(12) United States Patent
Friedrich et al.

(10) Patent No.: US 11,051,497 B2
(45) Date of Patent: *Jul. 6, 2021

(54) MANIPULATION OF IMMUNOGLOBULIN GENE DIVERSITY AND MULTI-ANTIBODY THERAPEUTICS

(71) Applicant: Kymab Limited, Cambridge (GB)

(72) Inventors: Glenn Friedrich, Cambridge (GB); E-Chiang Lee, Cambridge (GB); Jasper Clube, Cambridge (GB); Nicholas England, Cambridge (GB)

(73) Assignee: Kymab Limited, Cambridge (GB)

( * ) Notice: Subject to any disclaimer, the term of this patent is extended or adjusted under 35 U.S.C. 154(b) by 24 days.

This patent is subject to a terminal disclaimer.

(21) Appl. No.: 14/220,074

(22) Filed: Mar. 19, 2014

(65) Prior Publication Data

US 2014/0212416 A1   Jul. 31, 2014

Related U.S. Application Data

(63) Continuation of application No. PCT/GB2012/052298, filed on Sep. 18, 2012.

(30) Foreign Application Priority Data

| Sep. 19, 2011 | (GB) | 1116120 |
| Sep. 19, 2011 | (GB) | 1116122 |
| Feb. 24, 2012 | (GB) | 1203257 |
| Mar. 15, 2012 | (GB) | 1204592 |
| Mar. 29, 2012 | (GB) | 1205702 |
| May 18, 2012 | (GB) | 1208749 |
| Jul. 2, 2012 | (GB) | 1211692 |

(51) Int. Cl.
| *A01K 67/027* | (2006.01) |
| *C07K 16/18* | (2006.01) |
| *C07K 16/46* | (2006.01) |
| *C12N 15/85* | (2006.01) |
| *C07K 16/08* | (2006.01) |
| *C07K 16/12* | (2006.01) |
| *C07K 16/10* | (2006.01) |

(52) U.S. Cl.
CPC ......... *A01K 67/0278* (2013.01); *C07K 16/08* (2013.01); *C07K 16/12* (2013.01); *C07K 16/18* (2013.01); *C07K 16/462* (2013.01); *C12N 15/8509* (2013.01); *A01K 2217/072* (2013.01); *A01K 2217/15* (2013.01); *A01K 2227/105* (2013.01); *A01K 2267/01* (2013.01); *C07K 16/085* (2013.01); *C07K 16/088* (2013.01); *C07K 16/1018* (2013.01); *C07K 16/1045* (2013.01); *C07K 16/1217* (2013.01); *C07K 16/1232* (2013.01); *C07K 16/1242* (2013.01); *C07K 16/46* (2013.01); *C07K 2317/24* (2013.01); *C07K 2317/56* (2013.01); *C12N 2800/204* (2013.01)

(58) Field of Classification Search
CPC .......... A01K 67/0278; A01K 2217/072; A01K 2217/15; A01K 2227/105; A01K 2267/01; C12N 15/8509; C07K 16/462
USPC .................................... 800/6, 18; 530/387.3
See application file for complete search history.

(56) References Cited

U.S. PATENT DOCUMENTS

| 4,720,449 A | 1/1988 | Borror et al. |
| 5,169,939 A | 12/1992 | Gefter et al. |
| 5,545,806 A | 8/1996 | Lonberg et al. |
| 5,545,807 A | 8/1996 | Surani et al. |
| 5,565,321 A | 10/1996 | Spriggs et al. |
| 5,633,425 A * | 5/1997 | Lonberg ............. A01K 67/0276 536/23.1 |
| 5,770,429 A | 6/1998 | Lonberg et al. |
| 5,789,215 A | 8/1998 | Berns et al. |
| 5,807,715 A | 9/1998 | Morrison et al. |
| 5,939,598 A | 8/1999 | Kucherlapati et al. |
| 5,948,600 A | 9/1999 | Roschger et al. |

(Continued)

FOREIGN PATENT DOCUMENTS

| CA | 2307503 A1 | 11/2001 |
| CA | 2747534 A1 | 6/2010 |

(Continued)

OTHER PUBLICATIONS

Sun et al. (1999) Infection and Immunity, vol. 67(3), 1172-1179.*

(Continued)

*Primary Examiner* — Anne Marie S Wehbe

(74) *Attorney, Agent, or Firm* — Nutter McClennen & Fish LLP

(57) ABSTRACT

The invention provides improved non-human vertebrates and non-vertebrate cells capable of expressing antibodies comprising human variable region sequences. The present invention is directed to the provision of long HCDR3s from non-human vertebrates and cells. The present invention is also directed to the provision of novel V, D and J pairings in immunoglobulin heavy and light chain loci. Novel, biased antibody diversities and potentially expanded diversities are provided. The invention also provides for novel and potentially expanded diversity or diversity that is biased towards variable gene usage common to antibodies useful for treating and/or preventing certain diseases or conditions, such as infectious diseases. The invention also provides methods of generating antibodies using such vertebrates, as well as the antibodies per se, therapeutic compositions thereof and uses.

12 Claims, 9 Drawing Sheets

Specification includes a Sequence Listing.

(56) References Cited

U.S. PATENT DOCUMENTS

| | | | |
|---|---|---|---|
| 6,114,598 A | 9/2000 | Kucherlapati et al. | |
| 6,130,364 A | 10/2000 | Jakobovits et al. | |
| 6,162,963 A | 12/2000 | Kucherlapati et al. | |
| 6,319,906 B1 | 11/2001 | Bennett et al. | |
| 6,395,487 B1 | 5/2002 | Bradley et al. | |
| 6,461,818 B1 | 10/2002 | Bradley et al. | |
| 6,596,541 B2 * | 7/2003 | Murphy | A01K 67/0275 435/440 |
| 6,657,103 B1 | 12/2003 | Kucherlapati et al. | |
| 6,673,986 B1 | 1/2004 | Kucherlapati et al. | |
| 6,713,610 B1 | 3/2004 | Kucherlapati et al. | |
| 6,833,268 B1 | 12/2004 | Green et al. | |
| 6,914,128 B1 | 7/2005 | Salfeld et al. | |
| 6,992,235 B2 | 1/2006 | Bode et al. | |
| 6,998,514 B2 | 2/2006 | Bruggemann | |
| 7,105,348 B2 | 9/2006 | Murphy et al. | |
| 7,119,248 B1 | 10/2006 | Rajewsky et al. | |
| 7,205,140 B2 | 4/2007 | Gottschalk et al. | |
| 7,205,148 B2 | 4/2007 | Economides et al. | |
| 7,262,028 B2 | 8/2007 | Van Berkel et al. | |
| 7,294,754 B2 | 11/2007 | Poueymirou et al. | |
| 7,435,871 B2 | 10/2008 | Green et al. | |
| 7,501,552 B2 | 3/2009 | Lonberg et al. | |
| 7,605,237 B2 | 10/2009 | Stevens et al. | |
| 7,605,238 B2 | 10/2009 | Korman et al. | |
| 7,910,798 B2 | 3/2011 | Tanamachi et al. | |
| 7,932,431 B2 | 4/2011 | Bruggemann | |
| 8,158,419 B2 | 4/2012 | Lonberg et al. | |
| 8,502,018 B2 | 8/2013 | Murphy et al. | |
| 8,592,644 B2 | 11/2013 | Harriman et al. | |
| 8,642,835 B2 † | 2/2014 | Macdonald | |
| 8,697,940 B2 | 4/2014 | MacDonald et al. | |
| 8,754,287 B2 | 6/2014 | MacDonald et al. | |
| 8,771,988 B2 | 7/2014 | Goepfert et al. | |
| 8,791,323 B2 | 7/2014 | Murphy et al. | |
| 8,877,901 B2 | 11/2014 | Govindan | |
| 8,962,913 B2 | 2/2015 | Murphy et al. | |
| 9,253,965 B2 | 2/2016 | Liang et al. | |
| 9,434,782 B2 | 9/2016 | Bradley et al. | |
| 9,445,581 B2 | 9/2016 | Bradley et al. | |
| 9,447,177 B2 | 9/2016 | Bradley et al. | |
| 9,504,236 B2 | 11/2016 | Bradley et al. | |
| 9,505,827 B2 | 11/2016 | Bradley et al. | |
| 9,783,593 B2 | 10/2017 | Bradley et al. | |
| 9,783,618 B2 * | 10/2017 | Friedrich | C07K 16/468 |
| 9,788,534 B2 | 10/2017 | Bradley et al. | |
| 9,896,516 B2 | 2/2018 | Bradley et al. | |
| 9,924,705 B2 | 3/2018 | Liang et al. | |
| 9,938,357 B2 | 4/2018 | Bradley et al. | |
| 9,938,358 B2 | 4/2018 | Bradley et al. | |
| 9,963,716 B2 | 5/2018 | Bradley et al. | |
| 1,006,439 A1 | 9/2018 | Bradley et al. | |
| 1,014,946 A1 | 12/2018 | Lee et al. | |
| 10,149,462 B2 * | 12/2018 | Lee | C07K 16/462 |
| 10,165,763 B2 | 1/2019 | Bradley et al. | |
| 10,226,033 B2 | 3/2019 | Bradley et al. | |
| 10,251,377 B2 | 4/2019 | Clube | |
| 10,605,808 B2 | 3/2020 | Logtenberg et al. | |
| 10,667,501 B2 | 6/2020 | Germaschewski et al. | |
| 10,730,930 B2 * | 8/2020 | Bradley | C07K 16/00 |
| 10,774,155 B2 | 9/2020 | Bradley et al. | |
| 10,966,412 B2 | 4/2021 | Lee et al. | |
| 2002/0088016 A1 | 7/2002 | Bruggemann | |
| 2002/0183275 A1 | 12/2002 | Murphy et al. | |
| 2003/0070185 A1 | 4/2003 | Jakobovits et al. | |
| 2003/0108925 A1 | 6/2003 | Dix et al. | |
| 2003/0167489 A1 | 9/2003 | Rajewsky et al. | |
| 2003/0217373 A1 | 11/2003 | Green et al. | |
| 2004/0128703 A1 | 7/2004 | Shizuya | |
| 2004/0231012 A1 | 11/2004 | Bruggemann | |
| 2005/0048621 A1 | 3/2005 | Grasso et al. | |
| 2006/0008892 A1 | 1/2006 | Yacoby-Zeevi | |
| 2006/0015949 A1 | 1/2006 | Lonberg et al. | |
| 2006/0015957 A1 | 1/2006 | Lonberg et al. | |
| 2006/0021074 A1 | 1/2006 | Kellermann et al. | |
| 2006/0199204 A1 | 9/2006 | Dix et al. | |
| 2007/0280945 A1 | 12/2007 | Stevens et al. | |
| 2008/0098490 A1 | 4/2008 | Jakobovits et al. | |
| 2009/0083870 A1 | 3/2009 | Horn et al. | |
| 2009/0083879 A1 | 3/2009 | Dhugga | |
| 2009/0093059 A1 | 4/2009 | Baszczynski et al. | |
| 2009/0209036 A1 | 8/2009 | Reynaud et al. | |
| 2009/0307787 A1 | 12/2009 | Grosveld et al. | |
| 2010/0011450 A1 | 1/2010 | Garcia et al. | |
| 2010/0069614 A1 | 3/2010 | Houtzager et al. | |
| 2010/0146647 A1 | 6/2010 | Logtenberg et al. | |
| 2010/0196367 A1 | 8/2010 | Day | |
| 2010/0330676 A1 | 12/2010 | Horowitz et al. | |
| 2011/0119779 A1 | 5/2011 | Shizuya et al. | |
| 2011/0138489 A1 | 6/2011 | Tanamachi et al. | |
| 2011/0145937 A1 | 6/2011 | MacDonald et al. | |
| 2011/0195454 A1 | 8/2011 | McWhirter et al. | |
| 2011/0236378 A1 | 9/2011 | Green et al. | |
| 2011/0283376 A1 | 11/2011 | Murphy et al. | |
| 2012/0021409 A1 | 1/2012 | McWhirter et al. | |
| 2012/0070861 A1 | 3/2012 | MacDonald et al. | |
| 2012/0073004 A1 | 3/2012 | MacDonald et al. | |
| 2012/0096572 A1 * | 4/2012 | Macdonald | A01K 67/0275 800/18 |
| 2012/0167237 A1 * | 6/2012 | Bradley | C07K 16/00 800/9 |
| 2012/0195910 A1 | 8/2012 | Wu et al. | |
| 2012/0204278 A1 | 8/2012 | Bradley et al. | |
| 2012/0233715 A1 | 9/2012 | Kuroiwa et al. | |
| 2012/0322108 A1 | 12/2012 | MacDonald et al. | |
| 2013/0039850 A1 | 2/2013 | Lonberg et al. | |
| 2013/0096287 A1 | 4/2013 | MacDonald et al. | |
| 2013/0102031 A1 | 4/2013 | King et al. | |
| 2013/0160153 A1 | 6/2013 | MacDonald et al. | |
| 2013/0198879 A1 | 8/2013 | McWhirter et al. | |
| 2013/0212719 A1 | 8/2013 | MacDonald et al. | |
| 2013/0243759 A1 | 9/2013 | Friedrich et al. | |
| 2013/0247235 A1 | 9/2013 | McWhirter et al. | |
| 2013/0254911 A1 | 9/2013 | MacDonald et al. | |
| 2013/0263293 A1 | 10/2013 | Bradley et al. | |
| 2013/0323790 A1 | 12/2013 | MacDonald et al. | |
| 2013/0323791 A1 * | 12/2013 | Macdonald | C12N 15/8509 435/91.1 |
| 2013/0326647 A1 | 12/2013 | MacDonald et al. | |
| 2013/0333057 A1 | 12/2013 | MacDonald et al. | |
| 2014/0017228 A1 | 1/2014 | MacDonald et al. | |
| 2014/0017782 A1 | 1/2014 | Murphy et al. | |
| 2014/0041067 A1 | 2/2014 | Bradley et al. | |
| 2014/0120582 A1 | 5/2014 | Bradley et al. | |
| 2014/0130193 A1 | 5/2014 | MacDonald et al. | |
| 2014/0130194 A1 | 5/2014 | MacDonald et al. | |
| 2014/0137275 A1 | 5/2014 | MacDonald et al. | |
| 2014/0150125 A1 | 5/2014 | Bradley et al. | |
| 2014/0150126 A1 | 5/2014 | Bradley et al. | |
| 2014/0182003 A1 | 6/2014 | Bradley et al. | |
| 2014/0201854 A1 | 7/2014 | Bradley et al. | |
| 2014/0201856 A1 | 7/2014 | Bradley et al. | |
| 2014/0212416 A1 | 7/2014 | Friedrich et al. | |
| 2014/0213773 A1 | 7/2014 | MacDonald et al. | |
| 2014/0283150 A1 | 9/2014 | Bradley et al. | |
| 2014/0323327 A1 | 10/2014 | Bradley et al. | |
| 2014/0325690 A1 | 10/2014 | Bradley et al. | |
| 2014/0331339 A1 | 11/2014 | Bradley et al. | |
| 2014/0331343 A1 | 11/2014 | Bradley et al. | |
| 2014/0331344 A1 | 11/2014 | Friedrich et al. | |
| 2014/0356908 A1 | 12/2014 | Grosveld et al. | |
| 2014/0359797 A1 | 12/2014 | Bradley et al. | |
| 2015/0033369 A1 | 1/2015 | Bradley et al. | |
| 2015/0033372 A1 | 1/2015 | Bradley et al. | |
| 2015/0037337 A1 | 2/2015 | Friedrich et al. | |
| 2015/0040250 A1 | 2/2015 | Bradley et al. | |
| 2015/0082466 A1 | 3/2015 | Clube | |
| 2015/0113669 A1 | 4/2015 | Bradley et al. | |
| 2015/0133641 A1 | 5/2015 | Germaschewski et al. | |
| 2015/0196015 A1 | 7/2015 | MacDonald et al. | |
| 2015/0334998 A1 | 11/2015 | Bradley et al. | |
| 2016/0044900 A1 | 2/2016 | Bradley et al. | |
| 2016/0150768 A1 | 6/2016 | Bradley et al. | |
| 2016/0219846 A1 | 8/2016 | Liang et al. | |

(56) References Cited

U.S. PATENT DOCUMENTS

| | | |
|---|---|---|
| 2016/0249592 A1 | 9/2016 | Bradley et al. |
| 2016/0345551 A1 | 12/2016 | Bradley et al. |
| 2016/0345552 A1 | 12/2016 | Bradley et al. |
| 2016/0353719 A1 | 12/2016 | Friedrich et al. |
| 2017/0051045 A1 | 2/2017 | Bradley et al. |
| 2017/0071174 A1 | 3/2017 | Bradley et al. |
| 2017/0081423 A1 | 3/2017 | Bradley et al. |
| 2017/0094956 A1 | 4/2017 | Bradley et al. |
| 2017/0096498 A1 | 4/2017 | Bradley et al. |
| 2017/0099815 A1 | 4/2017 | Bradley et al. |
| 2017/0099816 A1 | 4/2017 | Bradley et al. |
| 2017/0099817 A1 | 4/2017 | Bradley et al. |
| 2017/0101482 A1 | 4/2017 | Bradley et al. |
| 2017/0101483 A1 | 4/2017 | Bradley et al. |
| 2017/0105396 A1 | 4/2017 | Bradley et al. |
| 2017/0135327 A1 | 5/2017 | Lee |
| 2017/0320936 A1 | 11/2017 | Bradley et al. |
| 2017/0354131 A1 | 12/2017 | Bradley et al. |
| 2018/0030121 A1 | 2/2018 | Bradley et al. |
| 2018/0142006 A1 | 5/2018 | Logtenberg et al. |
| 2018/0282761 A1 | 10/2018 | Bradley et al. |
| 2018/0295821 A1 | 10/2018 | Friedrich et al. |
| 2018/0298112 A1 | 10/2018 | Bradley et al. |
| 2019/0174729 A1 | 6/2019 | Lee et al. |
| 2019/0208753 A1 | 7/2019 | Clube |
| 2019/0327946 A1 | 10/2019 | Bradley et al. |
| 2020/0205384 A1 | 7/2020 | Friedrich et al. |
| 2020/0214274 A1 | 7/2020 | Lee et al. |
| 2020/0267952 A1 | 8/2020 | Germaschewski et al. |
| 2020/0317751 A1 | 10/2020 | Bradley et al. |
| 2020/0317752 A1 | 10/2020 | Bradley et al. |
| 2020/0337280 A1 | 10/2020 | Bradley et al. |
| 2020/0352144 A1 | 11/2020 | Bradley et al. |
| 2020/0352145 A1 | 11/2020 | Bradley et al. |
| 2020/0375158 A1 | 12/2020 | Bradley et al. |
| 2021/0079118 A1 | 3/2021 | Bradley et al. |

FOREIGN PATENT DOCUMENTS

| | | |
|---|---|---|
| CA | 2820824 A1 | 2/2012 |
| DE | 10251918 A1 | 5/2004 |
| EP | 1780272 A1 | 5/2007 |
| EP | 0937140 B1 | 9/2007 |
| EP | 2517556 B1 | 10/2012 |
| EP | 2517557 A2 | 10/2012 |
| EP | 2147594 A1 | 11/2013 |
| EP | 2480676 B1 | 4/2016 |
| GB | 2398784 A | 9/2004 |
| GB | 2403475 A | 1/2005 |
| JP | 2004524841 A | 8/2004 |
| JP | 2005510253 A | 4/2005 |
| JP | 2008507257 A | 3/2008 |
| JP | 2010512749 A | 4/2010 |
| JP | 2012521211 A | 9/2012 |
| KR | 20050042792 A | 5/2005 |
| WO | WO-9004036 A1 | 4/1990 |
| WO | WO-9100906 A1 | 1/1991 |
| WO | WO-9110741 A1 | 7/1991 |
| WO | WO-9203918 A1 | 3/1992 |
| WO | WO-9312227 A1 | 6/1993 |
| WO | WO-9402602 A1 | 2/1994 |
| WO | WO 9404667 A1 | 3/1994 |
| WO | WO-9425585 A1 | 11/1994 |
| WO | WO-9630498 A1 | 10/1996 |
| WO | WO-9824884 A1 | 6/1998 |
| WO | WO-9824893 A2 | 6/1998 |
| WO | 9850431 A2 | 11/1998 |
| WO | WO-9945962 A1 | 9/1999 |
| WO | WO-0026373 A1 | 5/2000 |
| WO | WO-0071585 A1 | 11/2000 |
| WO | WO-0208409 A2 | 1/2002 |
| WO | WO-0236789 A2 | 5/2002 |
| WO | WO-0243478 A2 | 6/2002 |
| WO | WO-02053596 A2 | 7/2002 |
| WO | WO-02059263 A2 | 8/2002 |
| WO | WO-02066630 A1 | 8/2002 |
| WO | WO-02070648 A2 | 9/2002 |
| WO | WO-03006639 A1 | 1/2003 |
| WO | WO-03047336 A2 | 6/2003 |
| WO | WO-03061363 A2 | 7/2003 |
| WO | 2004009618 A2 | 1/2004 |
| WO | WO-2004044150 A2 | 5/2004 |
| WO | WO-2004050838 A2 | 6/2004 |
| WO | WO-2005003364 A2 | 1/2005 |
| WO | WO-2005004592 A2 | 1/2005 |
| WO | WO-2005019463 A1 | 3/2005 |
| WO | WO-2005058815 A2 | 6/2005 |
| WO | WO-2005092926 A2 | 10/2005 |
| WO | WO-2006008548 A2 | 1/2006 |
| WO | WO-2006029459 A1 | 3/2006 |
| WO | WO-2006044492 A2 | 4/2006 |
| WO | WO-2006055704 A2 | 5/2006 |
| WO | WO-2006068953 A2 | 6/2006 |
| WO | WO-2006117699 A2 | 11/2006 |
| WO | WO-2006122442 A1 | 11/2006 |
| WO | WO-2007085837 A1 | 8/2007 |
| WO | WO-2007096779 A2 | 8/2007 |
| WO | WO-2007117410 A2 | 10/2007 |
| WO | WO-2007143168 A2 | 12/2007 |
| WO | WO-2008022391 A1 | 2/2008 |
| WO | WO-2008054606 A2 | 5/2008 |
| WO | WO-2008070367 A2 | 6/2008 |
| WO | WO-2008076379 A2 | 6/2008 |
| WO | WO-2008081197 A1 | 7/2008 |
| WO | WO-2008094178 A2 | 8/2008 |
| WO | WO-2008103474 A1 | 8/2008 |
| WO | WO-2008108918 A1 | 9/2008 |
| WO | WO-2008118970 A2 | 10/2008 |
| WO | WO-2008122886 A2 | 10/2008 |
| WO | WO-2008151081 A1 | 12/2008 |
| WO | WO-2009013620 A2 | 1/2009 |
| WO | WO-2009018411 A1 | 2/2009 |
| WO | WO-2009023540 A1 | 2/2009 |
| WO | WO-2009076464 A2 | 6/2009 |
| WO | WO-2009080254 A1 | 7/2009 |
| WO | WO-2009094178 A2 | 7/2009 |
| WO | WO-2009097006 A2 | 8/2009 |
| WO | WO-2009118524 A2 | 10/2009 |
| WO | WO-2009129247 A2 | 10/2009 |
| WO | WO-2009143472 A2 | 11/2009 |
| WO | WO-2009157771 A2 | 12/2009 |
| WO | WO-2010039900 A2 | 4/2010 |
| WO | WO-2010070263 A1 | 6/2010 |
| WO | WO-2010077854 A1 | 7/2010 |
| WO | WO-2010097385 A1 | 9/2010 |
| WO | WO-2010109165 A2 | 9/2010 |
| WO | WO-2010113039 A1 | 10/2010 |
| WO | WO-2011004192 A1 | 1/2011 |
| WO | WO-2011008093 A1 | 1/2011 |
| WO | WO-2011014469 A1 | 2/2011 |
| WO | WO-2011056864 A1 | 5/2011 |
| WO | WO-2011062206 A1 | 5/2011 |
| WO | WO-2011062207 A1 | 5/2011 |
| WO | WO-2011071957 A1 | 6/2011 |
| WO | WO-2011072204 A1 | 6/2011 |
| WO | WO-2011097603 A1 | 8/2011 |
| WO | WO-2011146121 A1 | 11/2011 |
| WO | WO-2011158009 A1 | 12/2011 |
| WO | WO-2011163311 A1 | 12/2011 |
| WO | WO-2011163314 A1 | 12/2011 |
| WO | 2012/018764 A1 † | 2/2012 |
| WO | WO-2012018764 A1 | 2/2012 |
| WO | WO-2012023053 A2 | 2/2012 |
| WO | WO-2012064682 A1 | 5/2012 |
| WO | WO-2012141798 A1 | 10/2012 |
| WO | WO-2012148873 A2 | 11/2012 |
| WO | WO-2013022782 A2 | 2/2013 |
| WO | WO-2013041844 A2 | 3/2013 |
| WO | WO-2013041845 A2 | 3/2013 |
| WO | WO-2013041846 A2 | 3/2013 |
| WO | WO-2013045916 A1 | 4/2013 |
| WO | WO-2013059230 A1 | 4/2013 |
| WO | WO-2013061078 A1 | 5/2013 |
| WO | WO-2013061098 A2 | 5/2013 |

(56) References Cited

FOREIGN PATENT DOCUMENTS

| WO | WO-2013079953 A1 | 6/2013 |
|---|---|---|
| WO | WO-2013096142 A1 | 6/2013 |
| WO | WO-2013116609 A1 | 8/2013 |
| WO | WO-2013130981 A1 | 9/2013 |
| WO | WO-2013134263 A1 | 9/2013 |
| WO | WO-2013144567 A1 | 10/2013 |
| WO | WO-2013166236 A1 | 11/2013 |
| WO | WO-2013171505 A2 | 11/2013 |
| WO | WO-2013176772 A1 | 11/2013 |
| WO | WO-2014093622 A2 | 6/2014 |
| WO | WO-2014130690 A1 | 8/2014 |
| WO | WO-2015049517 A2 | 4/2015 |
| WO | WO-2019008123 A2 | 1/2019 |

OTHER PUBLICATIONS

Rock et al. (1994) J. Exp. Med., vol. 179, 323-328.*
Shiokawa et al. (1999) J. Immunol., vol. 162, 6060-6070.*
U.S. Appl. No. 13/416,684, filed Mar. 9, 2012.
U.S. Appl. No. 13/433,084, filed Mar. 28, 2012.
U.S. Appl. No. 13/740,727, filed Jan. 14, 2013.
U.S. Appl. No. 13/843,528, filed Mar. 15, 2013.
U.S. Appl. No. 13/890,147, filed May 8, 2013.
U.S. Appl. No. 14/137,902, filed Dec. 20, 2013.
U.S. Appl. No. 14/935,010, filed Nov. 6, 2015.
Adams D.J., et al., "A Genome-Wide, End-Sequenced 129Sv BAC Library Resource for Targeting Vector Construction," Genomics, 2005, vol. 86 (6), pp. 753-758.
Affidavits Evidencing Murphy Slides as Printed Publication, 84 pages, dated Jun. 20, 2016.
Aguilera R.J. et al., "Characterization of immunoglobulin enhancer deletions in murine plasmacytomas," The EMBO Journal, 1985, vol. 4 (13B), pp. 3689-3693.
Ahmed T., "Sanofi-aventis and Regeneron Extend Therapeutic Antibody Agreement," PharmaDeals Review, Nov. 2009, vol. 11, p. 115.
Arnaout R., et al., "High-Resolution Description of Antibody Heavy-Chain Repertoires in Humans," Plos One, 2011, vol. 6 (8), pp. e22365-1-e22365-8.
Askew G.R., et al., "Site-Directed Point Mutations in Embryonic Stem Cells: A Gene-Targeting Tag-and-Exchange Strategy," Molecular and Cellular Biology, 1993, vol. 13 (7), pp. 4115-4124.
Atlas of Genetics and Cytogenetics in Oncology and Haematology, VPREB1 (pre-B lymphocyte 1), 5 pages. [Retrieved from the Internet online at http://atlasgeneticsoncolgy.org/Genes/GG_VPREB1.html on May 25, 2015].
Auerbach W., et al., "Establishment and Chimera Analysis of 129/SvEv- and C57BL/6-Derived Mouse Embryonic Stem Cell Lines," BioTechniques, 2000, vol. 29 (5), pp. 1024-1032.
Avery S., Attorney for Applicant, Third-Party Pre-Issuance Submission Under 37 CFR Section 1.290 in U.S. Appl. No. 14/517,755, dated Jun. 26, 2015, 16 pages.
Baker A.M., et al., "Adaptation of TCR Expression Vectors for the Construction of Mouse-Human Chimeric MBP-Specific TCR Transgenes," Journal of Neuroscience Research, 1996, vol. 45 (4), pp. 487-491.
Baker M.D., et al., "Homologous Recombination Between Transferred and Chromosomal Immunoglobulin Kappa Genes," Molecular and Cellular Biology, 1988, vol. 8 (10), pp. 4041- 4047.
Barreto V.M., et al., "AID from bony fish catalyzes class switch recombination," Journal of Experimental Medicine, 2005, vol. 202 (6), pp. 733-738.
Bates J.G., et al., "Chromosomal Position of a $V_H$ Gene Segment Determines its Activation and Inactivation as A Substrate for V(D)J Recombination," Journal of Experimental Medicine, 2007, vol. 204 (13), pp. 3247-3256.
Beard C., et al., "Efficient Method to Generate Single-Copy Transgenic Mice by Site-Specific Integration in Embryonic Stem Cells," Genesis, 2006, vol. 44 (1), pp. 23-28.
Beck E., et al., "Nucleotide Sequence and Exact Localization of the Neomycin Phosphotransferase Gene From Transposon Tn5," Genesis, 1982, vol. 19 (3), pp. 327-336.
Beerli R.R., et al., "Mining Human Antibody Repertoires," MAbs, Jul./Aug. 2010, vol. 2 (4), pp. 365-378.
Berg D.E., et al., "Inverted Repeats of Tn5 are Transposable Elements," Proceedings of the National Academy of Sciences U.S.A, 1982, vol. 79 (8), pp. 2632-2635.
Bethke B., et al., "Segmental Genomic Replacement by Cre-Mediated Recombination: Genotoxic Stress Activation of the p53 Promoter in Single-Copy Transformants," Nucleic Acids Research, 1997, vol. 25 (14), pp. 2828-2834.
Bhattacharya P., et al., "Switch Region Identity Plays an Important Role in Ig Class Switch Recombination," Journal of Immunology, 2010, vol. 184 (11), pp. 6242-6248.
Billiard F., et al., "Ongoing DII4-Notch Signaling is Required for T-Cell Homeostasis in the Adult Thymus," European Journal of Immunology, 2011, vol. 41 (8), pp. 2207-2216.
Blankenstein T. et al., "Immunoglobulin $V_H$ Region Genes of the Mouse are Organized in Overlapping Clusters," European Journal of Immunology, 1987, vol. 17 (9), pp. 1351-1357.
Board of Appeal of the European Patent Office, Datasheet for the Decision of Nov. 9, 2015 for Application No. 02709544.7, Case T 2220/14-3.3.08, 83 pages.
Bode J., et al., "The Transgeneticist's Toolbox: Novel Methods for the Targeted Modification of Eukaryotic Genomes," Biological Chemistry, 2000, vol. 381 (9-10), pp. 801-813.
Bogen B., et al., "A Rearranged $\lambda_2$ Light Gene Chain Retards but does not Exclude $\chi$ and $\lambda_1$ Expression," European Journal of Immunology, 1991, vol. 21 (10), pp. 2391-2395.
Bolland D.J., et al., "Antisense Intergenic Transcription Precedes Igh D-To-J Recombination and is Controlled by the Intronic Enhancer Eµ," Molecular and Cellular Biology, 2007, vol. 27 (15), pp. 5523-5533.
Bonin A., et al., "Isolation, Microinjection, and Transfer of Mouse Blastocysts," Methods in Molecular Biology, 2001, vol. 158, pp. 121-134.
Bottaro A., et al., "Deletion of the IgH Intronic Enhancer and Associated Matrix-Attachment Regions Decreases, But Does Not Abolish, Class Switching at the µ Locus," International Immunology, 1998, vol. 10 (6), pp. 799-806.
Bradley A., et al., "Formation of Germ-Line Chimaeras from Embryo-Derived Teratocarcinoma Cell Lines," Nature, 1984, vol. 309 (5965), pp. 255-256.
Bransteitter R., et al., "Activation-Induced Cytidine Deaminase Deaminates Deoxycytidine on Single-Stranded DNA but Requires the Action of RNase," Proceedings of the National Academy of Sciences, 2003, vol. 100 (7), pp. 4102-4107.
Breden F., et al., "Comparison of Antibody Repertoires Produced by HIV-1 Infection, Other Chronic and Acute Infections, and Systemic Autoimmune Disease," PLoS One, 2011, vol. 6 (3), pp. e16857.
Brezinschek H.P., et al., "Analysis of the Human $V_H$ Gene Repertoire," Journal of Clinical Investigation, 1997, vol. 99 (10), pp. 2488-2501.
Briney B.S., et al., "Human Peripheral Blood Antibodies with Long HCDR3s are Established Primarily at Original Recombination using a Limited Subset of Germline Genes," PLoS One, 2012, vol. 7 (5), pp. e36750-1-e36750-13.
Brocker C.N., et al., "Evolutionary Divergence and Functions of the ADAM and ADAMTS Gene Families," Human Genomics, 2009, vol. 4 (1), pp. 43-55.
Brüggemann M., et al., "A Repertoire of Monoclonal Antibodies with Human Heavy Chains from Transgenic Mice," Proceedings of the National Academy of Sciences U.S.A, 1989, vol. 86 (17), pp. 6709-6713.
Brüggemann M., et al., "Human Antibody Expression in Transgenic Mice," Archivum Immunologiae et Therapia Experimentalis, 2001, vol. 49 (3), pp. 203-208.
Brüggemann M., et al., "Human Antibody Production in Transgenic Mice: Expression from 100 Kb of the Human IgH Locus," European Journal of Immunology, 1991, vol. 21 (5), pp. 1323-1326.

(56) References Cited

OTHER PUBLICATIONS

Brüggemann M., et al., "Immunoglobulin Heavy Chain Locus of the Rat: Striking Homology to Mouse Antibody Genes," Proceedings of the National Academy of Sciences U.S.A, 1986, vol. 83 (16), pp. 6075-6079.
Brüggemann M., et al., "The Immunogenicity of Chimeric Antibodies," The Journal of Experimental Medicine, 1989, vol. 170 (6), pp. 2153-2157.
Brüggemann M., et al., "Strategies for Expressing Human Antibody Repertoires in Transgenic Mice," Immunology Today, 1996, vol. 17 (8), pp. 391-397.
Brüggemann M., et al., "Human Monoclonal Antibodies from Translocus Mice," Molecular Biology of B Cells, Chapter 34, 2003, pp. 547-561.
Buehr M., et al., "Capture of Authentic Embryonic Stem Cells from Rat Blastocysts," Cell, 2008, vol. 135 (7), pp. 1287-1298.
Butler J.E., et al., "Immunoglobulin Diversity, B-Cell and Antibody Repertoire Development in Large Farm Animals," Revue scientifique et technique (International Office of Epizootics), 1998, vol. 17 (7), pp. 43-70.
Cadiñanos J., et al., "Generation of an Inducible and Optimized PiggyBac Transposon System," Nucleic Acids Research, 2007, vol. 35 (12), pp. e87.
Carstea A.C., et al., "Germline Competence of Mouse ES and iPS Cell Lines: Chimera Technologies and Genetic Background," World Journal of Stem Cells, 2009, vol. 1 (1), pp. 22-29.
Casrouge A., et al., "Size Estimate of the αβ TCR Repertoire, of Naive Mouse Splenocytes," The Journal of Immunology, 2000, vol. 164 (11), pp. 5782-5787.
Chan A.C., et al., "Therapeutic Antibodies for Autoimmunity and Inflammation," Nature Reviews Immunology, 2010, vol. 10 (5), pp. 301-316.
Chen C., et al., "Immunoglobulin Heavy Chain Gene Replacement: A Mechanism of Receptor Editing," Immunity, 1995, vol. 3 (6), pp. 747-755.
Chen J., et al., "B Cell Development in Mice that Lack One or Both Immunoglobulin Kappa Light Chain Genes," The EMBO Journal, 1993, vol. 12 (3), pp. 821-830.
Chen Y., "*PiggyBac* Transposon-Mediated, Reversible Gene Transfer in Human Embryonic Stem Cells," Stem Cells and Development, Nov. 2010, vol. 19 (6), 9 pages.
Chinese Patent Office, First Office Action (English Translation) for Chinese Application No. 201180039668.1, dated Jan. 3, 2014, 6 pages.
Chinese Patent Office, First Office Action for Chinese Application No. 201180039668.1, dated Jan. 3, 2014, 6 pages.
Chinese Patent Office, Search Report, Chinese Application No. 201180039668.1, dated Jan. 3, 2014, 2 pages.
Chinese Patent Office, Search Report (English Translation), Chinese Patent Application No. 201180039668.1, dated Jan. 3, 2014, 1 page.
Cho C., "Testicular and Epididymal ADAMs: Expression and Function During Fertilization," Nature Reviews Urology, 2012, vol. 9 (10), pp. 550-560.
Choi I., et al., "Characterization and Comparative Genomic Analysis of Intronless Adams with Testicular Gene Expression," Genomics, 2004, vol. 83 (4), pp. 636-646.
Clark J ., et al., "A Future for Transgenic Livestock," Nature Reviews Genetics, 2003, vol. 4 (10), pp. 825-833.
Clark L.A., et al., "Trends in Antibody Sequence Changes During the Somatic Hypermutation Process," The Journal of Immunology, 2006, vol. 177 (1), pp. 333-340.
Clark M.R., "IgG Effector Mechanisms," Chemical Immunology, 1997, vol. 65, pp. 88-110.
Colbère-Garapin F., et al., "A New Dominant Hybrid Selective Marker for Higher Eukaryotic Cells," Journal of Molecular Biology, 1981, vol. 150 (1), pp. 1-14.
Collins F.S., et al., "A Mouse for All Reasons," Cell, 2007, vol. 128 (1), pp. 9-13.
Combriato G., et al., "Regulation of Human Igλ Light Chain Gene Expression by NF-KB[1]," 2002, vol. 168 (3), pp. 1259-1266.

Conrath K., et al., "Camel Single-domain Antibodies as Modular Building Units in Bispecific and Bivalent Antibody Constructs," The Journal of Biological Chemistry, 2001, vol. 276 (10), pp. 7346-7350.
Copeland N.G., et al., "Recombineering: A Powerful New Tool for Mouse Functional Genomics," Nature Reviews Genetics, 2001, vol. 2 (10), pp. 769-779.
Corbett S.J., et al., "Sequence of the Human Immunoglobulin Diversity (D) Segment Locus: A Systematic Analysis Provides No Evidence for the Use of DIR Segments, Inverted D Segments, "Minor" D Segments or D-D Recombination," Journal of Molecular Biology, 1997, vol. 270 (4), pp. 587-597.
Corti D., et al., "A Neutralizing Antibody Selected from Plasma Cells that Binds to Group 1 and Group 2 Influenza A Hemagglutinins," Science, 2011, vol. 333 (6044), pp. 850-856.
Crouch E.E., et al., "Regulation of AID expression in the Immune Response," Journal of Experimental Medicine, 2007, vol. 204 (5), pp. 1145-1156.
Cuesta A.M., et al., "Multivalent Antibodies: When Design Surpasses Evolution," Trends in Biotechnology, 2010, vol. 28 (7), pp. 355-362.
Davies N. P., et al., "Creation of Mice Expressing Human Antibody Light Chains by Introduction of a Yeast Artificial Chromosome Containing the Core Region of the Human Immunoglobulin 1 Locus," Nature Biotechnology, 1993, vol. 11 (8), pp. 911-914.
De Bono B., et al., "$V_H$ Gene Segments in the Mouse and Human Genomes," Journal of Molecular Biology, 2004, vol. 342 (1), pp. 131-143.
De Kruif J., et al., "Human Immunoglobulin Repertoires Against Tetanus Toxoid Contain a Large and Diverse Fraction of High-Affinity Promiscuous $V_H$ Genes," Journal of Molecular Biology, 2009, vol. 387 (3), pp. 548-558.
De Saint Vincent B.R., et al., "Homologous Recombination in Mammalian Cells Mediates Formation of a Functional Gene from Two Overlapping Gene Fragments," Proceedings of the National Academy of Sciences U.S.A, 1983, vol. 80 (7), pp. 2002-2006.
Dechiara T.M., et al., "Producing Fully ES Cell-Derived Mice from Eight-Cell Stage Embryo Injections," Methods in Enzymology, 2010, Chapter 16, vol. 476, pp. 285-294.
Dechiara T.M., et al., "VelociMouse: Fully ES Cell-Derived F0-Generation Mice Obtained from the Injection of ES Cells into Eight-Cell-Stage Embryos," Methods in Molecular Biology, 2009, Chapter 16, vol. 530, pp. 311-324.
Deng C., et al., "Reexamination of Gene Targeting Frequency as a Function of the Extent of Homology Between the Targeting Vector and the Target Locus," Molecular and Cellular Biology, 1992, vol. 12 (8), pp. 3365-3371.
Denome R.M., et al., "Patterns of Polyadenylation Site Selection in Gene Constructs Containing Multiple Polyadenylation Signals," Molecular and Cellular Biology, 1988, vol. 8 (11), pp. 4829-4839.
Di Noia, J.M., "Molecular Mechanisms of Antibody Somatic Hypermutation," Annual Review of Biochemistry, 2007, vol. 76, pp. 1-22.
Diez-Roux G., et al., "A High-Resolution Anatomical Atlas of the Transcriptome in the Mouse Embryo," PLoS Biology, 2011, vol. 9 (1), pp. 1-13.
Ding L., et al., "Generation of High-Affinity Fully Human Anti-Interleukin-8 Antibodies from its cDNA by Two-Hybrid Screening and Affinity Maturation in Yeast," Protein Science, 2010, vol. 19 (10), pp. 1957-1966.
Doetschman T., et al., "Establishment of Hamster Blastocyst-Derived Embryonic Stem (ES) Cells," Developmental Biology, 1988, vol. 127 (1), pp. 224-227.
Doetschman T., et al., "Targeted Mutation of the Hprt Gene in Mouse Embryonic Stem Cells," Proceedings of the National Academy of Sciences U.S.A, 1988, vol. 85 (22), pp. 8583-8587.
Donohoe M.E., et al., "Transgenic Human λ5 Rescues the Murine λ5 Nullizygous Phenotype," Journal of Immunology, 2000, vol. 164, pp. 5269-5276.
Doyle A., et al., "The Construction of Transgenic and Gene Knockout/Knockin Mouse Models of Human Disease," Transgenic Research, 2012, vol. 21 (2), pp. 327-349.

(56) References Cited

OTHER PUBLICATIONS

Durbin R., et al., "A Map of Human Genome Variation from Population-Scale Sequencing," Nature, 1000 Genomes Project Consortium, 2010, vol. 467 (7319), pp. 1061-1073.
Durdik J., et al., "Isotype Switching by a Microinjected μ Immunoglobulin Heavy Chain Gene in Transgenic Mice," Proceedings of the National Academy of Sciences U.S.A, 1989, vol. 86 (7), pp. 2346-2350.
Ebert A., et al., "The Distal $V_H$ Gene Cluster of the lgh Locus Contains Distinct Regulatory Elements with Pax5 Transcription Factor-Dependent Activity in Pro-B Cells.," Immunity, 2011, vol. 34 (2), pp. 175-187.
Edwards D.R., et al., "The ADAM Metalloproteinases," Molecular Aspects of Medicine, 2008, vol. 29 (5), pp. 258-289.
Eisener-Dorman A.F., "Cautionary Insights on Knockout Mouse Studies: The Gene or not the Gene?," Brain, Behavior, and Immunity, 2009, vol. 23 (3), pp. 318-324.
Ekiert D.C., et al., "A Highly Conserved Neutralizing Epitope on Group 2 Influenza A Viruses.," Science, 2011, vol. 333 (6044), pp. 843-850.
European Patent Office, International Search Report and Written Opinion for the International Searching Authority for Application No. PCT/GB2012/052297, dated Jun. 19, 2013, 24 pages.
European Patent Office, Alessandro Brero, Authorized Officer, International Search Report and Written Opinion of the International Searching Authority for Application No. PCT/GB2012/052298, dated Jun. 13, 2013, 21 pages.
European Patent Office, Examination Report for Application No. 12762378.3, dated Jun. 8, 2016, 5 pages.
European Patent Office, International Search Report and Written Opinion for the International Searching Authority for Application No. PCT/GB2012/052296, dated May 17, 2013, 30 pages.
European Patent Office, European Search Report for Application No. 12194977.0, dated Jul. 5, 2013, 4 pages.
European Patent Office, Extended European Search Report for Application No. 12171791.2, dated Jun. 18, 2013, 5 pages.
European Patent Office, Extended European Search Report for Application No. 12171793.8 dated Jun. 21, 2013, 8 pages.
European Patent Office, Extended European Search Report for Application No. 12194970.5, dated Jan. 23, 2013, 9 pages.
European Patent Office, Extended European Search Report for Application No. 12194977.0, dated Jul. 17, 2013, 8 pages.
European Patent Office, Extended European Search Report for Application No. 12195041.4, dated Nov. 18, 2013, 8 pages.
European Patent Office, Extended European Search Report for Application No. 14170196.1, dated Oct. 8, 2014, 8 pages.
European Patent Office, Extended European Search Report for Application No. 14176740.0, dated Oct. 15, 2014, 7 pages.
European Patent Office, Extended European Search Report for Application No. 15188522.5 dated Feb. 2, 2016, 15 pages.
European Patent Office, International Search Report and Written Opinion for Application No. PCT/GB2012/052380, dated Jan. 3, 2013, 17 pages.
European Patent Office, Gaby Brouns, Authorized Officer, International Search Report and Written Opinion for the International Searching Authority for Application No. PCT/GB2013/051280, dated Nov. 15, 2013, 19 pages.
European Patent Office, Gaby Brouns, Authorized officer, International Search Report and Written Opinion of the International Searching Authority for Application No. PCT/GB2013/050682, dated Sep. 25, 2013, 16 pages.
European Patent Office, International Search Report and Written Opinion for the International Searching Authority for Application No. PCT/GB2012/052956, dated Mar. 1, 2013, 14 pages.
European Patent Office, International Search Report and Written Opinion for the International Searching Authority for Application No. PCT/GB2012/052960, dated Apr. 29, 2013, 19 pages.
European Patent Office, International Search Report and Written Opinion for the International Searching Authority for Application No. PCT/GB2013/050683, dated Jul. 9, 2013, 11 pages.
European Patent Office, Examination Report for Application No. 12795841.1, dated Feb. 12, 2016, 5 pages.
European Patent Office, Examination Report for Application No. 13711119.1, dated Dec. 17, 2015, 6 pages.
European Patent Office, Examination Report for Application No. 13711119.1, dated Jul. 13, 2016, 6 pages.
European Patent Office, International Searching Authority, Examiners Report on Allowable Claims for Application No. PCT/GB2010/051122, dated Jan. 2004, 1 page.
European Patent Office, Extended European Search Report for Application No. 14196645.7, dated Jun. 26, 2015, 12 pages.
European Patent Office, International Search Report and Written Opinion for Application No. PCT/GB2012/052670, dated Feb. 14, 2013, 12 pages.
European Patent Office, Laurent Deleu, Authorized Officer, International Preliminary Report on Patentability Chapter II for Application No. PCT/GB2010/051122, date of completion Nov. 2, 2011, 33 pages.
European Patent Office, Laurent Deleu, Authorized Officer, International Search Report and Written Opinion for the International Searching Authority for Application No. PCT/GB2010/051122, dated Sep. 29, 2010, 9 pages.
European Patent Office, Examination Report for Application No. 14176740.0, dated Jun. 6, 2016, 5 pages.
European Patent Office, Examination Report for Application No. 12194970.5, dated Sep. 23, 2013, 6 pages.
European Patent Office, Examination Report forApplication No. 14176740.0, dated Oct. 23, 2015, 5 pages.
European Patent Office, International Search Report and Written Opinion for the International Searching Authority, Application No. PCT/GB2011/050019, dated May 16, 2011, 12 pages.
European Patent Office, Notice of opposition to a European patent, pertaining to Application No. 10734546.4, dated Jan. 23, 2013, 41 pages.
European Patent Office, Opposition against EP2421357 Animal Models and Therapeutic Molecules in the name of Kymab Limited pertaining to Application No. 10734546.4, dated Oct. 23, 2013, 44 pages.
European Patent Office, Statement of Fact and Arguments in Support of Opposition pertaining to Application No. 10734546.4, dated Oct. 22, 2013, 41 pages.
European Patent Office, Communication pursuant to Rule 114(2) EPC regarding 14772198.9, dated Mar. 30, 2016, 16 pages.
European Patent Office, Invitation to Pay Additional Fees and, Where Applicable, Protest Fee, Application No. PCT/GB2012/052296, dated Jan. 24, 2013, 9 pages.
Evans J.P., "Fertilin Beta and Other ADAMs as Integrin Ligands: Insights into Cell Adhesion and Fertilization," Bioessays, 2001, vol. 23 (7), pp. 628-639.
Featherstone K., et al., "The Mouse Immunoglobulin Heavy Chain V-D Intergenic Sequence Contains Insulators that May Regulate Ordered V(D)J Recombination," Journal of Biological Chemistry, 2010, vol. 285 (13), pp. 9327-9338.
Feeney A.J., "Genetic and Epigenetic Control of V Gene Rearrangement Frequency," Advances in Experimental Medicine and Biology, 2009, Chapter 6, vol. 650, pp. 73-81.
Fell H.P., "Homologous Recombination in Hybridoma Cells: Heavy Chain Chimeric Antibody Produced by Gene Targeting," Proceedings of the National Academy of Sciences U.S.A, 1989, vol. 86 (21), pp. 8507-8511.
Feng Y.Q., et al., "Site-Specific Chromosomal Integration in Mammalian Cells: Highly Efficient CRE Recombinase-Mediated Cassette Exchange," Journal of Molecular Biology, 1999, vol. 292 (4), pp. 779-785.
Feschotte C., et al., "DNA Transposons and the Evolution of Eukaryotic Genomes," Annual Review of Genetics, 2007, vol. 41, pp. 331-368.
Fleischer B., et al., "Reactivity of Mouse T-Cell Hybridomas Expressing Human Vβ Gene Segments With Staphylococcal and Streptococcal Superantigens," Infection and Immunity, 1996, vol. 64 (3), pp. 987-994.
Folger K.R., et al., "Patterns of Integration of DNA Microinjected into Cultured Mammalian Cells: Evidence for Homologous Recom-

(56) References Cited

OTHER PUBLICATIONS bination Between Injected Plasmid DNA Molecules," Molecular and Cellular Biology, 1982, vol. 2 (11), pp. 1372-1387.
Forconi F., et al., "The Normal IGHV1-69-Derived B-Cell Repertoire Contains Stereotypic Patterns Characteristic of Unmutated CLL," Blood, 2010, vol. 115 (1), pp. 71-77.
French Patent Office, INPI, International Search Report for Patent Application No. 1359518, dated Aug. 20, 2014, 3 pages.
Friedrich G., "Statement of Dr. Glenn Friedrich," Mar. 3, 2016, 4 pages.
Fujieda S., et al., "Multiple Types of Chimeric Germ-Line Ig Heavy Chain Transcripts in Human B Cells: Evidence for Trans-Splicing of Human Ig RNA," Journal of Immunology, 1996, vol. 157 (8), pp. 3450-3459.
Fukita Y., et al., "Somatic Hypermutation in the Heavy Chain Locus Correlates with Transcription," Immunity, 1998, vol. 9 (1), pp. 105-114.
Gallo M.L., et al., "The Human Immunoglobulin Loci Introduced into Mice: V (D) and J Gene Segment Usage Similar to that of Adult Humans," European Journal of Immunology, 2000, vol. 30 (2), pp. 534-540.
Gama Sosa M.A., et al., "Animal Transgenesis: An Overview," Brain Structure and Function, 2010, vol. 214 (2-3), pp. 91-109.
Gavilondo J.V., et al., "Antibody Engineering at the Millennium," BioTechniques, 2000, vol. 29 (1), pp. 128-145.
Genbank (D. Muzny et al.), "Rattus norvegicus clone CH230-30N12, * Sequencing in Progress *, 6 unordered pieces,", GenBank Accession No. AC111740, 42 pages, Nov. 9, 2002, XP55054806 [retrieved online on Feb. 28, 2013] [Retrieved from the Internet: http://www.ncbi.nlm.nlh.gov/nuccore/AC111740on Feb. 28, 2013.
Genbank, "DNA Sequence of the Human Immunoglobulin D Segment Locus," Accession No. x97051.1 S64822, Aug. 6, 2014, 29 pages [Retrieved from the Internet: http://www.ncbi.nlm.nih.gov/nuccore/X97051].
Genbank, "DNA Sequence of the Human Immunoglobulin D Segment Locus," Accession No. x97051.1 S64822,updated Mar. 3, 2015, 26 pages.
Genbank, "*Homo sapiens* immunoglobulin heavy-chain (IGHV2-5) gene, IGHV2-5*10 allele, partial sequence,"Accession No. KF698731.1, dated Nov. 18, 2013, 1 page.
Genbank, "Mus musculus strain 129S1/SvlmJ chromosome 12 genomic sca locus group 129S1/SvlmJ_MMCHR12_CTG1," NCBI Reference Sequence No. NT_114985.3, May 2014, 1 page.
Gerdes T., et al., "Physical Map of the Mouse Lambda Light Chain and Related Loci," Immunogenetics, 2002, vol. 54 (1), pp. 62-65.
Gerstein R.M., et al., "Isotype Switching of an Immunoglobulin Heavy Chain Transgene Occurs by DNA Recombination Between Different Chromosomes," Cell, 1990, vol. 63 (3), pp. 537-548.
Geurts A.M., et al., "Knockout Rats Via Embryo Microinjection of Zinc-Finger Nucleases," Science, 2009, vol. 325 (5939), p. 433.
Giallourakis C.C., et al., "Elements Between the IgH Variable (V) and Diversity (D) Clusters Influence Antisense Transcription and Lineage-Specific V(D)J Recombination," Proceedings of the National Academy of Sciences, 2010, vol. 107 (51), pp. 22207-22212.
Giraldo P., et al., "Size Matters: Use of YACs, BACs and PACs in Transgenic Animals," Transgenic Research, 2001, vol. 10 (2), pp. 83-103.
Giusti A.M., et al., "Hypermutation is Observed only in Antibody H Chain V Region Transgenes that have Recombined with Endogenous Immunoglobulin H DNA: Implications for the Location of Cis-Acting Elements Required for Somatic Mutation," The Journal of Experimental Medicine, 1993, vol. 177 (3), pp. 797-809.
Glanville J., et al., "Naive Antibody Gene-Segment Frequencies are Heritable and Unaltered by Chronic Lymphocyte Ablation," Proceedings of the National Academy of Sciences U.S.A, 2011, vol. 108 (50), pp. 20066-20071.
Gluzman Y., "SV40-Transformed Simian Cells Support the Replication of Early SV40 Mutants," Cell, 1981, vol. 23 (1), pp. 175-182.
Goldman I.L., et al., "Transgenic Animals in Medicine: Integration and Expression of Foreign Genes, Theoretical and Applied Aspects," Medical Science Monitor, 2004, vol. 10 (11), pp. RA274-RA285.
Goodhardt M., et al., "Rearrangement and Expression of Rabbit Immunoglobulin Kappa Light Chain Gene in Transgenic Mice," Proceedings of the National Academy of Sciences, 1987, vol. 84 (12), pp. 4229-4233.
Gorman Jr., et al., "The Ig(Kappa) 3 Enhancer Influences the Ratio of Ig(Kappa) Versus Ig(Lambda) B Lymphocytes," Immunity, 1996, vol. 5 (3), pp. 241-252.
Gorny M.K., et al., "Human Anti-V3 HIV-1 Monoclonal Antibodies Encoded by the VH5-51/VL Lambda Genes Define a Conserved Antigenic Structure," PLoS One, 2011, vol. 6 (12), pp. e27780-1-e27780-10. 0.
Goyenechea B., et al., "Cells Strongly Expressing Ig(Kappa) Transgenes Show Clonal Recruitment of Hypermutation: A Role for Both Mar and the Enhancers," EMBO Journal, 1997, vol. 16 (13), pp. 3987-3994.
Gratz S. et al., "Genome Engineering of *Drosophila* with the CRISPR RNA-Guided Cas9 Nuclease," Genetics, Aug. 2013, vol. 194, pp. 1029-1035.
Green L.L., "Antibody Engineering via Genetic Engineering of the Mouse: XenoMouse Strains are a Vehicle for the Facile Generation of Therapeutic Human Monoclonal Antibodies," Journal of Immunological Methods, 1999, vol. 231 (1-2), pp. 11-23.
Green L.L., et al., "Antigen-Specific Human Monoclonal Antibodies from Mice Engineered with Human Ig Heavy and Light Chain YACs," Nature Genetics, 1994, vol. 7 (1), pp. 13-21.
Green L.L., et al., "Regulation of B Cell Development by Variable Gene Complexity in Mice Reconstituted with Human Immunoglobulin Yeast Artificial Chromosomes," The Journal of Experimental Medicine, 1998, vol. 188 (3), pp. 483-495.
Grund M., European Patent Attorney, Grund Intellectual Property Group, Third-Party Observations according to Article 115 EPC regarding 11705964.2, dated Apr. 30, 2014, 4 pages.
Grund M., European Patent Attorney, Grund Intellectual Property Group, Third-Party Observations according to Article 115 EPC regarding 11705964.2, dated Oct. 9, 2013, 8 pages.
Grund M., European Patent Attorney, Grund Intellectual Property Group, Third-Party Observations according to Article 115 EPC regarding 12171791.2, dated Aug. 4, 2014, 6 pages.
Grund M., European Patent Attorney, Grund Intellectual Property Group, Third-Party Observations according to Article 115 EPC regarding 12171791.2, dated Dec. 19, 2014, 7 pages.
Grund M., European Patent Attorney, Grund Intellectual Property Group, Third-Party Observations according to Article 115 EPC regarding 12171791.2, dated Feb. 26, 2014, 9 pages.
Grund M., European Patent Attorney, Grund Intellectual Property Group, Third-Party Observations according to Article 115 EPC regarding 12171793.8, dated Jun. 25, 2014, 7 pages.
Grund M., European Patent Attorney, Grund Intellectual Property Group, Third-Party Observations according to Article 115 EPC regarding 12194970.5, dated Apr. 25, 2014, 6 pages.
Grund M., European Patent Attorney, Grund Intellectual Property Group, Third-Party Observations according to Article 115 EPC regarding 12194970.5, dated Aug. 12, 2014, 5 pages.
Grund M., European Patent Attorney, Grund Intellectual Property Group, Third-Party Observations according to Article 115 EPC regarding 12194970.5, dated Mar. 5, 2014, 9 pages.
Grund M., European Patent Attorney, Grund Intellectual Property Group, Third-Party Observations according to Article 115 EPC regarding 12194970.5, dated Nov. 15, 2013, 6 pages.
Grund M., European Patent Attorney, Grund Intellectual Property Group, Third-Party Observations according to Article 115 EPC regarding 12194977.0, dated May 12, 2015, 5 pages.
Grund M., European Patent Attorney, Grund Intellectual Property Group, Third-Party Observations according to Article 115 EPC regarding 12195041.4, dated Jul. 30, 2014, 5 pages.
Grund M., European Patent Attorney, Grund Intellectual Property Group, Third-Party Observations according to Article 115 EPC regarding 12762377.5, dated Feb. 12, 2016, 8 pages.

(56) References Cited

OTHER PUBLICATIONS

Grund M., European Patent Attorney, Grund Intellectual Property Group, Third-Party Observations according to Article 115 EPC regarding 12762377.5, dated May 22, 2015, 7 pages.
Grund M., European Patent Attorney, Grund Intellectual Property Group, Third-Party Observations according to Article 115 EPC regarding 12772122.3, dated Mar. 12, 2015, 5 pages.
Grund M., European Patent Attorney, Grund Intellectual Property Group, Third-Party Observations according to Article 115 EPC regarding 12772122.3, dated May 17, 2016, 7 pages.
Grund M., European Patent Attorney, Grund Intellectual Property Group, Third-Party Observations according to Article 115 EPC regarding 12795606.8, dated Feb. 26, 2014, 6 pages.
Grund M., European Patent Attorney, Grund Intellectual Property Group, Third-Party Observations according to Article 115 EPC regarding 12795606.8, dated Mar. 26, 2015, 4 pages.
Grund M., European Patent Attorney, Grund Intellectual Property Group, Third-Party Observations according to Article 115 EPC regarding 13711119.1, dated Dec. 9, 2015, 7 pages.
Grund M., European Patent Attorney, Grund Intellectual Property Group, Third-Party Observations according to Article 115 EPC regarding 13711119.1, dated Jul. 5, 2016, 7 pages.
Grund M., European Patent Attorney, Grund Intellectual Property Group, Third-Party Observations according to Article 115 EPC regarding 13711120.9, dated May 17, 2016, 11 pages.
Grund M., European Patent Attorney, Grund Intellectual Property Group, Third-Party Observations according to Article 115 EPC regarding 14176740.0, dated Aug. 10, 2015, 13 pages.
Grund M., European Patent Attorney, Grund Intellectual Property Group, Third-Party Observations according to Article 115 EPC regarding EP12194977.0, dated Mar. 26, 2014, 4 pages.
Grund M., European Patent Attorney, Grund Intellectual Property Group, Third-Party Observations regarding Application No. PCT/GB2012/052297, dated Jan. 17, 2014, 3 pages.
Grund M., European Patent Attorney, Grund Intellectual Property Group, Third-Party Observations regarding Application No. PCT/GB2012/052298, dated Jan. 17, 2014, 4 pages.
Grund M., European Patent Attorney, Grund Intellectual Property Group, Third-Party Observations regarding Application No. PCT/GB2012/052380, dated Jan. 24, 2014, 4 pages.
Grund M., European Patent Attorney, Grund Intellectual Property Group, Third-Party Observations regarding Application No. PCT/GB2012/052956, dated Mar. 26, 2014, 2 pages.
Grund M., European Patent Attorney, Grund Intellectual Property Group, Third-Party Observations regarding Application No. PCT/GB2012/052960, dated Apr. 2, 2014, 3 pages.
Grund M., European Patent Attorney, Grund Intellectual Property Group, Third-Party Observations regarding Application No. PCT/GB2013/050682, dated Jul. 28, 2014, 3 pages.
Grund M., European Patent Attorney, Grund Intellectual Property Group, Third-Party Observations regarding Application No. PCT/US2012/026416, dated Jun. 6, 2013, 2 pages.
Grund M., European Patent Attorney, Grund Intellectual Property Group, Third-Party Observations regarding PCT/GB2013/050683, dated Jul. 28, 2014, 2 pages.
Grund M., European Patent Attorney, Grund Intellectual Property Group, Third-Party Observations according to Article 115 EPC regarding 11705964.2, dated Feb. 26, 2015, 5 pages.
Gu H., et al., "Independent Control of Immunoglobulin Switch Recombination at Individual Switch Regions Evidenced Through Cre-loxP-Mediated Gene Targeting," Cell, 1993, vol. 73 (6), pp. 1155-1164.
Guerrero C., et al., "The Bleomycin Resistance Gene of Transposon Tn5 is an Excellent Marker for Transformation of Corynebacteria," Applied Microbiology and Biotechnology, 1992, vol. 36 (6), pp. 759-762.
Guirouilh-Barbat J. et al., "Is homologous recombination really an error-free process?", Frontiers in Genetics, Jun. 2014, vol. 5 (175), 15 pages.

Guntaka R.V., "Transcription Termination and Polyadenylation in Retroviruses," Microbiological Reviews, 1993, vol. 57 (3), pp. 511-521.
Hagiwara S., "Transgenic Expression of VpreB-3 Under the Control of the Immunoglobulin Heavy Chain Enhancer and SV40 Promoter," Kobe Journal of Medical Sciences, 1996, vol. 42 (1), pp. 43-59 (abstract only).
Han C., et al., "Comprehensive Analysis of Reproductive ADAMs: Relationship of ADAM4 and ADAM6 with an ADAM Complex Required for Fertilization in Mice," Biology of Reproduction, 2009, vol. 80 (5), pp. 1001-1008.
Harding F.A., et al., "Class Switching in Human ImmunoglobulinTransgenic Mice," Annals of the New York Academy of Sciences, 1995, vol. 764, pp. 536-546.
Hasty P., et al., "Target Frequency and Integration Pattern for Insertion and Replacement Vectors in Embryonic Stem Cells," Molecular and Cellular Biology, 1991, vol. 11 (9), pp. 4509-4517.
Hendricks J., et al., "Organization of the Variable Region of the Immunoglobulin Heavy-Chain Gene Locus of the Rat," Immunogenetics, 2010, vol. 62 (7), pp. 479-486.
Herschbach Jarrell B., Third-Party Pre-Issuance Submission Under 37 CFR Section 1.290 in U.S. Appl. No. 14/052,259, dated Aug. 6, 2014, 7 pages.
Hewitt S.L., et al., "Association Between the lgk and lgh Immunoglobulin Loci Mediated by the 3' lgk Enhancer Induces 'decontraction' of the lgh Locus in Pre-B Cells," Nature Immunology, 2008, vol. 9 (4), pp. 396-404.
Houdebine L.M., "The Methods to Generate Transgenic Animals and to Control Transgene Expression," Journal of Biotechnology, 2002, vol. 98 (2-3), pp. 145-160.
Houdebine L.M., "Transgenic Animal Models in Biomedical Research," Methods in Molecular Biology, Chapter 10, 2007, vol. 360, pp. 163-202.
Houldsworth J., et al., "Comparative Genomic Hybridization: An Overview," The American Journal of Pathology, 1994, vol. 145 (6), pp. 1253-1260.
Huang C.C., et al., "Structural Basis of Tyrosine Sulfation and $V_H$-Gene Usage in Antibodies that Recognize the HIV Type 1 Coreceptor-Binding Site on gp120," Proceedings of the National Academy of Sciences, 2004, vol. 101 (9), pp. 2706-2711.
Huber V.C. et al., "Distinct Contributions of Vaccine-Induced Immunoglobulin G1 (IgG1) and IgG2a Antibodies to Protective Immunity Against Influenza," Clinical and Vaccine Immunology, 2006, vol. 13 (9), pp. 981-990.
Hudziak R.M., et al., "Establishment of Mammalian Cell Lines Containing Multiple Nonsense Mutations and Functional Suppressor TRNA Genes," Cell, 1982, vol. 31 (1), pp. 137-146.
Huovila a.P., et al., "Shedding Light on ADAM Metalloproteinases," Trends in Biochemical Sciences, 2005, vol. 30 (7), pp. 413-422.
Iglesias-Ussel MD., et al., "Forced Expression of AID Facilitates the Isolation of Class Switch Variants from Hybridoma Cells," Journal of Immunological Methods, 2006, vol. 316 (1-2), pp. 59-66.
Ivics Z., et al., "The Expanding Universe of Transposon Technologies for Gene and Cell Engineering," Mobile DNA, 2010, vol. 1 (1), 15 pages.
Ivics Z., et al., "The *Sleeping Beauty* Transposable Element: Evolution, Regulation and Genetic Applications," Current Issues in Molecular Biology, 2004, vol. 6 (1), pp. 43-55.
Izsvák Z., et al., "*Sleeping Beauty* Transposition: Biology and Applications for Molecular Therapy," Molecular Therapy, 2004, vol. 9 (2), pp. 147-156.
Jacob H.J., et al., "Gene Targeting in the Rat: Advances and Opportunities," Trends in Genetics, 2010, vol. 26 (12), pp. 510-518.
Jakobovits A., et al., "From XenoMouse Technology to Panitumumab, the First Fully Human Antibody Product from Transgenic Mice," Nature Biotechnology, 2007, vol. 25 (10), pp. 1134-1143.
Jakobovits A., "Production of Fully Human Antibodies by Transgenic Mice," Current Opinion in Biotechnology, 1995, vol. 6 (5), pp. 561-566.
Jakobovits A., "The Long-Awaited Magic Bullets: Therapeutic Human Monoclonal Antibodies from Transgenic Mice," Expert Opinion Investigational Drugs, 1998, vol. 7 (4), pp. 607-614.

(56) References Cited

OTHER PUBLICATIONS

Janeway C.A. et al., "The rearrangement of antigen-receptor gene segments controls lymphocyte development," in Immunobiology, 5th Edition, Aug. 2015, 13 pages. [Retrieved from the Internet: http://www.ncbi.nlm.nih.gov/books/NBK27113/].
Janeway et al., "Structural Variation in Immunoglobulin Constant Regions," Immuobiology: The Immune System in Health and Disease, 5th Edition, 2001, 5 pages.
Janssens R., et al., "Generation of Heavy-Chain-only Antibodies in Mice," Proceedings of the National Academy of Sciences, 2006, vol. 103 (41), pp. 15130-15135.
Jasper, P.J., et al., "B lymphocyte deficiency in IgH-transgenic rabbits," European Journal of Immunology, 2007, vol. 37, pp. 2290-2299.
Jendreyko N., et al., "Intradiabodies, Bispecific, Tetravalent Antibodies for the Simultaneous Functional Knockout of Two Cell Surface Receptors," The Journal of Biological Chemistry, 2003, vol. 278 (48), pp. 47812-47819.
Jessen K.A., et al., "Molecular Analysis of Metastasis in a Polyomavirus Middle T Mouse Model: the Role of Osteopontin," Breast Cancer Research, 2004, vol. 6 (3), pp. R157-R169.
Johnston C.M., et al., "Complete Sequence Assembly and Characterization of the C57BL/6 Mouse Ig Heavy Chain V Region," The Journal of Immunology, 2006, vol. 176 (7), pp. 4221-4234.
Jung D., et al., "Mechanism and Control of V(D)J Recombination at the Immunoglobulin Heavy Chain Locus," Annual Review of Immunology, 2006, vol. 24, pp. 541-570.
Kaminski D.A., et al., "Antibody Class Switching differs among SJL, C57BL/6 and 129 Mice," International Immunology, 2007, vol. 19 (4), pp. 545-556.
Karu A.E., et al., "Recombinant Antibody Technolgy," ILAR Journal / National Research Council, Institute of Laboratory Animal Resources, 1995, vol. 37 (3), pp. 132-141.
Kaushik A., et al., "Novel Insight into Antibody Diversification from Cattle," Veterinary Immunology and Immunopathology, 2002, vol. 87 (3-4), pp. 347-350.
Kawasaki, K., et al., "One-Megabase Sequence Analysis of the Human Immunoglobulin λ Gene Locus," Genome Research, 1997, vol. 7, pp. 250-261.
Kellermann, et al., "Developing the XENOMOUSE® Technology for Evaluating Immunogenicity," AntibOZ 2: An International Forum to Predict the Next Wave of Protein-based Therapies and Immuno Diagnostics, 2004, AntibOZ 2 Conference, Austraila, 1 page (abstract only).
Kenter A.L., et al., "Three-Dimensional Architecture of the IgH Locus Facilitates Class Switch Recombination," Annals of the New York Academy of Sciences, 2012, vol. 1267, pp. 86-94.
Kim J.Y., et al., "CHO Cells in Biotechnology for Production of Recombinant Proteins: Current State and Further Potential," Applied Microbiology Biotechnology, 2012, vol. 93 (3), pp. 917-930.
Kim T., et al., "Expression and Relationship of Male Reproductive ADAMs in Mouse," Biology of Reproduction, 2006, vol. 74 (4), pp. 744-750.
Kingzette M., et al., "Trans-Chromosomal Recombination within the Ig Heavy Chain Switch Region in B Lymphocytes," Proceedings of the National Academy of Sciences, 1998, vol. 95 (20), pp. 11840-11845.
Kitamura D., et al., "A B Cell-Deficient Mouse by Targeted Disruption of the Membrane Exon of the Immunoglobulin Mu Chain Gene," Nature, 1991, vol. 350 (6317), pp. 423-426.
Köhrer C., et al., "Import of Amber and Ochre Suppressor tRNAs into Mammalian Cells: a General Approach to Site-Specific Insertion of Amino Acid Analogues into Proteins," Proceedings of the National Academy of Sciences, 2001, vol. 98 (25), pp. 14310-14315.
Kondo S., "Highly improved Gene Targeting by Germline-Specific Cas9 Expression in Drosophila," Genetics, vol. 195, Nov. 2013, pp. 715-721 (Abstract).

Kondo S., "Highly improved Gene Targeting by Germline-Specific Cas9 Expression in Drosophila," Genetics, vol. 195, Nov. 2013, pp. 715-721.
Kostenuik P.J., et al., "Denosumab, a Fully Human Monoclonal Antibody to RANKL, Inhibits Bone Resorption and Increases BMD in Knock-in Mice that Express Chimeric (Murine/Human) RANKL," Journal of Bone and Mineral Research, 2009, vol. 24 (2), pp. 182-195.
Kotzamanis G., et al., "Recombining Overlapping BACs into a Single Larger BAC," BMC Biotechnology, 2004, vol. 4 (1), 10 pages.
Kouskoff V., et al., "Cassette Vectors Directing Expression of T Cell Receptor Genes in Transgenic Mice," Journal of Immunological Methods, 1995, vol. 180 (2), pp. 273-280.
Krause J.C., et al., "Epitope-Specific Human Influenza Antibody Repertoires Diversify by B Cell Intraclonal Sequence Divergence and Interclonal Convergence," Journal of Immunology, 2011, vol. 187 (7), pp. 3704-3711.
Krutskikh A., et al., "Epididymal Protein Rnase10 is Required for Post-Testicular Sperm Maturation and Male Fertility," The FASEB Journal, 2012, vol. 26 (10), pp. 4198-4209.
Kucherlapati R.S., et al., "Homologous Recombination Between Plasmids in Mammalian Cells can be Enhanced by Treatment of Input DNA," Proceedings of the National Academy of Sciences, 1984, vol. 81 (10), pp. 3153-3157.
Kuraoka M., et al., "AID Expression During B-Cell Development: Searching for Answers," Immunologic Research, 2011, vol. 49 (1-3), pp. 3-13.
Kuroiwa Y., et al., "Sequential Targeting of the Genes Encoding Immunoglobulin-μ and Prion Protein in Cattle," Nature Genetics, 2004, vol. 36 (7), pp. 775-780.
Laffleur B., et al., "Production of Human or Humanized Antibodies in Mice," Chapter 9, Methods in Molecular Biology, 2012, vol. 901, pp. 149-159.
Laventie B.J., et al., "Heavy Chain-Only Antibodies and Tetravalent Bispecific Antibody Neutralizing Staphylococcus aureus Leukotoxins," Proceedings of the National Academy of Sciences, 2011, vol. 108 (39), pp. 16404-16409.
Le Mouellic H., et al., "Pattern of Transcription of the Homeo Gene Hox-3.1 in the Mouse Embryo," Genes & Development, 1988, vol. 2 (1), pp. 125-135.
Lee E.C., et al., "Complete Humanization of the Mouse Immunoglobulin Loci Enables Efficient Therapeutic Antibody Discovery," Nature Biotechnology, 2014, vol. 32 (4), pp. 356-363.
Lee E.C., et al., "The Application of Transgenic Mice for Therapeutic Antibody Discovery," Methods in Molecular Biology, Chapter 8, 2012, vol. 901, pp. 137-148.
Lee H., . et al, "Human C5aR Knock-in Mice Facilitate the Production and Assessment of Anti-Inflammatory Monoclonal Antibodies," Nature Biotechnology, 2006, vol. 24 (10), pp. 1279-1284.
Lefranc M.P., et al., "The Immunoglobulin Facts Book—Annex 3," IGHJ group, Academic Press, ISBN:9-12-441351-X, 2001, 4 pages.
Lefranc M.P., "Nomenclature of the Human Immunoglobulin Heavy (IGH) Genes," Experimental and Clinical Immunogenetics, 2001, vol. 18 (2), pp. 100-116.
Lefranc M.P., "Nomenclature of the Human Immunoglobulin Kappa (IGK) Genes," Experimental and Clinical Immunogenetics, 2001, vol. 18 (3), pp. 161-174.
Lefranc M.P., "Nomenclature of the Human Immunoglobulin Lambda (IGL) Genes," Experimental and Clinical Immunogenetics, 2001, vol. 18 (4), pp. 242-254.
Li H., et al., "Genetic Diversity of the Human Immunoglobulin Heavy Chain $V_H$ Region," Immunological Reviews, 2002, vol. 190, pp. 53-68.
Li L.P., et al., "Transgenic Mice with a Diverse Human T Cell Antigen Receptor Repertoire," Nature Medicine, 2010, vol. 16 (9), pp. 1029-1034.
Li M.A., et al., "Crafting Rat Genomes with Zinc Fingers," Nature Biotechnology, 2011, vol. 29 (1), pp. 39-41.
Li P., et al., "Germline Competent Embryonic Stem Cells Derived from Rat Blastocysts," Cell, 2008, vol. 135 (7), pp. 1299-1310.

(56) References Cited

OTHER PUBLICATIONS

Li X., et al., "The Minimum Internal and External Sequence Requirements for Transposition of the Eukaryotic Transformation Vector *PiggyBac*," Molecular Genetics & Genomics, 2001, vol. 266 (2), pp. 190-198.
Liao J., et al., "Generation of Induced Pluripotent Stem Cell Lines from Adult Rat Cells," Cell Stem Cell, 2009, vol. 4 (1), pp. 11-15.
Little M., et al., "Generation of a Large Complex Antibody Library from Multiple Donors," Journal of Immunological Methods, 1999, vol. 231 (1-2), pp. 3-9.
Liu L., et al., "Potent and Broad Anti-HIV-1 Activity Exhibited by a Glycosyl-Phosphatidylinositol-Anchored Peptide derived from the CDR H3 of Broadly Neutralizing Antibody PG16," Journal of Virology, 2011, vol. 85 (17), pp. 8467-8476.
Lonberg N.,"Fully Human Antibodies from Transgenic Mouse and Phage Display Platforms," Current Opinion in Immunology, 2008, vol. 20 (4), pp. 450-459.
Lonberg N.,"Human Antibodies from Transgenic Animals," Nature Biotechnology, 2005, vol. 23 (9), pp. 1117-1125.
Loveslati B.Y., et al., "A Study of Gm Allotypes and Immunoglobulin Heavy Gamma IGHG Genes in Berbers, Arabs and Sub-Saharan Africans from Jerba Island, Tunisia," European Journal of Immunogenetics, 2001, vol. 28 (5), pp. 531-538.
Luby T.M., et al., "The μ Switch Region Tandem Repeats are Important, but not Required, for Antibody Class Switch Recombination," The Journal of Experimental Medicine, 2001, vol. 193 (2), pp. 159-168.
Luciw P.A., et al., "Location and Function of Retroviral and SV40 Sequences that Enhance Biochemical Transformation after Microinjection of DNA," Cell, 1983, vol. 33 (3), pp. 705-716.
Luo G., et al., "Chromosomal Transposition of a Tc1/Mariner-like Element in Mouse Embryonic Stem Cells," Proceedings of the National Academy of Sciences, 1998, vol. 95 (18), pp. 10769-10773.
Lyon C., Attorney for Applicant, Third-Party Pre-Issuance Submission Under 37 CFR Sec. 1.290 in U.S. Appl. No. 14/056,700, dated Nov. 28, 2014, 6 pages.
Lyon C., Attorney for Applicant, Third-Party Pre-Issuance Submission Under 37 CFR Sec. 1.290 in U.S. Appl. No. 14/056,707, dated Nov. 28, 2014, 10 pages.
Lyon C., Attorney for Applicant, Third-Party Pre-Issuance Submission Under 37 CFR Sec. 1.290 in U.S. Appl. No. 13/846,672, dated Mar. 17, 2015, 32 pages.
Lyon C., Attorney for Applicant, Third-Party Pre-Issuance Submission Under 37 CFR Sec. 1.290 in U.S. Appl. No. 13/875,892, dated May 5, 2015, 49 pages.
Lyon C., Attorney for Applicant, Third-Party Pre-Issuance Submission Under 37 CFR Sec. 1.290 in U.S. Appl. No. 13/886,511, dated May 5, 2015, 18 pages.
Lyon C., Attorney for Applicant, Third-Party Pre-Issuance Submission Under 37 CFR Sec. 1.290 in U.S. Appl. No. 14/040,405, dated Jan. 16, 2015, 18 pages.
Lyon C., Attorney for Applicant, Third-Party Pre-Issuance Submission Under 37 CFR Sec. 1.290 in U.S. Appl. No. 14/040,427, dated Jan. 16, 2015, 20 pages.
Lyon C., Attorney for Applicant, Third-Party Pre-Issuance Submission Under 37 CFR Sec. 1.290 in U.S. Appl. No. 14/056,434, dated Dec. 15, 2014, 6 pages.
Lyon C., Attorney for Applicant, Third-Party Pre-Issuance Submission Under 37 CFR Sec. 1.290 in U.S. Appl. No. 14/080,630, dated Oct. 31, 2014, 8 pages.
Lyon C., Attorney for Applicant, Third-Party Pre-Issuance Submission Under 37 CFR Sec. 1.290 in U.S. Appl. No. 14/137,902, dated Nov. 13, 2014, 9 pages.
Lyon C., Attorney for Applicant, Third-Party Pre-Issuance Submission Under 37 CFR Sec. 1.290 in U.S. Appl. No. 14/220,080, dated Jul. 28, 2015, 28 pages.
Lyon C., Attorney for Applicant, Third-Party Pre-Issuance Submission Under 37 CFR Sec. 1.290 in U.S. Appl. No. 14/220,095, dated Aug. 4, 2015, 19 pages.
Lyon C., Attorney for Applicant, Third-Party Pre-Issuance Submission Under 37 CFR Sec. 1.290 in U.S. Appl. No. 14/220,099, dated Apr. 29, 2015, 43 pages.
Lyon C., Attorney for Applicant, Third-Party Pre-Issuance Submission Under 37 CFR Sec. 1.290 in U.S. Appl. No. 14/226,706, dated Jul. 28, 2015, 53 pages.
Lyon C., Attorney for Applicant, Third-Party Pre-Issuance Submission Under 37 CFR Sec. 1.290 in U.S. Appl. No. 14/263,158, dated Apr. 29, 2015, 16 pages.
Lyon C., Attorney for Applicant, Third-Party Pre-Issuance Submission Under 37 CFR Sec. 1.290 in U.S. Appl. No. 14/263,176, dated Apr. 29, 2015, 16 pages.
Lyon C., Attorney for Applicant, Third-Party Pre-Issuance Submission Under 37 CFR Sec. 1.290 in U.S. Appl. No. 14/497,054, dated Oct. 21, 2015, 81 pages.
Lyon C., Attorney for Applicant, Third-Party Pre-Issuance Submission Under 37 CFR Sec. 1.290 in U.S. Appl. No. 14/498,685, dated Sep. 18, 2015, 37 pages.
Lyon C., Attorney for Applicant, Third-Party Pre-Issuance Submission Under 37 CFR Sec. 1.290 in U.S. Appl. No. 14/516,461, dated Aug. 4, 2015, 27 pages.
Lyon C., Attorney for Applicant, Third-Party Pre-Issuance Submission Under 37 CFR Sec. 1.290 in U.S. Appl. No. 14/226,698, dated Jun. 3, 2015, 53 pages.
Ma B., et al., "Human Antibody Expression in Transgenic Rats: Comparison of Chimeric IgH Loci with Human $V_H$, D and $J_H$ but Bearing Different Rat C-Gene Regions," Journal of Immunological Methods, 2013, vol. 400-401, pp. 78-86.
Macdonald L., Curriculum Vitae of Lynn E. MacDonald, Ph.D., 3 pages.
Macdonald L., Declaration of Lynn E. MacDonald with Exhibits, dated Feb. 3, 2015, 13 pages, relating to International Application No. PCT/US02/04500 (Published as WO02/066630 A1).
Macdonald L., et al., Expanded Poster: Velocimmune Technology Extended to Humanization of Several Megabases of Complex, Sep. 2006, 6 pages.
Macdonald L., et al., Poster: "Velocimmune Technology Extended to Humanization of Several Megabases of Complex" and evidence of unavailability, Sep. 2006, 42 pages.
Macdonald L.E., et al., "Precise and in Situ Genetic Humanization of 6 Mb of Mouse Immunoglobulin Genes," Proceedings of the National Academy of Sciences, 2014, vol. 111 (14), pp. 5147-5152.
Mack M., et al., "A Small Bispecific Antibody Construct Expressed as a Functional Single-Chain Molecule with High Tumor Cell Cytotoxicity," Proceedings of the National Academy of Sciences, 1995, vol. 92 (15), pp. 7021-7025.
Magadán S., et al., "Production of Antigen-Specific Human Monoclonal Antibodies: Comparison of Mice Carrying IgH/kappa or IgH/kappa/lambda transloci," Biotechniques, 2002, vol. 33 (3), pp. 680, 682, 684 passim.
Maitta R.W., et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," Infection and Immunity, 2004, vol. 72 (1), pp. 196-208.
Makris J.C., et al., "Mutational Analysis of Insertion Sequence 50 (IS50) and Transposon 5 (Tn5) Ends," Proceedings of the National Academy of Sciences, 1988, vol. 85 (7), pp. 2224-2228.
Mallender W.D., et al., "Construction, Expression, and Activity of a Bivalent Bispecific Single-Chain Antibody," The Journal of Biological Chemistry, 1994, vol. 269 (1), pp. 199-206.
Manis J.P., et al., "Mechanism and Control of Class-Switch Recombination," Trends in Immunology, 2002, vol. 23 (1), pp. 31-39.
Marcello M.R., et al., "Lack of Tyrosylprotein Sulfotransferase-2 Activity Results in Altered Sperm-Egg Interactions and Loss of ADAM3 and ADAM6 in Epididymal Sperm," The Journal of Biological Chemistry, 2011, vol. 286 (15), pp. 13060-13070.
Mårtensson I.L., et al., "Role of the Surrogate Light Chain and the Pre-B-Cell Receptor in Mouse B-Cell Development," Immunology, 2000, vol. 101 (4), pp. 435-441.

(56) References Cited

OTHER PUBLICATIONS

Martinez-Jean C., et al., "Nomenclature and Overview of the Mouse (*Mus musculus* and *Mus* sp.) Immunoglobulin Kappa (IGK) Genes," Experimental and Clinical Immunogenetics, 2001, vol. 18 (4), pp. 255-279.

Matthews V.B., et al., "A Locus Affecting Immunoglobulin Isotype Selection (Igis1) Maps to the MHC Region in C57BL, BALB/c and NOD Mice," Immunology & Cell Biology, 2001, vol. 79 (6), pp. 576-582.

Mattila P.S., et al., "Extensive Allelic Sequence Variation in the J Region of the Human Immunoglobulin Heavy Chain Gene Locus," European Journal of Immunology, 1995, vol. 25 (9), pp. 2578-2582.

Maul R.W., et al., "AID and Somatic Hypermutation," Advances in Immunology, Chapter 6, 2010, vol. 105, pp. 159-191.

Mccreath K.J., et al., "Production of Gene-Targeted Sheep by Nuclear Transfer from Cultured Somatic Cells," Nature, 2000, vol. 405 (6790), pp. 1066-1069.

Mcmurry M.T., et al., "Enhancer Control of Local Accessibility to V(D)J Recombinase," Molecular and Cellular Biology, 1997, vol. 17 (8), pp. 4553-4561.

Mejía J.E., et al., "The Assembly of Large BACs by in Vivo Recombination," Genomics, 2000, vol. 70 (2), pp. 165-170.

Mendez M.J., et al., "Functional Transplant of Megabase Human Immunoglobulin Loci Recapitulates Human Antibody Response in Mice," Nature Genetics, 1997, vol. 15 (2), pp. 146-156.

Mills F., et al., "Enhancer Complexes Located Downstream of Both Human Immunoglobulin Cα Genes," The Journal of Experimental Medicine, Sep. 1997, vol. 186 (6), pp. 845-858.

Milner E.C., et al., "Polymorphism and Utilization of Human $V_H$ Genes," Annals of the New York Academy of Sciences, 1995, vol. 764, pp. 50-61.

Minaee S., et al., "Mapping and Functional Analysis of Regulatory Sequences in the Mouse Lambda5-VpreB1 Domain," Molecular Immunology, 2005, vol. 42 (11), pp. 1283-1292.

Mir K.U., "Sequencing Genomes: From Individuals to Populations," Briefings in Functional Genomics & Proteomics, 2009, vol. 8 (5), pp. 367-378.

Monaco A.P., et al., "YACs, BACs, PACs and MACs: Artificial Chromosomes as Research Tools," Trends in Biotechnology, 1994, vol. 12 (7), pp. 280-286.

Moran N., et al., "Mouse Platforms Jostle for Slice of Humanized Antibody Market," Nature Biotechnology, 2013, vol. 31 (4), pp. 267-268.

Moreau P., et al., "The SV40 72 Base Repair Repeat has a Striking Effect on Gene Expression Both in SV40 and Other Chimeric Recombinants," Nucleic Acids Research, 1981, vol. 9 (22), pp. 6047-6068.

Moreno R.D., et al., "The Emerging Role of Matrix Metalloproteases of the ADAM Family in Male Germ Cell Apoptosis," Spermatogenesis, 2011, vol. 1 (3), pp. 195-208.

Mortuza F.Y., et al., "Immunoglobulin Heavy-Chain Gene Rearrangement in Adult Acute Lymphoblastic Leukemia Reveals Preferential Usage of $J_H$-Proximal Variable Gene Segments," Blood, 2001, vol. 97 (9), pp. 2716-2726.

Müller U., "Ten Years of Gene Targeting: Targeted Mouse Mutants, from Vector Design to Phenotype Analysis," Mechanisms of Development, 1999, vol. 82 (1-2), pp. 3-21.

Mullins, L.J., et al., "Perspective Series: Molecular Medicine in Genetically Engineered Animals," Journal of Clinical Investigation, Apr. 1996, vol. 97 (7), pp. 1557-1560.

Murphy A., "Declaration of Andrew J. Murphy," including Slide Presentation dated Nov. 3, 2009, at Wellcome Trust Advanced Course: Genetic Manipulation of ES Cells, in Hirixton, UK, entitled "BAC-based Modifications of the Mouse Genome: The Big and the Backward," cited in an IDS in U.S. Appl. No. 14/192,051 of MacDonald et al., 62 pages, dated Oct. 6, 2014.

Murphy A., "VelocImmune: Immunoglobulin Variable Region Humanized Mice", Recombinant Antibodies for Immunotherapy, Chapter 8, 1st Edition, Cambridge: Cambridge University Press, 2009, pp. 100-108.

Murphy A.J., et al., "Mice with megabase humanization of their Immunoglobulin Genes Generate Antibodies as Efficiently as Normal Mice," Proceedings of the National Academy of Sciences, 2014, vol. 111 (14), pp. 5153-5158.

Muyrers J.P., et al., "Rapid Modification of Bacterial Artificial Chromosomes by ET-Recombination," Nucleic Acids Research, 1999, vol. 27 (6), pp. 1555-1557.

Nadel B., et al., "Sequence of the Spacer in the Recombination Signal Sequence Affects V(D)J Rearrangement Frequency and Correlates with Nonrandom $V_K$ Usage in Vivo," The Journal of Experimental Medicine, 1998, vol. 187 (9), pp. 1495-1503.

Nagle M., "Regeneron Helps Make Sanofi Velocimmune to its 'Weak' Pipeline," 2007, 2 pages.

Nandi A.K., et al., "Regulated Expression of Genes Inserted at the Human Chromosomal β-Globin Locus by Homologous Recombination," Proceedings of the National Academy of Sciences, 1988, vol. 85 (11), pp. 3845-3849.

Narayanan K., et al., "Bacterial Artificial Chromosome Mutagenesis Using Recombineering, Article ID: 971296," Journal of Biomedicine and Biotechnology, 2010, vol. 2011, Article ID No. 971296, 10 pages.

Narayanan K., et al., "Efficient and Precise Engineering of a 200 kb β-Globin Human/Bacterial Artificial Chromosome in *E. coli* DH10B using an Inducible Homologous Recombination System," Gene Therapy, 1999, vol. 6 (3), pp. 442-447.

Nelson A.L., et al., "Development Trends for Human Monoclonal Antibody Therapeutics," Nature Reviews Drug Discovery, 2010, vol. 9 (10), pp. 767-774.

Neuberger M.S., et al., "Isotype Exclusion and Transgene Down-Regulation in Immunoglobulin-Lambda Transgenic Mice," Nature, 1989, vol. 338 (6213), pp. 350-352.

Neuberger M.S., et al., "Somatic Hypermutation," Current Opinion in Immunology, 1995, vol. 7 (2), pp. 248-254.

Neuberger M.S., "Expression and regulation of immunoglobulin heavy chain gene transfected into lymphoid cells," The EMBO Journal, 1983, vol. 2 (8), pp. 1373-1378.

New Zealand Patent Office, Simon Maguire, Authorized Officer, Further Examination Report for Patent No. 623756, dated Sep. 9, 2015, 3 pages.

Nicholson I.C., et al., "Antibody Repertoires of Four- and Five-Feature Translocus Mice Carrying Human Immunoglobulin Heavy Chain and Kappa and Lambda Light Chain Yeast Artificial Chromosomes," Journal of Immunology, 1999, vol. 163 (12), pp. 6898-6906.

Niemann H., et al., "Transgenic Farm Animals: Present and Future," Rev. Sci Tech Off. Int Epiz., 2005, vol. 24 (1), pp. 285-298.

Nucleotide Sequence RID Y55HBK1W114, accessed Aug. 6, 2014, 2 pages.

Oancea A.E., et al., "Expression of the (recombinant) Endogenous Immunoglobulin Heavy-Chain Locus Requires the Intronic Matrix Attachment Regions," Molecular and Cellular Biology, 1997, vol. 17 (5), pp. 2658-2668.

Oberdoerffer P., et al., "Unidirectional Cre-Mediated Genetic Inversion in Mice using the Mutant loxP Pair lox66/lox71," Nucleic Acids Research, 2003, vol. 31 (22), pp. e140-1-e140.7.

Ohlin M., et al., "The Human Antibody Repertoire to Infectious Agents: Implications for Disease Pathogenesis," Molecular Immunology, 2003, vol. 40 (1), pp. 1-11.

Ohm-Laursen L., et al., "Identification of Two New Alleles, IGHV3-23*04 and IGHJ6*04, and the Complete Sequence of the IGHV3-h Pseudogene in the Human Immunoglobulin Locus and their Prevalences in Danish Caucasians," Immunogenetics, 2005, vol. 57 (9), pp. 621-627.

Osborn M.J., et al., "High-Affinity IgG Antibodies Develop Naturally in Ig-Knockout Rats Carrying Germline Human IgH/Igk/Igλ Loci Bearing the Rat $C_H$ Region," Journal of Immunology, 2013, vol. 190 (4), pp. 1481-1490.

Osoegawa K., et al., "Bacterial Artificial Chromosome Libraries for Mouse Sequencing and Functional Analysis," Genome Research, 2000, vol. 10 (1), pp. 116-128.

Parng C.L., et al., "Gene Conversion Contributes to LG Light Chain Diversity in Cattle," Journal of Immunology, 1996, vol. 157 (12), pp. 5478-5486.

(56) References Cited

OTHER PUBLICATIONS

Pavlicek, et al., "Ancient Transposable Elements, Processed Pseudogenes, and Endogenous Retroviruses," Genomic Disorders, Chapter 4, 2006, pp. 57-72.
Pear W.S., et al., "Localization of the Rat Immunoglobulin Heavy Chain Locus to Chromosome 6," Immunogenetics, 1986, vol. 23 (6), pp. 393-395.
Pelham H., et al., "Expression of a *Drosophila* Heat Shock Protein in Mammalian Cells: Transient Association with Nucleoli After Heat Shock," Philosophical Transactions of the Royal Society B: Biological Sciences, 1984, vol. 307 (1132), pp. 301-307.
Pera, M.F., et al., "Human embryonic stem cells," Journal of Cell Science, 2000, vol. 113, pp. 5-10.
Perlot T., et al., "Antisense Transcripts from Immunoglobulin Heavy-Chain Locus V(D)J and Switch Regions," Proceedings of the National Academy of Sciences, 2008, vol. 105 (10), pp. 3843-3848.
Perlot T., et al., "Cis-Regulatory Elements and Epigenetic Changes control genomic rearrangements of the IgH locus," Advances in Immunology, Chapter 1, 2008, vol. 99, pp. 1-32.
Pettersson S., et al., "A second B cell-specific enhancer 3' of the immunoglobulin heavy-chain locus," Nature, Mar. 1990, vol. 344, pp. 165-168.
Pettit S.J., et al., "Agouti C57BL/6N Embryonic Stem Cells for Mmouse Genetic Resources," Nature Methods, 2009, vol. 6 (7), pp. 493-495.
Plasterk R.H., et al., "Resident Aliens: the Tc1/Mariner Superfamily of Transposable Elements," Trends Genetics, 1999, vol. 15(8), pp. 326-332.
Poburksy K., Third-Party Pre-Issuance Submission Under 37 CFR 1.290 in U.S. Appl. No. 13/843,528, dated Mar. 18, 2014, 14 pages.
Poburksy K., Third-Party Pre-Issuance Submission Under 37 CFR 1.290 in U.S. Appl. No. 13/433,084, dated Apr. 1, 2014, 15 pages.
Poburksy K., Third-Party Pre-Issuance Submission Under 37 CFR 1.290 in U.S. Appl. No. 13/434,361, dated Apr. 1, 2014, 15 pages.
Poburksy K., Third-Party Pre-Issuance Submission Under 37 CFR 1.290 in U.S. Appl. No. 13/740,727, dated May 27, 2014, 25 pages.
Ponsel D., et al., "High Affinity, Developability and Functional Size: the Holy Grail of Combinatorial Antibody by Library Generation," Molecules, 2011, vol. 16 (5), pp. 3675-3700.
Popov A.V., et al., "A Human Immunoglobulin Lambda Locus is Similarly Well Expressed in Mice and Humans," The Journal of Experimental Medicine, 1999, vol. 189 (10), pp. 1611-1620.
Pramanik S., et al., "Segmental Duplication as One of the Driving Forces Underlying the Diversity of the Human Immunoglobulin Heavy Chain Variable Gene Region," BMC Genomics, 2011, vol. 12 (78), 12 pages.
Primakoff P., et al., "Penetration, Adhesion, and Fusion in Mammalian Sperm-Egg Interaction," Science, 2002, vol. 296 (5576), pp. 2183-2185.
Primakoff P., et al., "The ADAM Gene Family: Surface Proteins with Adhesion and Protease Activity," Trends Genetics, 2000, vol. 16 (2), pp. 83-87.
Prosser H.M., et al., "A Resource of Vectors and ES Cells for Targeted Deletion of MicroRNAs in Mice," Nature Biotechnology, 2011, vol. 29 (9), pp. 840-845.
Prosser H.M., et al., "Mosaic Complementation Demonstrates a Regulatory Role for Myosin VIIa in Actin Dynamics of Stereocilia," Molecular and Cellular Biology, 2008, vol. 28 (5), pp. 1702-1712.
Pruzina S., et al., "Human Monoclonal Antibodies to HIV-1 Gp140 from Mice Bearing YAC-Based Human Immunoglobulin Transloci," Protein Engineering, Design & Selection, 2011, vol. 24 (10), pp. 791-799.
Puente X.S., et al., "Comparative Genomic Analysis of Human and Chimpanzee Proteases," Genomics, 2005, vol. 86 (6), pp. 638-647.
Qi N.R., et al., "A New Transgenic Rat Model of Hepatic Steatosis and the Metabolic Syndrome," Hypertension, 2005, vol. 45 (5), pp. 1004-1011.
Qu S., et al., "Gene Targeting of ErbB3 Using a Cre-Mediated Unidirectional DNA Inversion Strategy," Genesis, 2006, vol. 44 (10), pp. 477-486.

Ramírez-Solis R., et al., "Chromosome Engineering in Mice," Nature, 1995, vol. 378 (6558), pp. 720-724.
Ramsden D.A., et al., "Conservation of Sequence in Recombination Signal Sequence Spacers," Nucleic Acids Research, 1994, vol. 22 (10), pp. 1785-1796.
Ray P., et al., "Ectopic Expression of a c-kit$^{W42}$ Minigene in Transgenic Mice: Recapitulation of W Phenotypes and Evidence for c-kit Function in Melanoblast Progenitors," Genes & Development, 1991, vol. 5 (12A), pp. 2265-2273.
Raynard S.J., et al., "Cis-Acting Regulatory Sequences Promote High-Frequency Gene Conversion between Repeated Sequences in Mammalian Ccells," Nucleic Acids Research, 2004, vol. 32 (19), pp. 5916-5927.
Reddy S.T., et al., "Monoclonal Antibiotics Isolated without Screening by Analysing the Variable-Gene Repertoire of Plasma Cells," Nature Biotechnology, 2010, vol. 28 (9), pp. 965-971.
Regeneron Pharmaceuticals, Inc., et al., "Big Pharma Vies for Mice," Nature Biotechnology, 2007, vol. 25 (6), pp. 613.
Regeneron Pharmaceuticals, Inc., Press Release—"Astellas Licenses Regeneron's Velocimmune Technology for Discovering Human Monoclonal Antibodies," dated Mar. 30, 2007, 2 pages.
Regeneron Pharmaceuticals, Inc., Press Release—"AstraZeneca Licenses Regeneron's VelocImmune Technology for Discovering Human Monoclonal Antibodies—AstraZeneca Is First Licensee of Novel Velocimmune Technology License Fees Total up to $120 Million Over Six Years," Feb. 5, 2007, 2 pages.
Regeneron Pharmaceuticals, Inc., Press Release—"Regeneron Initiates Major Global Collaboration wtih Sanofi-aventis of Develop and Commercialize Fully-Human Therapeutic Antibodies," Nov. 29, 2007, 2 pages.
Ren S.Y., et al., "Targeted Insertion Results in a Rhombomere 2-Specific Hoxa2 Knockdown and Ectopic Activation of Hoxa1 Expression," Developmental Dynamics, 2002, vol. 225 (3), pp. 305-315.
Retter I., et al., "Sequence and Characterization of the Ig Heavy Chain Constant and Partial Variable Region of the Mouse Strain 129S1," The Journal of Immunology, 2007, vol. 179 (4), pp. 2419-2427.
Ricker M., European Patent Attorney, Opposition against EP2421357B1 in the name of Kymab Limited Statement of Facts and Arguments pertaining to Application No. 10734546.4, dated Oct. 23, 2013, 29 pages.
Ristevski S., "Making Better Transgenic Models: Conditional, Temporal, and Spatial Approaches," Molecular Biotechnology, 2005, vol. 29 (2), pp. 153-163.
Rivera J., et al., "Genetic Background and the Dilemma of Translating Mouse Studies to Humans," Immunity, 2008, vol. 28 (1), pp. 1-4.
Rodriguez C.I., et al., "High-Efficiency Deleter Mice Show that FLPe is an Alternative to Cre-loxP," Nature Genetics, 2000, vol. 25 (2), pp. 139-140.
Rogozin I.B., et al., "Cutting edge: DGYW/WRCH is a Better Predictor of Mmutability at G:C bases in Lg Hypermutation than the Widely Accepted RGYW/WRCY Motif and Probably Reflects a Two-Step Activation-Induced Cytidine Deaminase-Triggered Process," The Journal of Immunology, 2004, vol. 172 (6), pp. 3382-3384.
Rosner K., et al., "Third Complementarity-Determining Region of Mutated $V_H$ Immunoglobulin Genes Contains Shorter V, D, J, P, and N Components than Non-Mutated Genes," Immunology, 2001, vol. 103 (2), pp. 179-187.
Rourke J., Declaration of Jeffrey Rourke, Registered Patent Attorney for Regeneron Pharmaceuticals, Inc.—in the matter of Patent Acceptance 2011266843 in the Name of Kymab Limited and in the Matter of Opposition thereto by Regeneron Pharmaceuticals, Inc., dated Jan. 29, 2016, 5 pages.
Rusk N., "Making Mice at High Speed," Nature Methods, 2007, vol. 4 (3), pp. 196-197.
Sabbattini P., et al., "Analysis of Mice with Single and Multiple Copies of Transgenes Reveals a Novel Arrangement for the Lambda5-$V_{preB1}$ Locus Control Region," Molecular and Cellular Biology, Jan. 1999, vol. 19 (1), pp. 671-679.

(56) References Cited

OTHER PUBLICATIONS

Sakai E., et al., "Recombination and Transcription of the Endogenous Ig Heavy Chain Locus is Effected by the Ig Heavy Chain Intronic Enhancer Core Region in the Absence of the Matrix Attachment Regions," Proceedings of the National Academy of Sciences, 1999, vol. 96 (4), pp. 1526-1531.

Sarkar A., et al., "Molecular Evolutionary Analysis of the Widespread *PiggyBac* Transposon Family and Related "Domesticated" Sequences," Molecular Genetics & Genomics, 2003, vol. 270 (2), pp. 173-180.

Sasso E.H., et al., "Ethnic Differences of Polymorphism of an Immunoglobulin $V_H3$ Gene," Journal of Clinical Investigation, 1995, vol. 96 (3), pp. 1591-1600.

Sasso E.H., et al., "Expression of the Immunoglobulin $V_H$ Gene 51p1 is Proportional to its Germline Gene Copy Number," Journal of Clinical Investigation, 1996, vol. 97 (9), pp. 2074-2080.

Sauer B., et al., "Cre-Stimulated Recombination at loxP-Containing DNA Sequences Placed into the Mammalian Genome," Nucleic Acids Research, 1989, vol. 17 (1), pp. 147-161.

Sauer B., et al., "Site-Specific DNA Recombination in Mammalian Cells by the Cre Recombinase of Bacteriophage P1," Proceedings of the National Academy of Sciences, 1988, vol. 85 (14), pp. 5166-5170.

Sauer B., "Functional Expression of the cre-lox Site-Specific Recombination System in the Yeast *Saccharomyces cerevisiae*," Molecular and Cellular Biology, 1987, vol. 7 (6), pp. 2087-2096.

Scapini P., et al., "Myeloid Cells, BAFF, and IFN-ɣ Establish an Inflammatory Loop that Exacerbates Autoimmunity in Lyn-Deficient Mice," The Journal of Experimental Medicine, 2010, vol. 207 (8), pp. 1757-1773.

Schlake T., et al., "Use of Mutated FLP Recognition Target (FRT) Sites for the Exchange of Expression Cassettes at Defined Chromosomal Loci," Biochemistry, 1994, vol. 33 (43), pp. 12746-12751.

Schnütgen F., et al., "A Directional Strategy for Monitoring Cre-Mediated Recombination at the Cellular Level in the Mouse," Nature Biotechnology, 2003, vol. 21 (5), pp. 562-565.

Schonewald, S.L., Attorney for Applicant, Third-Party Pre-Issuance Submission Under 37 CFR Sec. 1.290 in U.S. Appl. No. 14/750,870, dated Aug. 10, 2016, 34 pages.

Schonewald, S.L., Attorney for Applicant, Third-Party Pre-Issuance Submission Under 37 CFR Sec. 1.290 in U.S. Appl. No. 14/818,162, dated May 24, 2016, 47 pages.

Schröck E., et al., "Comparative Genomic Hybridization (CGH)—Detection of Unbalanced Genetic Aberrations Using Conventional and Micro-Array Techniques," Current Protocols in Cytometry, 2001, Chapter 8: Unit 8.12.1 Supplement 18, 30 pages.

Schroeder H.W Jr., et al., "Preferential Utilization of Conserved Immunoglobulin Heavy Chain Variable Gene Segments During Human Fetal Life," Proceedings of the National Academy of Sciences, 1990, vol. 87 (16), pp. 6146-6150.

Schweinfest C.W., et al., "A Heat-Shock-Inducible Eukaryotic Expression Vector," Gene, 1988, vol. 71 (1), pp. 207-210.

Scott C.T., "Mice with a Human Touch," Nature Biotechnology, 2007, vol. 25 (10), pp. 1075-1077.

Seals D.F., et al., "The ADAMs Family of Metalloproteases: Multidomain Proteins with Multiple Functions," Genes & Development, 2003, vol. 17 (1), pp. 7-30.

Seed B., "Purification of Genomic Sequences from Bacteriophage Libraries by Recombination and Selection in Vivo," Nucleic Acids Research, 1983, vol. 11 (8), pp. 2427-2445.

Seidl K.J., et al., "An Expressed Neo' Cassette Provides Required Functions of the $1_y2b$ Exon for Class Switching," International Immunology, 1998, vol. 10 (11), pp. 1683-1692.

Seidl K.J., et al., "Position-Dependent Inhibition of Class-Switch Recombination by PGk-Neo' Cassettes Inserted into the Immunoglobulin Heavy Chain Constant Region Locus," Proceedings of the National Academy of Sciences, 1999, vol. 96 (6), pp. 3000-3005.

Sekiguchi J., et al., "The Mechanism of V(D)J Recombination," Molecular Biology of B Cells, Chapter 5, Elsevier Academic Press, 2004, pp. 61-82.

Sen R., et al., "Multiple Nuclear Factors Interact with the Immunoglobulin Enhancer Sequences," Cell, 1986, vol. 46 (5), pp. 705-716.

Seong E., et al., "To Knockout in 129 or in C57BL/6: That is the Question," Trends in Genetics, 2004, vol. 20 (2), pp. 59-62.

Serwe M., et al., "V(D)J Recombination in B Cells is Impaired but not Blocked by Targeted Deletion of the Immunoglobulin Heavy Chain Intron Enhancer," The EMBO Journal, 1993, vol. 12 (6), pp. 2321-2327.

Sharon J., et al., "Expression of a VHC Kappa Chimaeric Protein in Mouse Myeloma Cells," Nature, 1984, vol. 309 (5966), pp. 364-367.

Shaul Y., et al., "Homologous Recombination Between a Defective Virus and a Chromosomal Sequence in Mammalian Cells," Proceedings of the National Academy of Sciences, 1985, vol. 82 (11), pp. 3781-3784.

Shi B., et al., "Comparative Analysis of Human and Mouse Immunoglobulin Variable Heavy Regions from IMGT/LIGM-DB with IMGT/HighV-QUEST," Theoretical Biology and Medical Modelling, 2014, vol. 11, pp. 1-11.

Shi Y.P., et al., "The Mapping of Transgenes by Fluorescence in Situ Hybridization on G-Banded Mouse Chromosomes," Mammalian Genome, 1994, vol. 5 (6), pp. 337-341.

Shin H., "Discovery Process for Antibody-Based Therapeutics," Development of Antibody-Based Therapeutics, Chapter 2, 2012, pp. 9-32.

Shimizu A., et al., "Immunoglobulin Double-Isotype Expression by Trans-mRNA in a Human Immunoglobulin Transgenic Mouse," Proceedings of the National Academy of Sciences, 1989, vol. 86 (20), pp. 8020-8023.

Shultz L.D., et al., "Humanized Mice in Translational Biomedical Research," Nature Reviews. Immunology, 2007, vol. 7 (2), pp. 118-130.

Sigmund C.D., "Viewpoint: Are Studies in Genetically Altered Mice Out of Control?," Arteriosclerosis, Thrombosis, and Vascular Biology, 2000, vol. 20 (6), pp. 1425-1429.

Simpson E.M., et al., "Genetic Variation Among 129 Substrains and its Importance for Targeted Mutagenesis in Mice," Nature Genetics, 1997, vol. 16 (1), pp. 19-27.

Sirac C., et al., "Role of the Monoclonal κ Chain V Domain and Reversibility of Renal Damage in a Transgenic Model of Acquired Fanconi Syndrome," Blood, 2006, vol. 108 (2), pp. 536-543.

Skarnes W.C., et al., "A Conditional Knockout Resource for the Genome-Wide Study of Mouse Gene Function," Nature, 2011, vol. 474 (7351), pp. 337-342.

Skoultchi A.I., et al., "Expression of Genes Inserted at the Human Beta-Globin Locus by Homologous Recombination," Progress in Clinical and Biological Research, 1987, vol. 251, pp. 581-594.

Smith K.R., "Gene Transfer in Higher Animals: Theoretical Considerations and Key Concepts," Journal of Biotechnology, 2002, vol. 99 (1), pp. 1-22.

Smithies O., "Direct Alteration of a Gene in the Human Genome," Journal of Inherited Metabolic Disease, 1986, vol. 9 (Suppl. 1), pp. 92-97.

Smithies O., et al., "Insertion of DNA Sequences into the Human Chromosomal 13-Globin Locus by Homologous Recombination," Nature, 1985, vol. 317 (6034), pp. 230-234.

Sohn J., et al., "Somatic Hypermutation of an Immunoglobulin μ Heavy Chain Transgene," The Journal of Experimental Medicine, 1993, vol. 177 (2), pp. 493-504.

Song K.Y., et al., "Accurate Modification of a Chromosomal Plasmid by Homologous Recombination in Human Cells," Proceedings of the National Academy of Sciences, 1987, vol. 84 (19), pp. 6820-6824.

Sonoda E., et al., "B Cell Development Under the Condition of Allelic Inclusion," Immunity, 1997, vol. 6 (3), pp. 225-233.

Soukharev S., et al., "Segmental Genomic Replacement in Embryonic Stem Cells by Double *Lox* Targeting," Nucleic Acids Research, 1999, vol. 27 (18), pp. e21.

(56) References Cited

OTHER PUBLICATIONS

Spanopoulou E., et al., "Functional Immunoglobulin Transgenes Guide Ordered B-Cell Differentiation in Rag-1-Deficient Mice," Genes & Development, 1994, vol. 8 (9), pp. 1030-1042.
Stavnezer J., et al., "Mechanism and Regulation of Class Switch Recombination," Annual Review of Immunology, 2008, vol. 26, pp. 261-292.
Stephen R., Kymab Limited Statement of Facts and Evidence in opposition to EP2550363, Olswang LLP, dated Sep. 10, 2015, 22 pages.
Stevens S., et al., Expanded Poster—VelocImmuneTM: Humanization of immunoglobulin loci using VolociGene technology, Sep. 2006, 6 pages.
Stevens S., et al., Poster: "VelocImmuneTM: Humanization of immunoglobulin loci using VolociGene technology" and evidence of unavailability, Sep. 2006, 42 pages.
Stevens S., "Human Antibody Discovery, VelocImune—A Novel Platform," Pharma Focus Asia, 2008, vol. 8, pp. 72-74.
Storb U., et al., "Physical Linkage of Mouse a Genes by Pulsed-Field Gel Electrophoresis Suggests that the Rearrangement Process Favors Proximate Target Sequences," Molecular and Cellular Biology, 1989, vol. 9 (2), pp. 711-718.
Suárez E., et al., "Rearrangement of only One Human IGHV Gene is Sufficient to Generate a Wide Repertoire of Antigen Specific Antibody Responses in Transgenic Mice," Molecular Immunology, 2006, vol. 43 (11), pp. 1827-1835.
Takeda S., et al., "Construction of Chimaeric Processed Immunoglobulin Genes Containing Mouse Variable and Human Constant Region Sequences," Nature, 1985, vol. 314 (6010), pp. 452-454.
Taki S., et al., "Targeted Insertion of a Variable Region Gene into the Immunoglobulin Heavy Chain Locus," Science, 1993, vol. 262 (5137), pp. 1268-1271.
Talbot P., et al., "Cell Adhesion and Fertilization: Steps in Oocyte Transport, Sperm-Zona Pellucida Interactions, and Sperm-Egg Fusion," Biology of Reproduction, 2003, vol. 68 (1), pp. 1-9.
Tan L.K., et al., "A Human-Mouse Chimeric Immunoglobulin Gene with a Human Variable Region is Expressed in Mouse Myeloma Cells," Journal of Immunology, 1985, vol. 135 (5), pp. 3564-3567.
Tanimoto Y., et al., "Embryonic Stem Cells Derived from C57BL/6J and C57BL/6N Mice," Comparative Medicine, 2008, vol. 58 (4), pp. 347-352.
Taylor L.D., et al., "Human Immunoglobulin Transgenes Undergo Rearrangement, Somatic Mutation and Class Switching in Mice that Lack Endogenous IgM," International Immunology, 1994, vol. 6 (4), pp. 579-591.
Te Riele H., et al., "Highly Efficient Gene Targeting in Embryonic Stem Cells through Homologous Recombination with Isogenic DNA Constructs," Proceedings of the National Academy of Sciences, 1992, vol. 89 (11), pp. 5128-5132.
The Jackson Laboratory, "Breeding Strategies for Maintaining Colonies of Laboratory Mice," A Jackson Laboratory Resource Manual, 2007, pp. 1-29.
Thomas K.R., et al., "High Frequency Targeting of Genes to Specific Sites in the Mammalian Genome," Cell, 1986, vol. 44 (3), pp. 419-428.
Thomas K.R., et al., "Introduction of Homologous DNA Sequences into Mammalian Cells Induces Mutations in the Cognate Gene," Nature, 1986, vol. 324 (6092), pp. 34-38.
Thomas K.R., et al., "Site-Directed Mutagenesis by Gene Targeting in Mouse Embryo-Derived Stem Cells," Cell, 1987, vol. 51 (3), pp. 503-512.
Thykjaer T., et al., "Gene Targeting Approaches Using Positive-Negative Selection and Large Flanking Regions," Plant Molecular Biology, 1997, vol. 35 (4), pp. 523-530.
Tomizuka K., et al., "Double Trans-Chromosomic Mice: Maintenance of Two Individual Human Chromosome Fragments Containing Ig Heavy and κ Loci and Expression of Fully Human Antibodies," Proceedings of the National Academy of Sciences, 2000, vol. 97 (2), pp. 722-727.

Tonegawa S., "Somatic Generation of Antibody Diversity," Nature, 1983, vol. 302 (5909), pp. 575-581.
Tong C., et al., "Production of p53 gene knockout rats by homologous recombination in embryonic stem cells," Nature, Sep. 2010, vol. 467 (7312), pp. 211-213.
Torres, et al., "Laboratory Protocols for Conditional Gene Targeting", Institute for Genetics, University of Cologne, 1997, pp. 37-40.
Tuaillon N., et al., "Human immunoglobulin heavy-chain minilocus recombination in transgenic mice: Gene-segment use in μ and γ transcripts," Proc. Natl. Acad. Sci. USA, Apr. 1993, vol. 90, pp. 3720-3724.
Tucker P.W., et al., "Mouse IgA Heavy Chain Gene Sequence: Implications for Evolution of Immunoglobulin Hinge Axons," Proceedings of the National Academy of Sciences, 1981, vol. 78 (12), pp. 7684-7688.
Ungrin M.D., et al., "Strict Control of Telomerase Activation Using Cre-Mediated Inversion," BMC Biotechnology, 2006, vol. 6, pp. 1-9, 2006.
United Kingdom Intellectual Property Office, Combined Search and Examination Report under Sections 17 and 18(3) for Application No. GB1317410.7, dated Nov. 21, 2013, 8 pages.
United Kingdom Intellectual Property Office, Combined Search and Examination Report under Sections 17 and 18(3) for Application No. GB1317447.9, dated Jan. 14, 2014, 7 pages.
United Kingdom Intellectual Property Office, Corrected International Search Report and Opinion for Application No. GB1122047.2, dated Apr. 20, 2012, 5 pages.
United Kingdom Intellectual Property Office, International Search Report for Application No. GB1116122.1, dated Feb. 2, 2012, 1 page.
Urquhart-Dykes & Lord LLP, Third-Party Observation for Application No. EP20140772198, dated Dec. 14, 2015, 8 pages.
USPTO, Excerpts from U.S. Appl. No. 14/682,859, filed Apr. 9, 2015, including Applicant-initiated Interview Summary; Amendments to the Claims and Information Disclosure Statement, 14 pages.
Valenzuela D.M., et al., "High-Throughput Engineering of the Mouse Genome Coupled with High-Resolution Expression Analysis," Nature Biotechnology, 2003, vol. 21 (6), pp. 652-659 and vol. 21 (7), p. 822.
Van Loo, P.F., et al., "Surrogate-Light-Chain Silencing Is Not Critical for the Limitation of Pre-B Cell Expansion but Is for the Termination of Constitutive Signaling," Immunity, Sep. 2007, vol. 27, pp. 468-480.
Van Snick J.L., et al., "Genetic Control of Rheumatoid Factor Production in the Mouse. Role of Genes Linked to the Immunoglobulin Heavy Chain Locus and to the Major Histocompatibility Complex," Arthritis and Rheumatism, 1983, vol. 26 (9), pp. 1085-1090.
Van Spriel A.B., et al., "Immunotherapeutic Perspective for Bispecific Antibodies," Immunology Today, 2000, vol. 21 (8), pp. 391-397.
Vasicek T.J., et al., "Structure and Expression of the Human Immunoglobulin λ Genes," The Journal of Experimental Medicine, 1990, vol. 172 (2), pp. 609-620.
Vassilieva S., et al., "Establishment of SSEA-1- and Oct-4-Expressing Rat Embryonic Stem-Like Cell Lines and Effects of Cytokines of the IL-6 Family on Clonal Growth," Experimental Cell Research, 2000, vol. 258 (2), pp. 361-373.
Venken K.J., et al., "P[acman]: a BAC Transgenic Platform for Targeted Insertion of Large DNA Fragments in *D. Melanogaster*," Science, 2006, vol. 314 (5806), pp. 1747-1751.
Vollmer J., et al., "Antigen Contacts by Ni-Reactive TCR: Typical αβ Chain Cooperation Versus Alpha Chain-Dominated Specificity," International Immunology, 2000, vol. 12 (12), pp. 1723-1731.
Vora K.A., et al., "Altering the Antibody Repertoire via Transgene Homologous Recombination: Evidence for Global and Clone-Autonomous Regulation of Antigen-Driven B Cell Differentiation," The Journal of Experimental Medicine, 1995, vol. 181 (1), pp. 271-281.
Wagner S.D., et al., "Antibodies Generated from Human Immunoglobulin Miniloci in Transgenic Mice," Nucleic Acids Research, 1994, vol. 22 (8), pp. 1389-1393.

(56) References Cited

OTHER PUBLICATIONS

Wallace H.A., et al., "Manipulating the Mouse Genome to Engineer Precise Functional Syntenic Replacements with Human Sequence," Cell, 2007, vol. 128 (1), pp. 197-209.
Wang M., et al., "AID Upmutants Isolated Using a High-Throughput Screen Highlight the Immunity/Cancer Balance Limiting DNA Deaminase Activity," Nature Structural & Molecular Biology, 2009, vol. 16 (7), pp. 769-776.
Wang M., et al., "Altering the Spectrum of Immunoglobulin V Gene Somatic Hypermutation by Modifying the Active Site of AID," The Journal of Experimental Medicine, 2010, vol. 207 (1), pp. 141-153.
Wang T.T., et al., "Catching a Moving Target," Science, 2011, vol. 333 (6044), pp. 834-835.
Wang W., et al., "Chromosomal Transposition of *PiggyBac* in Mouse Embryonic Stem Cells," Proceedings of the National Academy of Sciences, Jul. 2008, vol. 105 (27), pp. 9290-9295.
Wang Y., et al., "Many Human Immunoglobulin Heavy-Chain IGHV Gene Polymorphisms have been Reported in Error," Immunology and Cell Biology, 2008, vol. 86 (2), pp. 111-115.
Wasserman R., et al., "The Pattern of Joining ($J_H$) Gene Usage in the Human IgH Chain Is Established Predominantly at the B PreCursor Cell Stage," The Journal of Immunology, Jul. 1992, vol. 149 (2), pp. 511-516.
Waterhouse P., et al., "Combinatorial Infection and in Vivo Recombination: a Strategy for Making Large Phage Antibody Repertoires," Nucleic Acids Research, 1993, vol. 21 (9), pp. 2265-2266.
Waterston R.H., et al., "Initial Sequencing and Comparative Analysis of the Mouse Genome," Nature, 2002, vol. 420 (6915), pp. 520-562.
Weichhold G.M., et al., "Megabase Inversions in the Human Genome as Physiological Events," Nature, 1990, vol. 347 (6288), pp. 90-92.
Weichhold G.M., et al., "The Human Immunoglobulin κ Locus Consists of Two Copies that are Organized in Opposite Polarity," Genomics, 1993, vol. 16 (2), pp. 503-511.
Weiner L.M., "Fully Human Therapeutic Monoclonal Antibodies," Journal of Immunology, 2006, vol. 29 (1), pp. 1-9.
White J.K., et al., "Genome-Wide Generation and Systematic Phenotyping of Knockout Mice Reveals New Roles for Many Genes," Cell, 2013, vol. 154 (2), pp. 452-464.
Wikipedia, Monoclonal antibodies, Wikipedia, 2008, 8 pages.
Wikipedia, Polyclonal antibodies, Wikipedia, 2008, 5 pages.
Wilke K., et al., "Diagnosis of Haploidy and Triploidy Based on Measurement of Gene Copy Number By Real-Time PCR," Human Mutation, 2000, vol. 16 (5), pp. 431-436.
Wilkie T.M., et al., "Analysis of the Integrant in MyK-103 Transgenic Mice in which Males Fail to Transmit the Integrant," Molecular and Cellular Biology, 1987, vol. 7 (5), pp. 1646-1655.
Williams G.S., et al., "Unequal $V_H$ Gene Rearrangement Frequency within the Large $V_H$7183 Gene Family is not due to Recombination Signal Sequence Variation, and Mapping of the Genes Shows a Bias of Rearrangement Based on Chromosomal Location," Journal of Immunology, 2001, vol. 167 (1), pp. 257-263.
Williams K., Attorney for Applicant, Third-Party Pre-Issuance Submission Under 37 CFR 1.290 in U.S. Appl. No. 14/600,829, dated Apr. 1, 2016, 18 pages.
Williams K., Attorney for Applicant, Third-Party Pre-Issuance Submission Under 37 CFR 1.290 in U.S. Appl. No. 14/679,949, dated Apr. 1, 2016, 18 pages.
Wuerffel R., et al., "S-S Synapsis During Class Switch Recombination is Promoted by Distantly Located Transcriptional Elements and Activation-Induced Deaminase," Immunity, 2007, vol. 27 (5), pp. 711-722.
Xu L., et al., "Combinatorial Surrobody Libraries," Proceedings of the National Academy of Sciences, 2008, vol. 105 (31), pp. 10756-10761.
Xu Y., et al., "Deletion of the Igκ Light Chain Intronic Enhancer/Matrix Attachment Region Impairs but does not Abolish VκJκ Rearrangement," Immunity, 1996, vol. 4 (4), pp. 377-385.

Yamada M., et al., "Preferential Utilization of Specific Immunoglobulin Heavy Chain Diversity and Joining Segments in Adult Human Peripheral Boood B Lymphocytes," Journal of Experimental Medicine, Feb. 1991, vol. 173, pp. 395-407.
Yancopoulos G.D., et al., "Preferential Utilization of the Most $J_H$-Proximal $V_H$ Gene Segments in Pre-B-Cell Lines," Nature, 1984, vol. 311 (5988), pp. 727-733.
Yang X.W., et al., "Homologous Recombination Based Modification in *Escherichia coli* and Germline Transmission in Transgenic Mice of a Bacterial Artificial Chromosome," Nature Biotechnology, 1997, vol. 15 (9), pp. 859-865.
Yu C.C., et al., "Differential Usage of $V_H$ Gene Segments is Mediated by cis Elements," Journal of Immunology, 1998, vol. 161 (7), pp. 3444-3454.
Yu Y., et al., "Engineering Chromosomal Rearrangements in Mice," Nature Reviews Genetics, 2001, vol. 2 (10), pp. 780-790.
Zemlin M., et al., "Expressed Murine and Human CDR-H3 Intervals of Equal Length Exhibit Distinct Repertoires that Differ in their Amino Acid Composition and Predicted Range of Structures," Journal of Molecular Biology, 2003, vol. 334 (4), pp. 733-749.
Zhang Y., et al., "A New Logic for DNA Engineering Using Recombination in *Escherichia coli*," Nature Genetics, 1998, vol. 20 (2), pp. 123-128.
Zhao S., "A Comprehensive BAC Resource," Nucleic Acids Research, 2001, vol. 29 (1), pp. 141-143.
Zheng B., et al., "Engineering Mouse Chromosomes with Cre-loxP: Range, Efficiency, and Somatic Applications," Molecular and Cellular Biology, 2000, vol. 20 (2), pp. 648-655.
Zheng J., et al., "Immunoglobulin Gene Transcripts Have distinctive $V_HDJ_H$ Recombination Characteristics in Human Epithelial Cancer Cells", J. Bioi. Chem., Mar. 2009, vol. 284 (20), pp. 13610-13619.
Zou X., et al., "Removal of the BiP-Retention Domain in Cμ Permits Surface Deposition and Developmental Progression Without L-Chain," Molecular Immunology, 2008, vol. 45 (13), pp. 3573-3579.
Zou Y.R., et al., "Cre-loxP-Mediated Gene Replacement: a Mouse Strain Producing Humanized Antibodies," Current Biology, 1994, vol. 4 (12), pp. 1099-1103.
Deftos, M., et al., "Defining the Genetic Origins of Three Rheumatoid Synovium-derived IgG Rheumatoid Factors," *Journal of Clinical Investigations*, Jun. 1994, vol. 93, pp. 2545-2553.
Grund M., European Patent Attorney, Grund Intellectual Property Group, Third-Party Observations according to Article 115 EPC regarding 16189625.3, dated Mar. 23, 2017, 5 pages.
Guo, Y., et al., "A Preliminary Analysis of the Immunoglobulin Genes in the African Elephant (*Loxodonta Africana*)," *PLoS One*, Feb. 2011, vol. 6 (2), pp. e16889-1-e16889-14.
Huang, D., et al., "Sequence Analyses of Three Immunoglobulin G Anti-virus Antibodies Reveal Their Utilization of Autoantibody-related Immunoglobulin Vh Genes, but Not Vλ Genes," *Journal of Clinical Investigations*, Dec. 1992, vol. 90, pp. 2197-2208.
Jones, Brendan T., Attorney for Applicant, Third-Party Pre-Issuance Submission Under 37 CFR Sec. 1.290 in U.S. Appl. No. 15/232,122, filed Mar. 13, 2017, 32 pages.
Lefranc M.P., et al., Excerpts from "The Immunoglobulin FactsBook," IMGT, the international ImMunoGeneTics database, May 2001, 455 pages.
Macdonald L., et al., "Velocigene Technology Extended to Humanization of Several Megabases of Complex Gene Loci," (Abstract-21) 1st International MUGEN Conference on Animal Models for Human Immunological Disease, Athens Greece, Sep. 10-13, 2006, 1 page.
Shore, D.E., Attorney for Applicant, Third-Party Pre-Issuance Submission Under 37 CFR Sec. 1.290 in U.S. Appl. No. 14/543,359, filed Mar. 3, 2017, 16 pages.
Stevens S. et al., "Velocimmune: Humanization of Immunoglobulin Loci Using Velocigene Technology," (Abstract-4) Presented at 1st International MUGEN Conference on Animal Models for Human Immunological Disease, Athens, Greece, Sep. 10-13, 2006, 1 page.
U.S. Appl. No. 13/846,672, filed Mar. 18, 2013.
U.S. Appl. No. 13/875,892, filed May 2, 2013.
U.S. Appl. No. 14/220,095, filed Mar. 19, 2014.
U.S. Appl. No. 14/226,698, filed Mar. 26, 2014.

(56) References Cited

OTHER PUBLICATIONS

U.S. Appl. No. 15/018,670, filed Feb. 8, 2016.
U.S. Appl. No. 15/095,315, filed Apr. 11, 2016.
U.S. Appl. No. 15/383,196, filed Dec. 19, 2016.
U.S. Appl. No. 15/383,202, filed Dec. 19, 2016.
1st International MUGEN Conference on Animal Models for Human Immunological Disease, Sep. 10-13, 2006—Athens Greece (Abstracts 1-52), 52 pages.
Adams D.J. et al., "Contemporary approaches for modifying the mouse genome," Physiological Genomics, vol. 34, 2008, pp. 225-238.
Adams D.J. et al., "Mutagenic Insertion and Chromosome Engineering Resource (MICER)," Nature Genetics, vol. 36 (8), Aug. 2004, pp. 867-871.
Arthur J.S. et al., "Gene-Targeting Vectors," Chapter 9, Transgenesis Techniques, Principles and Protocols, Third edition, 2009 (24 pages, including cover sheet, copyright and preface pages and table of contents), pp. 127-144.
Asenbauer H. et al., "The immunoglobulin lambda light chain enhancer consists of three modules which synergize in activation of transcription," European Journal of Immunology, 1999, vol. 29, pp. 713-724.
Baer A. et al., "Coping with kinetic and thermodynamic barriers: RMCE, an efficient strategy for the targeted integration of transgenes," Current Opinions in Biotechnology, Oct. 2001, vol. 12 (5), pp. 473-480.
Beck J.A., et al., "Genealogies of mouse inbred strains," Nature Genetics, 2000, vol. 24, pp. 23-25 (with supporting table and chart).
Bentham, A., Attorneys for Regeneron Pharmaceuticals, Inc., Opposition against EP2421357B1 in the name of Kymab Ltd. pertaining to Application No. 10734546.4, dated Jan. 9, 2017, 13 pages.
Birling M.C. et al., "Site-Specific Recombinases for Manipulation of the Mouse Genome," Chapter 16, Transgenesis Techniques, Principles and Protocols, Third edition, 2009 (25 pages, including cover sheet, copyright and preface pages and table of contents), pp. 245-263.
Brault V., et al., "Modeling Chromosomes in Mouse to Explore the Function of Genes, Genomic Disorders, and Chromosomal Organization," PLoS Genetics, Jul. 2006, vol. 2 (7), pp. e86-1-e86-9.
Call L.M., et al., "A Cre-lox recombination system for the targeted integration of circular yeast artificial chromosomes into embryonic stem cells," Human Molecular Genetics, 2000, vol. 9 (12), pp. 1745-1751.
Carter T.C., et al., "Standardized Nomenclature for Inbred Strains of Mice," Cancer Research, 1952, vol. 12 (8), pp. 602-613.
Chia R., et al., "The origins and uses of mouse outbred stocks," Nature Genetics, 2005, vol. 37 (11), pp. 1181-1186.
Chinese Patent Office, Office Action (English Translation) for Chinese Patent Application No. 201380029744.1, dated Nov. 10, 2016, 2 pages.
Chinese Patent Office, Office Action for Chinese Patent Application No. 201380027944.1, dated Nov. 10, 2016, 5 pages.
De Wildt R.M. et al., "Analysis of Heavy and Light Chain Pairings Indicates that Receptor Editing Shapes the Human Antibody Repertoire," Journal of Molecular Biology, 1999, vol. 285, pp. 895-901.
Declerck P. et al., "Generation of Monoclonal Antibodies against autologous Proteins in Gene-inactivated Mice," The Journal of Biological Chemistry, Apr. 1995, vol. 270 (15), pp. 8397-8400.
Engel H., et al., "Expression level of a transgenic λ2 chain results in isotype exclusion and commitment to B1 cells," European Journal of Immunology, 1998, vol. 28, pp. 2289-2299.
European Patent Office, Opposition against EP2517557 Animal Models and Therapeutic Molecules in the name of Kymab Limited pertaining to Application No. 12171793.8, dated Jan. 17, 2017, 39 pages.
European Patent Office, Examination Report for Application No. 12778780.2, dated Oct. 14, 2016, 3 pages.
European Patent Office, Extended European Search Report for Application No. 16151215.7, dated Mar. 16, 2016, 11 pages.
European Patent Office, Extended European Search Report for Application No. 16189625.3, dated Nov. 23, 2016, 8 pages.
Festing, M.F.W., et al., "Revised nomenclature for strain 129 mice," Mammalian Genome, 1999, vol. 10, p. 836.
Glaser S. et al., "Current issues in mouse genome engineering," Nature Genetics, Nov. 2005, Vo. 37 (11), pp. 1187-1193.
Grippo V., et al., "The Heavy Chain Variable Segment Gene Repertoire in Chronic Chagas' Heart Disease," The Journal of Immunology, Dec. 2009, vol. 182 (12), pp. 8015-8025.
Grund M., European Patent Attorney, Grund Intellectual Property Group, Third-Party Observations according to Article 115 EPC regarding 11705964.2, dated Aug. 5, 2016, 11 pages.
Grund M., European Patent Attorney, Grund Intellectual Property Group, Third-Party Observations according to Article 115 EPC regarding 12194970.5, dated Sep. 9, 2013, 11 pages.
Grund M., European Patent Attorney, Grund Intellectual Property Group, Third-Party Observations according to Article 115 EPC regarding 12762378.3, dated Feb. 15, 2017, 7 pages.
Grund M., European Patent Attorney, Grund Intellectual Property Group, Third-Party Observations according to Article 115 EPC regarding 12795606.8, dated Aug. 22, 2014, 8 pages.
Grund M., European Patent Attorney, Grund Intellectual Property Group, Third-Party Observations according to Article 115 EPC regarding 14176740.0, dated Nov. 2, 2016, 4 pages.
Guan C. et al., "A Review of Current Large-Scale Mouse Knockout Efforts," Genesis, vol. 48, 2010, pp. 73-85.
Hamers-Caterman C. et al., "Naturally occurring antibodies devoid of light chains," Nature, Jun. 1993, vol. 363, pp. 446-448.
Hong J. et al., "Derivation and Characterization of Embryonic Stem Cells Lines Derived from Transgenic Fischer 344 and Dark Agouti Rats," Stem Cells and Development, 2012, vol. 21 (6), pp. 1571-1586.
Hsu E., et al., "The plasticity of immunoglobulin gene systems in evolution," Immunology Reviews, vol. 210, Apr. 2006, pp. 8-26.
Jones, Brendan T., Attorney for Applicant, Third-Party Pre-Issuance Submission Under 37 CFR Sec. 1.290 in U.S. Appl. No. 15/016,211, 59 pages, dated Oct. 4, 2016.
Jones, Brendan T., Attorney for Applicant, Third-Party Pre-Issuance Submission Under 37 CFR Sec. 1.290 in U.S. Appl. No. 15/018,670, 26 pages, dated Aug. 12, 2016.
Jones, Brendan T., Attorney for Applicant, Third-Party Pre-Issuance Submission Under 37 CFR Sec. 1.290 in U.S. Appl. No. 15/095,315, 26 pages, dated Sep. 16, 2016.
Jones, Brendan T., Attorney for Applicant, Third-Party Pre-Issuance Submission Under 37 CFR 1.290 in U.S. Appl. No. 15/214,963, Mar. 2, 2017, 42 pages.
Kindt T.J. et al., "Organization and Expression of Immunoglobulin Genes," Chapter 5, Immunology, Sixth edition, 2007 (36 pages, including cover sheet and copyright page), pp. 111-144.
Kuzin I.I. et al, "Requirement for enhancer specificity in immunoglobulin heavy chain locus regulation," Journal of Immunology, Jun. 2008, vol. 180 (11), pp. 7443-7450.
Largaespada D.A., "Transposon Mutagenesis in Mice," Methods in Molecular Biology, vol. 530, 2009, pp. 379-390.
Lefranc M., Appendix 1P, Abbreviations and Useful Data, "Nomenclature of the Human Immunoglobulin Genes," Current Protocols in Immunology, 2000, Supp. 40, pp. A.1P.1-A.1P.37.
Lefranc M.P. et al., "Immunoglobulin Lambda (IGL) Genes of Human and Mouse," Molecular Biology of B Cells, Chapter 4, p. 47, 2004 (Edtrs. Honjo et al.).
Levin A.M. et al., "Optimizing the affinity and specificity of proteins with molecular display," Molecular Biosystems, 2006, vol. 2, pp. 49-57.
Li M., Second Declaration of Dr. Meng (Amy) Li, dated Sep. 5, 2016, 2 pages.
Liang Q. et al., "Extensive genomic copy number variation in embryonic stem cells," Proceedings of the National Academy of Sciences of the U.S.A., Nov. 2008, vol. 105 (45), pp. 17453-17456.
Lyon C., Attorney for Applicant, Third-Party Pre-Issuance Submission Under 37 CFR Sec. 1.290 in U.S. Appl. No. 14/543,359, dated Nov. 13, 2015, 36 pages.
Macdonald L., Declaration of Lynne E. Macdonald, dated Jun. 29, 2016, 4 pages.

(56) References Cited

OTHER PUBLICATIONS

Marchalonis J.J. et al., "Emergence of the immunoglobulin family: conservation in protein sequence and plasticity in gene organization," Glycobiology, vol. 6, 1996, pp. 657-663.
Martinez C., et al., "The Mouse (*Mus musculus*) Immunoglobulin Kappa Variable (IGKV) Genes and Joining (IGKJ) Segments," Experimental and Clinical Immunogenetics, Jul. 1998, vol. 15, pp. 184-193.
Martinez P., et al., "Antibody Synthesis in Vitro," Encyclopedia of Life Sciences, 2005, pp. 1-8.
Mester G., European Patent Attorney, Grund Intellectual Property Group, Third-Party Observations according to Article 115 EPC regarding EP 12778780.2, dated Sep. 30, 2016, 5 pages.
MGI, "Guidelines for Nomenclature of Mouse and Rat Strains," International Committee on Standardized Genetic Nomenclature for Mice, Chairpersons: J.T. Eppig and G. Levan, Oct. 2011, 11 pages. [printed: Mar. 6, 2012-http://www.informatics.jax.org/mgihome/nomen/strains.shtml].
Moffatt S. et al., "PEGylated J591 mAb loaded in PLGA-PEG-PLGA tri-block copolymer for targeted delivery: In vitro evaluation in human prostate cancer cells," International Journal of Pharmaceutics, 2006, vol. 317, pp. 10-13.
Munoz M. et al., "Constraints to Progress in Embryonic Stem Cells from Domestic Species," Stem Cell Review and Reports, 2009, vol. 5, pp. 6-9.
Murphy D., "BAC-based Modifications of the Mouse Genome: The Big and the Backward," The Advanced Course: Genetic Manipulation of ES Cells, dated Nov. 3, 2009, VP Target Discovery, Regeneron Pharmaceuticals, 58 pages.
Murphy et al., The Generation of Lymphocyte Antigen Receptors, Ch. 4, excerpt from Janeway's Immunobiology, Seventh edition, 2008, p. 158.
Oumard A. et al., "Recommended method for chomosome exploitation: RMCE-based cassette-exchange systems in animal cell biotechnology," Cytotechnology, 2006, vol. 50, pp. 93-108.
Perez-Luz S. et al., "Factor VIII mRNA expression from a BAC carrying the intact locus made by homologous recombination," Genomics, 2007, vol. 90, pp. 610-619.
Presta L., "Molecular engineering and design of therapeutic antibodies," Current Opinion in Immunology, 2008, vol. 20, pp. 460-470.
Printout of PDF file available from the University of California website presented in support of European opposition in the name of Kymab Ltd. pertaining to Application No. EP12171793.8 as filed on Jan. 19, 2017, 4 pages. [http://www.research.uci.edu/facilities-services/tmf/presentations/Mouse_ES_CellLine].
Renaut L. et al., "Affinity Maturation of Antibodies: Optimized Methods to Generate High-Quality ScFv Libraries and Isolate IgG Candidates by High-Throughput Screening," Antibody Engineering: Methods and Protocols, Chapter 26, Second Edition, 2012, vol. 907, pp. 451-461.
Schroeder, Jr. H.W., "Similarity and divergence in the development and expression of the mouse and human antibody repertoires," Developmental and Comparative Immunology, vol. 30, 2006, pp. 119-135.
Sequence Listing to WO2008054606A2, 163 pages.
Sopher B. et al., "Efficient recombination-based methods for bacterial artificial chromosome fusion and mutagenesis," Gene, 2006, vol. 371, pp. 136-143.
Sorrell D.A. et al., "Targeted modification of mammalian genomes," Biotechnology Advances, vol. 23, 2005, pp. 431-469.
Stephen R., Olswang, Response to Examination Report dated Jun. 6, 2016 for EP Application No. 14176740.0 as filed with the European Patent Office dated Oct. 10, 2016, 4 pages.
Stephen R., Olswang, Response to Search Report dated Oct. 15, 2014 for Application No. 14176740.0, as filed with the European Patent Office on May 12, 2015, 4 pages.
Stephen R., Olswang, Response to Third-Party Observations dated Aug. 10, 2015 and Examination Report dated Oct. 23, 2015 for Application No. 14176740.0, as filed with the European Patent Office on Apr. 23, 2016, 6 pages.
Van Der Weyden L. et al., "Mouse Chromosome Engineering for Modeling Human Disease," Europe PMC Funders Group, Author Manuscript, Dec. 2008, 32 pages.
Van Dijk M., Declaration of Marcus Van Dijk with exhibits, Apr. 30, 2016, 139 pages.
Vieira P. et al., "The half-lives of serum immunoglobulins in adult mice," European Journal of Immunology, 1988, vol. 18, pp. 313-316.
Wang X., et al., "Recombination, transcription, and diversity of a partially germline-joined VH in a mammal," Immunogenetics, 2012, vol. 64, pp. 713-717.
Webpage corroborating non-confidential nature of 2006 MUGEN Conference, Athens (www.mugen.noe.org), accessed Aug. 9, 2016, 4 pages.
Zhang X. et al., "Combination of overlapping bacterial artificial chromosones by a two-step recombinogenic engineering method," Nucleic Acids Research, 2003, vol. 31 (15), pp. e81-1-e81-6.
Zhao Y. et al., "Physical Mapping of the Bovine Immunoglobulin Heavy Chain Constant Region Gene Locus," Journal of Biological Chemistry, Sep. 2003, vol. 278 (37), pp. 35024-35032.
Zou X., et al., "Subtle differences in antibody responses and hypermutation of λ light chains in mice with a disrupted χ contant region," European Journal of Immunology, 1995, vol. 25, pp. 2154-2162.
Grund M., European Patent Attorney, Grund Intellectual Property Group, Third-Party Observations according to Article 115 EPC regarding 16151215.17, dated Mar. 1, 2017, 4 pages.
U.S. Appl. No. 14/056,1434, filed Oct. 17, 2013.
U.S. Appl. No. 14/220,095, filed Mar. 19, 2014, issued Oct. 10, 2017 as 9,783,618.
European Patent Office, Examination Report for Application No. 13723933.1, dated Mar. 18, 2020, 7 pages.
European Patent Office, Examination Report for Application No. 17 174 426.1, dated Feb. 5, 2020 with Annex, 11 pages.
Ogle, Ph.D., J.M., European Patent Attorney of Hoffman Eitle, Statement of Grounds of Appeal (Corrected version) In re Opposition against EP2758535 dated Feb. 26, 2020, 83 pages.
Ogle, Ph.D., J.M., European Patent Attorney of Hoffman Eitle, Statement of Grounds of Appeal (original filed version) In re Opposition against EP2758535 dated Feb. 26, 2020, 80 pages.
Stephen R., Olswang LLP, Response to Grounds of Appeal dated Dec. 14, 2018 for Application No. 12171793.8 (Patent No. EP2517557), as filed with the European Patent Office on Apr. 29, 2019, 17 pages.
Stephen R., Olswang LLP, Response to Appeal filed by Regeneron Pharmaceuticals, Inc. for Application No. 14170196.1, as filed with the European Patent Office on Mar. 12, 2020, 23 pages.
Wozniak-Knopp G., et al., "Introducing antigen-binding sites in structural loops of immunoglobulin constant domains: Fc fragments with engineered HER2/neu-binding sites and antibody properties," Protein Engineering Design & Selection, 2010, vol. 23(4), pp. 289-297.
Yusa K., et al., "Generation of transgene-free induced pluripotent mouse stem cells by the piggyBac transposon," *Nature Methods*, May 2009, vol. 6, Issue No. 5, pp. 363-371.
Yusa K., et al., "Targeted gene correction of α1-antitrypsin deficiency in induced pluripotent stem cells," *Nature*, Oct. 2012, vol. 478, Issue No. 7369, pp. 391-394.
An Z., "Therapeutic Monoclonal Antibodies from Bench to Clinic," 2009, 4 pages.
Anderson P.S. et al., "Extensive restrictions in the VH sequence usage of the human antibody response against the Rhesus D Antigen," *Molecular Immunology*, vol. 44, pp. 412-422 (Jan. 2007).
Bostrom J. et al., Variants of the Antibody Herceptin That Interact with HER2 and VEGF at the Antigen Binding Site, *Science*, vol. 323, pp. 1610-1614 (Mar. 2009).
Canadian IP Office, Office Action for Application No. 2,857,569, dated Jan. 14, 2019, 6 pages.
Canadian IP Office, Protest and Submission of Prior Art, Application No. 2,802,591, dated Nov. 13, 2019, 18 pages.

(56) References Cited

OTHER PUBLICATIONS

Chapal N. et al., "Thyroid Peroxidase Autoantibodies Obtained from Random Single Chain Fv Libraries Contain the Same Heavy/Light Chain Combinations as Cccur in Vivo," *Endocrinology*, vol. 142(11), pp. 4710-4750 (2001).
Dewitt W.S., et al., A Public Database of Memory and Naïve B-Cell Receptor Sequences, *PLOS ONE*, 18 pages (Aug. 2016).
European Patent Office, Decision rejecting the opposition (Art. 101(2) EPC) for Application No. 10 010 741.6, dated Apr. 25, 2018, 44 pages.
European Patent Office, Irmgard Scheffzyk, Authorized officer, International Search Report for Application No. PCT/EP2018/068309, dated Jan. 15, 2019, 14 pages, together with the Written Opinion of the International Searching Authority.
Ewert H.T. et al., "Biophysical Properties of human antibody variable domains," *J. Mol. Biol.*, vol. 325(3), pp. 531-553 (Jan. 2003).
GENBANK, "Immunoglobulin Heavy Chain Variable Region (*Homo sapiens*)," Accession No. BAA75060, dated Jul. 2, 2008, 1 page.
Goodnow C.C., Declaration, (Evidence in Support of Opposition thereto by Regeneron Pharmaceuticals, Inc.) for Application No. 2011266843, dated Jan. 29, 2016, 21 pages.
Goodnow C.C., Second Declaration, (Evidence in Support of Opposition thereto by Regeneron Pharmaceuticals, Inc.) for Application No. 2011266843, dated Jul. 4, 2016, 9 pages.
Goodnow C.C., Declaration, (Evidence in Support of Opposition thereto by Regeneron Pharmaceuticals, Inc.) for Application No. 2011266843, dated Aug. 29, 2017, 7 pages.
Grund M., European Patent Attorney, Grund Intellectual Property Group, Third-Party Observations according to Article 115 EPC regarding 15188522.5, dated Mar. 13, 2019, 3 pages.
Grund M., European Patent Attorney, Grund Intellectual Property Group, Third-Party Observations according to Article 115 EPC regarding 17174426.1, dated Feb. 11, 2019, 5 pages.
Grund M., European Patent Attorney, Grund Intellectual Property Group, Third-Party Observations according to Article 115 EPC regarding 17196235.0, dated Nov. 27, 2018, 22 pages.
Ichihara Y., et al., "Organization of human immunoglobulin heavy chain diversity gene loci," *The EMBO Journal*, 1988, vol. 7, No. 13, pp. 4141-4150.
Ignatovich O., et al., "The creation of diversity in the human immunoglobulin V(lambda) repertoire," *Journal of Molecular Biology*, vol. 268, pp. 69-77 (Apr. 1997).
Ignatovich O., et al., "Dominance of intrinsic genetic factors in shaping the human immunoglobulin V repertoire", *Journal of Molecular Biology*, vol. 294, pp. 457-465 (Nov. 1999).
International Bureau of WIPO, Third-Party Observations regarding Application No. PCT/EP2018/068309, dated Aug. 14, 2019, 6 pages.
Japanese Patent Office, Notice of Reasons for Rejection—Application No. 2016-548441, dated Aug. 5, 2019, together with English translation, 12 pages.
Japanese Patent Office, Notice of Reasons for Rejection—Application No. 2017-017360, dated Mar. 19, 2018, together with English translation, 7 pages.
Japanese Patent Office, Notice of Reasons for Rejection—Application No. 2017-021028, dated Dec. 21, 2018, together with English translation, 11 pages.
Japanese Patent Office, Decision of Rejection—Application No. 2017-021028, dated Sep. 9, 2019, together with English translation, 9 pages.
Japanese Patent Office, Notice of Reasons for Rejection—Application No. 2018-088749, dated May 27, 2019, together with English translation, 11 pages.
Lee E-Chiang, Declaration of E-Chiang Lee, dated Jun. 13, 2016, 8 pages.
Lerner R.A., et al., "Rare antibodies from combinatorial libraries suggests an S.O.S. component of the human immunological repertoire," *Mol. BioSyst.*, vol. 7(4), pp. 1004-1012 (Apr. 2011).

Morrison S.L., et al. "Vectors and Approaches for the Eukaryotic Expression of Antibodies and Antibody Fusion Proteins" *Antibody Engineering*, 2nd Edition, Chapter 9, 1995, 31 pages.
Ogle, Ph.D., J.M., European Patent Attorney of Hoffman Eitle, Opposition to EP 2 792 236 (Application No. 14176740.0) dated Feb. 28, 2020, 56 pages.
Perera W.S., et al., "Comparison between hybridoma and Fab/phage anti-RhD: Their V gene usage and pairings," *Disease Markers*, vol. 16, pp. 15-19 (2000).
Richardson C. et al., "Molecular Basis of 9G4 B cell Autoreactivity in Human Systemic Lupus Erythematosus," *The Journal of Immunology*, vol. 191(10), pp. 4926-4939 (Nov. 2013).
Rock E.P., et al., "CDR3 Length in Antigen-specific Immune Receptors," *Journal of Experimental Medicine*, Jan. 1994, vol. 179, pp. 323-328.
Sabouri Z., et al., "Redemption of autoantibodies on anergic B cells by variable-region glycosylation and mutation away from self-reactivity," *Proceedings of the National Academy of Sciences of the United States of America*, Early Edition, pp. E2567-E2575 (May 2014).
Schaller M. et al., "The splenic autoimmune response to ADAMTS13 in thrombotic thrombocytopenic purpura contains recurrent antigen-binding CDR3 motifs," *Blood*, vol. 124(23), pp. 3469-3479 (Nov. 2014).
Shore D.E., Attorney for Applicant, Third-Party Pre-Issuance Submission Under 37 CFR Sec. 1.290 in U.S. Appl. No. 15/948,709, filed Jan. 10, 2019, 43 pages.
Shore D.E., Attorney for Applicant, Third-Party Pre-Issuance Submission Under 37 CFR Sec. 1.290 in U.S. Appl. No. 15/955,216, dated Feb. 5, 2019, 52 pages.
Shore D.E., Attorney for Applicant, Third-Party Pre-Issuance Submission Under 37 CFR Sec. 1.290 in U.S. Appl, No. 16/216,666, filed Dec. 11, 2019, 42 pages.
Shore D.E., Attorney for Applicant, Third-Party Pre-Issuance Submission Under 37 CFR Sec. 1.290 in U.S. Appl. No. 16/353,870, filed Dec. 20, 2019, 104 pages.
Siegel D.L. et al., "Section 5: Structural/genetic analysis of mAbs to blood group antigens. Coordinator's Report," *Transfus. Clin. Biol.*, vol. 9, pp. 83-97 (Jan. 2002).
Sleeman M.W., First Declaration, (Evidence in Support of Opposition thereto by Regeneron Pharmaceuticals, Inc.) for Application No. 2011266843, dated Jan. 29, 2016, 24 pages.
Sleeman M.W., Second Declaration, (Evidence in Support of Opposition thereto by Regeneron Pharmaceuticals, Inc.) for Application No. 2011266843, dated Jul. 4, 2016, 7 pages.
Sleeman M.W., Third Declaration, (Evidence in Support of Opposition thereto by Regeneron Pharmaceuticals, Inc.) for Application No. 2011266843, dated Jan. 5, 2018, 9 pages.
Stephen R., Olswang LLP, Patentee's Response to Search Report dated Oct. 15, 2014 to the European Patent Office with corresponding claims for Application No. 14176740.0, dated May 12, 2015, 10 pages.
Stephen R., Olswang LLP, Patentee's Response to Third-Party Observations dated Aug. 10, 2015 and Examination Report dated Oct. 23, 2015 to the European Patent Office with corresponding claims for Application No. 14176740.0, dated Apr. 23, 2016, 13 pages.
Stephen R., Olswang LLP, Patentee's Response to Examination Report dated Jun. 6, 2016 to the European Patent Office with corresponding claims for Application No. 14176740.0, dated Oct. 10, 2016, 11 pages.
Stephen R., Olswang LLP, Response to Examination Report dated Nov. 10, 2016 to the European Patent Office with corresponding claims for Application No. 14176740.0 dated Mar. 17, 2017, 13 pages.
Sun Y., et al., "Repertoire of Human Antibodies against the Polysaccharide Capsule of *Streptococcus pneumoniae* Serotype 6B," *Infection and Immunity*, Mar. 1999, vol. 67 (3), pp. 1172-1179.
Sullivan P.M., et al., "Targeted Replacement of the Mouse Apolipoprotein E Gene with the Common Human APOE3 Allele Enhances Diet-induced Hypercholesterolemia and Atherosclerosis," *The Journal of Biological Chemistry*, 1997, vol. 272, No. 2, pp. 17972-17980.

(56) References Cited

OTHER PUBLICATIONS

Traggiai E. et al., "An efficient method to make human monoclonal antibodies from memory B cells: potent neutralization of SARS coronavirus", Nature Medicine, vol. 10, pp. 871-875 (2004).
Van Dijk M., Third Declaration, dated Mar. 28, 2018, 6 pages (Evidence in Support of Opposition thereto by Regeneron Pharmaceuticals, Inc. for Application No. 2011266843).
Sharan S.K., et al., "Recombineering: a homologous recomination-based method of genetic engineering," Nature Protocols, 2009, vol. 4(2), pp. 206-223.
Shaw, D.J., J.A. Kemp, European Patent Attorney, Response to Summons to attend Oral Proceedings In re Opposition against EP2757875 in the name of Kymab Limited pertaining to Application No. 12762378.8, dated Apr. 16, 2020, 21 pages.
Shore, D.E., Attorney for Applicant, Third-Party Pre-Issuance Submission Under 37 CFR Sec. 1.290 in U.S. Appl. No. 16/296,033, filed Jul. 14, 2020, 75 pages.
Shore, D.E., Attorney for Applicant, Third-Party Pre-Issuance Submission Under 37 CFR Sec. 1.290 in U.S. Appl. No. 16/296,033, filed Jul. 14, 2020, 78 pages (2nd Submission).
Sosio M., et al., "Assembly of large genomic segments in artificial chromosomes by homologous recombination in Escherichia coli," Nucleic Acids Research, 2001, vol. 29(7), pp. e37-1-e37-8.
Stacey A., et al., "Use of Double-Replacement Gene Targeting to Replace the Murine α-Lactalbumin Gene with Its Human Counterpart in Embryonic Stem Cells and Mice," Molecular and Cellular Biology, Feb. 1994, vol. 14(2), pp. 1009-1016.
U.S. Patent and Trademark Office, Before the Patent and Appeal Board, AIA Review No. IPR2019-01577, Decision (Denying Institution of Inter Parties Review 35 U.S.C. Sec. 314), dated Apr. 1, 2020, 20 pages.
U.S. Patent and Trademark Office, Before the Patent and Appeal Board, AIA Review No. IPR2019-01578, Decision (Denying Institution of Inter Parties Review 35 U.S.C. Sec. 314), dated Apr. 1, 2020, 17 pages.
U.S. Patent and Trademark Office, Before the Patent and Appeal Board, AIA Review No. IPR2019-01579, Decision (Denying Institution of Inter Parties Review 35 U.S.C. Sec. 314), dated Mar. 20, 2020, 20 pages.
U.S. Patent and Trademark Office, Before the Patent and Appeal Board, AIA Review No. IPR2019-01580, Decision (Denying Institution of Inter Parties Review 35 U.S.C. Sec. 314), dated Mar. 18, 2020, 26 pages.
U.S. Patent and Trademark Office, Before the Patent and Appeal Board, AIA Review No. IPR2020-00389, Decision (Denying Institution of Inter Parties Review 35 U.S.C. Sec. 314), dated May 26, 2020, 21 pages.
Valancius V., et al., "Testing an "In-Out" Targeting Procedure for Making Subtle Genomic Modifications in Mouse Embryonic Stem Cells," Molecular and Cellular Biology, Mar. 1991, vol. 11(3), pp. 1402-1408.
Wu H., et al., Double replacement: Strategy for efficient introduction of subtle mutations into the murine Colla-1 gene by homologous recombination in embryonic stem cells, Proc. National Academy of Sciences of the U.S.A., Mar. 1994, vol. 91, pp. 2819-2823.
Xu Z., et al., "Site-specific recombination in Schizosaccharomyces pombe and systematic assembly of a 400kb transgene array iin mammalian cells using the integrase of Steptomyces phage φBt1," Nucleic Acids Research, Dec. 2007, vol. 36(1), pp. e9-1-e9-9.
Tung J.W., "Phenotypically distinct B cell development pathways map to the three B cell lineages in the mouse," Proceedings of the National Academy of Sciences of the U.S.A., Apr. 2006, vol. 103(16), pp. 6293-6298.
Defranco, Anthony L., Ph.D., Declaration, Interparties Review AIA No. IPR2019-01578 U.S. Pat. No. 9,505,827), dated Sep. 9, 2019, 121 pages.
Friedrich G., Statement of Dr. Glenn Friedrich, dated Mar. 31, 2014, 18 pages.
Friedrich G., Statement of Dr. Glenn Friedrich, dated Oct. 16, 2014, 9 pages.

Betz A.G., et al., "Elements Regulating Somatic Hypermutation of an Immunoglobulin κ Gene: Critical Role for the Intron Enhancer/Matrix Attachment Region," Cell, Apr. 1994, vol. 77, pp. 239-248.
Odegard V.H., et al., "Targeting of somatic hypermutation," Nature Reviews—Immunology, Aug. 2006, vol. 6, pp. 573-583.
[No Author Listed] IMGT Repertoire (IG and TR), Gene table: human (Homo sapiens) IGHD, created Apr. 18, 1997, last updated Jan. 17, 2020, 3 pages. [retrieved from the Internet under: http://www.imgt.org/IMGTrepertoire/].
Balbás P., et al., "Chromosomal Editing in Escherichia coli. Vectors for DNA Integration and Excision, " Molecular Biotechnology, Sep. 2001, vol. 19(1), pp. 1-12.
Bradley A., et al., "Modifying the Mouse: Design and Desire," Biotechnology, May 1992, vol. 10(5), pp. 534-539.
Brazilian Patent Office, Lúcia Aparecida Mendonca, Preliminary Office Action for Application No. BR112012000536-7, dated Jul. 7, 2010, 12 pages.
Brazilian Patent Office, Lúcia Aparecida Mendonca, Preliminary Office Action (English translation) for Application No. BR112012000536-7, dated Jul. 7, 2010, 1 page.
Carpenter A.J., et al., "Construction, Characterization, and Complementation of a Conditional-Lethal DNA Topoisomerase IIalpha Mutant Human Cell Line," Molecular Biology of the Cell, Dec. 2004, vol. 15(12), pp. 5700-5711.
Chinese Patent~Office, First Office Action for Application No. 201610821299.6, dated Jun. 23, 2020, 15 pages.
Chinese Patent Office, First Office Action (English translation) for Application No. 201610821299.6, dated Jun. 23, 2020, 19 pages.
Dafhnis-Calas F., et al., "Iterative in vivo assembly of large and complex transgenes by combining the activities of φC31 integrase and Cre recombinase," Nucleic Acids Research, Dec. 2005, vol. 33(22), pp. e189-1-e189-14.
Decloux, A.M., Attorney for Applicant, Amendment and Response After Final Rejection—U.S. Appl. No. 13/846,672, filed May 10, 2016, 20 pages.
Defranco, Anthony L., Ph.D., Declaration, Interparties Review AIA No. IPR2019-01577 U.S. Pat. No. 9,434,782), dated Sep. 9, 2019, 113 pages.
Deonarain R., et al., "Impaired Antiviral Response and Alpha/Beta Interferon Induction in Mice Lacking Beta Interferon," Journal of Virology, Apr. 2000, vol. 74(4), pp. 3404-3409.
Ejima D., "Effective elution of antibodies by arginine and arginine derivatives in affinity column chromatography," Analytical Biochemistry, 2005, vol. 345, pp. 250-257.
England, Nicholas Dr., 37 C.F.R. Rule 1.132 Declaration, dated Dec. 21, 2016, 6 pages.
European Patent Office, Notice of Opposition to a European Patent EP2758534 in the name of Kymab Limited pertaining to Application No. 12762377.5, dated May 4, 2020, 6 pages.
Finn, C.A., "Reproductive Capacity and Litter Size in Mice: Effect of Age and Environment," J. Reprod. Fertil., 1963, vol. 6, pp. 205-214.
GENBANK, "Human Ig germline J6-region, partial cds," Accession No. M63030, 1 page.
GENBANK, "H.sapiens immunoglobulin heavy chain J region, 131 C haplotype," Accession No. X86356, 2 pages.
Gibson D.G., et al., Complete Chemical Synthesis, Assembly, and Cloning of a Mycoplasma genitalium Genome, Science, Feb. 2008, vol. 319, pp. 1215-1220.
Gondo Y., et al., Next-generation gene targeting in the mouse for functional genomics, BMB reports, Jul. 2009, vol. 42(6), pp. 315-323.
Grund M., European Patent Attorney, Grund Intellectual Property Group, Third-Party Observations according to Article 115 EPC regarding 19207052.2, dated Aug. 19, 2020, 4 pages.
Gutterson N.I., et al., "Replacement and Amplification of Bacterial Genes With Sequences Altered in Vitro," Proc. Natl. Acad. Sci. USA, Aug. 1983, vol. 80(16), pp. 4894-4898.
Hasty P., et al., "Introduction of a Subtle Mutation Into the Hox-2.6 Locus in Embryonic Stem Cells," Nature, Mar. 1991, vol. 350(6315), pp. 243-246.

(56) References Cited

OTHER PUBLICATIONS

Hasty P., et al., "Gene targeting, principles, and practice in mammalian cells," Gene Targeting, A Practical Approach, 2nd Edition, Oxford, 2000, pp. 1-175, including cover pages (XP055500641).
Izhaki J.E., et al., "Construction by Gene Targeting in Human Cells of a 'Conditional' CDC2 Mutant That Rereplicates Its DNA,", Nature Genetics, Mar. 1997, vol. 15(3), pp. 258-265.
Izhaki J.E., et al., "Targeted Breakage of a Human Chromosome Mediated by Cloned Human Telomeric DNA," Nature Genetics, Dec. 1992, vol. 2(4), pp. 283-287.
Ivanov I.I., et al., "Development of the Expressed Ig CDR-H3 Repertoire Is Marked by Focusing of Constraints in Length, Amino Acid Use, and Charge That Are First Established in Early B Cell Progenitors," The Journal of Immunology, Jun. 2005, vol. 174, pp. 7773-7780.
Japanese Patent Office, Pre-Appeal Report—Application No. 2017-021028—Appeal No. 2020-000300, mailed Mar. 17, 2020, together with English translation, 13 pages.
Koller B.H., et al. "Altering Genes in Animals by Gene Targeting," Annu. Rev. Immunol., 1992, vol. 10, pp. 705-730.
Kotzamanis G., et al., "Construction of human artificial chromosome vectors by recombineering," Gene, 2005, vol. 351, pp. 29-38.
Kuzminov A., "DNA Replication Meets Genetic Exchange: Chromosomal Damage and Its Repair by Homologous Recombination," Proc. Natl. Acad. Sci. USA, Jul. 2001, vol. 98(15), pp. 8461-8468.
Law et al. "Antibodies Against Viruses: Passive and Active Immunization," Current Opinion in Immunology, Aug. 2008, vol. 20(4), pp. 486-492.
Logtenberg T., "Antibody Cocktails: Next-Generation Biopharmaceuticals With Improved Potency," Trends in Biotechnology, Sep. 2007, vol. 25(9), pp. 390-394.
Mitra R., et al., "PiggyBac can bypass DNA synthesis during cut and paste transposition," The EMBO Journal, 2008, vol. 27, pp. 1097-1109.
Muyrers J.P.P., et al., "Techniques: Recombinogenic engineering—new options for cloning and manipulating DNA," Trends in Biochemical Sciences, May 2001, vol. 26(5), pp. 325-331.
Ogle, Ph.D., J.M., European Patent Attorney of Hoffman Eitle, Written Submission in preparation to/during oral proceedings in re Opposition against EP2792236 dated Apr. 17, 2020, 14 pages.
Porter A., Resume Imperial College London, retrieved from the Internet under https://www.imperial.ac.uk/people/andy.porter on May 21, 2020, 2 pages.
Porter A.C., et al., "Role of the B Subunit of the *Escherichia coli* Proton-Translocating ATPase. A Mutagenic Analysis," Journal of Biological Chemistry, Jul. 1985, vol. 260(13), pp. 8182-8187.
Porter, Andrew, First Declaration (Evidence in Support of Opposition thereto by Regeneron Pharmaceuticals, Inc. for Application No. 14176740.0), dated Oct. 11, 2018, 31 pages.
Porter, Andrew, Second Declaration (Evidence in Support of Opposition thereto by Regeneron Pharmaceuticals, Inc. for Application No. 14176740.0), dated Apr. 14, 2020, 8 pages.
Porteus M., "Using Homologous Recombination to Manipulate the Genome of Human Somatic Cells," Biotechnology and Genetic Engineering Reviews, 2007, vol. 24, pp. 195-212.
Rojas G., et al., "Efficient Construction of a Highly Useful Phage-Displayed Human Antibody Repertoire", Biochemical and Biophysical Research Communications, Nov. 2005, vol. 336(4), pp. 1207-1213.
Rothstein R., "Targeting, Disruption, Replacement, and Allele Rescue: Integrative DNA Transformation in Yeast," Methods in Enzymology, 1991, vol. 194, pp. 281-301.
Rubinstein M., et al., "Introduction of a Point Mutation Into the Mouse Genome by Homologous Recombination in Embryonic Stem Cells Using a Replacement Type Vector With a Selectable Marker," Nucleic Acids Research, Jun. 1993, vol. 21(11), pp. 2613-2617.
Scherer S., et al., "Replacement of Chromosome Segments With Altered DNA Sequences Constructed in Vitro," Proc. Natl. Acad. Sci. USA, Oct. 1979, vol. 76(10), pp. 4951-4955.
Schonewald, Stephanie L., Choate Hall & Stewart LLP, Petition for Inter Parties Review—AIA Review No. IPR2019-01577, filed Sep. 20, 2019, 86 pages.
Schonewald, Stephanie L., Choate Hall & Stewart LLP, Petition for Inter Parties Review—AIA Review No. IPR2019-01578, filed Sep. 20, 2019, 83 pages.
Schonewald, Stephanie L., Choate Hall & Stewart LLP, Petition for Inter Parties Review—AIA Review No. IPR2019-01579, filed Sep. 20, 2019, 84 pages.
Schonewald, Stephanie L., Choate Hall & Stewart LLP, Petition for Inter Parties Review—AIA Review No. IPR2019-01580, filed Sep. 20, 2019, 87 pages.
Schonewald, Stephanie L., Choate Hall & Stewart LLP, Petition for Inter Parties Review—AIA Review No. IPR2020-00389, filed Jan. 3, 2020, 89 pages.
Liu X., et al., "Trisomy Eight in ES Cells Is a Common Potential Problem in Gene Targeting and Interferes With Germ Line Transmission," Developmental Dynamics, vol. 209, 1997, pp. 85-91.
Ozawa T., et al., "Amplification and analysis of cDNA generated from a single cell by 5'-RACE: application to isolation of antibody heavy and light chain variable gene sequences from single B cells,," BioTechniques—Short Technical Reports, 2006, vol. 40, Issue No. 4, pp. 469-478.
Sheng Y., et al., "Transformation of *Escherichia coli* with large DNA molecules by electroporation," Nucleic Acids Research, 1995, vol. 23, Issue No. 11, pp. 1990-1996.
U.S. Appl. No. 09/552,219, filed Apr. 19, 2000, issued May 28, 2002 as U.S. Pat. No. 6,395,487.
U.S. Appl. No. 09/552,626, filed Apr. 19, 2000, issued Oct. 8, 2002 as U.S. Pat. No. 6,461,818.
U.S. Appl. No. 13/310,431, filed Dec. 2, 2011.
U.S. Appl. No. 13/416,684, filed Mar. 9, 2012, issued Sep. 20, 2016 as U.S. Pat. No. 9,447,177.
U.S. Appl. No. 13/433,084, filed Mar. 28, 2012, issued Sep. 20, 2016 as U.S. Pat. No. 9,445,581.
U.S. Appl. No. 13/434,361, filed Mar. 29, 2012, issued Feb. 9, 2016 as U.S. Pat. No. 9,253,965.
U.S. Appl. No. 13/740,727, filed Jan. 14, 2013, issued Nov. 29, 2016 as U.S. Pat. No. 9,505,827.
U.S. Appl. No. 13/846,672, filed Mar. 19, 2014, issued Oct. 17, 2017 as U.S. Pat. No. 9,788,534.
U.S. Appl. No. 13/875,892, filed May 2, 2013, issued Oct. 10, 2017 as U.S. Pat. No. 9,783,593.
U.S. Appl. No. 13/886,511, filed May 3, 2013.
U.S. Appl. No. 14/040,405, filed Sep. 27, 2013.
U.S. Appl. No. 14/040,427, filed Sep. 27, 2013.
U.S. Appl. No. 14/052,259, filed Oct. 11, 2013.
U.S. Appl. No. 14/056,434, filed Oct. 17, 2013.
U.S. Appl. No. 14/056,700, filed Oct. 17, 2013.
U.S. Appl. No. 14/056,707, filed Oct. 17, 2013.
U.S. Appl. No. 14/080,630, filed Nov. 14, 2013.
U.S. Appl. No. 14/137,902, filed Dec. 20, 2013, issued Sep. 6, 2016 as U.S. Pat. No. 9,434,782.
U.S. Appl. No. 14/220,080, filed Mar. 19, 2014.
U.S. Appl. No. 14/220,095, filed Mar. 19, 2014, issued Oct. 10, 2017 as U.S. Pat. No. 9,783,618.
U.S. Appl. No. 14/220,099, filed Mar. 19, 2014.
U.S. Appl. No. 14/226,698, filed Mar. 26, 2014, issued May 8, 2018 as U.S. Pat. No. 9,963,716.
U.S. Appl. No. 14/226,706, filed Mar. 26, 2014.
U.S. Appl. No. 14/263,158, filed Apr. 28, 2014.
U.S. Appl. No. 14/263,176, filed Apr. 28, 2014.
U.S. Appl. No. 14/497,054, filed Sep. 25, 2014.
U.S. Appl. No. 14/498,685, filed Sep. 26, 2014.
U.S. Appl. No. 14/516,461, filed Oct. 16, 2014.
U.S. Appl. No. 14/543,359, filed Nov. 17, 2014.
U.S. Appl. No. 14/750,870, filed Jun. 25, 2015.
U.S. Appl. No. 14/818,162, filed Aug. 4, 2015.
U.S. Appl. No. 14/935,010, filed Nov. 6, 2015, issued Nov. 29, 2016 as U.S. Pat. No. 9,504,236.
U.S. Appl. No. 15/016,211, filed Feb. 4, 2016.
U.S. Appl. No. 15/018,670, filed Feb. 8, 2016, issued Mar. 27, 2018 as U.S. Pat. No. 9,924,705.

(56) References Cited

OTHER PUBLICATIONS

U.S. Appl. No. 15/088,805, filed Apr. 1, 2016.
U.S. Appl. No. 15/095,315, filed Apr. 11, 2016, issued Feb. 20, 2018 as U.S. Pat. No. 9,896,516.
U.S. Appl. No. 15/199,575, filed Jun. 30, 2016.
U.S. Appl. No. 15/214,963, filed Jul. 20, 2016.
U.S. Appl. No. 15/232,122, filed Aug. 9, 2016.
U.S. Appl. No. 15/251,969, filed Aug. 30, 2016.
U.S. Appl. No. 15/360,502, filed Nov. 23, 2016.
U.S. Appl. No. 15/369,595, filed Dec. 5, 2016.
U.S. Appl. No. 15/383,101, filed Dec. 19, 2016.
U.S. Appl. No. 15/383,188, filed Dec. 19, 2016.
U.S. Appl. No. 15/383,196, filed Dec. 19, 2016, issued Apr. 10, 2018 as U.S. Pat. No. 9,938,357.
U.S. Appl. No. 15/383,202, filed Dec. 19, 2016, issued Apr. 10, 2018 as U.S. Pat. No. 9,938,358.
U.S. Appl. No. 15/383,342, filed Dec. 19, 2016.
U.S. Appl. No. 15/383,353, filed Dec. 19, 2016.
U.S. Appl. No. 15/385,348, filed Dec. 20, 2016.
U.S. Appl. No. 15/385,372, filed Dec. 20, 2016.
U.S. Appl. No. 15/656,897, filed Jul. 21, 2017.
U.S. Appl. No. 15/690,183, filed Aug. 29, 2017.
U.S. Appl. No. 15/786,281, filed Oct. 17, 2017.
U.S. Appl. No. 15/948,709, filed Apr. 9, 2018.
U.S. Appl. No. 15/955,216, filed Apr. 17, 2018.
U.S. Appl. No. 15/973,376, filed May 7, 2018.
Bentham A., JA Kemp, Statement of Fact and Arguments in Support of Opposition pertaining to EP 2517557 for Application No. 12171793.8, dated Jan. 11, 2017, 32 pages.
Bentham A., JA Kemp, Final Written Submissions for Application No. 12171793.8, dated May 17, 2018, 20 pages.
European Patent Office, Extended European Search Report for Application No. 18153171.6, dated Jun. 28, 2018, 15 pages.
European Patent Office, Notice of Opposition to a European patent pertaining to Patent No. EP2517557 for Application No. 12171793.8, dated Jan. 11, 2017, 7 pages.
GENBANK, "*Homo sapiens* DNA, immunoglobulin heavy-chain variable region, complete sequence, 5 of 5," AB019441.1, dated Jun. 18, 2018, 36 pages.
Goding J.W., "Differences Between Conventional and Monoclonal Serology," *Monoclonal Antibodies: Principles and Practice, Production and Application of Monoclonal Antibodies in Cell Biology, Biochemistry and Immunology*,1996, Third Edition, Section 7.3, pp. 129-130.
Grund M., European Patent Attorney, Grund Intellectual Property Group, Third-Party Observations according to Article 115 EPC regarding 12171793.8, dated Oct. 10, 2013, 10 pages.
Grund M., European Patent Attorney, Grund Intellectual Property Group, Third-Party Observations according to Article 115 EPC regarding 12171793.8, dated Mar. 17, 2015, 4 pages.
Grund M., European Patent Attorney, Grund Intellectual Property Group, Third-Party Observations according to Article 115 EPC regarding 12171793.8, dated May 22, 2015, 5 pages.
Grund M., European Patent Attorney, Grund Intellectual Property Group, Third-Party Observations according to Article 115 EPC regarding 14781635.9, dated May 18, 2018, 4 pages.
Grund M., European Patent Attorney, Grund Intellectual Property Group, Third-Party Observations according to Article 115 EPC regarding 17174426.1, dated Jun. 27, 2018, 7 pages.
Janeway C.A. et al., "Structure of the Antibody Molecule and the Immunoglobulin Genes," excerpts from *Immunobiology: The Immune System in Health and Disease*, 4th Edition, 1999, 4 pages.
Kelley S.K., et al., "Preclinical pharmacokinetics, pharmacodynamics, and activity of a humanized anti-CD40 antibody (SGN-40) in rodents and non-human primates," *British Journal of Pharmacology*, 2006, vol. 148, pp. 1116-1123.
Kumar R., et al., "A novel strategy for efficient production of anti-V3 human scFvs against HIV-1 clade C," *BMC Biotechnology*, Nov. 2012, vol. 12 (1), 15 pages.

Li Z., et al., "The generation of antibody diversity through somatic hypermutation and class switch recombination," *Genes & Development*, vol. 18, pp. 1-11 (2004).
Macdonald L., Declaration of Lynne E. Macdonald, dated May 16, 2018, including Annex 1, 10 pages.
Muramatsu M., et al., "Specific Expression of Activation-induced Cytidine Deaminase (AID), a Novel Member of the RNA-editing Deaminase Family in Germinal Center B Cells," 1999, *The Journal of Biological Chemistry*, vol. 274 (26), pp. 18470-18476.
Newcombe C., et al., "Antibody production: Polyclonal-derived biotherapeutics," *Journal of Chromatography B*, 2007 vol. 848, pp. 2-7.
Shore D.E., Attorney for Applicant, Third-Party Pre-Issuance Submission Under 37 CFR Sec. 1.290 in U.S. Appl. No. 15/656,897, filed May 4, 2018, 55 pages.
Shore D.E., Attorney for Applicant, Third-Party Pre-Issuance Submission Under 37 CFR Sec. 1.290 in U.S. Appl. No. 15/786,281, filed Jun. 27, 2018, 63 pages.
Shore D.E., Attorney for Applicant, Third-Party Pre-Issuance Submission Under 37 CFR Sec. 1.290 in U.S. Appl. No. 15/786,281, filed Jun. 27, 2018 (Second Submission), 62 pages.
Shore D.E., Attorney for Applicant, Third-Party Pre-Issuance Submission Under 37 CFR Sec. 1.290 in U.S. Appl. No. 15/786,281, filed Jun. 27, 2018 (Third Submission), 53 pages.
Stephen R., Olswang LLP, Response to Third-Party Observations for Application No. 12171793.8, as filed with the European Patent Office on Apr. 17, 2015, 3 pages.
Stephen R., Olswang LLP, Response to Opposition (as filed by Regeneron Pharmaceuticals, Inc. on Jan. 11, 2017) for Application No. 12171793.8, as filed with the European Patent Office on Jun. 23, 2017, 8 pages.
Stephen R., Olswang LLP, Response to Opposition in the name of Kymab Limited filed against EP 2758535B1, dated Mar. 22, 2018, 26 pages.
Stephen R., Olswang LLP, Response to Summons and Preliminary Opinion pertaining to Patent No. EP 2517557 for Application No. 12171793.8, as filed with the European Patent Office dated May 17, 2018, 4 pages.
[No Author Listed] IMGT Repertoire (IG and TR), Gene table: human (*Homo sapiens*) IGHJ4, created Oct. 17, 1997, last updated Mar. 30, 2021, 606 pages. [retrieved from the internet under: http://www.imgt.org/IMGTrepertoire/Proteins/alleles/index.php?species=Homo%20sapiens&group=IGHJ&gene=IGHJ4].
Brevini T.A.L., "Embryonic Stem Cells in Domestic Animals, No shortcuts to pig embryonic stem cells," ScienceDirect/Theriogenology, vol. 74, 2010, pp. 544-550.
Daukss, Dana M., Third-Party Pre-Issuance Submission Under 37 CFR 1.290 in U.S. Appl. No. 16/725,707, dated Dec. 28, 2020, 46 pages.
Daukss, Dana M., Third-Party Pre-Issuance Submission Under 37 CFR 1.290 in U.S. Appl. No. 16/869,416, dated Apr. 6, 2021, 28 pages.
Daukss, Dana M., Third-Party Pre-Issuance Submission Under 37 CFR 1.290 in U.S. Appl. No. 16/870,365, dated Mar. 15, 2021, 36 pages.
Daukss, Dana M., Third-Party Pre-Issuance Submission Under 37 CFR 1.290 in U.S. Appl. No. 16/870,365, dated Mar. 15, 2021, 45 pages (Second Submission).
Daukss, Dana M., Third-Party Pre-Issuance Submission Under 37 CFR 1.290 in U.S. Appl. No. 16/886,057, dated Apr. 1, 2021, 31 pages.
Daukss, Dana M., Third-Party Pre-Issuance Submission Under 37 CFR 1.290 in U.S. Appl. No. 16/886,394, dated Apr. 1, 2021, 33 pages.
Daukss, Dana M., Third-Party Pre-Issuance Submission Under 37 CFR 1.290 in U.S. Appl. No. 16/905,557, dated Mar. 9, 2021, 67 pages.
Daukss, Dana M., Third-Party Pre-Issuance Submission Under 37 CFR 1.290 in U.S. Appl. No. 16/905,557, dated Mar. 9, 2021, 63 pages (Second Submission).
Daukss, Dana M., Third-Party Pre-Issuance Submission Under 37 CFR 1.290 in U.S. Appl. No. 16/721,326, dated Mar. 25, 2021, 36 pages.

(56) References Cited

OTHER PUBLICATIONS

Daukss, Dana M., Third-Party Pre-Issuance Submission Under 37 CFR 1.290 in U.S. Appl. No. 16/721,326, dated Mar. 25, 2021, 30 pages (Second Submission).

Defranco, Anthony L., Ph.D., Declaration, Interparties Review AIA No. IPR2019-01579 U.S. Pat. No. 9,447,177), dated Sep. 20, 2019, 103 pages.

European Patent Office, Examiner, Examination Report for Application No. 13723933.1, dated Feb. 21, 2019, 7 pages.

European Patent Office, Examination Report for Application No. 18743421.2, dated Feb. 26, 2021, 3 pages.

GENBANK, Mus musculus immunoglobulin heavy chain locus constant region and partial variable region, strain 129S1, NCBI Reference Sequence No. AJ851868.3, dated Jul. 26, 2007, 23 pages.

GENBANK, "Mus musculus Ig kappa germline J-C region: J1-5 and C genes, and flanks," GenBank No. L80040.1, dated Sep. 2, 2003, 5 pages.

GENBANK, *Homo sapiens* immunoglobulin heavy chain (Igh.1@) on chromosome 14, NCBI Ref. Sequence No. NG_001019.1, dated Jun. 26, 2002, 261 pages.

Ploegh, Hidde Dr., Declaration, submittted in U.S. Appl. No. 14/046,291 (now U.S. Pat. No. 10,526,630) dated Jul. 12, 2018, 123 pages.

Ronai D., et al., "Variegated Expression of the Endogenous Immunoglobulin Heavy-Chain Gene in the Absence of the Intronic Locus Control Region," Molecular and Cellular Biology, Oct. 1999, vol. 19, Issue No. 10, pp. 7031-7040.

Shiokawa S., et al., "IgM Heavy Chain Complementarity-Determining Region 3 Diversity Is Constrained by Genetic and Somatic Mechanisms Until Two Months After Birth," Journal of Immunology, May 1999, vol. 162, Issue No. 10, pp. 6060-6070.

Winter D.B., et al., "Insertion of 2 KB of Bacteriophage DNA Between an Immunoglobulin Promoter and Leader Exon Stops Somatic Hypermutation in a κ Transgene," Molecular Immunology, 1997, vol. 34, Issue No. 5, pp. 359-366.

U.S. Appl. No. 13/846,672, filed Mar. 18, 2013, issued Oct. 17, 2017 as U.S. Pat. No. 9,788,534.

1st International MUGEN Conference on Animal Models for Human Immunological Disease, Sep. 10-13, 2006—Athens Greece (Scientific Programme & Presentations), 4 pages.

Adekar S.P., et al., "A Natural Human IgM Antibody that Neutralizes Botulinum Neurotoxin in vivo," *Hybridoma*, 2008, vol. 27 (2), pp. 65-69.

Aizenshtein E., et al., "Immunological complex for enhancement of innate immune response in passive vaccination," *Vaccine*, Jan. 2013, vol. 31 (4), pp. 626-631 [abstract only—1 page].

Australian IP Office, Examination Report No. 1 for Standard Patent Application for Application No. 2016244295, dated Aug. 18, 2017, 4 pages.

Australian IP Office, Notification of material filed by a third-party for Application No. 2012311288 in the name of Kymab Ltd., Applicant, dated Nov. 20, 2017, 14 pages.

Baxendale H.E., et al., "Natural human antibodies to pneumococcus have distinctive molecular characteristics and protect against pneumococcal disease," *Clinical and Experimental Immunology*, 2007, vol. 151, pp. 51-60.

Bornstein G.G. et al., "Development of a new fully human anti-CD20 monoclonal antibody for the treatment of B-cell malignancies", *Investigational New Drugs*, 2010, vol. 28, pp. 561-574.

Boyd S.D., et al., "Individual Variation in the Germline Ig Gene Repertoire Inferred from Variable Region Gene Rearrangements," *The Journal of Immunology*, Jun. 2010, vol. 184 (12), pp. 6986-6992.

Bradley A., Declarations of Allan Bradley (Tanamachi/Grosveld), as submitted in U.S. Appl. No. 13/416,684, 5 pages.

Bradley A., Declaration of Allan Bradley (commercial success), with exhibits, as submitted in U.S. Appl. No. 13/416,684, dated Feb. 12, 2015, 15 pages.

Bradley A., Declaration of Allan Bradley (mouse strain), with exhibits, as submitted in U.S. Appl. No. 13/416,684, dated Feb. 12, 2015, 68 pages.

Bradshaw, et al., "*Handbook of Cell Signalling*," 2010, Chapter 5, p. 33 (excerpt).

Brüggemann M., et al., "Selection Strategies III: Transgenic Mice," in *Handbook of Therapeutic Antibodies—Technologies, Emerging Developments and Approved Therapeutics*, 2010, Chapter 4, pp. 69-91.

Brüggemann M., "The Preparation of Human Antibodies from Mice Harbouring Human Immunoglobulin Loci," *Transgenic Animals. Generation and Use*, 1997, Chapter 58, Part IV, Section A, pp. 397-402 pages (including cover and copyright pages).

Burton D.R., et al., "Antibody vs. HIV in a clash of evolutionary titans," *Proceedings of the National Academy of Sciences of the U.S.A*, Oct. 2005, vol. 102 (42), pp. 14943-14948.

Calame K., et al., "Regulation of immunoglobulin gene transcription," *Immunoglobulin Genes*, $2^{nd}$ edition, Chapter 18, 1995, pp. 397-422.

Camboni M., et al., "Active and passive immunization strategies based on the SDPM1 peptide demonstrate pre-clinical efficacy in the APPswePSEN1dE9 mouse model for Alzheimer's disease," *Neurobiology of Disease*, Feb. 2014, vol. 52, pp. 31-43 [abstract only—2 pages].

Collins A.M., et al., "The reported germline repertoire of human immunoglobulin kappa chain genes is relatively complete and accurate," *Immunogenetics*, 2008, vol. 60, pp. 669-676.

Collis A.V.J., et al., "Analysis of the Antigen Combining Site: Correlations Between Length and Sequence Composition of the Hypervariable Loops and the Nature of the Antigen," *Journal of Molecular Biology*, 2003, vol. 325, pp. 337-354.

Davis C.G., et al., "Production of Human Antibodies from Transgenic Mice," *Antibody Engineering, Methods and Protocols, Methods in Mol. Biol.*, Chapter 10, 2004, pp. 191-200.

Delves P.J., et al., "Antibodies," Chapter 3, *Roitt's Essential Immunology*, Eleventh edition, 2006, pp. 37-60.

D'Eustachio P., et al., "Mouse Chromosome 12," *Mammalian Genome*, 1998, vol. 8, pp. S241-S257.

Dörner T., et al., "Delineation of Selective Influences Shaping the Mutated Expressed Human Ig Heavy Chain Repertoire," *The Journal of Immunology*, Mar. 1998, vol. 160 (6), pp. 2831-2841.

Dörner T., et al., "Analysis of the targeting of the hypermutational machinery and the impact of subsequent selection on the distribution of nucleotide changes in human $V_H DJ_H$ rearrangements," *Immunologic Reviews*, Apr. 1998, vol. 162 (1), pp. 161-171.

Dörner T., et al., "Somatic hypermutation of human immunoglobulin heavy chain genes: targeting of RGYW motifs on both DNA strands," *European Journal of Immunology*, 1998, vol. 28, pp. 3384-3396.

Dübel S., "Therapeutic Antibodies—From Past to Future," in *Handbook of Therapeutic Antibodies—Technologies, Emerging Developments and Approved Therapeutics*, 2010, Chapter 1 (excerpt: pp. 3-5).

European Patent Office, Examination Report for Application No. 13723933.1, dated Jan. 17, 2018, 6 pages.

European Patent Office, Examination Report for Application No. 15188522.5, dated Aug. 11, 2017, 6 pages.

European Patent Office, Extended European Search Report for Application No. 17174426.1, dated Sep. 14, 2017, 10 pages.

European Patent Office, Extended European Search Report for Application No. 17196214.5, dated Jan. 2, 2018, 13 pages.

European Patent Office, Examination Report for Application No. 16151215.7, dated Jan. 23, 2017, 5 pages.

European Patent Office, Opposition against EP2604110 Animal Models and Therapeutic Molecules in the name of Kymab Limited pertaining to Application No. 12194777.0, dated Aug. 28, 2017, 73 pages.

European Patent Office, Opposition against EP2758535 Antibodies, Variable Domains and Chains Tailored for Human Use in the name of Kymab Limited pertaining to Application No. 12772122.3, dated Aug. 9, 2017, 75 pages.

(56) References Cited

OTHER PUBLICATIONS

European Patent Office, Opposition against EP2798950 Animal Models and Therapeutic Molecules in the name of Kymab Limited pertaining to Application No. 14170196.1, dated Jan. 18, 2018, 33 pages.
Evans M.J., Declaration of Martin J. Evans, with Appendices, dated Dec. 23, 2016, 99 pages.
Forsman A., et al., "Llama Antibody Fragments with Cross-Subtype Human Immunodeficiency Virus Type I (HIV-1)-Neutralizing Properties and High Affinity for HIV-1 gp120," *Journal of Virology*, Dec. 2008, vol. 82 (24), pp. 12069-12081.
Frigerio B., et al., "Antibody Engineering as Opportunity for Selection and Organization of Anti-HIV Therapeutic Agents," *The Open Autoimmunity Journal*, 2010, vol. 2, pp. 127-138.
GENBANK, "*Homo sapiens* partial IGHJ6 gene for immunoglobulin heavy joining 6, exon 1, allele 4," AJ879487.1, dated Jul. 26, 2016, 1 page.
Giudicelli V., et al., "IMGT/GENE-DB: a comprehensive database for human and mouse immunoglobulin and T cell receptor genes," *Nucleic Acids Research*, 2005, vol. 33, pp. D256-D261.
Grandea A.G., III., et al., "Human antibodies reveal a protective epitope that is highly conserved among human and nonhuman influenza A viruses," *Proceedings of the National Academy of Sciences of the U.S.A.*, Jul. 2010, vol. 107 (28), pp. 12658-12663.
Grund M., European Patent Attorney, Grund Intellectual Property Group, Third-Party Observations according to Article 115 EPC regarding 12762377.5, dated Jun. 20, 2017, 4 pages.
He Y., et al., "Efficient Isolation of Novel Human Monoclonal Antibodies with Neutralizing Activity Against HIV-1 from Transgenic Mice Expressing Human Ig Loci," *The Journal of Immunology*, 2002, vol. 169, pp. 595-605.
HGNC (HUGO Gene Nomenclature Committee), "Gene Family: Immunoglobulin Heavy Locus at 14q32.33 (IGH)," 4 pages. [retrieved on Jul. 31, 2017 at http://www.genenames.org/cgi-bin/genefamilies/set/349].
Hülseweh B., et al, "Human-like antibodies neutralizing Western equine encephalitis virus," *mAbs*, May/Jun. 2014, vol. 6 (3), pp. 718-727.
IMBIMBO B.P., et al., "Solanezumab for the treatment of mild-to-moderate Alzheimer's disease," *Expert Review of Clinical Immunology*, Feb. 2012, vol. 8 (2), pp. 135-149 [abstract only—1 page].
IMGT, the International ImMunoGeneTics Information system database, IMGT/GENE-DB entry for *Homo sapiens* IGHD3-9, 2007, 2 pages.
IMGT, the International ImMunoGeneTics Information system database, "Alignment of alleles: Human IGHJ6," dated Jun. 29, 2011, 1 page.
IMGT, the International ImMunoGeneTics Information system database, IMGT/GENE-DB entry for *Homo sapiens* IGHJ6, dated Jul. 26, 2017, version 3.1.17, 4 pages.
IMGT, the International ImMunoGeneTics Information system database, "IMGT/GENE-DB reference sequences," Nucleotide sequences of the four human IGHJ6 alleles, dated Jul. 26, 2017, version 3.1.17, 1 page.
IMGT, the International ImMunoGeneTics Information system database, "IMGT/GENE-DB reference sequences," Amino acid sequences of the four human IGHJ6 alleles, dated Jul. 26, 2017, version 3.1.17, 7 pages.
Jackson S.M., et al., "Human B Cell Subsets," *Advances in Immunology*, Chapter 5, 2008, vol. 98, pp. 151-224.
Jones B.T., Attorney for Applicant, Third-Party Pre-Issuance Submission Under 37 CFR Sec. 1.290 in U.S. Appl. No. 15/251,969, filed May 4, 2017, 22 pages.
Jones B.T., Attorney for Applicant, Third-Party Pre-Issuance Submission Under 37 CFR Sec. 1.290 in U.S. Appl. No. 15/360,502, filed May 8, 2017, 40 pages.
Jones B.T., Attorney for Applicant, Third-Party Pre-Issuance Submission Under 37 CFR Sec. 1.290 in U.S. Appl. No. 15/383,101, filed May 30, 2017, 32 pages.
Jones B.T., Attorney for Applicant, Third-Party Pre-Issuance Submission Under 37 CFR Sec. 1.290 in U.S. Appl. No. 15/383,188, filed May 30, 2017, 33 pages.
Jones B.T., Attorney for Applicant, Third-Party Pre-Issuance Submission Under 37 CFR Sec. 1.290 in U.S. Appl. No. 15/383,196, filed May 8, 2017, 25 pages.
Jones B.T., Attorney for Applicant, Third-Party Pre-Issuance Submission Under 37 CFR Sec. 1.290 in U.S. Appl. No. 15/383,202, filed May 3, 2017, 23 pages.
Kim S.J., et al., "Antibody Engineering for the Development of Therapeutic Antibodies," *Mol. Cells*, 2005, vol. 20 (1), pp. 17-29.
Kriangkum J., et al., "Molecular Characterization of Waldenstrom's Macroglobulinemia Reveals Frequent Occurrence of Two B-Cell Clones Having Distinct IgH VDJ Sequences," *Clinical Cancer Research*, Apr. 2007, vol. 13 (7), pp. 2005-2013.
Lee E., et al., "Use of IGHJ and IGHD gene mutations in analysis of immunoglobulin sequences for the prognosis of chronic lymphocytic leukemia," *Leukemia Research*, 2007, vol. 31, pp. 1247-1252.
Lonberg N., et al., "Antigen-specific human antibodies from mice comprising four distinct genetic modifications," *Nature*, Apr. 1994, vol. 368, pp. 856-859.
Lonberg N., et al., "Human Antibodies from Transgenic Mice," *Intern. Rev. Immunol.*, 1995, vol. 13, pp. 65-93.
Lonberg N., "Human Monoclonal Antibodies from Transgenic Mice," *Therapeutic Antibodies. Handbook of Experimental Pharmacology*, 2008, pp. 69-97.
Magdelaine-Beuzelin C., et al., "Structure-function relationships of the variable domains of monoclonal antibodies approved for cancer treatment," *Critical Reviews in Oncology/Hematology*, 2007, vol. 64, pp. 210-225.
Mårtensson I.L., et al., "The pre-B-cell receptor," *Current Opinion in Immunology*, 2007, vol. 19, pp. 137-142.
Meier I.D., et al., "Short DNA sequences inserted for gene targeting can accidentally interfere with off-target gene expression," *The FASEB Journal*, Research Communication, Jun. 2010, vol. 24, pp. 1714-1724.
Missirlis P.I., et al., "A high-throughout screen identifying sequence and promiscuity characteristics of the loxP spacer region in Cre-mediated recombination," *BMC Genomics*, Apr. 2006, vol. 7(73), 13 pages.
O'Dea, T.P., Attorney for Applicant, Third-Party Pre-Issuance Submission Under 37 CFR Sec. 1.290 in U.S. Appl. No. 15/383,342, filed Aug. 7, 2017, 32 pages.
O'Dea, T.P., Attorney for Applicant, Third-Party Pre-Issuance Submission Under 37 CFR Sec. 1.290 in U.S. Appl. No. 15/385,348, filed Jul. 28, 2017, 48 pages.
O'Dea, T.P., Attorney for Applicant, Third-Party Pre-Issuance Submission Under 37 CFR Sec. 1.290 in U.S. Appl. No. 15/385,372, filed Jul. 28, 2017, 48 pages.
Okada A., et al., "The variable region gene assembly mechanism," *Immunoglobulin Genes*, 2$^{nd}$ edition, Chapter 10, 1995, pp. 205-234.
Pinaud E., et al., "The IgH Locus 3' Regulatory Region: Pulling the Strings from Behind," *Advances in Immunology*, Chapter 2, 2011, vol. 11, pp. 27-70.
Potter K.N., et al., "Features of the overexpressed V1-69 genes in the unmutated subset of chronic lymphocytic leukemia are distinct from those in the healthy elderly repertoire," *Blood*, Apr. 2003, vol. 101 (8), pp. 3082-3084.
Prak E.T.L, et al., "B cell receptor editing in tolerance and autoimmunity," *Annals of the New York Academy of Sciences*, Jan. 2011, vol. 1217, pp. 96-121.
Raaphorst F.M., et al., "Human Ig heavy chain CDR3 regions in adult bone marrow pre-B cells display an adult phenotype of diversity: evidence for structural selection of $D_H$ amino acid sequences," *International Immunology*, Oct. 1997, vol. 9 (10), pp. 1503-1515.
Ren L., et al., "Silencing of the immunoglobulin heavy chain locus by removal of all eight constant-region genes in a 200-kb region," *Genomics*, Aug. 2004, vol. 84, pp. 686-695.
Ricker M., European Patent Attorney, Opposition against EP2758535 in the name of Kymab Limited Statement of Facts and Arguments pertaining to Application No. 12772122.3, dated Aug. 9, 2017, 42 pages.

(56) References Cited

OTHER PUBLICATIONS

Rudolf M.P., et al., "Molecular basis for nonanaphylactogenicity of a monoclonal anti-IgE antibody," *Journal of Immunology*, Jul. 2010, vol. 165 (2), pp. 813-819.
Ruiz M., et al, "The Human Immunoglobulin Heavy Diversity (IGHD) and Joining (IGHJ) Segments," *Experimental and Clinical Immunogenetics*, 1999, vol. 16, pp. 173-184.
Russell N.D., et al., "Production of Protective Human Antipneumococcal Antibodies by Transgenic Mice with Human Immunoglobulin Loci," *Infection and Immunity*, Apr. 2000, vol. 68 (4), pp. 1820-1826.
Schonewald S.L., Attorney for Applicant, Third-Party Pre-Issuance Submission Under 37 CFR Sec. 1.290 in U.S. Appl. No. 14/935,010, dated Aug. 19, 2016, 27 pages.
Shore D.E., Attorney for Applicant, Third-Party Pre-Issuance Submission Under 37 CFR Sec. 1.290 in U.S. Appl. No. 15/088,805, filed Nov. 17, 2017, 44 pages.
Shore D.E., Attorney for Applicant, Third-Party Pre-Issuance Submission Under 37 CFR Sec. 1.290 in U.S. Appl. No. 15/199,575, filed May 31, 2017, 37 pages.
Shore D.E., Attorney for Applicant, Third-Party Pre-Issuance Submission Under 37 CFR Sec. 1.290 in U.S. Appl. No. 15/690,183, filed Feb. 28, 2018, 60 pages.
Siman-Tov D.D., et al., "Differentiation of a passive vaccine and the humoral immune response toward infection: Analysis of phage displayed peptides," *Vaccine*, Jan. 2006, vol. 24, pp. 607-612.
Stein R., et al., "Characterization of a humanized IgG4 anti-HLA-DR monoclonal antibody that lacks effector cell functions but retains direct antilymphoma activity and increases the potency of rituximab," *Blood*, Oct. 2006, vol. 108 (8), pp. 2736-2744.
Suárez E., et al., "Human monoclonal antibodies produced in transgenic BABκ,λ mice recognising idiotypic immunoglobulins of human lymphoma cells," *Molecular Immunology*, 2004, vol. 41, pp. 519-526.
Taylor L.D., et al., "A transgenic mouse that expresses a diversity of human sequence heavy and light chain immunoglobulins," *Nucleic Acids Research*, 1992, vol. 20 (23), pp. 6287-6295.
Table S1 (from Breden F., et al., "Comparison of Antibody Repertoires Produced by HIV-1 Infection, Other Chronic and Acute Infections, and Systemic Autoimmune Disease," *PLoS One*, 2011, vol. 6 (3), pp. e16857-1—e16857—11.), 60 pages.
Table S2 (from Breden F., et al., "Comparison of Antibody Repertoires Produced by HIV-1 Infection, Other Chronic and Acute Infections, and Systemic Autoimmune Disease," *PLoS One*, 2011, vol. 6 (3), pp. e16857-1-e16857—11.), 14 pages.
Xiao X., et al., "Germline-like predecessors of broadly neutralizing antibodies lack measurable binding to HIV-1 envelope glycoproteins: Implications for evasion of immune responses and design of vaccine immunogens," *Biochemical and Biophysical Communications*, 2009, vol. 390, pp. 404-409.
Zhu Z., et al., "Cross-Reactive HIV-1-Neutralizing Human Monoclonal Antibodies Identified from a Patient with 2F5-Like Antibodies," *Journal of Virology*, Nov. 2011, vol. 85 (21), pp. 11401-11408.
Zwick M.B., et al., "The Long Third Complementarity-Determining Region of the Heavy Chain Is Important in the Activity of the Broadly Neutralizing Anti-Human Immunodeficiency Virus Type 1 Antibody 2F5," *Journal of Virology*, Mar. 2004, vol. 78 (6), pp. 3155-3161. 0.
U.S. Appl. No. 14/080,630, filed Nov. 14, 2013, issued Jan. 1, 2019 as U.S. Pat. No. 10,165,763.
U.S. Appl. No. 14/498,685, filed Sep. 26, 2014, issued Apr. 9, 2019 as U.S. Pat. No. 10,251,377.
U.S. Appl. No. 14/516,461, filed Oct. 16, 2014, issued Sep. 4, 2018 as U.S. Pat. No. 10,064,398.
U.S. Appl. No. 14/543,359, filed Nov. 17, 2014, issued Jun. 2, 2020 as U.S. Pat. No. 10,667,501.
U.S. Appl. No. 15/088,805, filed Apr. 1, 2016, issued Dec. 11, 2018 as U.S. Pat. No. 10,149,462.
U.S. Appl. No. 15/656,897, filed Jul. 21, 2017, issued Aug. 4, 2020 as U.S. Pat. No. 10,730,930.
U.S. Appl. No. 15/690,183 filed Aug. 29, 2017, issued Mar. 12, 2019 as U.S. Pat. No. 10,226,033.
U.S. Appl. No. 15/948,709, filed Apr. 9, 2018, issued Sep. 15, 2020 as U.S. Pat. No. 10,774,155.
U.S. Appl. No. 16/216,666, filed Dec. 11, 2018.
U.S. Appl. No. 16/296,033, filed Mar. 7, 2019.
U.S. Appl. No. 16/353,870, filed Mar. 14, 2019.
U.S. Appl. No. 16/721,326, filed Dec. 19, 2019.
U.S. Appl. No. 16/725,707, filed Dec. 23, 2019.
U.S. Appl. No. 16/869,416, filed May 7, 2020.
U.S. Appl. No. 16/870,365, filed May 8, 2020.
U.S. Appl. No. 16/870,413, filed May 8, 2020.
U.S. Appl. No. 16/886,057, filed May 28, 2020.
U.S. Appl. No. 16/886,394, filed May 28, 2020.
U.S. Appl. No. 16/905,537, filed Jun. 18, 2020.
U.S. Appl. No. 16/905,557, filed Jun. 18, 2020.
U.S. Appl. No. 17/020,997, filed Sep. 15, 2020.
U.S. Appl. No. 17/180,258, filed Feb. 18, 2021.
Huang, et al. Dec. 1992. Sequence Analyses of Three Immunoglobulin G Anti-virus Antibodies Reveal Their Utilization of Autoantibody-related Immunoglobulin Vh Genes, but Not V.lambda. Genes. J. Clin. Invest. 90: 2197-2208.†
Deftos, et al., Jun. 1994, Defining the Genetic Origins of Three Rheumatoid Synovium-derived IgG Rheumatoid Factors, J. Clin. Invest., 93: 2545-2553.†
Guo, et al., Feb. 2011, A Preliminary Analysis of the Immunoglobulin Genes in the African Elephant (*Loxodonta africana*), PLoS ONE, 6(2):e16889.†
Macdonald, et al., 2006, Sep. 10-13, Velocigene Technology Extended to Humanization of Several Megabases of Complex Gene Loci, Presented at 1st International MUGEN Conference on Animal Models for Human Immunological Disease, Athens, Greece.†
Stevens, et al., Sep. 10-13, 2006, Velocimmune: Humanization of Immunoglobulin Loci Using Velocigene Technology, Abstract of poster presented at 1st International MUGEN Conference on Animal Models for Human Immunological Disease, Athens, Greece.†
Lefranc, Marie-Paule, and Gérard Lefranc. Immunoglobulin Facts Book. London: Academic Press, 2001. Print. 457 pages.†

\* cited by examiner
† cited by third party

Figure 5 (part 1 of 4)

Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

Figure 5 (part 2 of 4)

Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

Figure 5 (part 3 of 4)

Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

Figure 5 (part 4 of 4)

Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

SEQUENCE LISTING

<160> NUMBER OF SEQ ID NOS: 2

<210> SEQ ID NO 1
<211> LENGTH: 296

```
<212> TYPE: DNA
<213> ORGANISM: Homo sapiens

<400> SEQUENCE: 1
caggtgcagc tggtgcagtc tggggctgag gtgaagaagc ctgggtcctc ggtgaaggtc      60
tcctgcaagg cttctggagg cacccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaga        296

<210> SEQ ID NO 2
<211> LENGTH: 98
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

MANIPULATION OF IMMUNOGLOBULIN GENE DIVERSITY AND MULTI-ANTIBODY THERAPEUTICS

CROSS REFERENCE

This application claims the benefit of U.S. provisional application 61/818,121 filed May 1, 2013, which is herein incorporated by reference.

The attached sequence listing is hereby incorporated by reference.

FIELD OF THE INVENTION

The present invention relates to the provision of antibodies with long HCDR3 lengths. The present invention is also directed to the provision of novel V, D and J pairings in immunoglobulin heavy and light chain loci. Novel, biased antibody diversities and potentially expanded diversities are provided. The invention also provides for novel and potentially expanded diversity or diversity that is biased towards variable gene usage common to antibodies useful for treating and/or preventing certain diseases or conditions, such as infectious diseases. This ability to bias the antibody repertoire also provides methods of simplifying the production of antibody mixtures, such as polyclonal antibody therapeutics useful for the treatment and/or prevention of infectious diseases where a polyclonal approach to target multiple pathogen antigens is desirable. To this end, the present invention also provides bispecific antibodies that are capable of binding to more than one antigen (eg, multiple infectious antigens expressed by the same pathogen), thus providing advantages (such as manufacturing, dosing and administration advantages) not possible with polyclonal antibody mixtures.

The present invention provides vertebrates and cells, such as transgenic mice or rats or transgenic mouse or rat cells. Furthermore, the invention relates to methods of using the vertebrates to isolate antibodies or nucleotide sequences encoding antibodies. Antibodies, nucleotide sequences, pharmaceutical compositions and uses are also provided by the invention.

BACKGROUND

The state of the art provides non-human vertebrates (eg, mice and rats) and cells comprising transgenic immunoglobulin loci, such loci comprising human variable (V), diversity (D) and/or joining (J) segments, and optionally human constant regions. Alternatively, endogenous constant regions of the host vertebrate (eg, mouse or rat constant regions) are provided in the transgenic loci. Methods of constructing such transgenic vertebrates and use of these to generate antibodies and nucleic acids thereof following antigen immunisation are known in the art, eg, see U.S. Pat. No. 7,501,552 (Medarex), U.S. Pat. No. 5,939,598 (Abgenix), U.S. Pat. No. 6,130,364 (Abgenix), WO02/066630 (Regeneron), WO2011004192 (Genome Research Limited), WO2009076464, WO2009143472 and WO2010039900 (Ablexis), the disclosures of which are explicitly incorporated herein. Such transgenic loci in the art include varying amounts of the human V(D)J repertoire.

Existing transgenic immunoglobulin loci tend to be based on a single human DNA source. The potential diversity of human antibody variable regions in non-human vertebrates bearing such transgenic loci is thus confined by the repertoire used.

It would be desirable to provide for novel and potentially expanded repertoire and diversity of human variable regions in transgenic immunoglobulin loci and non-human vertebrates harbouring these, as well as in antibodies produced following immunisation of such animals.

SUMMARY OF THE INVENTION

The present inventors have discovered, by way of construction of transgenic non-human vertebrates, immunisation, antibody heavy chain collection and deep bioinformatics analysis, how to rationally design for VH domains, heavy chains and antibodies having long HCDR3s. These are useful for addressing antigens (such as infectious disease pathogen antigens, receptors and enzyme clefts) where a longer CDR better addresses the target.

The present inventors also realised the possibility of providing combinations of V, D and J gene segments in new ways to provide synthetic gene segment combinations in immunoglobulin loci that are not found in nature or in state-of-the-art loci. The inventors realised the importance of this to provide for novel and potentially expanded repertoire and diversity of human variable regions in transgenic immunoglobulin loci and non-human vertebrates harbouring these, as well as in antibodies produced following immunisation of such animals. In one aspect, the inventors realised that it would be desirable to bias the novel repertoire for the production of antibodies having improved affinity and/or biophysical characteristics/, and/or wherein the range of epitope specificities produced by means of such repertoire is novel, provides for antibodies to epitopes that have hitherto been intractable by prior transgenic immunoglobulin loci or difficult to address. For example, the inventors envisaged a specific application to bias the novel repertoire for the production of antibodies useful in the therapy and/or prevention of infectious disease.

To this end, in a first configuration of the invention, there is provided

A non-human vertebrate (optionally a mouse or a rat) or vertebrate cell whose genome comprises:
(a) An immunoglobulin heavy chain locus comprising one or more human V gene segments, one or more human D gene segments and one or more human J gene segments upstream of a constant region; optionally wherein the heavy chain locus is according to any configuration of the invention described below; and
(b) An immunoglobulin light chain locus comprising either
(i) one or more human VH gene segments and one or more human J gene segments upstream of a constant region (optionally a rearranged VHJLCL or VHJλCL, wherein the CL is Cλ or $C_\kappa$); or
(ii) one or more human VL gene segments, one or more human D gene segments and one or more human JH gene segments upstream of a constant region (optionally a rearranged VLDJHCL or VλDJHCL, wherein the CL is Cλ or $C_\kappa$); or
(iii) one or more human VL gene segments selected from the group consisting of: a VλII gene family member, VλVII 4A, VλII 2.1, VλVII 4A, a Vλ1 gene family member, a Vλ3 gene family member, IGLV1S2, Vλ3-cML70, Ialh2, IaIvI, Ia3h3, Kv325, a VκI gene family member, κI-15A (KL012), VκII family member, a VκIII family member, a VκI gene family member, κI-15A (KL012), VκII A2 (optionally the Ata allele), Vκ A27 (Humkv325) and a gene segment at least 80% identical thereto, and one or more human JL gene segments upstream of a constant region;

Wherein the gene segments in the heavy chain locus are operably linked to the constant region thereof, and the gene segments in the light chain locus are operably linked to the constant region thereof, so that upon immunisation the mouse is capable of producing an antibody comprising heavy chains produced by recombination of the heavy chain locus and light chains produced by recombination of the light chain locus.

In one aspect, in (b)(i) the V gene segment repertoire of the light chain locus comprises or consists of one or more VH gene segments selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hvv1f10, VH4.11, 71-4, VH251, VH1-69 and a gene segment at least 80% identical thereto; or in (b)(iii) the light chain locus V gene segment repertoire consists of one VL gene segment type (optionally and one or mutants thereof), wherein the VL gene segment is selected from said group of VL gene segments.

In a second configuration of the present invention, there is provided

A non-human vertebrate (optionally a mouse or a rat) or vertebrate cell whose genome comprises:

(a) An immunoglobulin heavy chain locus comprising one or more human V gene segments, one or more human D gene segments and one or more human J gene segments upstream of a constant region; and (b) (i) An unrearranged immunoglobulin light chain locus comprising one or more human VH gene segments and one or more human J gene segments upstream of a constant region, wherein each human VH gene segment is a human gene segment identical to (or mutant of) a human VH gene segment used to produce a rearranged VDJ encoding a heavy chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism); or (ii) An immunoglobulin light chain locus comprising a rearranged VJ region or VDJ region upstream of a constant region, wherein the nucleotide sequence of the recombined region is identical to a nucleotide sequence produced by the recombination of a human J gene segment and optionally a human D gene segment with a human VH gene segment that is identical to (or mutant of) the human VH gene segment used to produce a rearranged VDJ encoding a heavy chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism);

(c) Wherein the gene segments in the heavy chain locus are operably linked to the constant region thereof, and the gene segments or VJ or VDJ in the light chain locus are operably linked to the constant region thereof, so that upon immunisation the mouse is capable of producing an antibody comprising heavy chains produced by recombination of the heavy chain locus and light chains derived from the light chain locus;

(d) Optionally when (b)(i) applies, each said VH gene segment in the light chain locus is selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto;

(e) Optionally when (b)(ii) applies, the nucleotide sequence of the recombined region is identical to a nucleotide sequence produced by the recombination of a human J gene segment and optionally a human D gene segment with a human VH gene segment selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto.

In one aspect, the V gene segment repertoire of the light chain locus comprises or consists of one human VH gene segment; optionally germline VH and one or more polymorphic variants thereof, eg, where each polymorphic variant differs from the germline VH nucleotide sequence by 1, 2, 3, 4, 5, 6, 7, 8, 9 or 10 positions. In one aspect, the V gene segment repertoire of the light chain locus comprises or consists of human VH1-69 gene segment; optionally germline VH1-69 and one or more polymorphic variants thereof, eg, where each polymorphic variant differs from the germline VH1-69 nucleotide sequence by 1, 2, 3, 4, 5, 6, 7, 8, 9 or 10 positions. An example of constructing an immunoglobulin locus comprising VH1-69 and polymorphic variants is given below. By using a particular gene segment (eg, one commonly found in human antibodies raised in humans against an infection or other condition) and one or more polymorphic variants thereof, it is possible to provide a repertoire of genes and yet still bias the antibody gene repertoire to a gene segment that is relevant to the disease (eg, an infectious disease, such as a bacterial or viral disease, eg, influenza). This provides a useful pool of genes from which to ultimately generate and isolate a lead antibody for a therapeutic/prophylactic against the disease in question. In an example, the polymorphic variants are natural variants seen in human beings or human populations. The skilled person will know of sources of human antibody gene sequences, such as IMGT (www.imgt.org), GenBank (www.ncbi.nlm.nih.gov/genbank) and the 1000 Genomes databases (www.1000genomes.org). Bioinformatics tools for database manipulation are also readily available and known to the skilled person, eg, as publicly available from the 1000 Genomes Project/EBI (www.1000genomes.org)

In another aspect, the genome of said vertebrate or cell is homozygous for light chain locus (b)(i) or (ii); optionally wherein:

the V gene segment repertoire of the light chain loci consists of one or more human VH gene segments selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto; or the recombined VJ or VDJ repertoire of the light chain loci consists of sequences identical to one or more nucleotide sequences produced by the recombination of a human VH gene segment selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto, with a human J gene segment and optionally a human D gene segment.

In another aspect, each immunoglobulin light chain locus of said vertebrate or cell is according to (b)(i) and comprises only a single human VH gene segment selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto, optionally wherein the genome of the vertebrate or cell is homozygous for said light chain so that all light chain loci comprise the same, single human VH gene segment.

The invention provides a first method of isolating an antibody that binds a predetermined antigen, the method comprising
(a) providing a vertebrate (optionally a mouse or rat) according to any preceding configuration or aspect;
(b) immunising said vertebrate with said antigen (optionally wherein the antigen is an antigen of an infectious disease pathogen);
(c) removing B lymphocytes from the vertebrate and selecting one or more B lymphocytes expressing antibodies that bind to the antigen;
(d) optionally immortalising said selected B lymphocytes or progeny thereof, optionally by producing hybridomas therefrom; and
(e) isolating an antibody (eg, and IgG-type antibody) expressed by the B lymphocytes.

A second method is provided comprising carrying out the first method and the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

An aspect provides method of producing a polyclonal antibody mixture, the method comprising carrying out the first method by separately immunising first and second vertebrates (optionally first and second mice or first and second rats) with antigen and combining the anti-antigen antibodies isolated from each vertebrate (or mutants or derivatives of said antibodies) to produce a polyclonal antibody mixture; optionally wherein the following apply separately or in combination ((i) and (ii); or (i) and (iii)):
(i) the vertebrates are immunised with the same antigen or different antigens (optionally wherein the different antigens are expressed by the same pathogenic organism (or a family member thereof));
(ii) prior to immunisation the light chain loci of the vertebrates contain the identical VH gene repertoire (optionally a single VH gene) and optionally the identical 1 repertoire; optionally the light chain loci of the mammals are identical prior to immunisation;
(iii) prior to immunisation the light chain loci of the vertebrates contain the identical rearranged VJ or VDJ repertoire (optionally a single VJ or VDJ); optionally the light chain loci of the vertebrates are identical prior to immunisation.

An aspect provides method of producing a polyclonal antibody mixture, the method comprising carrying out the first method by immunising one or a plurality of vertebrates (optionally mice or rats) with first and second antigens and combining the anti-antigen antibodies isolated from each vertebrate (or mutants or derivatives of said antibodies) to produce a polyclonal antibody mixture; optionally wherein the following apply separately or in combination ((i) and (ii); or(i) and (iii)):
(i) the antigens are expressed by the same pathogenic organism (or a family member thereof));
(ii) prior to immunisation the light chain loci of the vertebrates contain the identical VH gene repertoire (optionally a single VH gene) and optionally the identical J repertoire; optionally the light chain loci of the mammals are identical prior to immunisation;
(iii) prior to immunisation the light chain loci of the vertebrates contain the identical rearranged VJ or VDJ repertoire (optionally a single VJ or VDJ); optionally the light chain loci of the vertebrates are identical prior to immunisation.

An aspect provides method of producing host cells capable of expressing a polyclonal antibody mixture, the method comprising, in the second method:—
(a) immunising one or a plurality of vertebrates (optionally mice or rats) with first and second antigens (optionally wherein the different antigens are expressed by the same pathogenic organism (or a family member thereof));
(b) isolating nucleic acid encoding first and second anti-antigen antibodies from B lymphocytes from said vertebrates;
(c) determining the nucleotide sequences of the heavy and light chain variable regions of the first antibody;
(d) determining the nucleotide sequence of the heavy variable region and optionally the light chain variable region of the second antibody;
(e) inserting the heavy chain variable region coding sequence of each antibody into a heavy chain expression vector; optionally wherein the constant region coding sequence of each heavy chain is exchanged for a nucleotide sequence that encodes a human or humanised constant region;
(f) inserting the light chain variable region coding sequence of the first antibody into a light chain expression vector; optionally wherein the constant region coding sequence of the light chain of the first antibody is exchanged for a nucleotide sequence that encodes a human or humanised constant region;
(g) optionally inserting the light chain variable region coding sequence of the second antibody into a light chain expression vector; optionally wherein the constant region coding sequence of the light chain of the second antibody is exchanged for a nucleotide sequence that encodes a human or humanised constant region; and
(h) introducing each expression vector into a host cell and co-expressing antibody chains in a mixture of said host cells to produce antibodies, each antibody comprising one or both of said heavy chain variable regions and a light chain; optionally wherein the expression vectors are introduced together into the same host cell (eg, a CHO or HEK293 cell) so that the cell is capable of expressing antibody light chains and heavy chains, such that the cell or a plurality of the host cells express antibodies, each comprising one or both of said heavy chain variable regions and a light chain;
(i) optionally:
prior to immunisation the light chain loci of the vertebrates contain the identical VH gene repertoire (optionally a single VH gene segment) and optionally the identical J repertoire (optionally a single J gene segment); optionally the light chain loci of the vertebrates are identical prior to immunisation; or prior to immunisation the light chain loci of the vertebrates contain the identical rearranged VJ or VDJ repertoire (optionally a single VJ or VDJ); optionally the light chain loci of the vertebrates are identical prior to immunisation.

The invention also provides a method of producing a monoclonal or polyclonal antibody mixture, optionally for use in medicine, optionally for the treatment and/or prevention of an infectious disease, wherein optionally wherein each antibody binds an antigen of an infectious disease pathogen, preferably the same antigen. The invention also provides the use of an isolated, monoclonal or polyclonal antibody, or a mutant or derivative antibody thereof in the manufacture of a medicament for the treatment and/or prevention of an infectious disease, optionally wherein the infectious disease is a disease caused by a bacterial or viral pathogen.

The invention further provides an isolated antibody (eg, IgG-type antibody) obtainable or obtained by a method of the invention, or a mutant or derivative antibody thereof wherein (i) the isolated antibody comprises two copies of the heavy chain variable region of said first antibody paired with two copies of the light chain variable region of said first antibody; or (ii) the isolated antibody comprises two copies of the heavy chain variable region of said second antibody paired with two copies of the light chain variable region of said first antibody; or (iii) the isolated antibody is a bispecific antibody comprising one copy of the heavy chain variable region of said first antibody paired with a copy of the light chain variable region of the first antibody, and one copy of the heavy chain variable region of said the antibody paired with a copy of the light chain variable region of the first antibody, optionally wherein the bispecific antibody binds to said first and second antigens are expressed by the same pathogenic organism (or a family member thereof; optionally for use in medicine, optionally for the treatment and/or prevention of an infectious disease.

In an aspect, there is provided a nucleotide sequence encoding an antibody of the invention, optionally wherein the nucleotide sequence is part of a vector.

In an aspect, there is provided a pharmaceutical composition comprising the antibody or antibodies of the invention and a diluent, excipient or carrier.

In a third configuration of the invention, there is provided
A non-human vertebrate (optionally a mouse or a rat) or vertebrate cell whose genome comprises:
(a) An immunoglobulin heavy chain locus comprising either:—
(i) one or more human VL gene segments, one or more human D gene segments and one or more human J gene segments upstream of a constant region (optionally a rearranged VLDJHCH or VλDJHCH); or
(ii) one or more human VH gene segments selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII1-VH2-1, VH4.18, ha4h3, Hv1051, 71-2, Hv1f10, VH4.11, 71-4, VH251, VH1-69 and a gene segment at least 80% identical; one or more human D gene segments and one or more human JH gene segments upstream of a constant region; and
(b) An immunoglobulin light chain locus comprising one or more human V gene segments and one or more human J gene segments upstream of a constant region, optionally wherein the light chain locus is according to (b)(i) or (b)(ii) of the first configuration of the invention;
Wherein the gene segments in the heavy chain locus are operably linked to the constant region thereof, and the gene segments in the light chain locus are operably linked to the constant region thereof, so that upon immunisation the mouse is capable of producing an antibody comprising heavy chains produced by recombination of the heavy chain locus and light chains produced by recombination of the light chain locus.

In a fourth configuration of the invention, there is provided
A non-human vertebrate (optionally a mouse or a rat) or vertebrate cell whose genome comprises:
(a) (i) An unrearranged immunoglobulin heavy chain locus comprising one or more human VL gene segments, one or more human D gene segments and one or more JH gene segments upstream of a constant region, wherein each human VL gene segment is a human gene segment identical to (or mutant of) a human VL gene segment used to produce a rearranged VJ encoding a light chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism); or
(ii) An immunoglobulin heavy chain locus comprising a rearranged VJ region or VDJ region upstream of a constant region, wherein the nucleotide sequence of the recombined region is identical to a nucleotide sequence produced by the recombination of a human J gene segment and optionally a human D gene segment with a human VL gene segment that is identical to (or mutant of) the human VL gene segment used to produce a rearranged VJ encoding a light chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism);
(b) An immunoglobulin light chain locus comprising one or more human V gene segments and one or more human J gene segments upstream of a constant region; and
(c) Wherein the gene segments in the light chain locus are operably linked to the constant region thereof, and the gene segments or VJ or VDJ in the heavy chain locus are operably linked to the constant region thereof, so that upon immunisation the mouse is capable of producing an antibody comprising light chains produced by recombination of the light chain locus and heavy chains derived from the heavy chain locus;
(d) Optionally when (a)(i) applies, each said VL gene segment in the heavy chain locus is selected from the group consisting of a VL gene segment selected from the group consisting of a VλII gene family member, VλVII 4A, VλII 2.1, VλVII 4A, a Vλ1 gene family member, a Vλ3 gene family member, IGLV1S2, Vλ3-cML70, IaIh2, IaIyI, Ia3h3, Kv325, a VκI gene family member, κI-15A (KL012), VκII family member, a VκIII family member, a VκI gene family member, κI-15A (KL012), VκII A2 (optionally the A2a allele), Vκ A27 (Humkv325) and a gene segment at least 80% identical thereto;

(e) Optionally when (a)(ii) applies, the nucleotide sequence of the recombined region is identical to a nucleotide sequence produced by the recombination of a human J gene segment and optionally a human D gene segment with a human VL gene segment selected from the group consisting of a VL gene segment selected from the group consisting of a VλII gene family member, VλVII 4A, VλII 2.1, VλVII 4A, a Vλ1 gene family member, a Vλ3 gene family member, IGLV1S2, Vλ3-cML70, IaIh2, IaIyI, Ia3h3, Kv325, a VκI gene family member, κI-15A (KL012), VκII family member, a VκIII family member, a VκI gene family member, κI-15A (KL012), VκII A2 (optionally the A2a allele), Vκ A27 (Humkv325) and a gene segment at least 80% identical thereto.

In one aspect of the fourth configuration of the invention, the genome of said vertebrate or cell is homozygous for heavy chain locus (a)(i) or (ii); optionally wherein:

the V gene segment repertoire of the heavy chain loci consists of one or more human VL gene segments selected from the group consisting of a VL gene segment selected from the group consisting of a VλII gene family member, VλVII 4A, VλII 2.1, VλVII 4A, a Vλ1 gene family member, a Vλ3 gene family member, IGLV1S2, Vλ3-cML70, IaIh2, IaIyI, Ia3h3, Kv325, a VκI gene family member, κI-15A (KL012), VκII family member, a VκIII family member, a VκI gene family member, κI-15A (KL012), VκII A2 (optionally the A2a allele), Vκ A27 (Humkv325) and a gene segment at least 80% identical thereto; or the recombined VJ or VDJ repertoire of the heavy chain loci consists of sequences identical to one or more nucleotide sequences produced by the recombination of a human VL gene segment selected from the group consisting of a VL gene segment selected from the group consisting of a VλII gene family member, VλVII 4A, VλII 2.1, VλVII 4A, a Vλ1 gene family member, a Vλ3 gene family member, IGLV1S2, Vλ3-cML70, IaIh2, IaIyI, Ia3h3, Kv325, a VκI gene family member, κI-15A (KL012), VκII family member, a VκIII family member, a VκI gene family member, κI-15A (KL012), VκII A2 (optionally the A2a allele), Vκ A27 (Humkv325) and a gene segment at least 80% identical thereto with a human J gene segment and optionally a human D gene segment.

The invention provides a monoclonal or polyclonal antibody composition prepared by immunisation of at least one vertebrate (eg, mouse or rat) according to any preceding configuration or aspect with an antigen, optionally wherein the antigen is an antigen of an infectious disease pathogen, optionally wherein the same antigen is used to immunise all the vertebrates; optionally wherein the antibody or antibodies are IgG-type.

The invention also provides an isolated chimaeric antibody for treating and/or preventing an infectious disease or condition, the antibody comprising a non-human vertebrate (optionally a mouse or rat) heavy chain constant regions and human variable regions that bind an antigen of an infectious disease pathogen, wherein the antibody is obtainable or obtained in a method comprising immunisation of a non-human vertebrate of the invention with said antigen.

The invention also provides an isolated human antibody for treating and/or preventing an infectious disease or condition, the antibody comprising human heavy chain constant regions and human variable regions that bind an antigen of an infectious disease pathogen, wherein the antibody is obtainable or obtained in a method comprising affinity maturation of antibody variable regions in vivo in a transgenic non-human vertebrate (eg, mouse or rat) when said variable regions are operably linked to heavy chain constant regions of said vertebrate (eg, mouse or rat heavy chain constant regions) by (a) immunisation of a vertebrate of the invention with said antigen, (b) isolation of nucleic acid encoding a chimaeric antibody according to the invention, (c) replacing the nucleotide sequences of the nucleic acid that encode the non-human vertebrate heavy chain constant regions with nucleotide sequence encoding human heavy chain constant regions to produce nucleic acid encoding a human antibody; (d) expressing the human antibody in vitro (optionally from CHO or HEK293 cells harbouring the human nucleic acid) and (e) isolating the human antibody (optionally with further affinity maturation of the antibody and/or producing a derivative thereof).

An aspect provides a mixture of first and second human antibodies, each antibody being capable of binding to an antigen of an infectious disease pathogen (optionally wherein the first antibody binds a first antigen and the second antibody binds a second antigen, said antigens being from the same pathogen; or wherein the antigens are the same). In an embodiment, a common light chain is used which enables simplified manufacture of the antibody mixture. Thus, there is provided in the mixture, the light chain amino acid sequence of the first antibody that is identical to the light chain amino acid sequence of the second antibody, or has up to 15 amino acid changes therefrom.

The invention further provides a host cell comprising one or more expression vectors encoding 3 or more first and second antibody heavy and light chains.

In a fifth configuration of the invention, there is provided A synthetic immunoglobulin locus comprising one or more variable and 0.1 gene segments (and optionally one or more D gene segments) operably linked 5' of a constant region, wherein the locus comprises a 5' to 3' V(D)J arrangement selected from the group consisting of immunoglobulin locus can be constructed with one or more of the following arrangements (5' to 3'):—

(a) [V (heavy, lambda or kappa)]-[two-turn RSS]-[one-turn RSS]-[D]-[JH], wherein said RSSs are in an opposite orientation;

(b) [VH]-[D]-[two-turn RSS]-[one-turn RSS]-[J lambda], wherein said RSSs are in an opposite orientation;

(c) [VH]-[D]-[one-turn RSS]-[two-turn RSS]-[J kappa], wherein said RSSs are in an opposite orientation;

(d) [VH or V kappa]-[two-turn RSS]-[one-turn RSS]-[J lambda], wherein said RSSs are in an opposite orientation;

(e) [V kappa]-[one-turn RSS]-[two-turn RSS]-[JH or J lambda], wherein said RSSs are in an opposite orientation;

(f) [V (heavy, lambda or kappa)]-[one-turn RSS]-[two-turn RSS]-[D]-[JH], wherein said RSSs are in an opposite orientation;

(g) [VH]-[D]-[one-turn RSS]-[two-turn RSS]-[J lambda], wherein said RSSs are in an opposite orientation;

(h) [VH]-[D]-[two-turn RSS]-[one-turn RSS]-[J kappa], wherein said RSSs are in an opposite orientation;

(i) [VH or V kappa]-[one-turn RSS]-[two-turn RSS]-[J lambda], wherein said RSSs are in an opposite orientation;

(j) [V kappa]-[two-turn RSS]-[one-turn RSS]-[JH or J lambda], wherein said RSSs are in an opposite orientation.

In a sixth configuration, the invention also provides means for generating VH domains, heavy chains and antibodies having a long HCDR3 length. In this context, the invention provides:—

A non-human vertebrate (eg, a mouse or a rat) or a non-human vertebrate cell (eg, a mouse cell or a rat cell) whose genome comprises a human immunoglobulin D gene segment repertoire that is biased to the human D2 and/or D3 family or biased to one, more or all human D gene segments selected from the group D1-26, D2-2, D3-9, D3-10, D3-22, D4-17, D6-13 and D6-19.

A non-human vertebrate (eg, a mouse or a rat) or a non-human vertebrate cell (eg, a mouse cell or a rat cell), optionally according to any preceding claim, whose genome comprises a human immunoglobulin VH gene segment repertoire that is biased to one, more or all of gene segments selected from the group VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1.

A non-human vertebrate (eg, a mouse or a rat) or a non-human vertebrate cell (eg, a mouse cell or a rat cell) whose genome comprises a human immunoglobulin JH gene segment repertoire that is biased to human JH6.

A monoclonal or polyclonal antibody composition or a population of antibody-producing cells for producing such composition, wherein the composition or population is prepared by immunising at least one vertebrate according to any preceding claim with an antigen, wherein the antibody or antibodies have human heavy chain variable regions comprising non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)—pattern junctional mutations when compared to corresponding human germline V, D and J sequences; wherein the composition comprises at least one antigen-specific antibody having a HCDR3 length of at least 20 amino acids (according to IMGT).

A repertoire of antibody heavy chains (eg, provided by antibodies) comprising one or more heavy chains whose variable domain HCDR3 has a length of at least 20 amino acids (according to IMGT) and derived from the recombination of a human VH, D and JH, wherein the VH is selected from the group
VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01 and
the D is selected from the group
D2-2*02, D3-9*01, D3-10*01 and D3-22*01, or
D2-2*02, D3-9*01 and D3-10*01, or
D3-9*01 and D3-10*01, or
D1-26, D2-2, D3-9, D3-10, D3-22, D4-17, 06-13 and D6-19, or
D1-26*01, D2-2*02, D3-9*01, D3-10*01, D3-22*01, D4-17*01, D6-13*01 and D6-19*01, or
D2-2, D3-9, D3-10, D3-22, D4-17, D6-13 and D6-19, or
D2-2*02, D3-9*01, D3-10*01, D3-22*01, D4-17*01, D6-13*01 and D6-19*01, or
D1-26, D2-2, D3-10 and 06-19, or
D2-2, D3-9 and D3-10; and optionally the JH is JH6 (eg, JH6*02);

Wherein
(a) the heavy chain variable domain has been produced in vivo in a non-human vertebrate (eg, a mouse or a rat); and/or
(b) the heavy chain variable domain comprises non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)—pattern junctional mutations when compared to corresponding human germline V, D and J sequences.

BRIEF DESCRIPTION OF THE FIGURES

FIG. 5 (in 4 parts): Alignment of 13 IGHV1-69 alleles showing the variable (V) coding region only. Nucleotides that differ from VH1-69 allele *01 are indicated at the appropriate position whereas identical nucleotides are marked with a dash. Where nucleotide changes result in amino acid differences, the encoded amino acid is shown above the corresponding triplet. Boxed regions correspond to CDR1, CDR2 and CDR3 as indicated.

DETAILED DESCRIPTION OF THE INVENTION

Figure 1:
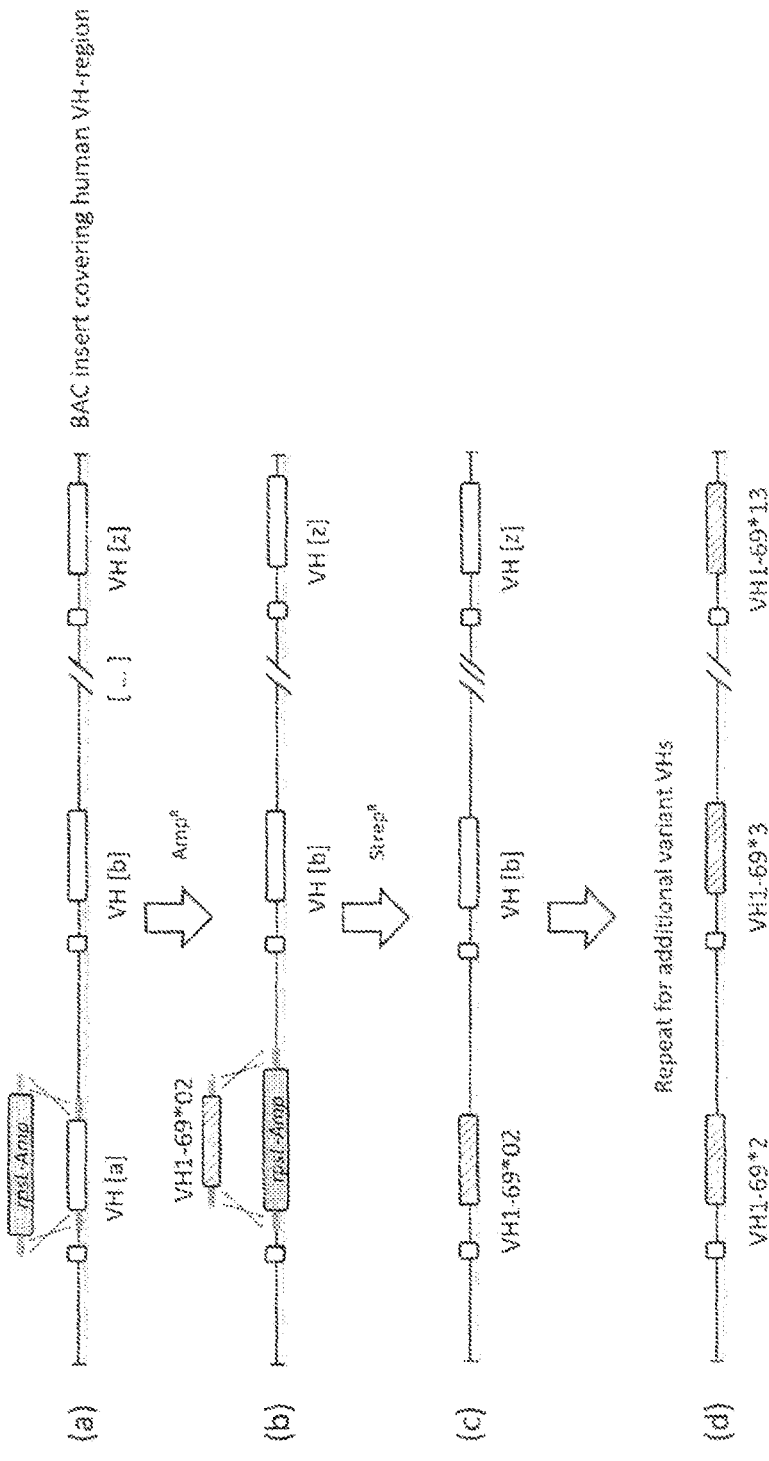
FIGS. 1 to 3: Schematic illustrating a protocol for producing recombineered BAC vectors to add V gene segments into a mouse genome.

A source for human V, D and J gene segments is Bacterial Artificial Chromosomes (RPCI-11 BACs) obtained from Roswell Park Cancer Institute (RPCI)/Invitrogen. See http://bacpac.chori.org/hmale11.htm, which describes the BACs as follows: —

"RPCI-11 Human Male BAC Library

The RPCI-11 Human Male BAC Library (Osoegawa et al., 2001) was constructed using improved cloning techniques (Osoegawa et al., 1998) developed by Kazutoyo Osoegawa. The library was generated by Kazutoyo Osoegawa. Construction was funded by a grant from the National Human Genome Research Institute (NHGRI, NIH) (#1R01RG01165-03). This library was generated according to the new NHGRI/DOE "Guidance on Human Subjects in Large-Scale DNA Sequencing . . .

"Male blood was obtained via a double-blind selection protocol. Male blood DNA was isolated from one randomly chosen donor (out of 10 male donors)".

Osoegawa K, Mammoser A G, Wu C, Frengen E, Zeng C, Catanese J J, de Jong P J; Genome Res. 2001 March; 11(3):483-96; "A bacterial artificial chromosome library for sequencing the complete human genome";

Osoegawa, K., Woon, P. Y., Zhao, B., Frengen, E., Tateno, M., Catanese, J J, and de Jong, P. J. (1998); "An Improved Approach for Construction of Bacterial Artificial Chromosome Libraries"; Genomics 52, 1-8.

As a source of antibody gene segment sequences, the skilled person will also be aware of the following available databases and resources (including updates thereof):—
1.1. The Kabat Database (G. Johnson and T. T. Wu, 2002; http://www.kabatdatabase.com). Created by E. A. Kabat and T. T. Wu in 1966, the Kabat database publishes aligned sequences of antibodies, T-cell receptors, major histocompatibility complex (MHC) class I and II molecules, and other proteins of immunological interest. A searchable interface is provided by the Seqhuntll tool, and a range of utilities is available for sequence alignment, sequence subgroup classification, and the generation of variability plots. See also Kabat, E. A., Wu, T. T., Perry, H., Gottesman, K., and Foeller, C. (1991) Sequences of Proteins of Immunological Interest, 5th ed., NIH Publication No. 91-3242, Bethesda, Md., which is incorporated herein by reference, in particular with reference to human gene segments for use in the present invention.

1.2. KabatMan (A. C. R. Martin, 2002; http://www.bioinf.org.uk/abs/simkab.html). This is a web interface to make simple queries to the Kabat sequence database.

1.3. IMGT, the International ImMunoGeneTics Information System®; M.-P. Lefranc, 2002; http://imgt.cines.fr). IMGT is an integrated information system that specializes in antibodies, T cell receptors, and MHC molecules of all vertebrate species. It provides a common portal to standardized data that include nucleotide and protein sequences, oligonucleotide primers, gene maps, genetic polymorphisms, specificities, and two-dimensional (2D) and three-dimensional (3D) structures. IMGT includes three sequence databases (IMGT/LIGM-DB, IMGT/MHC-DB, IMGT/PRIMERDB), one genome database (IMGT/GENE-DB), one 3D structure database (IMGODstructure-DB), and a range of web resources ("IMGT Marie-Paule page") and interactive tools.

1.4. V-BASE (I. M. Tomlinson, 2002; http://www.mrc-cpe.cam.ac.uk/vbase). V-BASE is a comprehensive directory of all human antibody germline variable region sequences compiled from more than one thousand published sequences. It includes a version of the alignment software DNAPLOT (developed by Hans-Helmar Althaus and Werner Müller) that allows the assignment of rearranged antibody V genes to their closest germline gene segments.

1.5. Antibodies—Structure and Sequence (A. C. R. Martin, 2002; http://www.bioinf.org.uk/abs). This page summarizes useful information on antibody structure and sequence. It provides a query interface to the Kabat antibody sequence data, general information on antibodies, crystal structures, and links to other antibody-related information. It also distributes an automated summary of all antibody structures deposited in the Protein Databank (PDB). Of particular interest is a thorough description and comparison of the various numbering schemes for antibody variable regions.

1.6. AAAAA—AHo's Amazing Atlas of Antibody Anatomy (A. Honegger, 2001; http://www.unizh.ch/~antibody). This resource includes tools for structural analysis, modeling, and engineering. It adopts a unifying scheme for comprehensive structural alignment of antibody and T-cell-receptor sequences, and includes Excel macros fUr antibody analysis and graphical representation.

1.7. WAM—Web Antibody Modeling (N. Whitelegg and A. R. Rees, 2001; http://antibodv.both.ac.uk). Hosted by the Centre for Protein Analysis and Design at the University of Bath, United Kingdom. Based on the AbM package (formerly marketed by Oxford Molecular) to construct 3D models of antibody Fv sequences using a combination of established theoretical methods, this site also includes the latest antibody structural information.

1.8. Mike's Immunoglobulin Structure/Function Page (M. R. Clark, 2001; http://www.path.cam.ac.uk/~mrc7/mikeimages.html) These pages provide educational materials on immunoglobulin structure and function, and are illustrated by many colour images, models, and animations. Additional information is available on antibody humanization and Mike Clark's Therapeutic Antibody Human Homology Project, which aims to correlate clinical efficacy and anti-immunoglobulin responses with variable region sequences of therapeutic antibodies.

1.9. The Antibody Resource Page (The Antibody Resource Page, 2000; http://www.antibodyresource.com). This site describes itself as the "complete guide to antibody research and suppliers." Links to amino acid sequencing tools, nucleotide antibody sequencing tools, and hybridoma/cell-culture databases are provided.

1.9. Humanization bY Design (J. Saldanha, 2000; http://people.cryst.bbk.ac.uk/~ubcq07s). This resource provides an overview on antibody humanization technology. The most useful feature is a searchable database (by sequence and text) of more than 40 published humanized antibodies including information on design issues, framework choice, framework back-mutations, and binding affinity of the humanized constructs.

See also Antibody Engineering Methods and Protocols, Ed. Benny K C Lo, Methods in Molecular Biology™, Human Press. Also at http://www.blogsua.com/pdf/antibody-engineering-methods-and-protocolsantibody-engineering-methods-and-protocols.pdf In one embodiment throughout the present text, "germline" refers to the canonical germline gene segment sequence.

The present invention is directed to the provision of novel V, D and J pairings in immunoglobulin heavy and light chain loci. Novel, biased antibody diversities and potentially expanded diversities are provided. One aspect of the invention exploits the natural pairing of compatible recombination signal sequences (RSSs) during antibody V(D)J recombination in vivo, and this aspect of the invention provides new, synthetic combinations of V, D and J gene segments using the observation of RSS compatibility.

Another aspect of the invention is based on the observation of V, D and J usage bias in naturally-occurring human antibodies raised against infectious disease pathogens. The invention is useful for manipulating the antibody gene diversity in transgenic non-human animals, thus providing for novel and potentially expanded diversity or diversity that is biased towards variable gene usage common to antibodies useful for treating and/or preventing certain diseases or conditions, such as infectious diseases. This ability to bias the antibody repertoire also provides methods of simplifying the production of antibody mixtures, such as polyclonal antibody therapeutics useful for the treatment and/or prevention of infectious diseases where a polyclonal approach to target multiple pathogen antigens is desirable. To this end, the present invention also provides bispecific antibodies that are capable of binding to more than one antigen (eg, multiple infectious antigens expressed by the same pathogen), thus providing advantages (such as manufacturing, dosing and administration advantages) not possible with polyclonal antibody mixtures.

The present invention provides vertebrates and cells, such as transgenic mice or rats or transgenic mouse or rat cells. Furthermore, the invention relates to methods of using the vertebrates to isolate antibodies or nucleotide sequences encoding antibodies. Antibodies, nucleotide sequences, pharmaceutical compositions and uses are also provided by the invention.

To this end, the present invention provides, in a first configuration

A non-human vertebrate (optionally a mouse or a rat) or vertebrate cell whose genome comprises:
(a) An immunoglobulin heavy chain locus comprising one or more human V gene segments (optionally a plurality of VH), one or more human D gene segments and one or more human J gene segments upstream of a constant region; optionally wherein the heavy chain locus is according to (a) of the second configuration described below; and
(b) An immunoglobulin light chain locus comprising either
  (i) one or more human VH gene segments and one or more human J gene segments upstream of a constant region (optionally a rearranged $V_H J_L C_L$ or $V_H J_\lambda C_L$, wherein the $C_L$ is $C_\lambda$ or Cκ); or
  (ii) one or more human VL gene segments, one or more human D gene segments and one or more human $J_H$ gene segments upstream of a constant region (optionally a rearranged $V_L DJ_H C_L$ or $V_A DJ_R C_L$, wherein the $C_L$ is $C_\lambda$ or Cκ); or
  (iii) one or more human VL gene segments selected from the group consisting of: a $V_\lambda II$ gene family member, $V_\lambda VII$ 4A, $V_\lambda II$ 2.1, $V_\lambda VII$ 4A, a $V_\lambda 1$ gene family member, a $V_\lambda 3$ gene family member, IGLV1S2, $V_\lambda 3$-cML70, Ialh2, IaIyI, Ia3h3, Kv325, a VκI gene family member, κI-15A (KL012), $V_\kappa II$ family member, a $V_\kappa III$ family member, a VκI gene family member, κI-15A (KL012), $V_\kappa II$ A2 (optionally the A2a allele), $V_\kappa A27$ (Humkv325) and a gene segment at least 80% identical thereto, and one or more human $J_L$ gene segments upstream of a constant region; optionally the one or more VL gene segments are selected from List A1, A2, A1.1, A1.2, A2.1, A2.2, A2.3 or A2.4 below.

Wherein the gene segments in the heavy chain locus are operably linked to the constant region thereof, and the gene segments in the light chain locus are operably linked to the constant region thereof, so that upon immunisation the mouse is capable of producing an antibody comprising heavy chains produced by recombination of the heavy chain locus and light chains produced by recombination of the light chain locus.

This configuration of the invention, thus, provides for the possibility of novel, synthetic antibody and gene repertoires in a transgenic non-human vertebrate, such as a mouse or rat. Such new repertoires are desirable, since they provide for the possibility of a novel pool of antibodies from which lead antibodies can be selected following immunisation of the vertebrate with a predetermined antigen. This, therefore, provides for a pool from which antibodies with desirable characteristics can be isolated, for example, antibodies with relatively high affinity for specific target antigen binding. It is desirable to isolate high affinity antibodies directly from the immunised vertebrate, since this can provide for an antibody lead that is potentially useful as a therapeutic and/or prophylactic medicament without the need for further extensive affinity maturation (eg, by in vitro antibody display such as ribosome display or phage display). Modification of the effector portions of the antibody can be made as desired (eg, humanisation of the constant region), without the need to manipulate the sequences of the variable regions. Alternatively, or additionally, the pool of antibodies may allow for selection of a lead antibody with desirable biophysical characteristics and/or epitope specificity. The latter may be important for finding lead antibodies against epitopes that have not previously raised therapeutic and/or prophylactic antibodies or epitopes that are difficult to reach by antibodies generated by antibody gene diversities generated by prior non-human vertebrates bearing transgenic immunoglobulin loci, eg, those based on the single human genome represented by the RPCI-11 BACs.

The cells of the invention (according to any aspect or configuration) is, for example, a B-cell, hybridoma or a stem cell, optionally an embryonic stem cell or haematopoietic stem cell. In one aspect the ES cell is derived from the mouse C57BL/6N, C57BL/6J, 129S5 or 129Sv strain. In one aspect the non-human vertebrate is a rodent, suitably a mouse, and cells of the invention, are rodent cells or ES cells, suitably mouse ES cells. The ES cells of the present invention can be used to generate animals using techniques well known in the art, which comprise injection of the ES cell into a blastocyst followed by implantation of chimaeric blastocystys into females to produce offspring which can be bred and selected for homozygous recombinants having the required insertion. In one aspect the invention relates to a transgenic animal comprised of ES cell-derived tissue and host embryo derived tissue. In one aspect the invention relates to genetically-altered subsequent generation animals, which include animals having a homozygous recombinants for the VDJ and/or VJ regions.

Vertebrates bearing one or more light chain loci according to (b)(i) and (ii) provide for novel and potentially expanded antibody and gene repertoires by exploiting synthetic, non-naturally-occurring, combinations of immunoglobulin gene segments (V, D, J, C). In this respect, the present inventors have realised the desirability and possibility of providing for antibody and gene repertoires that mix heavy chain gene segments with those of light chain loci. This is based on observations of the inventors: Firstly, nature suggests the possibility of functional antibodies having VH-VH or VL-VL pairings (as opposed to more classical VH-VL pairings). For example, reference is made to heavy chain antibodies of Camelidae which produce antibodies with paired VH domains and is devoid of light chain VL domains (eg, see Nature. 1993 Jun. 3; 363(6428):446-8; Naturally occurring antibodies devoid of light chains; Hamers-Casterman C, Atarhouch T, Muyldermans S, Robinson G, Hamers C, Songa E B, Bendahman N, Hamers R). These antibodies function to specifically bind antigen, such antibodies being found in the blood of such Camelidae (eg, llamas, camels, alpacas). Such antibodies with VH pairs can also be synthetically produced to provide therapeutic and prophylactic medicaments (eg, see WO1994004678, WO2004041862, WO2004041863). Transgenic mice also can produce such heavy chain antibodies and the in vivo production of the antibodies allows the mouse's immune system to select for VH-VH pairings, sometimes selecting for such pairings in which mutations have been introduced in vivo by the mouse to accommodate the pairing (WO2010109165A2). Thus, the inventors realised that the adoption of an in vivo antibody production system (rather than an in vitro system such as phage or ribosome display of antibodies) is desirable to accommodate the synthetic immunoglobulin gene segment combinations that are now contemplated by the present invention.

Figure 6:
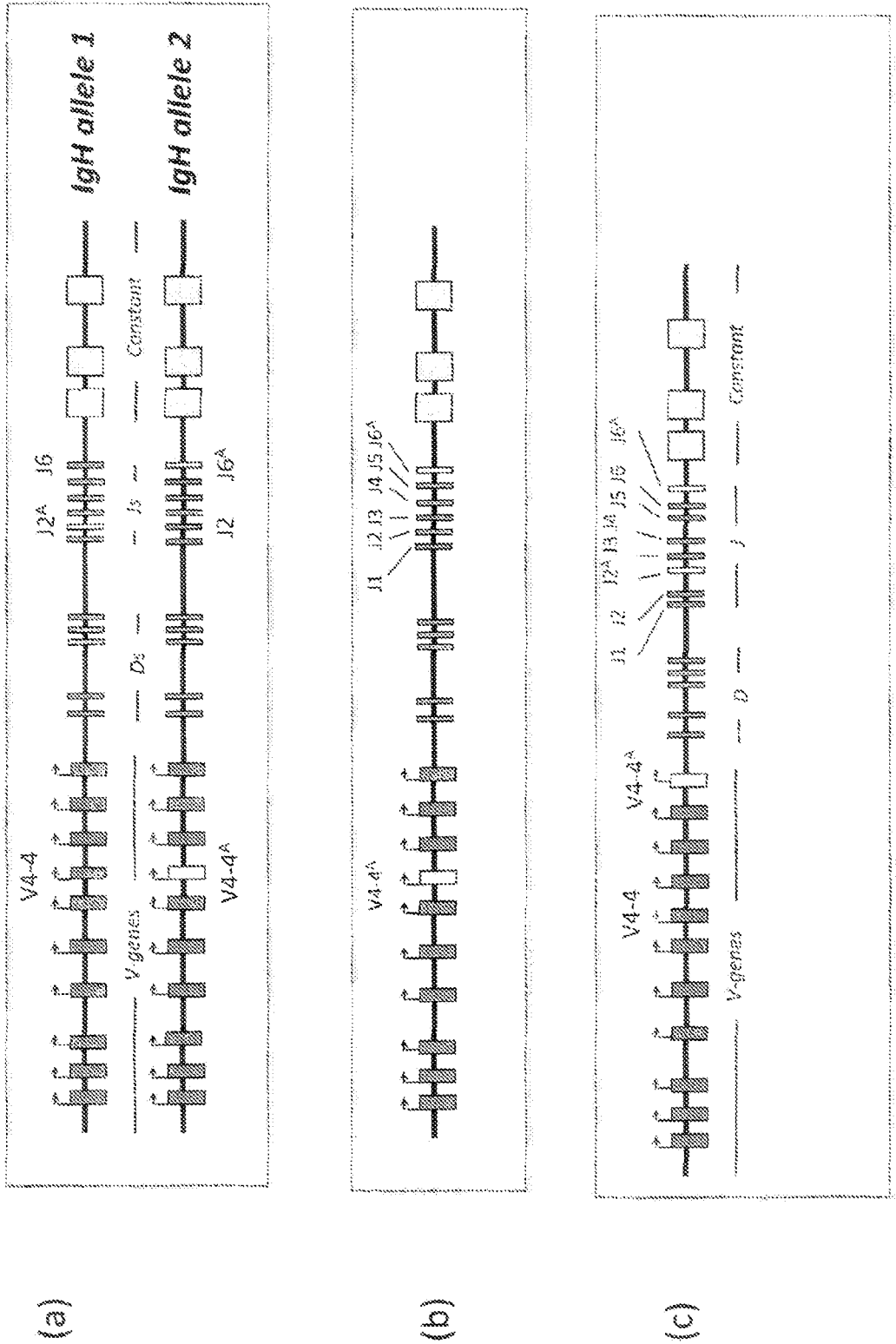
FIG. 6: RSS structure and recombination schematic.

A second observation of the present inventors lies in the architecture of naturally-occurring immunoglobulin loci, and in particular the arrangement of recombination signal sequences (RSSs) that mediate V(D)J recombination in vivo (see, eg, Cell. 2002 April; 109 Suppl:S45-55. The mechanism and regulation of chromosomal V(D)J recombination; Bassing C H, Swat W, Alt F W, the disclosure of which is incorporated herein by reference). As illustrated in FIG. 6, two types of RSS element have been identified: a one-turn RSS (12-RSS) and a two-turn RSS (23-RSS). In natural VJ recombination in the lambda light chain locus, recombination if effected between a two-turn RSS that lies 3' of a V lambda and a one-turn RSS that lies 5' of a J lambda, the RSSs being in opposite orientation. In natural VJ recombination in the kappa light chain locus, recombination if effected between a one-turn RSS that lies 3' of a V kappa and a two-turn RSS that lies 5' of a J kappa, the RSSs being in opposite orientation. In natural VD recombination in the heavy chain locus, recombination if effected between a two-turn RSS that lies 3' of a VH and a one-turn RSS that lies 5' of a D, the RSSs being in opposite orientation. In natural DJ recombination in the heavy chain locus, recombination if effected between a one-turn RSS that lies 3' of a D and a two-turn RSS that lies 5' of a 1H, the RSSs being in opposite orientation. Thus, generally a two-turn RSS is compatible with a one-turn RSS in the opposite orientation. The inventors realised that they could use this observation in constructing transgenic immunoglobulin loci such that a 5' gene segment can recombine with a 3' gene segment (eg, a V with a J; or a V with a D) when there is provided a two-turn RSS and a one-turn RSS in the opposite orientation, with each RSS adjacent a respective one of the gene segments. Thus, the inventors realised in one embodiment that an immunoglobulin locus can be constructed with one or more of the following arrangements (5' to 3'):—

(k) [V (heavy, lambda or kappa)]-[two-turn RSS]-[one-turn RSS]-[D]-[JH], wherein said RSSs are in an opposite orientation;

(l) [VH]-[D]-[two-turn RSS]-[one-turn RSS]-[J lambda], wherein said RSSs are in an opposite orientation;

(m) [VH]-[D]-[one-turn RSS]-[two-turn RSS]-[J kappa], wherein said RSSs are in an opposite orientation;

(n) [VH or V kappa]-[two-turn RSS]-[one-turn RSS]-[J lambda], wherein said RSSs are in an opposite orientation;

(o) [V kappa]-[one-turn RSS]-[two-turn RSS]-[JH or J lambda], wherein said RSSs are in an opposite orientation;

(p) [V (heavy, lambda or kappa)]-[one-turn RSS]-[two-turn RSS]-[D]-[JH], wherein said RSSs are in an opposite orientation;

(q) [VH]-[D]-[one-turn RSS]-[two-turn RSS]-[J lambda], wherein said RSSs are in an opposite orientation;

(r) [VH]-[D]-[two-turn RSS]-[one-turn RSS]-[1 kappa], wherein said RSSs are in an opposite orientation;

(s) [VH or V kappa]-[one-turn RSS]-[two-turn RSS]-[J lambda], wherein said RSSs are in an opposite orientation;

(t) [V kappa]-[two-turn RSS]-[one-turn RSS]-[JH or J lambda], wherein said RSSs are in an opposite orientation.

The skilled person will realise that standard molecular biology techniques can be used to provide vectors comprising synthetic combinations of RSS with V, D or J for use in this aspect of the invention, such that the vectors can be used to build a transgenic immunoglobulin locus (eg, using homologous recombination and/or recombinase mediated cassette exchange as known in the art, eg, see U.S. Pat. No. 7,501,552 (Medarex), U.S. Pat. No. 5,939,598 (Abgenix), U.S. Pat. No. 6,130,364 (Abgenix), WO02/066630 (Regeneron), WO2011004192 (Genome Research Limited), WO2009076464, WO2009143472 and WO2010039900 (Ablexis), the disclosures of which are explicitly incorporated herein. For example, such synthetic combinations with RSS and gene segments can be made using standard recombineering techniques in *E. coli* to construct BAC vectors harbouring the synthetic combination prior to insertion in embryonic stem cells using homologous recombination or RMCE (eg, using cre/lox site-specific recombination). Details of recombineering can be found at www.genebridges.com and in EP1034260 and EP1204740 the disclosures of which are explicitly incorporated herein.

In one embodiment of (b)(i), all of the light chain locus V gene segments are human VH gene segments (optionally with one or more human V lambda gene segments).

In one embodiment of (b)(i), the constant region is a mouse, rat or human CL, eg, Cλ. In one embodiment, the J and constant regions are provided by one or more human JλCλ.

Although having utility generally to any antigen and disease setting, vertebrates bearing one or more light chain loci according to (b)(iii) are useful, in particular, for generating antibody leads against infectious disease pathogens. In this respect, the present inventors have realised the desirability and possibility of providing for antibody and gene repertoires that are biased to immunoglobulin gene segments commonly found in natural antibody reactions of humans to infectious disease pathogens. The inventors realised that it would be desirable to provide for vertebrates, cells, methods etc for the production of therapeutic and/or prophylactic antibodies based on natural human immune responses to antigens, such as antigens of infectious disease pathogens. In this respect, the literature observes frequently used immunoglobulin gene segments to raise anti-infective responses in humans (Table 1).

TABLE 1

Immunoglobulin Gene Usage in Human Antibody Responses to Infectious Disease Pathogens

| GENE | ANTIGEN | ORGANISM | REFERENCES [Human Ab Source] |
|---|---|---|---|
| BACTERIAL PATHOGENS | | | |
| KAPPA V GENES<br>Vk II germline gene A2 + JK3<br>Vk II family gene + JK4<br>94% identical to the A27<br>(Humkv325) germ line gene<br>a VκI gene family member; κI-<br>15A (KL012)<br>LAMBDA V GENES<br>Four Vλ VII family members that<br>are 96-98% identical to each<br>other<br>Vλ II family members (82, 89 and | *Haemophilus influenzae* type b polysaccharide (Hib PS) | *Haemophilus influenzae* | 1. Lonberg, Nat Biotech 2005; [human PBMCs]<br>2. Adderson et al, J Clin Invest 1992; [Human PBLs]<br>3. Chung et al, J Immunol 1993<br>4. Nadel et al, J Immunol 1998<br>5. Feeney et al, J Clin Invest 1996<br>6. Lucas et al, Infect Immun 1994; [Human PBLs]<br>7. Adderson et al, J Clin Invest 1993; [Human PBLs]<br>8. Granoff et al, J Clin Invest 1993; |

TABLE 1-continued

Immunoglobulin Gene Usage in Human Antibody Responses to Infectious Disease Pathogens

| GENE | ANTIGEN | ORGANISM | REFERENCES [Human Ab Source] |
|---|---|---|---|
| 91% homologous to Vλ2.1 gene) + VHIII segments closely homologous to germline gene 9.1 | | | [human PBLs] 9. Azmi et al, Infect Immun 1994; [human tonsil cells] |
| V$_λ$VII 4A All with Jλ homologous to germline Jλ2 and Jλ3 | | | |
| VH GENES | | | |
| VH 96% identical to the VH germ line gene segment DP77 (V3-21) LSG6.1, LSG12.1, V$_H$III VH26, V$_H$III 9.1 | | | |
| VH and VL COMBINATIONS | | | |
| V$_H$III 9.1 + V$_λ$VII 4A V$_H$III 9.1 + V$_λ$II 2.1 V$_H$III 9.1 + V$_κ$II A2 V$_H$III VH26 + V$_λ$II 2.1 V$_H$III 9.1; V$_H$III H11; V$_H$III VH26 κI 15A Vλ2.1 | Polysaccharide capsule of E coli K1 Meningococcal B polysaccharide; Poly[α(2→8)-N-acetylneuramic acid | E coli K1 Neisseria meningitidis Group B | 9. Azmi et al, Infect Immun 1994 |
| | | VIRAL PATHOGENS | |
| VHIII or VHIV family member Vλ I or Vλ3 member VH26 + Dk1 + JH6 with IGLV1S2 + Jλ2 VH4.18 VH2-1 (VH3) + D region Dxp'1 + JH5 with Vλ3 cML70 + Jλ3 VH1GRR + JH3 + Dn4r or D2r with IGLV1S2 + Jλ2 For VZV Abs: ha3h2 (VH3) with Ialh2 (Vλ); or ha1c1 (VH1) with Ialvl (Vλ1) For VZV Abs: ha4h3 (VH4) with Ia3h3 (Vλ3) | HSV 120-kD glycoprotein 116-, 105-, 64-kD glycoproteins of VZV | Herpes family virus Herpes simplex virus (HSV); HSV-1; HSV-2 Varicella zoster virus (VZV) | 10. Huang et al, J Clin Invest 1992; [human tonsils] |
| Hv1051 (VH) Kv325 (Vk) | | Cytomegalovirus (CMV) | 10. Huang et al, J Clin Invest 1992; |
| 71-2 (VH) Hv1f10 (VH) VH4.11 71-4 (VH) VH251 VH1-69 | | HIV | 10. Huang et al, J Clin Invest 1992; 11. Wang & Palese, Science 2011 |
| VH1-69 | Haemagglutinin (HA) | Influenza virus, eg, Group 1 and/or Group 2 Infulenza A virus; eg, H1N1, H2N2, or H3N2 or H7N2 or H7N7 influenza virus | 12. Ekiert et al, Science 2009 13. Throsby et al, PLoS One 2008 14. Sui et al, Nat Struct Mol Biol 2009 15. Ekiert et al, Science 2011 |

REFERENCES

1. Nat. Biotechnol. 2005 September; 23(9):1117-25; Human antibodies from transgenic animals; Lonberg N.
2. J Clin Invest. 1992 March; 89(3):729-38; Immunoglobulin light chain variable region gene sequences for human antibodies to *Haemophilus influenzae* type b capsular polysaccharide are dominated by a limited number of V kappa and V lambda segments and VJ combinations; Adderson E E, Shackelford P G, Insel R A, Quinn A, Wilson P M, Carroll W L
3. J. Immunol. 1993 Oct. 15; 151(8):4352-61; Clonal characterization of the human IgG antibody repertoire to *Haemophilus influenzae* type b polysaccharide. V. In vivo expression of individual antibody clones is dependent on Ig CH haplotypes and the categories of antigen; Chung G H, Scott M G, Kim K H, Kearney J, Siber G R, Ambrosino D M, Nahm M H.
4. J. Immunol. 1998 Dec. 1; 161(11):6068-73; Decreased frequency of rearrangement due to the synergistic effect of nucleotide changes in the heptamer and nonamer of the recombination signal sequence of the V kappa gene Alb, which is associated with increased susceptibility of Navajos to *Haemophilus influenzae* type b disease; Nadel B, Tang A, Lugo G, Love V, Escuro G, Feeney A J.
5. J Clin Invest. 1996 May 15; 97(10):2277-82; A defective V kappa A2 allele in Navajos which may play a role in increased susceptibility to *Haemophilus influenzae* type b disease; Feeney A J, Atkinson M J, Cowan M J, Escuro G, Lugo G.
6. Infect Immun. 1994 September; 62(9):3873-80; Variable region sequences of a protective human monoclonal antibody specific for the *Haemophilus influenzae* type b capsular polysaccharide; Lucas A H, Larrick J W, Reason D C.

7. J Clin Invest. 1993 June; 91(6):2734-43; Restricted immunoglobulin VH usage and VDJ combinations in the human response to *Haemophilus influenzae* type b capsular polysaccharide. Nucleotide sequences of monospecific anti-Haemophilus antibodies and polyspecific antibodies cross-reacting with self antigens; Adderson E E, Shackelford P G, Quinn A, Wilson P M, Cunningham M W, Insel R A, Carroll W L.

8. J Clin Invest. 1993 March; 91(3):788-96; Variable region expression in the antibody responses of infants vaccinated with *Haemophilus influenzae* type b polysaccharide-protein conjugates. Description of a new lambda light chain-associated idiotype and the relation between idiotype expression, avidity, and vaccine formulation. The Collaborative Vaccine Study Group; Granoff D M, Shackelford P G, Holmes S J, Lucas A K 9. Infect Immun. 1994 May; 62(5):1776-86; Variable region sequences and idiotypic expression of a protective human immunoglobulin M antibody to capsular polysaccharides of *Neisseria meningitidis* group B and *Escherichia coli* K1; Azmi F H, Lucas A H, Raff H V, Granoff D M.

10. J Clin Invest. 1992 December; 90(6):2197-208; Sequence analyses of three immunoglobulin G anti-virus antibodies reveal their utilization of autoantibody-related immunoglobulin Vh genes, but not V lambda genes; Huang D F, Olee T, Masuho Y, Matsumoto Y, Carson D A, Chen P P.

11. Science. 2011 Aug. 12; 333(6044):834-5, Biochemistry. Catching a moving target, Wang T T, Palese P 12. Science. 2009 Apr. 10; 324(5924)246-51. Epub 2009 Feb. 26; Antibody recognition of a highly conserved influenza virus epitope; Ekiert D C, Bhabha G, Elsliger M A, Friesen R H, Jongeneelen M, Throsby M, Goudsmit J, Wilson I A.

13. PLoS One. 2008; 3(12):e3942. Epub 2008 Dec. 16; Heterosubtypic neutralizing monoclonal antibodies cross-protective against H5N1 and H1N1 recovered from human IgM+ memory B cells; Throsby M, van den Brink E, Jongeneelen M, Poon L L, Alard P, Cornelissen L, Bakker A, Cox F, van Deventer E, Guan Y, Cinatl J, ter Meulen J, Lasters I, Carsetti R, Peiris M, de Kruif J, Goudsmit J.

14. Nat Struct Mol. Biol. 2009 March; 16(3):265-73. Epub 2009 Feb. 22, Structural and functional bases for broad-spectrum neutralization of avian and human influenza A viruses, Sui J, Hwang W C, Perez S, Wei G, Aird D, Chen L M, Santelli E, Stec B, Cadwell G, All M, Wan H, Murakami A, Yammanuru A, Han T, Cox N J, Bankston L A, Donis R O, Liddington R C, Marasco W A.

15. Science. 2011 Aug. 12; 333(6044):843-50. Epub 2011 Jul. 7, A highly conserved neutralizing epitope on group 2 influenza A viruses, Ekiert D C, Friesen R H, Bhabha G, Kwaks T, Jongeneelen M, Yu W, Ophorst C, Cox F, Korse H J, Brandenburg B, Vogels R, Brakenhoff J P, Kompier R, Koldijk M H, Cornelissen L A, Poon L L, Peiris M, Koudstaal W, Wilson I A, Goudsmit J.

In one embodiment, in (b)(i) the J gene segments of the light chain locus are $J_\lambda$ gene segments and optionally the constant region of the light chain locus is a lambda constant region; or in (b)(ii) the VL is a $V_\lambda$ and optionally the constant region of the light chain locus is a lambda constant region. Alternatively, the constant region is C kappa.

In one embodiment, in (b)(i) the V gene segment repertoire of the light chain locus comprises or consists of one or more VH gene segments selected from the group consisting of: a $V_H$III gene family member (optionally, a VHIIIa or VHIIIb family member), a $V_H$IV gene family member, $V_H$III 9.1 (VH3-15), $V_H$III VH26 (VH3-23), $V_H$3-21, LSG6.1, LSG12.1, DP77 (V3-21), $V_H$ H11, VH1GRR, ha3h2, $V_H$III-VH2-1, VH4.18, ha4h3, Hv1051, 71-2, Hv1f10, VH4.11, 71-4, VH251, VH1-69 and a gene segment at least 80% identical thereto. These gene segments are useful because they expand the repertoire in vivo to VH gene segments that are found in natural human immune responses to antigens, such as antigens of infectious disease pathogens. This is useful, for example, when the vertebrate is immunised with an antigen of an infectious disease pathogen, for generation and isolation of an antibody for treating and/or preventing a disease or condition mediated by said pathogen. In one example, in (b)(i) the V gene segment repertoire of the light chain locus comprises or consists of only VH gene segment selected from the group consisting of: a $V_H$III gene family member (optionally, a VHIIIa or VHIIIb family member), a $V_H$IV gene family member, $V_H$III 9.1 (VH3-15), $V_H$III VH26 (VH3-23), $V_H$3-21, LSG6.1, LSG12.1, DP77 (V3-21), $V_H$ H11, VH1GRR, ha3h2, $V_H$I-ha1c1, $V_H$III-VH2-1, VH4.18, ha4h3, Hv1051, 71-2, Hv1f10, VH4.11, 71-4, VH251, VH1-69 and a gene segment at least 80% identical thereto. This is useful to bias the immune response of the vertebrate (and thus resultant lead antibodies) to a predetermined gene segment, eg, one known to be commonly used in natural human immune responses to antigens, such as antigens of infectious disease pathogens. For example, VH1-69 is commonly used to produce antibodies in humans against Infulenza virus (see Table 1); it is possible, therefore, to confine the single VH segment to VH1-69 in embodiment (b)(i) of the invention.

In one embodiment, in (b)(iii) the light chain locus V gene segment repertoire consists of only one (optionally only two, three or four) VL gene segment type (optionally and one or mutants thereof), wherein the VL gene segment is selected from said group of VL gene segments. This is useful to bias the immune response of the vertebrate (and thus resultant lead antibodies) to a predetermined gene segment, eg, one known to be commonly used in natural human immune responses to antigens, such as antigens of infectious disease pathogens.

In one embodiment, in (a) said constant region is a heavy chain endogenous non-human vertebrate (optionally host mouse or rat) constant region and/or in (b) said constant region is a light chain endogenous non-human vertebrate (optionally host mouse or rat) constant region.

In one embodiment in any configuration of the invention, the genome has been modified to prevent or reduce the expression of fully-endogenous antibody. Examples of suitable techniques for doing this can be found in PCT/GB2010/051122, U.S. Pat. Nos. 7,501,552, 6,673,986, 6,130,364, WO2009/076464, EP1399559 and U.S. Pat. No. 6,586,251, the disclosures of which are incorporated herein by reference. In one embodiment, the non-human vertebrate VDJ region of the endogenous heavy chain immunoglobulin locus, and optionally VJ region of the endogenous light chain immunoglobulin loci (lambda and/or kappa loci), have been inactivated. For example, all or part of the non-human vertebrate VDJ region is inactivated by inversion in the endogenous heavy chain immunoglobulin locus of the mammal, optionally with the inverted region being moved upstream or downstream of the endogenous Ig locus (see, eg, WO2011004192, the disclosure of which is incorporated herein by reference). For example, all or part of the non-human vertebrate VJ region is inactivated by inversion in the endogenous kappa chain immunoglobulin locus of the mammal, optionally with the inverted region being moved upstream or downstream of the endogenous Ig locus. For example, all or part of the non-human vertebrate VJ region is inactivated by inversion in the endogenous lambda chain immunoglobulin locus of the mammal, optionally with the inverted region being moved upstream or downstream of the endogenous Ig locus. In one embodiment the endogenous heavy chain locus is inactivated in this way as is one or both of the endogenous kappa and lambda loci.

Additionally or alternatively, the vertebrate has been generated in a genetic background which prevents the production of mature host B and T lymphocytes, optionally a RAG-1-deficient and/or RAG-2 deficient background. See U.S. Pat. No. 5,859,301 for techniques of generating RAG-1 deficient animals.

Thus, in one embodiment of any configuration or aspect of the invention herein, endogenous heavy and light chain expression has been inactivated.

In a second configuration of the invention, there is provided

A non-human vertebrate (optionally a mouse or a rat) or vertebrate cell whose genome comprises:
(a) An immunoglobulin heavy chain locus comprising one or more human V gene segments (eg, a plurality of VH), one or more human D gene segments and one or more human J gene segments upstream of a constant region; and
(b) (i) An unrearranged immunoglobulin light chain locus comprising one or more human VH gene segments and one or more human J gene segments upstream of a constant region, wherein each human VH gene segment is a human gene segment identical to (or mutant of, eg, having up to 15 or 10 nucleotide changes from the human gene segment) a human VH gene segment (eg, a germline VH gene segment; eg, a gene segment selected from List A1, A2, A1.1, A1.2, A2.1, A2.2, A2.3 or A2.4 below.) used to produce a rearranged VDJ encoding a heavy chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism); or
(ii) An immunoglobulin light chain locus comprising a rearranged VJ region or VDJ region upstream of a constant region, wherein the nucleotide sequence of the recombined region is identical to a nucleotide sequence produced by the recombination of a human J gene segment and optionally a human D gene segment with a human VH gene segment that is identical to (or mutant of; eg, having up to 15 or 10 nucleotide changes from the human gene segment)) the human VH gene segment (eg, germline VH gene segment; eg, a gene segment selected from List A1, A2, A1.1, A1.2, A2.1, A2.2, A2.3 or A2.4 below.) used to produce a rearranged VDJ encoding a heavy chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism);
(c) Wherein the gene segments in the heavy chain locus are operably linked to the constant region thereof, and the gene segments or VJ or VDJ in the light chain locus are operably linked to the constant region thereof, so that upon immunisation the mouse is capable of producing an antibody comprising heavy chains produced by recombination of the heavy chain locus and light chains derived from the light chain locus;
(d) Optionally when (b)(i) applies, each said VH gene segment in the light chain locus is selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VF12-1, VH4.18, ha4h3, Hv1051, 71-2, Hv1f10, VH4.11, 71-4, VH251, VH1-69 and a gene segment at least 80% identical thereto; optionally each VH gene segment is selected from List A1, A2, A1.1, A1.2, A2.1, A2.2, A2.3 or A2.4 below.
(e) Optionally when (b)(ii) applies, the nucleotide sequence of the recombined region is identical to a nucleotide sequence produced by the recombination of a human J gene segment and optionally a human D gene segment with a human VH gene segment selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hvlf10, VH4.11, 71-4, VH251, VH1-69 and a gene segment at least 80% identical thereto; optionally each VH gene segment is selected from List A1, A2, A1.1, A1.2, A2.1, A2.2, A2.3 or A2.4 below.

In one embodiment, the antigen is an antigen expressed by a bacterial or viral infectious disease pathogen, eg, any of the pathogens listed in Table 1. For example, the antigen is an antigen selected from the antigens listed in Table 1.

In one embodiment of any aspect, configuration or embodiment of the invention herein, the "human individual harbouring said organism" is a patient that has natural resistance to the pathogen and produces antibodies that bind to the pathogen or an antigen expressed thereby.

In one embodiment of the second configuration, the J gene segments of the light chain locus are $J_\lambda$ gene segments and optionally the constant region of the light chain locus is a lambda constant region. Alternatively, the constant region is C kappa.

In one embodiment of the second configuration, the V gene segment repertoire of the light chain locus comprises or consists of one or more VH gene segments selected from the group consisting of: a $V_H$III gene family member (optionally, a VHIIIa or VHIIIb family member), a $V_H$IV gene family member, $V_H$III 9.1 (VH3-15), $V_H$III VH26 (VH3-23), $V_H$3-21, LSG6.1, LSG12.1, DP77 (V3-21), $V_H$ H11, VH1GRR, ha3h2, $V_H$I-ha1c1, $V_H$II-VH2-1, VH4.18, ha4h3, Hv1051, 71-2, Hv1f10, VH4.11, 71-4, VH251, VH1-69 and a gene segment at least 80% identical thereto. These gene segments are useful because they expand the repertoire in vivo to VH gene segments that are found in natural human immune responses to antigens, such as antigens of infectious disease pathogens. This is useful, for example, when the vertebrate is immunised with an antigen of an infectious disease pathogen, for generation and isolation of an antibody for treating and/or preventing a disease or condition mediated by said pathogen. In one example, in (b)(i) the V gene segment repertoire of the light chain locus comprises or consists of only VH gene segment selected from the group consisting of: a $V_H$III gene family member (optionally, a VHIIIa or VHIIIb family member), a $V_H$IV gene family member, V$_H$III 9.1 (VH3-15), V$_H$III VH26 (VH3-23), V$_H$3-21, LSG6.1, LSG12.1, DP77 (V3-21), V$_H$ H11, VH1GRR, ha3h2, V$_H$ I-ha1c 1, V$_H$III-VH2-1, VH4.18, ha4h3, Hv1051, 71-2, Hv1f10, VH4.11, 71-4, VH251, VH1-69 and a gene segment at least 80% identical thereto. This is useful to bias the immune response of the vertebrate (and thus resultant lead antibodies) to a predetermined gene segment, eg, one known to be commonly used in natural human immune responses to antigens, such as antigens of infectious disease pathogens. For example, VH1-69 is commonly used to produce antibodies in humans against Infulenza virus (see Table 1); it is possible, therefore, to confine the single VH segment to VH1-69 in embodiment (b)(i) of the invention.

In one embodiment of the second configuration, in (a) said constant region is a heavy chain endogenous non-human vertebrate (optionally host mouse or rat) constant region.

In one embodiment of the second configuration, in (b) said constant region is a light chain endogenous non-human vertebrate (optionally host mouse or rat) constant region.

In one embodiment of the second configuration, the genome of said vertebrate or cell is homozygous for light chain locus (b)(i) or (ii); optionally wherein:
the V gene segment repertoire of the light chain loci consists of one or more human VH gene segments selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto; or the recombed VJ or VDJ repertoire of the light chain loci consists of sequences identical to one or more nucleotide sequences produced by the recombination of a human VH gene segment selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VH1-ha1c1, VHIII-VH2-1, VH4.18, ha4h3, Hv1051, 71-2, Hv1f10, VH4.11, 71-4, VH251, VH1-69 and a gene segment at least 80% identical thereto, with a human J gene segment and optionally a human D gene segment. In one embodiment, all of the light chain locus V gene segments are from this group.

In one embodiment of the second configuration, endogenous heavy and light chain expression has been inactivated, and wherein light chain loci according to the second configuration are the only functional light chain loci in the genome of the vertebrate or cell.

In one embodiment of the second configuration, each immunoglobulin light chain locus of said vertebrate or cell is according to (b)(i) and comprises only a single human VH gene segment selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical thereto, optionally wherein the genome of the vertebrate or cell is homozygous for said light chain so that all light chain loci comprise the same, single human VH gene segment. In this embodiment (and generally in other embodiments, configurations and aspects of the invention), confinement of heavy and/or light chain locus architecture is useful for biasing or controlling the antibody and gene repertoire, eg, to mirror human immune responses as mentioned above. Provision of a single light or heavy chain variable (and optionally D and/or J) gene segment (or only this with closely related mutants thereof)—or confinement in embodiments below to a single rearranged V(D)J region or single heavy or light chain—is advantageous for simplifying the expression and production of therapeutic/prophylactic antibodies since this restricts the number of antibody species produced during downstream manufacture. A common heavy or light chain is advantageous to enable co-expression of a plurality (eg, two, three or more) different antibodies in the same expression medium, for example from the same host cell. See, eg, EP1523496 (Merus BV) and WO2011097603 (Regeneron Pharmaceuticals, Inc).

In one embodiment of the second configuration, each immunoglobulin light chain locus of said vertebrate or cell is according to (b)(ii) and comprises only a single rearranged VJ or VDJ region, optionally wherein the genome of the vertebrate or cell is homozygous for said light chain so that all light chain loci comprise the same, single rearranged VJ or VDJ region.

In one embodiment of the second configuration, each immunoglobulin light chain locus further comprises a VH gene segment or rearranged region that is a mutant (eg, having up to 15 or 10 nucleotide changes from the VH gene segment) respectively of said selected human VH gene segment or rearranged region, optionally wherein the genome of the vertebrate or cell is homozygous for said light chain mutant VH gene segment or rearranged region.

In one embodiment of the second configuration, each immunoglobulin light chain locus comprises only two or three human VH gene segments selected from said group, optionally wherein the genome of the vertebrate or cell is homozygous for said two or three light chain human VH gene segments.

In one embodiment of the second configuration, each immunoglobulin light chain locus comprises only two or three of said rearranged VJ or VDJ regions, optionally wherein the genome of the vertebrate or cell is homozygous for said two or three light chain rearranged VJ or VDJ regions.

The invention provides a monoclonal or polyclonal antibody composition prepared by immunisation of at least one vertebrate (eg, mouse or rat) according to any configuration, aspect or embodiment of the invention, optionally wherein the antigen is an antigen of an infectious disease pathogen (eg, a bacterial or viral pathogen antigen or an antigen listed in Table 1), optionally wherein the same antigen is used to immunise all the vertebrates; optionally wherein the antibody or antibodies are IgG-type (eg, IgG1).

The invention provides a first method of isolating an antibody that binds a predetermined antigen (eg, a bacterial or viral pathogen antigen or an antigen listed in Table 1), the method comprising
(a) providing a vertebrate (optionally a mouse or rat) according to according to any configuration, aspect or embodiment of the invention;
(b) immunising (eg, using a standard prime-boost method) said vertebrate with said antigen (optionally wherein the antigen is an antigen of an infectious disease pathogen);
(c) removing B lymphocytes from the vertebrate and selecting one or more B lymphocytes expressing antibodies that bind to the antigen;

(d) optionally immortalising said selected B lymphocytes or progeny thereof, optionally by producing hybridomas therefrom; and (e) isolating an antibody (eg, and IgG-type antibody) expressed by the B lymphocytes.

In a first embodiment of the first method of the invention, the method comprises the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host. The skilled person will be aware of standard molecular biology techniques to do this. For example, see Harlow, E. & Lane, D. 1998, 5$^{th}$ edition, Antibodies: A Laboratory Manual, Cold Spring Harbor Lab. Press, Plainview, N.Y.; and Pasqualini and Arap, Proceedings of the National Academy of Sciences (2004) 101:257-259 for standard immunisation. Joining of the variable regions of an antibody to a human constant region can be effected by techniques readily available in the art, such as using conventional recombinant DNA and RNA technology as will be apparent to the skilled person. See e.g. Sambrook, J and Russell, D. (2001, 3' d edition) Molecular Cloning: A Laboratory Manual (Cold Spring Harbor Lab. Press, Plainview, N.Y.).

In one embodiment of the first method of the invention, the method comprisesfurther making a mutant or derivative of the antibody.

A method of producing a polyclonal antibody mixture is provided, the method comprising carrying out the first method of the invention by separately immunising first and second vertebrates (optionally first and second mice or first and second rats) with antigen and combining the anti-antigen antibodies isolated from each vertebrate (or mutants or derivatives of said antibodies) to produce a polyclonal antibody mixture; optionally wherein the following apply separately or in combination ((i) and (ii); or (i) and (iii)):
(i) the vertebrates are immunised with the same antigen or different antigens (optionally wherein the different antigens are expressed by the same pathogenic organism (or by family members or different strains of the organism));
(ii) prior to immunisation the light chain loci of the vertebrates contain the identical VH gene repertoire (optionally a single VH gene) and optionally the identical J repertoire; optionally the light chain loci of the mammals are identical prior to immunisation;
(iii) prior to immunisation the light chain loci of the vertebrates contain the identical rearranged VJ or VDJ repertoire (optionally a single VJ or VDJ); optionally the light chain loci of the vertebrates are identical prior to immunisation.

A method of producing a polyclonal antibody mixture is provided, the method comprising carrying out the first method of the invention by immunising one or a plurality of vertebrates (optionally mice or rats) with first and second antigens and combining the anti-antigen antibodies isolated from each vertebrate (or mutants or derivatives of said antibodies) to produce a polyclonal antibody mixture; optionally wherein the following apply separately or in combination ((i) and (ii); or (i) and (iii)):
(i) the antigens are expressed by the same pathogenic organism (or by family members or different strains of the organism));
(ii) prior to immunisation the light chain loci of the vertebrates contain the identical VH gene repertoire (optionally a single VH gene) and optionally the identical J repertoire; optionally the light chain loci of the mammals are identical prior to immunisation;
(iii) prior to immunisation the light chain loci of the vertebrates contain the identical rearranged VJ or VDJ repertoire (optionally a single VJ or VDJ); optionally the light chain loci of the vertebrates are identical prior to immunisation.

The Invention Provides a Second Method:

A method of producing host cells (eg, Chinese Hamster Ovary (CHO) or HEK293 cells) capable of expressing a polyclonal antibody mixture is provided, the method comprising, in a method according to said first embodiment of the first method of the invention:—

(a) immunising one or a plurality of vertebrates (optionally mice or rats) with first and second antigens (optionally wherein the different antigens are expressed by the same pathogenic organism (or a family member thereof));

(b) isolating nucleic acid encoding first and second anti-antigen antibodies from B lymphocytes from said vertebrates;

(c) determining the nucleotide sequences of the heavy and light chain variable regions (optionally the entire heavy and/or light chain sequences) of the first antibody;

(d) determining the nucleotide sequence of the heavy variable region and optionally the light chain variable region of the second antibody;

(e) inserting the heavy chain variable region coding sequence of each antibody into a heavy chain expression vector; optionally wherein the constant region coding sequence of each heavy chain is exchanged for a nucleotide sequence that encodes a human or humanised constant region;

(f) inserting the light chain variable region coding sequence of the first antibody into a light chain expression vector; optionally wherein the constant region coding sequence of the light chain of the first antibody is exchanged for a nucleotide sequence that encodes a human or humanised constant region;

(g) optionally inserting the light chain variable region coding sequence of the second antibody into a light chain expression vector; optionally wherein the constant region coding sequence of the light chain of the second antibody is exchanged for a nucleotide sequence that encodes a human or humanised constant region; and (h) introducing each expression vector into a host cell and co-expressing antibody chains in a mixture of said host cells to produce antibodies, each antibody comprising one or both of said heavy chain variable regions and a light chain; optionally wherein the expression vectors are introduced together into the same host cell (eg, a CHO or HEK293 cell) so that the cell is capable of expressing antibody light chains and heavy chains, such that the cell or a plurality of the host cells express antibodies (eg, two, three, four or more different antibodies), each comprising one or both of said heavy chain variable regions and a light chain;

(i) optionally:
prior to immunisation the light chain loci of the vertebrates contain the identical VH gene repertoire (optionally a single VH gene segment) and optionally the identical J repertoire (optionally a single J gene segment); optionally the light chain loci of the vertebrates are identical prior to immunisation; or
prior to immunisation the light chain loci of the vertebrates contain the identical rearranged VJ or VDJ repertoire (optionally a single VJ or VDJ); optionally the light chain loci of the vertebrates are identical prior to immunisation.
(j) optionally:
producing a monoclonal or polyclonal antibody mixture, by expressing a monoclonal antibody or polyclonal mixture of said antibodies; optionally followed by isolating an antibody comprising the heavy chain variable region of the first and/or second antibodies.

The invention also provides a monoclonal or polyclonal antibody mixture so produced or a derivative antibody or mixture thereof, eg, where one or more constant region has been changed (eg, replaced with a different constant region such as a human constant region; or mutated to enhance or ablate Fc effector function). (optionally the entire heavy and/or light chain sequences)

In any of the methods of the invention, optionally each vertebrate used for immunisation is provided by
(a) isolating from a human blood or tissue (eg, B lymphocytes (PBLs), peripheral blood mononuclear cells (PBMCs), bone marrow, spleen, tonsil or lymph node) sample a B lymphocyte that expresses an antibody that binds a predetermined antigen (eg, an antigen expressed by an infectious disease pathogen; optionally wherein said serum or tissue was from a human individual suffering, susceptible to, or recovered from, a disease or condition caused or mediated by an organism harbouring or secreting said antigen; or from a human individual harbouring said organism);
(b) determining which human germline VH gene segment was recombined in the human to produce the nucleotide sequence of said B lymphocyte that encodes the heavy chain variable region of the antibody;
(c) constructing a transgenic vertebrate wherein said human germline VH gene segment is provided in a light chain locus thereof according the first or second configuration of the invention; and
(d) providing said transgenic vertebrate for immunisation in the first method of the invention.

The term "Human blood" herein includes a human blood product minus one or more non-B lymphocyte cellular populations, provided that the product retains antibody-producing cells, eg, PBLs.

In an embodiment of the first method of the invention, each vertebrate used for immunisation is provided by
(a) isolating from a human blood or tissue (eg, B lymphocytes, PBMCs, bone marrow, spleen, tonsil or lymph node) sample a B lymphocyte that expresses an antibody that binds a predetermined antigen (eg, an antigen expressed by an infectious disease pathogen; optionally wherein said serum or tissue was from a human individual suffering, susceptible to, or recovered from, a disease or condition caused or mediated by an organism harbouring or secreting said antigen; or from a human individual harbouring said organism);
(b) determining a nucleotide sequence of said B lymphocyte that encodes a rearranged VDJ or VJ region of the antibody;
(c) constructing a transgenic vertebrate wherein said rearranged VDJ or VJ region is provided in a light chain locus thereof according to the first or second configuration of the invention; and
(d) providing said transgenic vertebrate for immunisation in the first method of the invention.

Common Light Chain Antibodies & Bispecifics (Eg, to Two Pathogen Antigens for Infectious Diseases)

The invention provides an isolated antibody (eg, IgG-type, such as IgG1-type, antibody) obtainable or obtained by the second method of the invention (including step (j), or a mutant or derivative antibody thereof wherein (i) the isolated antibody comprises two copies of the heavy chain variable region of said first antibody paired with two copies of the light chain variable region of said first antibody; or (ii) the isolated antibody comprises two copies of the heavy chain variable region of said second antibody paired with two copies of the light chain variable region of said first antibody; or (iii) the isolated antibody is a bispecific antibody comprising one copy of the heavy chain variable region of said first antibody paired with a copy of the light chain variable region of the first antibody, and one copy of the heavy chain variable region of said the antibody paired with a copy of the light chain variable region of the first antibody, optionally wherein the bispecific antibody binds to said first and second antigens recited in claim 24; optionally for use in medicine, optionally for the treatment and/or prevention of an infectious disease.

In an aspect of the invention, there is provided a monoclonal or polyclonal antibody mixture (eg, IgG-type antibody or antibodies), wherein the monoclonal antibody or mixture is according to any configuration, aspect, embodiment or example of the invention, or a mutant or derivative antibody thereof optionally for use in medicine, optionally for the treatment and/or prevention of an infectious disease, wherein optionally wherein each antibody binds an antigen of an infectious disease pathogen, preferably the same antigen.

In an aspect of the invention, there is provided the use of an isolated, monoclonal or polyclonal antibody according to any configuration, aspect, embodiment or example of the invention, or a mutant or derivative antibody thereof in the manufacture of a medicament for the treatment and/or prevention of an infectious disease, optionally wherein the infectious disease is a disease caused by a bacterial or viral pathogen.

An example of a mutant antibody is one that bears up to 15 or 10 amino acid mutations in its variable regions relative to an isolated antibody (eg, IgG-type, such as IgG1-type, antibody) obtainable or obtained by the second method of the invention (including step (j). An example of a derivative is one that has been modified to replace a constant region with a different constant region such as a human constant region; or mutated to enhance or ablate Fc effector function.

Examples of infectious diseases are diseases caused or mediated by a bacterial or viral pathogen, eg, a pathogen listed in Table 1. Examples of antigens are those listed in Table 1.

For example, the infectious disease is selected from the group consisting of a disease caused by a pathogen selected from the group consisting of *Haemophilus influenza, E. coli, Neisseria meningitidis*, a herpes family virus, cytomegalovirus (CMV), HIV and influenza virus.

The invention further provides a nucleotide sequence encoding an antibody according to any configuration, aspect, embodiment or example of the invention, optionally wherein the nucleotide sequence is part of a vector.

The invention further provides a pharmaceutical composition comprising the antibody or antibodies of any configuration, aspect, embodiment or example of the invention and a diluent, excipient or carrier.

In a Third Configuration of the Invention, there is Provided
A non-human vertebrate (optionally a mouse or a rat) or vertebrate cell whose genome comprises:
(a) An immunoglobulin heavy chain locus comprising either:—
(i) one or more human VL gene segments, one or more human D gene segments and one or more human J gene segments upstream of a constant region (optionally a rearranged $V_L DJ_H C_H$ or $V_\lambda DJ_H C_H$); or (ii) one or more human VH gene segments selected from the group consisting of: a VHIII gene family member (optionally, a VHIIIa or VHIIIb family member), a VHIV gene family member, VHIII 9.1 (VH3-15), VHIII VH26 (VH3-23), VH3-21, LSG6.1, LSG12.1, DP77 (V3-21), VH H11, VH1GRR, ha3h2, VHI-ha1c1, VHIII-VH2-1, VH4.18, ha4h3, Hv1051, 71-2, Hv1f10, VH4.11, 71-4, VH251, VH1-69 and a gene segment at least 80% identical; one or more human D gene segments and one or more human $J_H$ gene segments upstream of a constant region; optionally each VH gene segment (and optionally each D) is selected from List A1, A2, A1.1, A1.2, A2.1, A2.2, A2.3 or A2.4 below; and (b) An immunoglobulin light chain locus comprising one or more human V gene segments (eg, a plurality of VL) and one or more human J gene segments upstream of a constant region, optionally wherein the light chain locus is according to (b)(i) or (b)(ii) of the first configuration of the invention;

Wherein the gene segments in the heavy chain locus are operably linked to the constant region thereof, and the gene segments in the light chain locus are operably linked to the constant region thereof, so that upon immunisation the mouse is capable of producing an antibody comprising heavy chains produced by recombination of the heavy chain locus and light chains produced by recombination of the light chain locus.

In one example, in (a)(i) all of the heavy chain locus V gene segments are human VL gene segments.

In one embodiment of the third configuration, the V gene segment repertoire of the light chain locus comprises or consists of one or more VL gene segments selected from the group consisting of a $V_\lambda II$ gene family member, $V_\lambda VII$ 4A, $V_\lambda II$ 2.1, $V_\lambda VII$ 4A, a $V_\lambda 1$ gene family member, a $V_\lambda 3$ gene family member, IGLV1S2, $V_\lambda 3$-cML70, IaIh2, IaIyI, Ia3h3, Kv325, a VκI gene family member, κI-15A (KL012), $V_\kappa II$ family member, a $V_\kappa III$ family member, a VκI gene family member, κI-15A (KL012), $V_\kappa II$ A2 (optionally the Ata allele), $V_\kappa$ A27 (Humkv325) and a gene segment at least 80% identical thereto; optionally each VL gene segment is selected from List A1, A2, A1.1, A1.2, A2.1, A2.2, A2.3 or A2.4 below; and/or wherein or in (a)(ii) the heavy chain locus V gene segment repertoire consists of only one (or two, three or four) VH gene segment type (optionally and one or mutants thereof), wherein the VH gene segment is selected from said group of VH gene segments. This is useful to bias the immune response of the vertebrate (and thus resultant lead antibodies) to a predetermined gene segment, eg, one known to be commonly used in natural human immune responses to antigens, such as antigens of infectious disease pathogens.

In one embodiment of the third configuration, in (a) said constant region is a heavy chain endogenous non-human vertebrate (optionally host mouse or rat) constant region and/or in (b) said constant region is a light chain endogenous non-human vertebrate (optionally host mouse or rat) constant region.

In one embodiment of the third configuration, endogenous heavy and light chain expression has been inactivated.

A Fourth Configuration of the Present Invention Provides

A non-human vertebrate (optionally a mouse or a rat) or vertebrate cell whose genome comprises:

(a) (i) An unrearranged immunoglobulin heavy chain locus comprising one or more human VL gene segments, one or more human D gene segments and one or more $J_H$ gene segments upstream of a constant region, wherein each human VL gene segment is a human gene segment identical to (or mutant of, eg, having up to 15 or 10 nucleotide changes from the human gene segment) a human VL gene segment (eg, a germline VL gene segment; eg, a VL gene segment selected from List A1, A2, A1.1, A1.2, A2.1, A2.2, A2.3 or A2.4 below) used to produce a rearranged VJ encoding a light chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism); or (ii) An immunoglobulin heavy chain locus comprising a rearranged VJ region or VDJ region upstream of a constant region, wherein the nucleotide sequence of the recombined region is identical to a nucleotide sequence produced by the recombination of a human J gene segment and optionally a human D gene segment with a human gene segment identical to (or mutant of, eg, having up to 15 or 10 nucleotide changes from the human gene segment) a human VL gene segment (eg, a germline VL gene segment; eg, a VL gene segment selected from List A1, A2, A1.1, A1.2, A2.1, A2.2, A2.3 or A2.4 below) used to produce a rearranged VJ encoding a light chain variable region of a human antibody from an antibody-expressing cell wherein said antibody binds to an antigen of an infectious disease pathogen (optionally the variable regions of said antibody being identical to an antibody from a human individual suffering, susceptible to, or recovered from, a disease or condition caused or mediated by an organism harbouring or secreting said antigen; or from a human individual harbouring said organism);

(b) An immunoglobulin light chain locus comprising one or more human V gene segments (eg, a plurality of VL) and one or more human J gene segments upstream of a constant region; and (c) Wherein the gene segments in the light chain locus are operably linked to the constant region thereof, and the gene segments or VJ or VDJ in the heavy chain locus are operably linked to the constant region thereof, so that upon immunisation the mouse is capable of producing an antibody comprising light chains produced by recombination of the light chain locus and heavy chains derived from the heavy chain locus;

(d) Optionally when (a)(i) applies, each said VL gene segment in the heavy chain locus is selected from the group consisting of a VL gene segment selected from the group consisting of a VλII gene family member, VλVII 4A, VλII 2.1, VλVII 4A, a Vλ1 gene family member, a Vλ3 gene family member, IGLV1S2, Vλ3-cML70, IaIh2, IaIvI, Ia3h3, Kv325, a VκI gene family member, κI-15A (KL012), VκII family member, a VκIII family member, a VκI gene family member, κI-15A (KL012), VκII A2 (optionally the A2a allele), Vκ A27 (Humkv325) and a gene segment at least 80% identical thereto; optionally each VL gene segment is selected from List A1, A2, A1.1, A1.2, A2.1, A2.2, A2.3 or A2.4 below;

(e) Optionally when (a)(ii) applies, the nucleotide sequence of the recombined region is identical to a nucleotide sequence produced by the recombination of a human J gene segment and optionally a human D gene segment with a human. VL gene segment selected from the group consisting of a VλIIgene family member, VλVII 4A, VλII 2.1, VλVII 4A, a Vλ1 gene family member, a Vλ3 gene family member, IGLV1S2, Vλ3-cML70, IaIh2, IaIyI, Ia3h3, Kv325, a VκI gene family member, κI-15A (KL012), VκII family member, a VκIII family member, a VκI gene family member, κI-15A (KL012), VκII A2 (optionally the A2a allele), Vκ A27 (Humkv325) and a gene segment at least 80% identical thereto.

The group of VL gene segments is useful to bias the immune response of the vertebrate (and thus resultant lead antibodies) to a predetermined gene segment, eg, one known to be commonly used in natural human immune responses to antigens, such as antigens of infectious disease pathogens.

In an embodiment of the fourth configuration, the VL gene segments of the heavy chain locus are $V_A$ gene segments.

In an embodiment of the fourth configuration, in (a) said constant region is a heavy chain endogenous non-human vertebrate (optionally host mouse or rat) constant region.

In an embodiment of the fourth configuration, in (b) said constant region is a light chain endogenous non-human vertebrate (optionally host mouse or rat) constant region.

In an embodiment of the fourth configuration, the genome of said vertebrate or cell is homozygous for heavy chain locus (a)(i) or (ii); optionally wherein:
  the V gene segment repertoire of the heavy chain loci consists of one or more (or consists only of) human VL gene segments selected from the group consisting of a VL gene segment selected from the group consisting of a $V_\lambda$II gene family member, $V_\lambda$VII 4A, VII 2.1, $V_\lambda$VII 4A, a $V_\lambda$1 gene family member, a $V_\lambda$3 gene family member, IGLV1S2, $V_\lambda$3-cML70, IaIh2, IaIyI, Ia3h3, Kv325, a VκI gene family member, κI-15A (KL012), $V_\kappa$II family member, a $V_\kappa$III family member, a VκI gene family member, id-15A (KL012), $V_\kappa$II A2 (optionally the A2a allele), $V_\kappa$A27 (Humkv325) and a gene segment at least 80% identical thereto; or
  the recombined VJ or VDJ repertoire of the heavy chain loci consists of sequences identical to one or more nucleotide sequences produced by the recombination of a human VL gene segment selected from the group consisting of a VL gene segment selected from the group consisting of a VλII gene family member, VλVII 4A, VλII 2.1, VλVII 4A, a Vλ1 gene family member, a Vλ3 gene family member, IGLV1S2, Vλ3-cML70, IaIh2, IaIyI, Ia3h3, Kv325, a VκI gene family member, κI-15A (KL012), VκII family member, a VκIII family member, a VκI gene family member, κI-15A (KL012), VκII A2 (optionally the A2a allele), Vκ A27 (Humkv325) and a gene segment at least 80% identical thereto with a human J gene segment and optionally a human D gene segment.

In an embodiment of the fourth configuration, endogenous heavy and light chain expression has been inactivated, and wherein heavy chain loci according to the fourth configuration are the only functional heavy chain loci in the genome of the vertebrate or cell.

In an embodiment of the fourth configuration, each immunoglobulin heavy chain locus of said vertebrate or cell is according to (a)(i) and comprises only a single human VL gene segment selected from the group consisting of a VL gene segment selected from the group consisting of a VλII gene family member, VλVII 4A, VλII 2.1, VλVII 4A, a Vλ1 gene family member, a Vλ3 gene family member, IGLV1S2, Vλ3-cML70, IaIh2, IaIyI, Ia3h3, Kv325, a VκI gene family member, κI-15A (KL012), VκII family member, a VκIII family member, a VκI gene family member, κI-15A (KL012), VκII A2 (optionally the A2a allele), Vκ A27 (Humkv325) and a gene segment at least 80% identical thereto, optionally wherein the genome of the vertebrate or cell is homozygous for said heavy chain so that all heavy chain loci comprise the same, single human VL gene segment.

In an embodiment of the fourth configuration, each immunoglobulin heavy chain locus of said vertebrate or cell is according to (a)(ii) and comprises only a single rearranged VJ or VDJ region, optionally wherein the genome of the vertebrate or cell is homozygous for said heavy chain so that all heavy chain loci comprise the same, single rearranged VJ or VDJ region.

In an embodiment of the fourth configuration, each immunoglobulin heavy chain locus further comprises a VL gene segment or rearranged region that is a mutant respectively of said selected human VL gene segment or rearranged region, optionally wherein the genome of the vertebrate or cell is homozygous for said light chain mutant VL gene segment or rearranged region.

In all configurations, aspects, examples and embodiments of the invention, where a "mutant" is mentioned, this includes a mutant sequence that is identical to a reference sequence (eg, reference VH, VL, VJ or VDJ) but with 1, 2, 3, 4, 5, 6, 7, 8, 9 or 10 nucleotide or amino acid changes therefrom.

In an embodiment of the fourth configuration, each immunoglobulin heavy chain locus comprises only two or three human VL gene segments selected from said group, optionally wherein the genome of the vertebrate or cell is homozygous for said two or three heavy chain human VL gene segments.

In an embodiment of the fourth configuration, each immunoglobulin heavy chain locus comprises only two or three of said rearranged VJ or VDJ regions, optionally wherein the genome of the vertebrate or cell is homozygous for said two or three heavy chain rearranged VJ or VDJ regions.

The invention provides a monoclonal or polyclonal antibody composition prepared by immunisation of at least one vertebrate (eg, mouse or rat) according to the third or fourth embodiment of the invention with an antigen, optionally wherein the antigen is an antigen of an infectious disease pathogen, optionally wherein the same antigen is used to immunise all the vertebrates; optionally wherein the antibody or antibodies are IgG-type.

The invention provides a third method: A method of isolating an antibody (eg, IgG-type, such as IgG1) that binds a predetermined antigen, the method comprising
(a) providing a vertebrate (optionally a mouse or rat) according to the third or fourth embodiment of the invention;
(b) immunising (eg, using standard prime-boost) said vertebrate with said antigen (optionally wherein the antigen is an antigen of an infectious disease pathogen);
(c) removing B lymphocytes from the vertebrate and selecting one or more B lymphocytes expressing antibodies that bind to the antigen;
(d) optionally immortalising said selected B lymphocytes or progeny thereof, optionally by producing hybridomas therefrom; and
(e) isolating an antibody (eg, and IgG-type antibody) expressed by the B lymphocytes;
(f) Optionally, the third method comprises the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

Optionally, the third method further comprises making a mutant or derivative of the antibody.

The invention provides a fourth method: A method of producing a polyclonal antibody mixture, the method comprising carrying out the third method by separately immunising first and second vertebrates (optionally first and second mice or first and second rats) with antigen (eg, any antigen disclosed herein) and combining the anti-antigen antibodies isolated from each vertebrate (or mutants or derivatives of said antibodies) to produce a polyclonal antibody mixture; optionally wherein the following apply separately or in combination ((i) and (ii); or (i) and (iii)):

(i) the vertebrates are immunised with the same antigen or different antigens (optionally wherein the different antigens are expressed by the same pathogenic organism (or different family members thereof or different strains of the organism));

(ii) prior to immunisation the heavy chain loci of the vertebrates contain the identical VL gene repertoire (optionally a single VL gene) and optionally the identical D and/or J repertoire; optionally the heavy chain loci of the mammals are identical prior to immunisation;

(iii) prior to immunisation the heavy chain loci of the vertebrates contain the identical rearranged VJ or VDJ repertoire (optionally a single VJ or VDJ); optionally the heavy chain loci of the vertebrates are identical prior to immunisation.

The invention provides a fifth method: A method of producing a polyclonal antibody mixture, the method comprising carrying out the third method by immunising one or a plurality of vertebrates (optionally mice or rats) with first and second antigens and combining the anti-antigen antibodies isolated from each vertebrate (or mutants or derivatives of said antibodies) to produce a polyclonal antibody mixture; optionally wherein the following apply separately or in combination ((i) and (ii); or (i) and (iii)):

(i) the antigens are expressed by the same pathogenic organism (or different family members thereof or different strains of the organism);

(ii) prior to immunisation the heavy chain loci of the vertebrates contain the identical VL gene repertoire (optionally a single VL gene) and optionally the identical D and/or J repertoire; optionally the heavy chain loci of the mammals are identical prior to immunisation;

(iii) prior to immunisation the heavy chain loci of the vertebrates contain the identical rearranged VJ or VDJ repertoire (optionally a single VJ or VDJ); optionally the heavy chain loci of the vertebrates are identical prior to immunisation.

The invention provides a sixth method: A method of producing host cells capable of expressing a polyclonal antibody mixture, the method comprising, in the third method wherein step (f) is carried out:—

(a) immunising one or a plurality of vertebrates (optionally mice or rats) with first and second antigens (optionally wherein the different antigens are expressed by the same pathogenic organism (or a family member thereof));

(b) isolating nucleic acid encoding first and second anti-antigen antibodies from B lymphocytes from said vertebrates;

(c) determining the nucleotide sequences of the heavy and light chain variable regions (optionally the entire heavy and/or light chain sequences) of the first antibody;

(d) determining the nucleotide sequence of the light variable region and optionally the heavy chain variable region of the second antibody;

(e) inserting the light chain variable region coding sequence of each antibody into a light chain expression vector; optionally wherein the constant region coding sequence of each light chain is exchanged for a nucleotide sequence that encodes a human or humanised constant region;

(f) inserting the heavy chain variable region coding sequence of the first antibody into a heavy chain expression vector; optionally wherein the constant region coding sequence of the heavy chain of the first antibody is exchanged for a nucleotide sequence that encodes a human or humanised constant region;

(g) optionally inserting the heavy chain variable region coding sequence of the second antibody into a heavy chain expression vector; optionally wherein the constant region coding sequence of the heavy chain of the second antibody is exchanged for a nucleotide sequence that encodes a human or humanised constant region; and (h) introducing each expression vector into a host cell and co-expressing antibody chains in a mixture of said host cells to produce antibodies, each antibody comprising one or both of said light chain variable regions and a heavy chain; optionally wherein the expression vectors are introduced together into the same host cell (eg, a CHO or HEK293 cell) so that the cell is capable of expressing antibody light chains and heavy chains, such that the cell or a plurality of the host cells express antibodies (eg, two, three or four different antibodies), each comprising one or both of said light chain variable regions and a heavy chain; optionally:

prior to immunisation the heavy chain loci of the vertebrates contain the identical VL gene repertoire (optionally a single VL gene segment) and optionally the identical D and/or J repertoire (optionally a single D and J gene segment); optionally the heavy chain loci of the vertebrates are identical prior to immunisation; or prior to immunisation the heavy chain loci of the vertebrates contain the identical rearranged VJ or VDJ repertoire (optionally a single VJ or VDJ); optionally the heavy chain loci of the vertebrates are identical prior to immunisation.

The invention also provides a monoclonal or polyclonal antibody mixture so produced or a derivative antibody or mixture thereof, eg, where one or more constant region has been changed (eg, replaced with a different constant region such as a human constant region; or mutated to enhance or ablate Fc effector function).

The invention provides a seventh method: A method of producing a monoclonal antibody or polyclonal antibody mixture, the method comprising carrying out the sixth method and expressing a monoclonal antibody or polyclonal mixture of said antibodies; optionally followed by isolating an antibody comprising the light chain variable region of the first and/or second antibodies.

Optionally, each vertebrate used for immunisation is provided by (a) isolating from a human blood or tissue (eg, B lymphocytes, PBMCs, bone marrow, spleen, tonsil or lymph node) sample a B lymphocyte that expresses an antibody that binds a predetermined antigen (eg, an antigen expressed by an infectious disease pathogen; optionally wherein said serum or tissue was from a human individual suffering, susceptible to, or recovered from, a disease or condition caused or mediated by an organism harbouring or secreting said antigen; or from a human individual harbouring said organism);

(b) determining which human germline VL gene segment was recombined in the human to produce the nucleotide sequence of said B lymphocyte that encodes the light chain variable region of the antibody;
(c) constructing a transgenic vertebrate wherein said human germline VL gene segment is provided in a heavy chain locus thereof according to the third or fourth configuration of the invention; and
(d) providing said transgenic vertebrate for immunisation in the fourth, fifth or sixth method of the invention.

In another embodiment, each vertebrate used for immunisation is provided by
(a) isolating from a human blood or tissue (eg, B lymphocytes, PBMCs, bone marrow, spleen, tonsil or lymph node) sample a B lymphocyte that expresses an antibody that binds a predetermined antigen (eg, an antigen expressed by an infectious disease pathogen; optionally wherein said serum or tissue was from a human individual suffering, susceptible to, or recovered from, a disease or condition caused or mediated by an organism harbouring or secreting said antigen; or from a human individual harbouring said organism);
(b) determining a nucleotide sequence of said B lymphocyte that encodes a rearranged VDJ or VJ region of the antibody;
(c) constructing a transgenic vertebrate wherein said rearranged VDJ or VJ region is provided in a heavy chain locus thereof according the third or fourth configuration of the invention; and
(d) providing said transgenic vertebrate for immunisation in the method of the fourth, fifth or sixth method of the invention.

Common Heavy Chain Antibodies & Bispecifics (Eg, to Two Pathogen Antigens for Infectious Diseases)

The invention provides an isolated antibody (eg, IgG-type antibody) obtainable or obtained by the seventh method, or a mutant or derivative antibody thereof wherein (i) the isolated antibody comprises two copies of the heavy chain variable region of said first antibody paired with two copies of the light chain variable region of said first antibody; or (ii) the isolated antibody comprises two copies of the heavy chain variable region of said second antibody paired with two copies of the light chain variable region of said first antibody; or (iii) the isolated antibody is a bispecific antibody comprising one copy of the heavy chain variable region of said first antibody paired with a copy of the light chain variable region of the first antibody, and one copy of the heavy chain variable region of said the antibody paired with a copy of the light chain variable region of the first antibody, optionally wherein the bispecific antibody binds to said first and second antigens described above; optionally for use in medicine, optionally for the treatment and/or prevention of an infectious disease.

The invention provides a monoclonal or polyclonal antibody mixture (eg, IgG-type antibody or antibodies), wherein the monoclonal antibody or mixture comprises or consists of antibodies produced by the fourth, fifth, sixth or seventh method, or a mutant or derivative antibody thereof optionally for use in medicine, optionally for the treatment and/or prevention of an infectious disease, wherein optionally wherein each antibody binds an antigen of an infectious disease pathogen, preferably the same antigen.

The following embodiments relate to antibodies, host cells, nucleic acids and compositions and apply to such elements obtained or obtainable by any previous configuration or method of the invention:—

The invention provides an isolated chimaeric antibody for treating and/or preventing an infectious disease or condition, the antibody comprising a non-human vertebrate (optionally a mouse or rat) heavy chain constant regions and human variable regions that bind an antigen of an infectious disease pathogen, wherein the antibody is obtainable or obtained in a method comprising immunisation of a vertebrate according to of any one of the first to seventh methods of the invention with said antigen. The antigen is, for example, any antigen mentioned above. The disease or condition is, for example, any disease or condition mentioned above.

The invention provides an isolated human antibody for treating and/or preventing an infectious disease or condition, the antibody comprising human heavy chain constant regions and human variable regions that bind an antigen of an infectious disease pathogen, wherein the antibody is obtainable or obtained in a method comprising affinity maturation of antibody variable regions in vivo in a transgenic non-human vertebrate (eg, mouse or rat) when said variable regions are operably linked to heavy chain constant regions of said vertebrate (eg, mouse or rat heavy chain constant regions) by (a) immunisation of a vertebrate of any configuration of the invention with said antigen, (b) isolation of nucleic acid encoding a chimaeric antibody as described above, (c) replacing the nucleotide sequences of the nucleic acid that encode the non-human vertebrate heavy chain constant regions with nucleotide sequence encoding human heavy chain constant regions to produce nucleic acid encoding a human antibody; (d) expressing the human antibody in vitro (optionally from CHO or HEK293 cells harbouring the human nucleic acid) and (e) isolating the human antibody (optionally with further affinity maturation of the antibody and/or producing a derivative thereof). The invention provides a mixture of first and second such human antibodies (an optionally also third and optionally fourth antibodies), each antibody being capable of binding to an antigen of an infectious disease pathogen (optionally wherein the first antibody binds a first antigen and the second antibody binds a second antigen, said antigens being from the same pathogen; or wherein the antigens are the same). Optionally, the light chain amino acid sequence of the first antibody is identical to the light chain amino acid sequence of the second antibody, or has up to 15 amino acid changes therefrom. The advantages of such a common (or closely-related) chain are explained above, and include relative ease of manufacture.

The antigen is, for example, any antigen mentioned above. The disease or condition is, for example, any disease or condition mentioned above. The pathogen is, for example, any pathogen mentioned above.

The invention provides an antibody comprising human variable domains that bind a predetermined antigen (eg, an antigen expressed by a bacterial or viral pathogen), wherein the variable domain sequences are encoded by rearranged VDJ and VJ regions, each of the VDJ and/or VJ being a hybrid region produced by the in vivo rearrangement of human heavy and light chain variable region gene segments (V and J and optionally D segments); optionally wherein the antibody comprises human constant regions.

The invention provides a method of producing an isolated human antibody for treating and/or preventing an infectious disease or condition, the antibody comprising human heavy chain constant regions and human variable regions that bind an antigen of an infectious disease pathogen, wherein the method comprises affinity maturing antibody variable regions in vivo in a transgenic non-human vertebrate (eg, mouse or rat) when said variable regions are operably linked to heavy chain constant regions of said vertebrate (eg, mouse or rat heavy chain constant regions) by (a) immunisation of a vertebrate of any configuration of the invention with said antigen, (b) isolation of nucleic acid encoding a chimaeric antibody as described above, (c) replacing the nucleotide sequences of the nucleic acid that encode the non-human vertebrate heavy chain constant regions with nucleotide sequence encoding human heavy chain constant regions to produce nucleic acid encoding a human antibody; (d) expressing the human antibody in vitro (optionally from CHO or HEK293 cells harbouring the human nucleic acid) and (e) isolating the human antibody (optionally with further affinity maturation of the antibody and/or producing a derivative thereof). The antigen is, for example, any antigen mentioned above. The disease or condition is, for example, any disease or condition mentioned above. The pathogen is, for example, any pathogen mentioned above.

The invention provides the use of any isolated, monoclonal or polyclonal antibody or mixture of the invention as described above, in the manufacture of a medicament for the treatment and/or prevention of an infectious disease, optionally wherein the infectious disease is a disease caused by a bacterial or viral pathogen. The disease or condition is, for example, any disease or condition mentioned above. The pathogen is, for example, any pathogen mentioned above. For example, the infectious disease is selected from the group consisting of a disease caused by a pathogen selected from the group consisting of *Haemophilus influenza, E. coli, Neisseria meningitidis*, a herpes family virus, cytomegalovirus (CMV), HIV and influenza virus.

The invention provides first and second nucleotide sequences (eg, DNA, RNA, mRNA, cDNA) encoding the heavy and light chains of an antibody according to any configuration, aspect, example or embodiment of the invention or at least the variable regions thereof, optionally wherein each nucleotide sequence is part of a vector.

The invention provides a host cell comprising one or more expression vectors encoding the heavy chains of the first and second antibodies mentioned above, and the light chain of the first antibody mentioned above (and optionally also the light chain of the second antibody). Again, reference is made to the discussion above about the advantages of having a common antibody chain for the production of antibody mixtures.

The invention provides a pharmaceutical composition comprising the antibody or antibodies of any configuration, aspect, example or embodiment of the invention and a diluent, excipient or carrier; optionally wherein the composition is provided in a container connected to an IV needle or syringe or in an IV bag. The skilled person will know standard diluents, excipients and carriers suitable for pharmaceutical application.

Throughout this description, where it is mentioned "at least 80% identical", there is contemplated in the alternative one of the following identities: at least 85%, 90, 95, 96, 97, 98 or 99 identical and the disclosure herein contemplates that one or more of these identities may be recited in a claim herein in place of "at least 80% identical".

Tailoring V(D)J Incorporation into Immunoglobin Loci for the Generation of Antibodies Against Infectious Disease In the various configurations, aspects, embodiments and examples above, the invention provides the skilled addressee with the possibility of choosing immunoglobulin gene segments in a way that tailors or biases the repertoire for application to generating antibodies to treat and/or prevent infectious diseases. The inventors have categorised the following groups of gene segments for use in the invention according to the desired application of resultant antibodies.

List A:
Immunoglobulin Gene Segments for Antibodies that Bind an Antigen Expressed by a Pathogen
(a) a VL gene segment selected from the group consisting of a $V_\lambda$II gene family member, $V_\lambda$VII 4A, $V_\lambda$II 2.1, $V_\lambda$VII 4A, a $V_\lambda$1 gene family member, a $V_\lambda$3 gene family member, IGLV1S2, $V_\lambda$3-cML70, IaIh2, IaIyI, Ia3h3, Kv325, a VκI gene family member, κI-15A (KL012), $V_\kappa$II family member, a $V_\kappa$III family member, a VκI gene family member, κI-15A (KL012), $V_\kappa$II A2 (optionally the A2a allele), $V_\kappa$ A27 (Humkv325) and a gene segment at least 80% identical thereto.
(b) a $V_\lambda$ gene segment selected from a $V_\lambda$II gene family member, $V_\lambda$VII 4A, $V_\lambda$II 2.1, $V_\lambda$VII 4A, a $V_\lambda$1 gene family member, a $V_\lambda$3 gene family member, IGLV1S2, $V_\lambda$3-cML70, IaIh2, IaIyI, Ia3h3 and a gene segment at least 80% identical thereto.
(c) a $V_\kappa$ gene segment selected from Kv325, a VκI gene family member, κI-15A (KL012), $V_\kappa$II family member, a $V_\kappa$III family member, a VκI gene family member, κI-15A (KL012), $V_\kappa$II A2 (optionally the A2a allele), $V_\kappa$ A27 (Humkv325) and a gene segment at least 80% identical thereto.
(d) a $V_\kappa$ gene segment a $V_H$III gene family member (optionally, a VHIIIa or VHIIIb family member), a $V_H$IV gene family member, $V_H$III 9.1 (VH3-15), $V_H$III VH26 (VH3-23), $V_H$3-21, LSG6.1, LSG12.1, DP77 (V3-21), $V_H$ H11, VH1GRR, ha3h2, $V_H$I-ha1c1, $V_H$III-VH2-1, VH4.18, ha4h3, Hv1051, 71-2, Hv1f1, VH4.11, 71-4, VH251, VH1-69 and a gene segment at least 80% identical thereto.
(e) a $J_\lambda$ gene segment selected from $J_\lambda$2, $J_\lambda$3 and a gene segment at least 80% identical thereto.
(f) a D gene segment selected from Dk1, Dxp'1, Dn4r, D2r and a gene segment at least 80% identical thereto.

List A1:
Immunoglobulin Gene Segments for Antibodies that Bind an Antigen Expressed by a Bacterial Pathogen
(a) a $V_\lambda$ gene segment selected from a $V_\lambda$II gene family member, $V_\lambda$VII 4A, $V_\lambda$II 2.1, $V_\lambda$VII 4A and a gene segment at least 80% identical thereto.
(b) a $V_\lambda$ gene segment selected from a VκI gene family member, κI-15A (KL012), $V_\kappa$II family member, a $V_\kappa$III family member, a VκI gene family member, κI-15A (KL012), $V_\kappa$II A2 (optionally the A2a allele), $V_\kappa$ A27 (Humkv325) and a gene segment at least 80% identical thereto.
(c) a $V_H$ gene segment a VH3 gene family member (optionally, a VHIIIa or VHIIIb family member), $V_H$III 9.1 (VH3-15), $V_H$III VH26 (VH3-23), $V_H$3-21, LSG6.1, LSG12.1, DP77 (V3-21), $V_H$ H11 and a gene segment at least 80% identical thereto.
(d) a $J_\lambda$ gene segment selected from $J_\lambda$2, $J_\lambda$3 and a gene segment at least 80% identical thereto.
(e) a $J_H$ gene segment selected from $J_H$2, $J_H$3, $J_H$4 and a gene segment at least 80% identical thereto.

List A1.1:
Immunoglobulin Gene Segments for Antibodies that Bind an Antigen Expressed by H Influenza
(a) a $V_\lambda$ gene segment selected from a $V_\lambda$II gene family member, $V_\lambda$VII 4A, $V_\lambda$II 2.1, $V_\lambda$VII 4A and a gene segment at least 80% identical thereto.
(b) a $V_\kappa$ gene segment selected from a $V_\kappa$II family member, a $V_\kappa$III family member, a VκI gene family member, κI-15A (KL012), $V_\kappa$II A2 (optionally the Ata allele), $V_\kappa$ A27 (Humkv325) and a gene segment at least 80% identical thereto.

(c) a $V_H$ gene segment a VH3 gene family member (optionally, a VHIIIb family member), $V_H$III 9.1 (VH3-15), $V_H$III VH26 (VH3-23), $V_H$3-21, LSG6.1, LSG12.1, DP77 (V3-21) and a gene segment at least 80% identical thereto.

(d) a $J_\lambda$ gene segment selected from $J_\lambda 2$, $J_\lambda 3$ and a gene segment at least 80% identical thereto.

List A1.2:

Immunoglobulin Gene Segments for Antibodies that Bind an Antigen Expressed by *E. Coli* or *Neisseria meningitidis*

(a) a VH gene segment a VH3 gene family member (optionally a VHIIIa or VHIIIb member), $V_H$III 9.1 (VH3-15), $V_H$ H11, $V_H$III VH26 (VH3-23) a gene segment at least 80% identical thereto, eg, $V_H$III 9.1+$J_H$3; or $V_H$ H11+$J_H$4; or $V_H$III VH26+$J_H$2.

(b) a $V_\kappa$ gene segment selected from a VκI gene family member, κI-15A (KL012) and a gene segment at least 80% identical thereto.

(c) a $V_\lambda$ gene segment selected from a $V_\lambda$II gene family member, $V_\lambda$II 2.1 and a gene segment at least 80% identical thereto.

(d) a $J_H$ gene segment selected from $J_H 2$, $J_H 3$, $J_R 4$ and a gene segment at least 80% identical thereto.

A2:

Immunoglobulin Gene Segments for Antibodies that Bind an Antigen Expressed by a Viral Pathogen (a) a $V_H$ gene segment selected from a $V_H$III gene family member, a $V_H$IV gene family member, $V_H$III-VH26 (VH3-23), VH1GRR, ha3h2, $V_H$I-ha1c1, $V_H$III-VH2-1, VH4.18, ha4h3, Hv1051, 71-2, Hv1f10, VH4.11, 71-4, VH251, VH1-69 and a gene segment at least 80% identical thereto.

(b) a $V_\lambda$ gene segment selected from a $V_\lambda 1$ gene family member, a $V_\lambda 3$ gene family member, IGLV1S2, $V_\lambda 3$-cML70, IaIh2, IaIyI, Ia3h3 and a gene segment at least 80% identical thereto.

(c) a Vk gene segment selected from Kv325 and a gene segment at least 80% identical thereto.

(d) a $J_H$ gene segment selected from $J_H 3$, $J_H 5$, $J_H 6$ and a gene segment at least 80% identical thereto.

(e) a D gene segment selected from Dk1, Dxp'1, Dn4r, D2r and a gene segment at least 80% identical thereto.

(f) a $J_\lambda$ gene segment selected from $J_\lambda 2$, $J_\lambda 3$ and a gene segment at least 80% identical thereto.

A2.1:

Immunoglobulin Gene Segments for Antibodies that Bind an Antigen Expressed by Herpes Virus Family (eg, VZV or HSV)

(a) a $V_H$ gene segment selected from a $V_H$III gene family member, a $V_H$IV gene family member, $V_H$III-VH26 (VH3-23), VH1GRR, ha3h2, $V_H$I-ha1c1, $V_H$III-VH2-1, VH4.18, ha4h3, and a gene segment at least 80% identical thereto.

(b) a $V_\lambda$ gene segment selected from a $V_\lambda 1$ gene family member, a $V_\lambda 3$ gene family member, IGLV1S2, $V_\lambda 3$-cML70, IaIh2, IaIyI, Ia3h3 and a gene segment at least 80% identical thereto.

(c) a JH gene segment selected from $J_H 3$, $J_H 5$, $J_H 6$ and a gene segment at least 80% identical thereto.

(d) a D gene segment selected from Dk1, Dxp'1, Dn4r, D2r and a gene segment at least 80% identical thereto.

(e) a $J_\lambda$ gene segment selected from $J_\lambda 2$, $J_\lambda 3$ and a gene segment at least 80% identical thereto.

A2.2:

Immunoglobulin Gene Segments for Antibodies that Bind an Antigen Expressed by CMV (a) a $V_H$ gene segment selected from Hv1051 and a gene segment at least 80% identical thereto.

(b) a Vk gene segment selected from Kv325 and a gene segment at least 80% identical thereto.

A2.3:

Immunoglobulin Gene Segments for Antibodies that Bind an Antigen Expressed by HIV (a) a $V_H$ gene segment selected from 71-2, Hv1f10, VH4.11, 71-4, VH251, VH1-69 and a gene segment at least 80% identical thereto.

A2.4:

Immunoglobulin Gene Segments for Antibodies that Bind an Antigen Expressed by Influenza Virus (a) a $V_H$ gene segment selected from VH1-69 and a gene segment at least 80% identical thereto.

Thus,

Where one wishes to generate an antibody or antibody mixture to treat and/or prevent an infectious disease, one or more V, D and/or or all J gene segments used in any configuration, aspect, method, example or embodiment of the invention can be selected from List A1. Thus, for example in (a) of the first configuration of the invention, the recited heavy chain V gene segment is selected from the VH gene segments in List A, optionally with a D in that list.

Where one wishes to generate an antibody or antibody mixture to treat and/or prevent an infectious disease caused or mediated by a bacterial pathogen, one or more or all V, D and/or J gene segments used in any configuration, aspect, method, example or embodiment of the invention can be selected from List A1.

Where one wishes to generate an antibody or antibody mixture to treat and/or prevent an infectious disease caused or mediated by a viral pathogen, one or more or all V, D and/or J gene segments used in any configuration, aspect, method, example or embodiment of the invention can be selected from List A2.

Where one wishes to generate an antibody or antibody mixture to treat and/or prevent an infectious disease caused or mediated by H influenza, one or more or all V, D and/or J gene segments used in any configuration, aspect, method, example or embodiment of the invention can be selected from List A1.1.

Where one wishes to generate an antibody or antibody mixture to treat and/or prevent an infectious disease caused or mediated by *E. Coli* or *Neisseria meningitidis*, one or more or all V, D and/or J gene segments used in any configuration, aspect, method, example or embodiment of the invention can be selected from List A1.2.

Where one wishes to generate an antibody or antibody mixture to treat and/or prevent an infectious disease caused or mediated by Herpes Virus Family (eg, VZV or HSV), one or more or all V, D and/or J gene segments used in any configuration, aspect, method, example or embodiment of the invention can be selected from List A2.1.

Where one wishes to generate an antibody or antibody mixture to treat and/or prevent an infectious disease caused or mediated by CMV, one or more or all V, D and/or J gene segments used in any configuration, aspect, method, example or embodiment of the invention can be selected from List A2.2.

Where one wishes to generate an antibody or antibody mixture to treat and/or prevent an infectious disease caused or mediated by HIV, one or more or all V, D and/or J gene segments used in any configuration, aspect, method, example or embodiment of the invention can be selected from List A2.3.

Where one wishes to generate an antibody or antibody mixture to treat and/or prevent an infectious disease caused or mediated by Influenza Virus, one or more or all V, D and/or 1 gene segments used in any configuration, aspect, method, example or embodiment of the invention can be selected from List A2.4.

Optionally each VH segment in the locus of the invention is selected from List A1, A2, A1.1, A1.2, A2.1, A2.2, A2.3 or A2.4.

Optionally each VL segment in the locus of the invention is selected from List A1, A2, A1.1, A1.2, A2.1, A2.2, A2.3 or A2.4

Optionally each D segment in the locus of the invention is selected from List A1, A2, A1.1, A1.2, A2.1, A2.2, A2.3 or A2.4.

Optionally each $J_L$ segment in the locus of the invention is selected from List A1, A2, A1.1, A1.2, A2.1, A2.2, A2.3 or A2.4.

Long HCDR3 Binding Sites &Tailoring Gene Segments to Pathogens & Other Antigens

This aspect of the invention relates to the development of vertebrates, cells, methods and antibodies with relatively long HCDR3 binding sites. There is also provided embodiments in which genomes and antibodies are tailored in terms of their gene segments usage to address infectious disease pathogen antigens or other antigens which are advantageously addressed with a longer HCDR3 length for binding or neutralisation. Antibodies may be raised in the vertebrates by immunisation with a non-pathogen target antigen, eg, an antigen bearing an epitope in a cleft requiring a long CDR for contact, or an antigen from a pathogen that causes or is implicated in harmful human disease or conditions. Examples are bacterial or viral pathogens and the target antigen may be a bacterial cell-surface antigen or a viral surface-exposed antigen (eg, coat protein). Additionally or alternatively, the antigen may be an antigen that is released (eg, secreted) from a pathogenic bacterium or virus. The invention is not limited to addressing pathogen antigens, but is also useful for addressing other antigens where a long CDR3 would be useful for binding (eg, an enzyme active site or receptor cleft).

Figure 2:
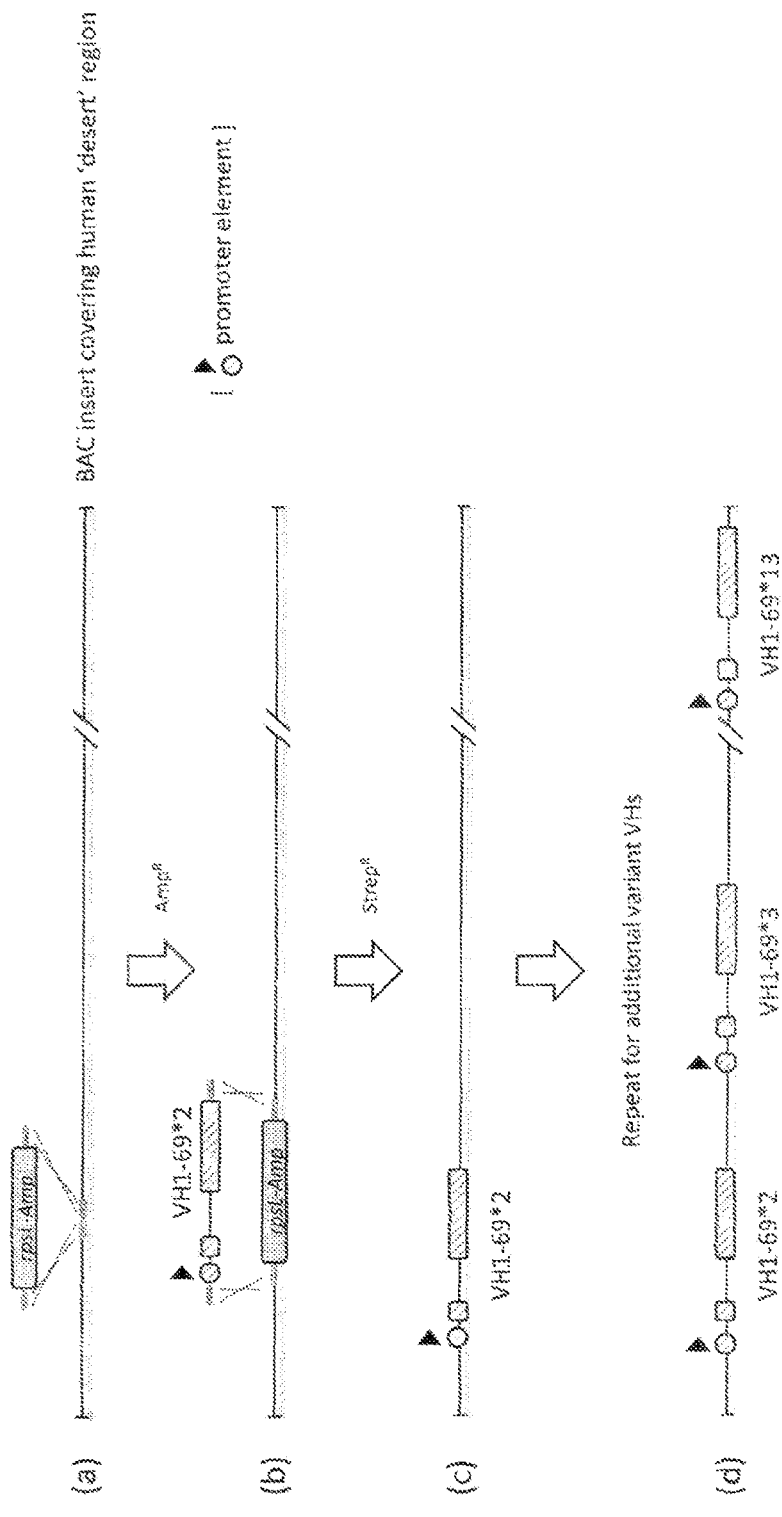

Antibodies with long HCDR3 (at least 20 amino acids according to IMGT nomenclature) have been shown to effectively neutralise a variety of pathogens including HIV, Influenza virus, malaria and Africa trypanosomes. Reference is also made to naturally-occurring Camelid (eg, llama or camel) heavy chain-only antibodies which bear long HCDR3s for reaching relatively inaccessible epitopes (see, eg, EP0937140). Long HCDR3s can form unique stable subdomains with extended loop structure that towers above the antibody surface to confer fine specificity. In some cases, the long HCDR3 itself is sufficient for epitope binding and neutralization (Liu, L et al; Journal of Virology. 2011. 85: 8467-8476, incorporated herein by reference). The unique structure of the long HCDR3 allows it to bind to cognate epitopes within inaccessible structure or extensive glycosylation on a pathogen surface. In human peripheral blood, there is around 3.5% of naïve B antibodies or 1.9% of memory B IgG antibodies containing the HCDR3s with lengths of more than 24 amino acids (Briney, B S et al, referenced given below) (FIG. 1 of Briney, B S et al). The usage analysis indicates that these antibodies have the preference to use human VH1-69, D2-2, D3-3, D2-15 and JH6 segments (FIGS. 2-5 of Briney, B S et al). There are around 20% of all HCDR3 length antibodies using JH6. However, in those antibodies with more than 24 amino acids of HCDR3, there are 70% using JH6 (FIG. 2 of Briney, B S et al). Human VH5-51 is also commonly used for anti-HIV antibodies (see Gorny et al, PLoS One. 2011; 6(12):e27780. Epub 2011 Dec. 2.

Human anti-V3 HIV-1 monoclonal antibodies encoded by the VH5-51/VL lambda genes define a conserved antigenic structure, incorporated herein by reference).

Supplementing these observations, the inventors have found (see examples) that other selected human heavy chain variable region gene segments (V, D, J) recombine in transgenic non-human vertebrates to produce long HCDR3 (at least 20 amino acids).

Thus, as explained further in the examples, the inventors constructed transgenic IgH loci in ES cells, wherein the loci purposely included selected human heavy chain variable region gene segments (V, D, J) that recombine to produce long HCDR3 (at least 20 amino acids). From the ES cells, the inventors generated transgenic non-human vertebrates (both naïve and immunised with a range of different target antigen types—disease pathogen and human antigenic species), isolated antibodies and heavy chain sequences based on the selected gene segments as well as B-cells expressing these and made hybridomas expressing antigen-specific antibodies that are based on the selected gene segments.

There is a need in the art for genetically modified non-human animals that prefer to make human antibodies that have long HCDR3s, as well as antibodies that can be selected from such animals wherein the antibodies can address target epitopes more easily accessed by long HCDR3s. Long CDRH3 is also useful for penetrating highly glycan-covered epitope sites (eg, virus epitopes or any glycoprotein targets, eg, see Nature. 2011 Dec. 14; 480 (7377):324-5. doi: 10.1038/480324a;

Vaccinology: "A sweet cleft in HIV's armour", Sattentau Q J, incorporated herein by reference), and the target antigen can comprise such a target epitope.

The present invention provides vertebrates that can artificially simulate those naturally-occurring human long HCDR3 antibodies, and can provide antibody, heavy chain and variable domain repertoires from which can be selected an antibody, heavy chain or variable domain having a long HCDR3 (eg, having a HCDR3 length of 20, 21, 22, 23, 24, 25, 26, 27, 28, 29, 30 or more amino acids (according to IMGT). The invention provides for the combination of human VH, D and 1 gene repertoires upstream of non-human vertebrate (eg, mouse or rat, eg, endogenous mouse or rat) constant region in heavy chain loci comprised by the vertebrate genomes. This enables the recombination, maturation and selection of the human gene segments in the context of endogenous or other non-vertebrate constant regions which enhances the development of good sized antibody, heavy chain and variable domain repertoires from which to select long HCDR3-type binding sites. Thus, in an example of any configuration of the invention, the human gene segments are provided in a heavy chain locus upstream of a non-human vertebrate (eg, endogenous) constant region. Similarly any antibody of the invention comprises human variable domains and non-human vertebrate (eg, endogenous) domains. The latter can be replaced by human constant domains after selection and isolation.

For example, the following antibodies of the invention are contemplated (eg, produced in a vertebrate of this aspect of the invention by a method disclosed herein) or a copy or derivative of an antibody so produced:—

An isolated, synthetic or recombinant antibody comprising human heavy chain variable domains having a HCDR3 length of 20, 21, 22, 23, 24, 25, 26, 27, 28, 29, 30 or more amino acids (according to IMGT), the heavy chain variable domains being derived from the recombination of a human VH gene segment selected from a VH group disclosed herein with a human D gene segment and a human JH gene segment (optionally a JH6), wherein the antibody binds a target antigen; wherein the heavy chain variable domains have non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)-pattern junctional mutations when compared to corresponding human germline V, D and J sequences. In an example, the antibody of the invention has a HCDR3 length of 20, 21, 22, 23, 24, 25, 26, 27, 28, 29 or 30 amino acids (according to IMGT). In an example, the antigen is an antigen of a pathogen that causes or is implicated in a human infectious disease or condition, eg, a pathogen listed in Table 1. In an example, the antibody specifically binds an active site or cleft of an antigen (eg, an enzyme active site or receptor cleft). This can be determined, eg, using standard X-ray crystallography of a complex of the antibody (or heavy chain or VH domain) with the cognate antigen, as is known to the skilled person.

Mouse AID-pattern somatic hypermutations and/or mouse dTd-pattern mutations can be provided, for example, wherein VH domain is produced in a mouse comprising mouse AID and/or mouse TdT (eg, endogenous AID or TdT). See also Annu. Rev. Biochem. 2007. 76:1-22; Javier M. Di Noia and Michael S, Neuberger, "Molecular Mechanisms of Antibody Somatic Hypermutation" (in particular FIG. 1 and associated discussion on AID hotspots in mouse); and Curr Opin Immunol. 1995 April; 7(2):248-54, "Somatic hypermutation", Neuberger M S and Milstein C (in particular, discussion on hotspots in mouse), the disclosures of which are incorporated herein by reference. Such mice can be made using corresponding mouse ES cell technology.

In an example, the antibody specifically binds to a HIV antigen. Several naturally-occurring human antibodies are known to be neutralising of HIV and have rather long HCDR3 lengths (20 amino acids or more according to IMGT; see Breden et al, PLoS One. 2011 Mar. 30; 6(3): e16857; "Comparison of antibody repertoires produced by HIV-1 infection, other chronic and acute infections, and systemic autoimmune disease" (incorporated herein by reference)—VH1-69 preferred for long HCDR3). See also PLoS One. 2012; 7(5):e36750. Epub 2012 May 9; "Human peripheral blood antibodies with long HCDR3s are established primarily at original recombination using a limited subset of germline genes"; Briney B S e al (incorporated herein by reference). Thus, it is desirable to provide antibodies of the invention that have similarly long HCDR3 lengths. The antibody of the invention is, in one example, provided for treating and/or preventing HIV infection, eg, chronic. HIV infection, in a human. The invention also provides a method of treating and/or preventing HIV infection, eg, chronic HIV infection, in a human, the method comprising administering a pharmaceutically acceptable dose of the antibody of the invention. The dose can be split into one or more administration aliquots, eg, administered over a time course according to a medically-determined regimen, as the skilled person will be able to determine.

In an example, the antibody specifically binds to *Hemophilus influenza* type b polysaccharide. The antibody of the invention is, in one example, provided for treating and/or preventing *Hemophilus influenza* infection, eg, chronic *Hemophilus influenza* infection, in a human. The invention also provides a method of treating and/or preventing *Hemophilus influenza* infection, eg, chronic *Hemophilus influenza* infection, in a human, the method comprising administering a pharmaceutically acceptable dose of the antibody of the invention. The dose can be split into one or more administration aliquots, eg, administered over a time course according to a medically-determined regimen, as the skilled person will be able to determine.

In an example, the antibody specifically binds to a rotavirus antigen (eg, protein 6 or 7). The antibody of the invention is, in one example, provided for treating and/or preventing rotavirus infection, eg, chronic rotavirus infection, in a human. The invention also provides a method of treating and/or preventing rotavirus infection, eg, chronic rotavirus infection, in a human, the method comprising administering a pharmaceutically acceptable dose of the antibody of the invention. The dose can be split into one or more administration aliquots, eg, administered over a time course according to a medically-determined regimen, as the skilled person will be able to determine.

In an example, the antibody specifically binds to a cytomegalovirus antigen (eg, cytomegalovirus gB antigen). The antibody of the invention is, in one example, provided for treating and/or preventing cytomegalovirus infection, eg, chronic cytomegalovirus infection, in a human. The invention also provides a method of treating and/or preventing cytomegalovirus infection, eg, chronic cytomegalovirus infection, in a human, the method comprising administering a pharmaceutically acceptable dose of the antibody of the invention. The dose can be split into one or more administration aliquots, eg, administered over a time course according to a medically-determined regimen, as the skilled person will be able to determine.

The invention also provides a vertebrate or cell for expressing such an antibody; thus the invention provides a non-human vertebrate (eg, a mouse or a rat) or a non-human vertebrate cell (eg, a mouse cell or a rat cell) whose genome comprises a human immunoglobulin VH gene segment repertoire that is biased to one, more or all human VH gene segments selected from a VH group disclosed herein.

The invention also provides
a method of isolating an antibody that binds a HIV antigen, *Hemophilus influenza* type b polysaccharide, cytomegalovirus antigen or rotavirus antigen, the method comprising
(a) providing the human VH biased vertebrate of the invention;
(b) immunising said vertebrate with said HIV antigen, *Hemophilus influenza* type b polysaccharide, cytomegalovirus antigen or rotavirus antigen;
(c) removing B lymphocytes from the vertebrate and selecting one or more B lymphocytes expressing antibodies that bind to the antigen;
(d) optionally immortalising said selected B lymphocytes or progeny thereof, optionally by producing hybridomas therefrom; and
(e) isolating an antibody (eg, and IgG-type antibody) expressed by the B lymphocytes, wherein the antibody has a HCDR3 length of 20 amino acids or more.

Optionally, the method further comprises the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

Optionally, the method further comprises making a copy, mutant or derivative (eg, humanised version) of the antibody produced by the method.

This aspect of the invention also provides

A pharmaceutical composition comprising the anti-HIV antibody, for treating and/or preventing HIV in a human (eg, an infant human).

A pharmaceutical composition comprising the anti-*Hemophilus influenza* type b polysaccharide antibody, for treating and/or preventing *Haemophilus influenza* in a human (eg, an infant human).

A pharmaceutical composition comprising the anti-rotavirus antibody, for treating and/or preventing rotavirus in a human (eg, an infant human).

A pharmaceutical composition comprising the anti-cytomegalovirus antibody, for treating and/or preventing cytomegalovirus in a human (eg, an infant human).

The invention also provides a method of generating such an antibody (eg, any one of embodiments (i) et seq above) by immunising a vertebrate of the invention with the target antigen and isolating the antibody from the vertebrate, optionally also making a copy or derivative of the antibody. In a further step, a B-cell capable of expressing the antibody is isolated from the vertebrate. In a further step, a nucleic acid encoding the antibody (or a VH domain thereof) is isolated from the vertebrate (eg, a nucleic acid PCR cloned from a B-cell isolated from the vertebrate).

In an example, the antibody of the invention is a neutralising antibody. In an example, the antibody of the invention has a HCDR3 length of 20, 21, 22, 23, 24, 25, 26, 27, 28, 29, 30 or more amino acids (according to IMGT). In an example, the antibody of the invention has a HCDR3 length of 20, 21, 22, 23, 24, 25, 26, 27, 28, 29 or 30 amino acids (according to IMGT). In an example, the antibody of the invention is isolated from a non-human vertebrate (eg, a mouse or a rat), for example a vertebrate of the invention; or the antibody is a copy or derivative (eg, humanised version) thereof. In an example, the antibody of the invention has non-human vertebrate constant regions (eg, mouse or rat constant regions); these may be replaced using standard recombinant DNA technology with human constant regions, so the invention also provides for human versions of the antibodies recited above, wherein the human antibody comprises human variable and constant regions, wherein the variable regions bind the antigen. In an example, the antibody of the has lambda-type human light chain variable domains. In another example, the antibody of the invention has kappa-type human light chain variable domains.

Antibody competition can be determined, for example, by ELISA or surface plasmon resonance (SPR; eg, by competition Biacore™ or Proteon) as is standard.

The invention also provides the following embodiments (recited below as numbered clauses):—

D Bias

1. A non-human vertebrate (eg, a mouse or a rat) or a non-human vertebrate cell (eg, a mouse cell or a rat cell) whose genome comprises a human immunoglobulin D gene segment repertoire that is biased to the human D2 and/or D3 family or biased to one, more or all human D gene segments selected from the group D1-26, D2-2, D3-9, D3-10, D3-22, D4-17, D6-13 and D6-19.

For example, the repertoire consists of only human D gene segments from the D2 and/or D3 family.

Optionally the repertoire is biased to one or more of human D2-2, 02-15, D3-3, D3-9, D3-10 and D3-22, or the repertoire consists of one, more or all of these D gene segments. These produce long HCDR3 lengths (eg, see Table 2 and references cited herein).

For example, the repertoire is biased to one or more of human of D2-2*02, D3-9*01, D3-10*01 and D3-22*01, or the repertoire consists of one, more or all of these D gene segments.

For example, the repertoire is biased to one or more of human D2-2*02, D3-9*01 and D3-10*01, or the repertoire consists of one, more or all of these D gene segments.

For example, the repertoire is biased to D3-9*01 and D3-10*01, or consists of one, more or all of these D gene segments.

Optionally the repertoire consists of one, more or all of human D1-26, D2-2, D3-9, D3-10, D3-22, D4-17, D6-13 and D6-19. These produce long HCDR3 lengths (eg, see Table 2).

Optionally the repertoire is biased to one or more of human D1-26*01, D2-2*02, D3-9*01, D3-10*01, D3-22*01, D4-17*01, D6-13*01 and D6-19*01, or the repertoire consists of one, more or all of these D gene segments.

Optionally the repertoire is biased to one or more of human D2-2, D3-9, D3-10, D3-22, D4-17, 06-13 and D6-19, or the repertoire consists of one, more or all of these D gene segments. Optionally the repertoire is biased to one or more of human D2-2*02, D3-9*01, D3-10*01, D3-22*01, D4-17*01, D6-13*01 and D6-19*01, or the repertoire consists of one, more or all of these D gene segments. These produce long HCDR3 lengths in naïve repertoires (eg, see Table 2).

Optionally the repertoire is biased to one or more of human D1-26, D2-2, D3-10 and D6-19, or the repertoire consists of one, more or all of these D gene segments. Optionally the repertoire is biased to one or more of human D1-26*01, D2-2*02, D3-10*01 and D6-19*01, or the repertoire consists of one, more or all of these D gene segments. These produce long HCDR3 lengths in immunised repertoires (eg, see Table 2).

Optionally the repertoire is biased to one or more of human D2-2, D3-9 and D3-10, or the repertoire consists of one, more or all of these D gene segments. Optionally the repertoire is biased to one or more of human D2-2*02, D3-9*01 and D3-10*01, or the repertoire consists of one, more or all of these D gene segments. These produce long HCDR3 lengths in antigen-specific repertoires (eg, see Table 2).

IMGT nomenclature is used for all gene segments.

Throughout this text, Genbank is a reference to Genbank release number 185.0 or 191.0; the 1000 Genomes database is Phase 1, release v3, 16 Mar. 2012; the Ensembl database is assembly GRCh37.p8 (Oct. 4, 2012); the IMGT database is available at www.imgt.org. The sequences of all VH gene segments explicitly mentioned herein are disclosed herein in their entirety (for possible inclusion in clauses in conjunction with any aspect of the invention as clauseed), such sequences being those in the IMGT and 1000 Genomes databases.

In one embodiment, the genome comprises an IgH locus comprising a targeted insertion of said human D gene segments. In an example, the IgH locus comprises (in 5' to 3' order) one or more human VH gene segments, said D gene segment repertoire, one or more human JH gene segments and a constant region (eg, wherein the constant region is a human constant region or a non-human (eg, endogenous, eg, mouse or rat) constant region).

In another embodiment, the genome comprises said human D gene segments randomly inserted therein. This can be effected, eg, by incorporating human DNA borne by YACS into the genome of ES cells (followed optionally by generation of a non-human vertebrate therefrom, as is standard).

Optionally, the human D gene segment repertoire further comprises no more than 5 additional human D gene segments, for example, the repertoire includes 1, 2, 3, 4 or 5 additional human D gene segments.

2. The vertebrate or cell of clause 1, wherein the D gene segment repertoire consists of or substantially consists of one, two or three human gene segments selected from the group D1-26, D2-2, D3-9, D3-10, D3-22, D4-17, D6-13 and D6-19.

3. The vertebrate or cell of clause 1 or 2, wherein the genome comprises an unrearranged immunoglobulin heavy chain locus comprising (in 5' to 3' order) human VH, D and JH gene segments and said human D gene segments recited in clause 1 are spaced from the VH gene segment(s) by no more than four other D gene segments (eg, by no D gene segments).

This provides for bias wherein proximal D gene segments (those more 3', ie, closer to the constant region) are likely to be more frequently used than those segments from distal (ie, 5' or further away from the constant region).

4. The vertebrate or cell of any preceding clause, wherein the genome comprises an unrearranged immunoglobulin heavy chain locus comprising said human D gene segments and there are no other D gene segments in the locus between said human D gene segments.

This is another way of biasing the repertoire of D gene segments. Thus, the desired Ds are provided in tandem, aimed to promote use in recombination.

5. The vertebrate or cell of any preceding clause, wherein the genome comprises three or more copies of a human D gene segment selected from D1-26, D2-2, D2-15, D3-3, D3-9, D3-10, D3-22, D4-17, D6-13 and D6-19.

For example, the genome comprises three or more copies of a human D gene segment selected from D1-26, D2-2, D3-9, D3-10, D3-22, D4-17, D6-13 and D6-19.

This is another way of biasing the repertoire of D gene segments.

6. The vertebrate or cell of clause 5, wherein the genome comprises first and second human D gene segments selected from D1-26, D2-2, D2-15, D3-3, D3-9, D3-10, D3-22, D4-17, D6-13 and
D6-19 when the first D gene segment is present as three or more copies and wherein the second D gene segment is present as three or more copies.

For example, the first and second gene segments are selected from D1-26, D2-2, D3-9, D3-10, D3-22, D4-17, D6-13 and D6-19.

The various gene segment biasing techniques described herein can be performed using conventional DNA manipulation in the construction of transgenic vertebrates or cells of the invention, which techniques (eg, recombineering and recombinant DNA technology) will be known to the skilled person. For example, BACs can be constructed using these techniques in which the desired combination of human gene segments is provided, and these BACs can be introduced into ES cells for incorporation of the human gene segments into the genomes thereof (eg, by targeted insertion into Ig loci). The ES cells can be used to generate transgenic vertebrates as is standard and cells (eg, B-cells) can be isolated from these wherein the genome is as per the invention.

In one embodiment, the biased D gene segment(s) are selected from the IMGT database of variants or the 1000 Genomes database.

7. The vertebrate or cell of any preceding clause, wherein the D gene segments are selected from D2-2*02, D3-9*01, D3-10*01 and D3-22*01, or selected from D1-26*01, D2-2*02, D3-9*01, D3-10*01, D3-22*01, D4-17*01, D6-13*01 and D6-19*01.

VH Bias

8. A non-human vertebrate (eg, a mouse or a rat) or a non-human vertebrate cell (eg, a mouse cell or a rat cell), optionally according to any preceding clause, whose genome comprises a human immunoglobulin VH gene segment repertoire that is biased to one, more or all of gene segments selected from the group VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1.

These produce long HCDR3 lengths (see Table 2 and references cited herein).

For example, the VH repertoire is biased to one, more or all of VH1-2, VH1-3, VH1-8, VH1-18, VH2-5, VH3-7, VH3-9, VH3-11, VH3-13, VH3-20, VH3-21, VH3-23, VH4-4, VH6-1 and VH7-4-1. These produce long HCDR3 lengths (see Table 2), or the repertoire consists of one, more or all of these VH gene segments. For example, the VH repertoire is biased to one, more or all of VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01, or the repertoire consists of one, more or all of these VH gene segments.

For example, the VH repertoire is biased to one, more or all of VH1-2*02, VH1-8*01, VH1-18*01, VH1-3*01, VH2-5*10, VH3-7*01, VH3-9*01, VH3-13*01, VH3-21*03, VH3-23*04, VH4-4*02, VH6-1*01 and VH7-4-1*01, or the repertoire consists of one, more or all of these VH gene segments. These produce long HCDR3 lengths in naïve repertoires (see Table 2).

For example, the VH repertoire is biased to one, more or all of VH4-4*02, VH3-11*01 and VH3-7*01, or the repertoire consists of one, more or all of these VH gene segments. These produce long HCDR3 lengths in immunised repertoires (see Table 2).

For example, the VH repertoire is biased to one, more or all of VH1-3*01, VH1-8*01, VH3-7*01, VH3-9*01, VH3-11*01 and VH4-4*02, or the repertoire consists of one, more or all of these VH gene segments. These produce long HCDR3 lengths in antigen-specific repertoires (see Table 2).

Optionally, the human VH gene segment repertoire further comprises no more than 5 additional human VH gene segments, for example, the repertoire includes 1, 2, 3, 4 or 5 additional human VH gene segments.

In one embodiment, the genome comprises an IgH locus comprising a targeted insertion of said human VH gene segments. In an example, the IgH locus comprises (in 5' to 3' order) said VH gene segment repertoire, one or more human D gene segments, one or more human JH gene segments and a constant region (eg, wherein the constant region is a human constant region or a non-human (eg, endogenous, eg, mouse or rat) constant region).

In another embodiment, the genome comprises said human VH gene segments randomly inserted therein. This can be effected, eg, by incorporating human DNA borne by YACS into the genome of ES cells (followed optionally by generation of a non-human vertebrate therefrom, as is standard).

9. The vertebrate or cell of clause 8, wherein the VH gene segment repertoire substantially consists of or substantially consists of one, two or three human gene segments selected from VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1.

For example, the VH gene segment repertoire substantially consists of or substantially consists of one, two or three human gene segments selected from the group consisting of VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01.

10. The vertebrate or cell of clause 8 or 9, wherein the genome comprises an unrearranged immunoglobulin heavy chain locus comprising (in 5' to 3' order) human VH, D and JH gene segments and said human VH gene segments are spaced from the D gene segment(s) by no more than four other VH gene segments (eg, by no VH gene segments).

This provides for bias wherein proximal VH gene segments (those more 3', ie, closer to the constant region) are likely to be more frequently used than those segments from distal (ie, 5' or further away from the constant region).

11. The vertebrate or cell of any one of clauses 8 to 10, wherein the genome comprises an unrearranged immunoglobulin heavy chain locus comprising said human VH gene segments and there are no other VH gene segments in the locus between said human VH gene segments.

This is another way of biasing the repertoire of VH gene segments.

12. The vertebrate or cell of any one of clauses 8 to 11, wherein the genome comprises three or more copies of a human VH gene segment selected from the group consisting of VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1.

For example, the genome comprises three or more copies of a human VH gene segment selected from the group consisting of VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01.

This is another way of biasing the repertoire of VH gene segments.

13. The vertebrate or cell of clause 12, wherein the genome comprises first and second human VH gene segments selected from the group consisting of VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1 when the first VH gene segment is present as three or more copies and wherein the second VH gene segment is present as three or more copies.

For example, the genome comprises first and second human VH gene segments selected from the group consisting of VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01 when the first VH gene segment is present as three or more copies and wherein the second VH gene segment is present as three or more copies.

In an embodiment, all or substantially all of VH gene segments are present as three or more copies each.

The various gene segment biasing techniques described herein can be performed using conventional DNA manipulation in the construction of transgenic vertebrates or cells of the invention, which techniques (eg, recombineering and recombinant DNA technology) will be known to the skilled person. For example, BACs can be constructed using these techniques in which the desired combination of human gene segments is provided, and these BACs can be introduced into ES cells for incorporation of the human gene segments into the genomes thereof (eg, by targeted insertion into Ig loci). The ES cells can be used to generate transgenic vertebrates as is standard and cells (eg, B-cells) can be isolated from these wherein the genome is as per the invention.

In one embodiment, the biased D gene segment(s) are selected from the IMGT database of variants or the 1000 Genomes database.

14. The vertebrate or cell of any one of clauses 8 to 13, wherein the VH gene segments are selected from the group consisting of VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01.

In an embodiment, the genome comprises a human immunoglobulin VH gene segment repertoire that is biased to VH1-69.

In an embodiment, the human immunoglobulin VH gene segment repertoire substantially consists of one or more human VH1-69 gene segments.

The gene segments are provided in one or more immunoglobulin loci. For example, the gene segment repertoire (D and/or VH) is provided in both IgH loci (ie, in a homozygous state).

15. The vertebrate or cell of any one of clauses 8 to 16, comprising an immunoglobulin heavy chain locus comprising two or more copies of a VH gene segment selected from said group.

Thus, at least one of said copies is closer to the constant region of the locus than the germline distance in a human from a human constant region. The aim is to provide by bias by providing more than one copy on the same locus. Also as at least one of the copies is closer (more proximal to) the constant region and J-C intron (which includes regulatory elements such as the Emu enhancer region), this may favour use of the gene segment, thus contributing to the desired bias.

Optionally, the genome is homozygous for the heavy chain locus.

Optionally the two or more copies of gene segments are identical (eg, all VH1-69*01, using IMGT nomenclature). In another example, copies are variants of each other, eg, naturally-occurring human variants. Alterntatively, synthetic variants may be used with or without a naturally-occurring variant.

In any embodiment of the invention, the vertebrate is naïve or immunised with a target antigen.

16. The vertebrate or cell of any clause, wherein the genome comprises a human JH gene segment repertoire consisting of one or more human JH6 gene segments.

This biases the JH repertoire for the production of long HCDR3, since this is the longest naturally-occurring human JH gene segment type and is commonly found in naturally-occurring human antibodies having long HCDR3.

For example, the repertoire comprises two or more different JH6 variants. In an example, the repertoire comprises two or more JH6*02 variants (IMGT nomenclature).

17. The vertebrate or cell of any preceding clause, wherein the genome comprises a human immunoglobulin JH gene segment repertoire that is biased to JH6, optionally JH6*02.

18. The vertebrate or cell of clause 17, wherein the JH gene segment repertoire consists or substantially consists of three or more human JH6 gene segments.

19. The vertebrate or cell of any preceding clause, wherein the sequence of each of said human gene segments is a human germline gene segment sequence.

20. The vertebrate or cell of any preceding clause, wherein one, more or all of the selected gene segments are present in the genome as two or more copies, the copies being variants of each other.

Thus, one, more or all of the human V, D and JH gene segments of said genome is present in two or more variant versions, such as naturally-occurring human variants, eg, variants found in the 1000 Genomes database and/or IMGT database. In another example, one or more of the variants may be a synthetic variant.

21. The vertebrate or cell of any preceding clause, wherein said human gene segments are provided by homozygous immunoglobulin heavy chain loci.

In an example, no other (non-human) active heavy chain VH, D or JH gene segments are present in heavy chain loci of the genome. Additionally, in an example no active non-human light chain VL or JL gene segments are present in the genome.

This is useful for ensuring that endogenous (non-human) variable region expression is inactivated. Thus, all heavy chains produced by the vertebrate or cell will have human variable regions, which is useful for producing drugs for administration to humans.

22. A non-human vertebrate (eg, a mouse or a rat) or a non-human vertebrate cell (eg, a mouse cell or a rat cell) whose genome comprises a human immunoglobulin VH gene segment repertoire, one or more human D gene segments and one or more human JH gene segments, wherein the VH repertoire does not comprise one, more or all VH gene segments selected from the group VH1-2, VH1-3, VH1-8, VH1-18, VH5-51, VH1-69, VH2-5, VH3-7, VH3-9, VH3-11, VH3-13, VH3-20, VH3-21, VH3-23, VH4-4, VH6-1 and VH7-4-1.

23. A non-human vertebrate (eg, a mouse or a rat) or a non-human vertebrate cell (eg, a mouse cell or a rat cell) whose genome comprises a human immunoglobulin D gene segment repertoire, one or more human VH gene segments and one or more human JH gene segments, wherein the D repertoire does not comprise one, more or all D gene segments selected from the group D1-26, D2-2, D3-9, D3-10, D3-22, D4-17, D6-13 and D6-19.

In instances it has been observed in that the art that certain human gene usage may dominate the immune response to infectious disease pathogen antigens or other antigens. While this may yield many specific antibodies, typically these may not be neutralising and thus the immune response is relatively ineffective. This may happen, for example, where the antigen is a decoy antigen expressed by the pathogen. The present embodiments of the invention where specific gene segments are omitted are useful for avoiding dominance of certain human gene segments, such as those omitted from the genome. In this way, the genome human gene segment repertoire is biased away from the dominance and this enables better use and sampling of the remaining human gene segment sequence space, thereby providing the chance of producing antibodies that may not be normally raised in a natural setting. Antigen specific antibodies can be selected from vertebrates and cells with such genomes. In some examples, this may yield neutralising antibodies.

It is advantageous to include a plurality of different human VH gene segments, making up the human VH gene segment repertoire. This provides for good diversities of rearranged human variable regions from which to select leads. It is possible, for example, to include an otherwise complete, functional repertoire of human VH gene segments. To this end, the human VH gene segment repertoire comprises, in one example, a plurality of human VH gene segments, eg, at least 7, 10, 15, 20, 15, 30, 35, 40 or 45 different human VH gene segments. This can be achieved, for example, using BACs harbouring stretches of unrearranged human variable region DNA comprising VH gene segments—homologous recombination and/or sRMCE being used to insert several stretches of such DNA from serial BACs into an endogenous heavy chain locus upstream of the constant region thereof in the genome of a non-human vertebrate ES cell (eg, mouse or rat ES cell), followed by development of one or more progeny vertebrates from such cells (and optional breeding to homozygosity of the heavy chain locus). In one embodiment, human DNA is inserted that includes a first human VH (eg, VH1-69 and/or VH1-2) and flanking VH gene segments upstream and downstream of these. In a second ES cell genomic manipulation, the first VH is deleted from the genome, eg, using standard homolgous recombination techniques as is known in the art. In this way, one or more VH gene segments usually upstream and/or downstream of the deleted gene segment(s) in a wild-type human germline genome are retained so that they can be available to contribute to the subsequent rearranged human V region repertoire that is used for selection of leads. In another example, the initial insertion of human DNA is made using stretches of DNA that already omit the first VH (eg, by deleting such stretches using recombineering of BACs in *E. coli*, as is known in the art). Similar techniques can be used (with appropriate BACs) for the omission of human D and/or J gene segments.

Thus, in an embodiment, VH gene segments that normally are upstream and/or downstream of the omitted human VH gene segments (or omitted D or J as per other embodiments) in a wild-type germline human genome are included in the vertebrate or cell of the invention. For example, the human VH gene segment repertoire of the genome in the invention does not comprise VH1-69, but does comprise one, two, three or four human VH gene segments selected from VH2-10, VH3-72, VH3-73 and VH3-74. These are gene segments that are immediately upstream of VH1-69 in a wild-type human germline heavy chain locus (see IMGT). For example, additionally or alternatively the human VH gene segment repertoire of the genome in the invention does not comprise VH1-69, but does comprise one, two, three, four or more (or all of) human VH gene segments selected from VH3-66, VH3-64, VH4-61, VH4-59, VH1-58, VH3-53, VH3-49, VH3-48, VH1-46 and VH1-45. These are gene segments that are immediately downstream of VH1-69 in a wild-type human germline heavy chain locus (see IMGT). Additionally or alternatively, the human VH gene segment repertoire of the genome in the invention does not comprise VH1-69, but does comprise one, two, three, four or more (or all of) human VH gene segments selected from VH2-5, 7-41, 4-4, 1-3, 1-2 and 6-1. Additionally or alternatively, the human VH gene segment repertoire of the genome in the invention does not comprise VH1-69, but does comprise one, two, three, four, 5, 6, 7, 8, 9, 10 or more (or all of) human VH gene segments selected from VH2-5, 7-41, 4-4, 1-3, 1-2, 6-1, 3-7, 1-8, 3-9, 3-11 and 3-13. Additionally or alternatively, the human VH gene segment repertoire of the genome in the invention does not comprise VH1-69, but does comprise one, two, three, four, 5, 6, 7, 8, 9, 10, 11, 12, 13, 14, 15, 16, 17 or more (or all of) human VH gene segments selected from VH2-5, 7-41, 4-4, 1-3, 1-2, 6-1, 3-7, 1-8, 3-9, 3-11, 3-13, 3-15, 1-18, 3-20, 3-21, 3-23, 1-24 and 2-26. Additionally or alternatively, the human VH gene segment repertoire of the genome in the invention does not comprise VH1-69, but does comprise VH6-1 (which is commonly used in human immune responses, VH6-1 being the most proximal to the constant region in a wild-type human germline heavy chain locus) and/or VH3-23 (which is commonly used in human immune responses). In embodiment (eg, for generating VH, heavy chains or antibodies for treating and/or preventing an infectious disease, eg, HIV infection, in a human), VH1-2 is omitted in the genome or locus. In this case one, two, three or all human VH gene segments immediately 5' and 3' of VH1-2 in a wild-type germline human IgH locus (eg, see IMGT) are included in the genome, such as comprised by the same IgH locus upstream of human D and JH gene segments and a constant region.

24. The vertebrate or cell of clause 22 or 23, wherein the genome comprises a human JH gene segment repertoire that does not comprise JH6.

JH Bias

25. A non-human vertebrate (eg, a mouse or a rat) or a non-human vertebrate cell (eg, a mouse cell or a rat cell) whose genome comprises a human immunoglobulin JH gene segment repertoire that is biased to human JH6.

In an example, the repertoire is biased to human JH6*02 (IMGT nomenclature).

So, the inventors made a choice of human JH6*02 on the basis of
(i) Containing YYG and YYGXDX motifs that is conserved across several vertebrate species;
(ii) Provision of one less TAC codon than other human JH6 variant (an AID hotspot that risks stop codons) and a choice instead of a codon that preserves the YYG and YYGXDX motifs;
(iii) Avoidance of a GGCA AID hotspot in the region of the HCDR3/FW4 junction; and
(iv) Common occurrence (and thus conservation and acceptability) in humans of the JH6*02 variant.

26. The vertebrate or cell of clause 25, wherein the genome comprises an unrearranged immunoglobulin heavy chain locus comprising a plurality of human JH6 gene segments; optionally wherein the genome is homozygous for said locus.

In an example, the plurality comprises or consists of a plurality of JH6*02 gene segments.

27. The vertebrate or cell of clause 26, wherein the heavy chain locus comprises (in 5' to 3' order) human VH, D and JH gene segments and said JH6 gene segments are spaced from the D gene segment(s) by no more than two other JH gene segments.

28. The vertebrate or cell of clause 25, 26 or 27, wherein are no other JH gene segments in the locus between said human JH6 gene segments.

29. A non-human vertebrate (eg, a mouse or a rat) or a non-human vertebrate cell (eg, a mouse cell or a rat cell) whose genome comprises a human immunoglobulin JH gene segment repertoire that consists of one or more human JH6 gene segments.

In an example, all of the gene segments are JH6*02 gene segments.

30. The vertebrate or cell of any one of clauses 25 to 29, wherein all of said gene segments are human germline gene segments.

31. The vertebrate or cell of any one of clauses 25 to 30, comprising different variant JH6 gene segments.

In an example, the variants are all naturally-occurring (eg, appearing in the IMGT or 1000 Genome databases). In an other example, one or more variant is synthetic.

32. The vertebrate or cell of any one of clauses 25 to 31, wherein said gene segments are provided by homozygous immunoglobulin heavy chain loci.

In one embodiment, the biased JH gene segment(s) are selected from the IMGT database of variants or the 1000 Genomes database.

33. A monoclonal or polyclonal antibody composition or a population of antibody-producing cells for producing such composition, wherein the composition or population is prepared by immunising at least one vertebrate according to any preceding clause with an antigen, wherein the antibody or antibodies have human heavy chain variable regions comprising non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)—pattern junctional mutations when compared to corresponding human germline V, D and J sequences; wherein the composition comprises at least one antigen-specific antibody having a HCDR3 length of at least 20 amino acids (according to IMGT).

As will be readily apparent to the skilled person, AID and TdT mutations can be determined using bioinformatics analysis to find the closest matching human germline gene segment(s) that correspond to a given variable domain sequence, aligning the sequences and determining the differences. AID has known hotspots for mutation (eg, see Annu. Rev. Biochem. 2007.76:1-22; Javier M. Di Noia and Michael S, Neuberger, "Molecular Mechanisms of Antibody Somatic Hypermutation" (in particular FIG. 1 and associated discussion on AID hotspots in mouse); and Curr Opin Immunol. 1995 April; 7(2):248-54, "Somatic hypermutation", Neuberger M S and Milstein C (in particular, discussion on hotspots in mouse), the disclosures of which are incorporated herein by reference). By carrying out the standard bioinformatics analysis, TdT mutations (eg, to provide junctional muatations and diversity) can be determined, as will be familiar to the skilled person.

Corresponding human germline V, D and J sequences can be according to the IMGT database or 1000 Genomes database, for example.

For example, the HCDR3 length is at least 20, 21, 22, 23, 24, 25, 26, 27, 28, 29 or 30 amino acids.

For example, the HCDR3 length is from 20 to 23 or 24 to 30, eg, from 28 to 30 amino acids.

For example, the cells are B cells (eg, immortalised B cells) or hybridomas.

Optionally the antibodies of any aspect of the invention comprise human light chain variable regions. For example, the human light chain variable regions have non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)—pattern junctional mutations when compared to corresponding human germline V, D and J sequences.

34. An isolated antibody that specifically binds an antigen, the antibody comprising human heavy chain variable regions and non-human constant regions, wherein the variable regions are derived from the recombination in a non-human vertebrate of (i) a human VH gene segment selected from the group recited in clause 8 with (ii) a human D gene segment selected from the group recited in clause 1 and with a human JH gene segment (optionally JH6); wherein the antibody has a HCDR3 length of at least 20 amino acids (according to IMGT); and non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)—pattern junctional mutations when compared to corresponding human germline V, D and J sequences.

In examples, the VH is selected from the group VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01 and/or
the D is selected from the group
D2-2*02, D3-9*01, D3-10*01 and D3-22*01, or
D2-2*02, D3-9*01 and D3-10*01, or
D3-9*01 and D3-10*01, or
D1-26, D2-2, D3-9, D3-10, D3-22, D4-17, D6-13 and 06-19, or
D1-26*01, D2-2*02, D3-9*01, D3-10*01, D3-22*01, D4-17*01, D6-13*01 and D6-19*01, or
D2-2, D3-9, D3-10, D3-22, 04-17, D6-13 and D6-19, or
D2-2*02, D3-9*01, D3-10*01, D3-22*01, D4-17*01, D6-13*01 and D6-19*01, or
D1-26, D2-2, D3-10 and D6-19, or
D2-2, D3-9 and D3-10.

35. The antibody of clause 34, wherein the antibody is obtained or obtainable from a vertebrate according to any one of clauses 1 to 32.

In an embodiment, the antibody is obtained from said vertebrate, or is a copy of such an antibody.

36. A method of isolating an antibody that binds a predetermined antigen, the method comprising
  (a) providing a vertebrate (optionally a mouse or rat) according to any one of clauses 1 to 32;
  (b) immunising said vertebrate with said antigen;
  (c) removing B lymphocytes from the vertebrate and selecting one or more B lymphocytes expressing antibodies that bind to the antigen;
  (d) optionally immortalising said selected B lymphocytes or progeny thereof, optionally by producing hybridomas therefrom; and
  (e) isolating an antibody (eg, and IgG-type antibody) expressed by the B lymphocytes.

37. The method of clause 36, wherein in step (e) wherein the antibody has a HCDR3 length of at least 20 amino acids (according to IMGT).

The length can be 20, 21, 22, 23, 24, 25, 26, 27, 28, 29 or 30 amino acids (according to IMGT), eg, from 20 to 23 amino acids (a produced in the examples).

38. The method of clause 36 or 37, comprising the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

39. The method of clause 36, 37 or 38, further comprising making a copy, mutant or derivative (eg, humanised version) of the antibody produced by the method.

Humanisation can entail making the constant regions human.

40. The antibody composition, cell population, antibody or method of any one of clauses 33 to 39, wherein the antigen is an antigen of an infectious disease pathogen; optionally wherein the pathogen is a virus or bacterium.

41. The antibody composition, cell population, antibody or method of clause 40, wherein pathogen is selected from the group consisting of *Haemophilus influenza, E. coli, Neisseria meningitidis*, a herpes family virus, cytomegalovirus (CMV), HIV and influenza virus.

42. The antibody composition, cell population, antibody or method of any one of clauses 33 to 41, wherein the antigen is a HIV gp120 antigen or a HIV gp41 antigen.

43. The antibody composition, cell population, antibody or method of any one of clauses 33 to 40, wherein the antigen comprises an active site or cleft, wherein the antibody having a HCDR3 length of at least 20 amino acids specifically binds to the active site or cleft of the antigen.

44. A pharmaceutical composition comprising an antibody or antibody composition according to any one of clauses 33 to 35 and 40 to 43, or an antibody produced by the method of any one of clauses 36 to 38, for treating and/or preventing an infectious disease in a human (eg, wherein the infectious disease is caused by a pathogen selected from the group consisting of *Haemophilus influenza, E. coli, Neisseria meningitidis*, a herpes family virus, cytomegalovirus (CMV), HIV and influenza virus).

45. A repertoire of antibody heavy chains (eg, provided by antibodies) comprising one or more heavy chains whose variable domain HCDR3 has a length of at least 20 amino acids (according to IMGT) and derived from the recombination of a human VH, D and JH, wherein the VH is selected from the group
VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01 and
the D is selected from the group
D2-2*02, D3-9*01, D3-10*01 and D3-22*01, or
D2-2*02, D3-9*01 and D3-10*01, or
D3-9*01 and D3-10*01, or
D1-26, D2-2, D3-9, D3-10, D3-22, 04-17, 06-13 and D6-19, or
D1-26*01, D2-2*02, D3-9*01, D3-10*01, D3-22*01, D4-17*01, D6-13*01 and D6-19*01, or
D2-2, D3-9, D3-10, D3-22, D4-17, 06-13 and D6-19, or
D2-2*02, D3-9*01, D3-10*01, D3-22*01, D4-17*01, D6-13*01 and D6-19*01, or
D1-26, D2-2, D3-10 and D6-19, or
D2-2, D3-9 and D3-10;
and optionally the JH is JH6 (eg, JH6*02);
Wherein
(a) the heavy chain variable domain has been produced in vivo in a non-human vertebrate (eg, a mouse or a rat); and/or
(b) the heavy chain variable domain comprises non-human vertebrate AID-pattern somatic hypermutations, (eg, mouse or rat AID-pattern mutations) when compared to corresponding human germline V, D and J sequences and/or non-human (eg, mouse or rat) terminal deoxynucleotidyl transferase (TdT)—pattern junctional mutations when compared to corresponding human germline V, D and J sequences.

In an example, the heavy chain (or all heavy chains in the repertoire) comprise non-human vertebrate constant regions (eg, mouse or rat constant regions). For example, the constant regions are gamma-type constant regions (eg, gamma-1, gamma-2 or gamma-4 type).

In an example, the repertoire is a naïve repertoire. This is shown in the examples section herein.

In an example, the repertoire is an immunised repertoire. This is shown in the examples section herein.

In an example, the repertoire is an antigen-specific repertoire (eg, provided by a plurality of hybridomas). This is shown in the examples section herein.

The repertoire can be provided by B cells (eg, immortalised B cells).

The repertoire can be provided by hybridomas.

In an example, the vectors are harboured by host cells (eg, CHO or HEK293 cells or yeast cells).

The HCDR3 length can be 20, 21, 22, 23, 24, 25, 26, 27, 28, 29 or 30 amino acids (according to IMGT), eg, from 20 to 23 amino acids (a produced in the examples).

In an example, in (a) the vertebrate is a vertebrate according to the invention.

46. A nucleic acid collection encoding the heavy chain repertoire of clause 45.

In an example, the nucleic acids are provided in respective vectors (eg, expression vectors, eg, *E. coli* or CHO or HEK293 vectors).

47. A method of obtaining an antigen-specific heavy chain (eg, provided by an antibody), the method comprising exposing the repertoire of clause 45 to a predetermined antigen and selecting one or more heavy chains that specifically bind to the antigen, wherein one or more heavy chains is isolated that has a HCDR3 length of at least 20 amino acids.

Optionally, when the heavy chain has a non-human constant region, this is swapped for a human constant region, as is conventional in the art. Thus, the invention provides a human antibody heavy chain so produced (eg, provided in combination with a human light chain to produce a human antibody which is useful for human therapeutic and/or prophylactic use, eg, to treat and/or prevent an infectious disease in a human patient).

In an example of the vertebrate or cell of any aspect of the invention, the genome comprises an immunoglobulin light chain locus comprising one or more human V gene segments and one or more human J gene segments upstream of a constant region (eg, a human or a mouse lambda or kappa constant region).

For rearrangement and expression of heavy chains, the locus comprises control elements, such as an Eµ and Sµ between the J gene segment(s) and the constant region as is known by the skilled person. In one example, a mouse Eµ and Sµ is included in the heavy chain locus between the JH repertoire and the constant region (ie, in 5' to 3' order the locus comprises the JH gene segment(s), Eµ and Sµ and constant region). In an example, the Eµ and Sµ are Eµ and Sµ of a mouse 129-derived genome (eg, a 129Sv-derived genome, eg, 129Sv/EV (such as 129S7Sv/Ev (such as from AB2.1 or AB2.2 cells obtainable from Baylor College of Medicine, Texas, USA) or 129S6Sv/Ev))); in another example, the Eµ and Sµ are Eµ and Sµ of a mouse C57BL/6-derived genome. In this respect, the locus can be constructed in the IgH locus of the genome of a cell selected from AB2.1, AB2.2, VGF1, C17 and FH14. VGF1 cells were established and described in Auerbach W, Dunmore J H, Fairchild-Huntress V, et al; Establishment and chimera analysis of 129/SvEv- and C57BL/6-derived mouse embryonic stem cell lines. Biotechniques 2000; 29:1024-8, 30, 32, incorporated herein by reference.

Additionally or alternatively, the constant region (or at least a Cµ; or Cµ and gamma constant regions thereof) is a constant region (or Cµ; or µ and gamma constant regions thereof) is of a genome described in the paragraph immediately above.

A suitable source of human DNA sequences or gene segments will be readily apparent to the skilled person. For example, it is possible to collect a DNA sample from a consenting human donor (eg, a cheek swab sample as per the Example herein) from which can be obtained suitable DNA sequences for use in constructing a locus of the invention. Other sources of human DNA are commercially available, as will be known to the skilled person. Alternatively, the skilled person is able to construct gene segment sequence by referring to one or more databases of human Ig gene segment sequences disclosed herein.

In an example, the genome comprises all or some of the following human VH gene segments
IGHV6-1
IGHV3-7
IGHV1-8
IGHV3-9
IGHV3-11
IGHV3-13
IGHV1-18
IGHV3-30
IGHV4-31
IGHV4-39
IGHV4-59
  Optionally also (i) and/or (ii)
  (i)
IGHV1-2
IGHV2-5 and
IGHV3-21
  (ii)
IGHV1-2
IGHV2-5
IGHV3-21
IGHV1-24

For example, the genome comprises all or some of the following human VH gene segment variants
IGHV6-1*01
IGHV3-7*01
IGHV1-8*01
IGHV3-9*01
IGHV3-11*01
IGHV3-13*01
IGHV1-18*01
IGHV3-30*18
IGHV4-31*03
IGHV4-39*01 and
IGHV4-59*01;
  Optionally also (iii) or (iv)
  (ii)
IGHV1-2*04
IGHV2-5*10 and
IGHV3-21*03
  (iv)
IGHV1-2*02
IGHV2-5*01
IGHV3-21*01 and
IGHV1-24*01

For example, the genome comprises all or some of the following human JH gene segment variants
IGHJ2*01
IGHJ3*02
IGHJ4*02
IGHJ5*02 and
IGHJ6*02

For example, the genome comprises all or some of the following human D gene segments
IGHD1-1
IGHD2-2
IGHD3-9

IGHD3-10
IGH D5-12
IGHD6-13
IGHD1-14
IGHD2-15
IGHD3-16
IGHD4-17
IGHD6-19
IGHD2-21
IGHD5-24
IGHD1-26 and
IGHD7-27
and optionally also (v) or (vi)
(v)
IGHD3-3
(vi)
IGHD3-3
IGHD4-4
IGHD5-5
IGHD6-6
IGHD1-7
IGHD2-8 and
IGHD2-8

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting Examples (Examples 1-3 being prophetic). Example 4 is a worked example.

EXAMPLES

Example 1

Recombineered BAC Vectors to Add Polymorphic V-Regions to the Mouse Genome

Figure 3:
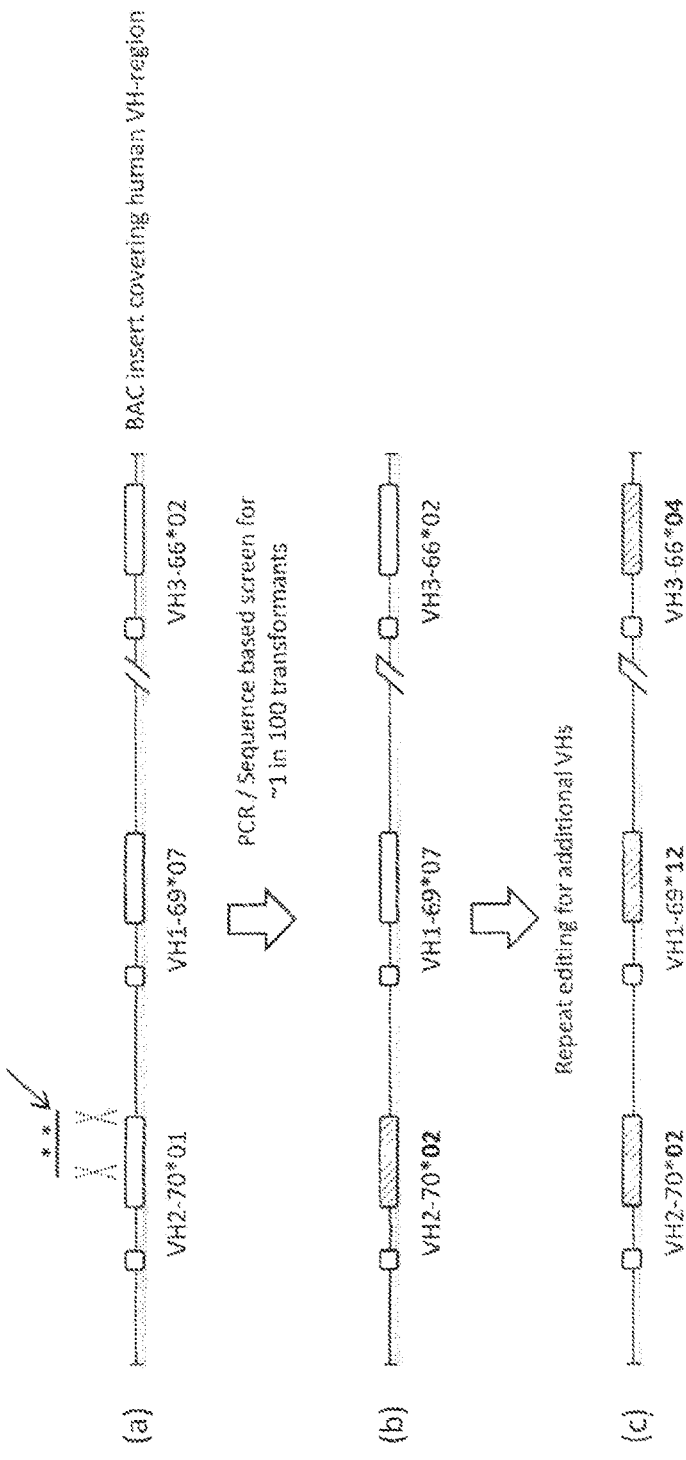

FIG. 1 through 3 depict recombineering methods (see references above) that can be used to introduce polymorphic V-gene regions into genomic DNA. In one embodiment, a genomic fragment from the human heavy chain region is inserted into a bacterial artificial chromosome (BAC) vector by standard techniques. Preferably, such a BAC, which can range in size from 20-kb to 200-kb or more, can be isolated from libraries of BACs by standard techniques including sequence searches of commercially available libraries or by hybridization to bacterial colonies containing BACs to identify those with a BAC of interest.

A BAC is chosen that has several VH gene segments; in FIG. 1, these are generically identified as VH[a] through VH[z] for example. One skilled in the art will readily identify appropriate genomic fragments, for example, an approximately 120-kb fragment from human VH5-78 through VH1-68 which includes 5 endogenous active VH gene segments and 7 VH psuedogenes. Using recombineering techniques, the endogenous VH gene segments can be replaced by polymorphic VH or VL gene segments. In this example, two steps are required. The first step replaces the V-region coding exon of an endogenous VH gene segment with a positive-negative selection operon, in this example, an operon encoding an ampicillin resistance gene (Amp) and a streptomycin-sensitizing ribosomal protein (rpsL). Certain strains of bacteria can be selected for the absence of the rpsL gene by resistance to streptomycin. Short stretches of DNA homologous to sequences flanking the endogenous VH gene exon are placed 5' and 3' of the rpsL-Amp operon. In the presence of appropriate recombination factors per standard recombineering techniques (see references above) recombination between the operon fragment and the BAC will result in replacement of the endogenous VH gene exon with the operon (FIG. 1*a*) which are selected by resistance to ampicillin. The second step uses the same homologous sequences in order to replace the inserted operon with a desired polymorphic VH gene segment. In this example, a human VI-1'-69 gene is inserted (FIGS. 1b and 1c). In particular the *02 allele of VH1-69 is used [ref IMGT and FIG. 5]. Successful integrations of the polymorphic VH gene segment are selected in bacteria that become resistant to streptomycin due to the loss of the operon, specifically the rpsL portion.

In this example, the two step process as described can be repeated for each of the endogenous VH gene segments or for as many endogenous gene segments that one wishes to replace with polymorphic V gene segments (FIG. 1d).

As is apparent, any polymorphic V gene segment can be inserted in this manner and any endogenous V gene segment can act as a target, including pseudogenes. V gene segments in each of the heavy chain and two light chain loci can be replaced using this technique with appropriate genomic fragments available as BAC inserts.

FIG. 2 depicts another method for creating a genomic fragment encoding polymorphic V gene segments. In this example, polymorphic V gene segments are inserted into a region of genomic DNA devoid of other genes, control elements or other functions. Such 'desert' regions can be selected based on sequence analysis and corresponding DNA fragments cloned into BACs or identified in existing BAC libraries. Starting with such a genomic fragment, recombineering techniques can be used to insert polymorphic V gene segments at intervals of, for example, 10-kb. In this example, a 150-kb genomic fragment might accommodate insertion of up to 15 polymorphic V gene segments. Insertion of the segments is a two-step process. The first recombineering step inserts the rpsL-Amp operon at a specific site. Sequences homologous to a specific site are used to flank the operon. These are used by the recombineering system to insert the element specifically into the BAC genomic fragment and positive events are selected by resistance to ampicillin (FIG. 2a). The second step replaces the operon in the genomic fragment with a polymorphic V gene segment by a similar recombineering step using the same sequence homology (FIG. 2b). In this example, both exons and promoter element of a polymorphic VH gene segment are inserted, resulting in replacement of the rpsL-Amp operon and therefore resistance to streptomycin (FIG. 2c).

The two step technique for inserting polymorphic V gene segments into a specific site on the genomic fragment can be repeated multiple times resulting in a BAC genomic fragment with several polymorphic gene segments, including their promoter elements. It is apparent that the examples shown in FIGS. 1 and 2 can be combined wherein the technique for insertion can be used to add extra polymorphic V gene segments to a BAC genomic fragment as depicted in FIG. 1. One might choose to add these extra segments to an IG genomic fragment since such a fragment would be more amenable to proper IG gene expression once inserted into a non-human mammal's genome. It is known that a genomic fragment can have elements such as enhancers or elements that contribute to certain chromatin conformations, both important in wild-type gene expression.

FIG. 3 depicts an additional method to create genomic fragments with polymorphic V gene segments. This method depends upon the efficiency with which short (around 50 to 150 bases, preferably 100 bases) single stranded DNA fragments recombine with a homologous sequence using recombineering (Nat Rev Genet. 2001 October; 2(10):769-79; Recombineering: a powerful new tool for mouse functional genomics; Copeland N G, Jenkins N A, Court D L). The recombinases used in recombineering preferentially bind and use such short single-stranded fragments of DNA as a substrate for initiating homologous recombination. The efficiency can be as high as 10-2, that is, a positive event can be found in approximately 100 randomly picked (not selected) clones resulting from recombineering. A positive event in this example occurring when one or more single nucleotide changes introduced into the single-stranded fragment get transferred to the BAC insert containing V gene segments and surrounding genomic DNA, said nucleotide change or changes occurring at a homologous sequence on the BAC.

Polymorphic V gene segments can differ from endogenous V gene segments by only 1 or 2, or up to 10 or 15 nucleotide changes, for example. An example of such nucleotide polymorphisms are depicted in FIG. 5. Short single stranded regions that encompass the polymorphic nucleotide changes can be chemically synthesized using standard techniques. The resulting single stranded DNA fragments are introduced into bacteria and via recombineering techniques approximately 1 in 100 BAC fragments will have incorporated the polymorphic nucleotides via homologous incorporation of the single stranded fragment (FIG. 3a). BACs with the desired nucleotide change can be identified by screening for example several hundred individual clones by polymerase chain reaction (PCR) amplification and sequencing, both by standard techniques. In the example, two nucleotide changes will convert a VH1-69*01 gene segment into a VH1-69*02 gene segment (FIG. 3b).

It is clear that this process can be repeated for multiple endogenous V gene segments contained on a single BAC genomic fragment. In addition, the techniques depicted in FIG. 2 can be used to add additional polymorphic V gene segments by insertion into regions between existing V gene segments. As would be evident to one skilled in the art, a combination of these techniques can be used to create numerous variations of both polymorphic and endogenous human V gene segments. And it would be evident that several different genomic fragments with engineered polymorphic V gene segments and endogenous human V gene segments can be combined to create even more variations.

Example 2

Adding Polymorphic V-Regions to the Genome Using SRMCE of Modified BACs

Modified BACs with polymorphic V gene segments created using the methods described in Example 0.1 can be used to alter the genome of non-human mammals. These alterations can result in an intact IG locus in which normal immunoglobin region recombination results in VDJ or VJ combinations which includes the human V gene segments. An example of how such an animal can be created is by altering the genome of, for example, mouse embryonic stem (ES) cells using the strategy outlined in FIG. 4.

One technique to integrate modified BACs with polymorphic V gene segments into a genome is sequential recombinase mediated cassette exchange (SRMCE). The technique is described in WO2011004192 (Genome Research Limited), which is incorporated here in its entirety by reference.

Figure 4:
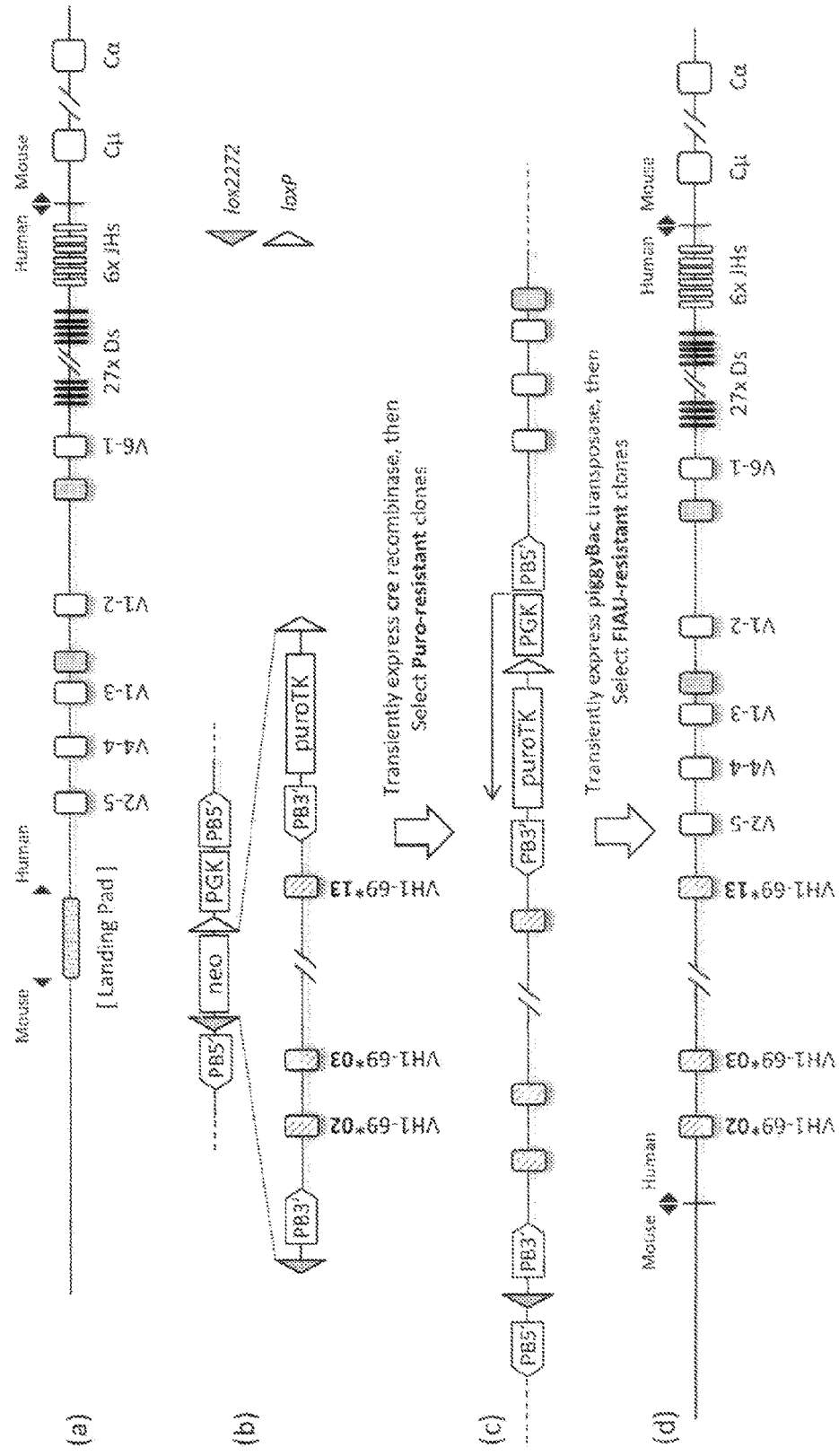
FIG. 4: Schematic illustrating a protocol for adding V gene segments to a mouse genome using sequential recombinase mediated cassette exchange (sRMCE)

SRMCE provides for a locus modified with a 'landing pad' inserted at a specific location. This insertion can either be de novo via homologous recombination or as a consequence of a previous BAC insertion. In this example, the landing pad is inserted in the mouse IGH locus between the most 3'J gene segment and the Cμ gene segment and a previous BAC insertion via SRMCE techniques have resulted in the addition of 5 human V gene segments and 2 V region pseudogenes. The landing pad has elements as shown in FIG. 4 that will allow the selection of correct insertion of a second targeting BAC fragment. The specificity of this insertion is provided by cre recombinase-mediated exchange between permissive lox sites. A lox site is permissive for recombination only with a compatible lox site. In this example, the loxP site will only recombine with loxP and lox2272 will only recombine with lox2272. This provides directionality to the insertion of the BAC fragment as depicted in FIGS. 4b and 4c.

ES cell clones with correct insertions are selected from a pool of clones without insertions or with non-productive insertions by resistance to puromycin. Resistance to puromycin results from the juxtaposition of an active promoter element, PGK, with the puroTK coding region. Correct insertions are verified by standard techniques including PCR of junctions, PCR of internal elements, Southern blotting, comparative genomic hybridization (CGH), sequencing and etc. In the example, correct lox2272-lox2272 and loxP-IoxP recombination also results in two intact sets of piggyBac elements that did not exist prior to insertion. An intact piggyBac element is comprised of a set of inverted repeats which are depicted in the figure by "PB5'" and "PB3'". An appropriated oriented set of piggyBac elements are the substrate of piggyBac transposase which can catalyse recombination between the elements, resulting in deletion of intervening sequences as well as both elements. The DNA remaining after a piggyBac transposition is left intact and is lacking any remnant of the piggyBac element. In the example, ES cell clones with successful piggyBac transposition are selected by loss of the active puroTK element which renders the cells resistant to the drug FIAU (FIGS. 4c and 4d).

The final product of the SRMCE method in this example is a IGH locus with several polymorphic V gene segments inserted along with a set of endogenous unmodified VH gene segments between sequences of the mouse genome on the 5' side and the mouse IGH constant region gene segments on the 3' side. The polymorphic V gene segments are positioned such that they can participate in the recombination events associated with B cell maturation yielding VDJ gene segments. These gene segments can then be transcribed and spliced to the mouse constant region. Translation of these transcripts will result in the production of an antibody heavy chain encoded by the polymorphic V gene segment, a human DH gene segment, a human JH gene segment and a mouse constant heavy chain gene segment.

As is well known to those skilled in the art, an ES cell clone can be used to create a line of genetically modified mice via injection of said cells into a mouse blastocyst embryo, transferring the injected embryo to a suitable recipient and breeding the chimeric offspring that result. The modified gene locus can be propagated through breeding and made either heterozygous or homozygous depending on the genetic cross.

It is evident from the structure of the IGH locus provided in this example and by knowledge of the mechanisms involved in B cell receptor (BCR) and antibody gene rearrangements that a large set of different combinations of polymorphic V gene segments with various DH and JH gene segments will result and these can contribute to a large repertoire of functional antibody genes in a population of B cells in genetically modified animals. In this example, several different human VH1-69 polymorphs are incorporated to provide superhuman VH diversity. This particular VH gene segment is known to be prevalent in antibodies that bind infectious disease pathogens (such as influenza virus) and therefore the antibody repertoire of a mouse with the genetic modification of this example would be expected to produce antibodies with a bias in favour of those that bind infectious disease pathogens. The repertoire, in other words, would have a larger subset of antibodies with superior affinities for pathogen antigens. Examples of such pathogens include influenza virus, hepatitis C virus (HCV) and human immunodeficiency virus-1 (HIV-1) (see also table above).

Example 3

Alignment of 13 VH1-69 Alleles

Building a more diverse antibody repertoire by incorporating additional V gene segment polymorphs requires availability of polymorphic alleles of V gene segments. One source of such alleles include sequence databases. In this example, 13 distinct alleles of the VH1-69 gene segment are provided. These allele sequences and comparisons are drawn from the "IMmunoGeneTics" IMGT Information System (www.imgt.com) database. FIG. 5 is a diagram of the alignment of alleles *02 through *13 with the *01 allele. The VH1-69*01 nucleotide and amino acid sequence is provided at the top of the figure. Where the remaining alleles are identical to the *01 allele sequence a dash is inserted below the sequence. Nucleotide differences are noted alongside the appropriate allele and if the sequence change results in a protein coding change, the amino acid change is indicated above the triplet.

FIG. 5 depicts between 1 and 4 amino acid changes for each allele in comparison to the *01 allele. All of the amino acid changes occur in the part of the heavy chain protein encoding the complementarity determining regions (CDRs). These regions are responsible for antigen specificity and the affinity of the antibody for the antigen. It is evident that providing additional polymorphic CDRs in a repertoire of antibodies will increase the likelihood of there being an antibody with superior binding characteristics for various antigens. In several reports, it has been observed that the VH1-69-encoded variable region of the heavy chain is often found in antibodies that bind influenza virus, HCV and HIV-1 antigens (see table above). Therefore incorporating the polymorphic V gene segments of this example into a transgenic animal model using the methods of Examples 1 and 2 would likely result in an antibody repertoire in said transgenic animal with more antibodies that bind to antigens associated with these and other pathogens. And as is known in the art, a larger repertoire increases the probability of finding monoclonal antibodies using, for example, hybridoma technology, that bind with high affinity and specificity to a desired antigen.

This disclosure therefore describes in these examples a transgenic mouse model which can be immunized with pathogen or other antigens. Plasma B cells from such an immunized mouse can be used to make a hybridoma library that can be screened for production of antibodies that bind the pathogen antigens. This library will be superior to libraries from traditional transgenic mice for finding such antibodies given the addition of polymorphic VH1-69 gene segments to the IGH locus in said transgenic mouse.

These examples are not limiting to the human polymorphic V gene segments that can be chosen or to the methods used to introduce them into an animal model. The method can be used to construct a transgenic locus with immunoglobulin D and/or J segments. The V, D, J segments can be from a plurality of human sources (optionally more than one human ethnic population).

Example 4

Transgenic Mice, B-Cells, Hybridomas, Antibodies & Heavy Chains Based on Human JH6*02

A functional human gene segment repertoire (from $V_H2$-26 to 46, see the IMGT database for the structure of the human IgH locus; http://www.imgt.org./IMGTrepertoire/index.php?section=LocusGenes&repertoire=locus&species=human&kroup=IGK) was sectored by the inventors to produce two different transgenic heavy chain alleles (denoted S2F and S3F) and corresponding mice. The transgenic alleles were expressed in the mice and the heavy chain repertoires were assessed at the RNA transcript level. Deep sequence analysis was carried out using Bioinformatics methods to assess V, D and JH gene usage, including in variable domain sequences having a HCDR3 length of at least 20 amino acids. Endogenous, mouse variable region gene segments were inactivated by inversion (as per the method described in WO2011004192 this disclosure being incorporated herein by reference).

Sequencing of Human Donor DNA Samples: Identification of Conserved JH6*02 Variant DNA samples from 9 anonymised consenting human donors were obtained by taking cheek swabs.

The samples were processed and the DNA Samples were extracted follow the protocol of QIAamp DNA Mini Kit (Cat. No. 51304, Qiagen).

PCR reactions were set up to amplify the JH6 region and PCR products were sequenced (PCR Oligos sequence: Fwd. 5'-AGGCCAGCAGAGGGTTCCATG-3' (SEQ ID NO: 444), Rev. 5'-GGCTCCCAGATCCTCAAGGCAC-3' (SEQ ID NO: 445)).

Sequence analysis was carried out by comparing to the JH6 reference sequence from IMGT annotated database (http://www.imgt.org/), and this identified that all 9 donor genomes contained the human JH6*02 variant, with this variant being in the homozygous state in 7 out of the 9 donors. The inventors also consulted the genomic sequences publicly available for Jim Watson and Craig Venter at Ensembl human genome database [http://www.ensembl.org/]. These too contained the human JH6*02 variant. This confirmed to the inventors that human JH6*02 is a common, conserved variant in humans, and thus a good candidate for construction of a transgenic IgH locus as per the invention Identification of Suitable Human DNA Sequence BACs A series of human bacterial artificial chromosome (BAC) clones were identified from Ensemble (http://ensembl.org/index.html) or UCSC (http://genome.ucsc.edu/) human database searches based on gene name (IGH) or location (chromosome 14: 106026574-107346185). Seven human RP11 BAC clones were selected, RP11-1065N8 BAC carrying human JH6*02. In total, the following BACs were identified as sources of human IgH locus DNA: RP11-1065N8, RP11-659B19, RP11-14117, RP-112H5, RP11-101G24, RP11-12F16 and RP11-47P23.

With a similar approach, different BAC clones (eg, different RP11 clone IDs or different sources from RP11) or genetically engineered BACs can be selected for insertion into the mouse IGH locus to provide different sets of human repertoires in the transgenic mouse.

Construction of Transgenic IgH Loci

Insertion of human heavy gene segments from a 1st IGH BAC(RP11-1065 N8) into the IGH locus of mouse AB2.1 ES cells (Baylor College of Medicine) was performed to create a heavy chain allele denoted the S1 allele. The inserted human sequence corresponds to the sequence of human chromosome 14 from position 106494908 to position 106328951 and comprises functional heavy gene segments $V_H2$-5, $V_H7$-4-1, $V_H4$-4, $V_H1$-3, $V_H1$-2, $V_H6$-1, D1-1, D2-2, D3-9, D3-10, D4-11, D5-12, D6-13, D1-14, D2-15, D3-16, D4-17, D5-18, D6-19, D1-20, D2-21, D3-22, D4-23, D5-24, D6-25, D1-26, D7-27, $J_H1$, $J_H2$, $J_H3$, $J_H4$, 45 and $J_H6$ (in 5' to 3' order), wherein the JH6 was chosen to be the human JH6*02 variant. The insertion was made between positions 114666435 and 114666436 on mouse chromosome 12, which is upstream of the mouse Cu region. The mouse $V_H$, D and $J_H$ gene segments were retained in the locus, immediately upstream of (5' of) the inserted human heavy chain DNA.

A second allele, S2 was constructed in which more human functional $V_H$ gene segments were inserted upstream (5') of the 5'-most $V_H$ inserted in the S1 allele by the sequential insertion of human DNA from a second BAC (BAC2). The inserted human sequence from BAC2 corresponds to the sequence of human chromosome 14 from position 106601551 to position 106494909 and comprises functional heavy chain gene segments $V_H3$-13, $V_H3$-11, $V_H3$-9, $V_H1$-8, $V_H3$-7. The mouse $V_H$, D and $J_H$ gene segments were retained in the locus, immediately upstream of (5' of) the inserted human heavy chain DNA. In a subsequent step, these were inverted to inactivate them, thereby producing S2F mice in which only the human heavy chain variable region gene segments are active.

A third allele, S3 was constructed in which more human functional $V_H$ gene segments were inserted upstream (5') of the 5'-most $V_H$ inserted in the S2 allele by the sequential insertion of human DNA from a third BAC (BAC3). The inserted sequence corresponds to the sequence of human chromosome 14 from position 106759988 to position 106609301, and comprises functional heavy chain gene segments, $V_H2$-26, $V_H1$-24, $V_H3$-23, $V_H3$-21, $V_H3$-20, $V_H1$-18, and $V_H3$-15. The mouse $V_H$, D and $J_H$ gene segments were retained in the locus, immediately upstream of (5' of) the inserted human heavy chain DNA. In a subsequent step, these were inverted to inactivate them, thereby producing S3F mice in which only the human heavy chain variable region gene segments are active.

Mice bearing either the S2F or S3F insertion into an endogenous heavy chain locus were generated from the ES cells using standard procedures. The other endogenous heavy chain locus was inactivated in the mice by insertion of an inactivating sequence comprising $neo^R$ into the mouse $J_H$-Cµ intron (to produce the "HA" allele).

Specifically, the following alleles were included:—
VH1-2*02, VH1-3*01, VH1-8*01, VH1-18*01, VH2-5*10, VH3-7*01, VH3-9*01, VH3-11*01, VH3-13*01, VH3-21*03, VH3-23*04, VH4-4*02, VH6-1*01 and VH7-4-1*01
D1-26*01, D2-2*02, D3-9*01, D3-10*01, D3-22*01, D4-17*01, D6-13*01 and D6-19*01

Immunisation Procedure

Transgenic mice of the S2F or S3F genotype were primed with 20-40 ug recombinant proteins obtained commercially or produced in house with Antigen 1. (OVA (Sigma A7641); Antigen 2 (a human infectious disease pathogen antigen) and Antigen 3 (a human antigen) via the ip route in complete Freunds adjuvant (Sigma F 5881) and 10 ug/animal CpG (CpG oligo; Invivogen, San Diego, Calif., USA) and then boosted twice in about two weekly intervals with about half the amount of antigen in incomplete Freunds adjuvant (Sigma F 5506) and 10 ug/animal CpG. Final boosts were administered two weeks later iv without any adjuvant and contained 5-10 ug protein in PBS.

Hebridoma Fusion Procedure

Spleens were taken 3 days after the final boost and spleenocytes were treated with CpG (25 µm final concentration) for and left until the following day. Cells were then fused with SPO/2 Ag14 myeloma cells (HPA Cultures Cat No 85072401) using a BTX ECM2001 electrofusion instrument. Fused cells were left to recover for 20 minutes then seeded in a T75 flask until next morning. Then the cells were spun down and plated out by dilution series on 96-well culture plates and left for about 10 days before screening. Media was changed 1-3 times during this period.

Screening

Culture supernatants of the hybridoma wells above were screened using homogenious time resolved fluorescence assay (htrf) using Europium cryptate labelled anti-mouse IgG (Cisbio anti-mouse Ig Europium Cryptate) and a biotin tagged target antigen with a commercially available streptavidin conjucated donor (Cisbio; streptaviding conjugated D2) or by IgG-specific 384 well ELISA. Positive wells identified by htrf were scaled to 24-well plates or immediately counterscreened using an IgG-specific detection ELISA method. Positives identified by primary ELISA screen were immediately expanded to 24-well plates. Once cultures were expanded to 24-well stage and reached confluency, supernatants were re-tested using htrf or IgG-specific ELISA to confirm binding to target antigen. Supernatant of such confirmed cultures were then also analysed by surface plasmon resonance using a BioRad ProteOn XPR36 instrument. For this, antibody expressed in the hybridoma cultures was captured on a biosensor GLM chip (BioRad 176-512) which had an anti-mouse IgG (GE Healthcare BR-1008-38)) covalently coupled the biosensor chip surface. The antigen was then used as the analyte and passed over the captured hybridoma antibody surface. For Antigen 2 and Antigen 3, concentrations of 256 nM, 64 nM, 16 nM, 4 nM and 1 nM were typically used, for Antigen 1, concentrations of 1028 nM, 256 nM, 64 nM, 16 nM and 4 nM were typically used, binding curves were double referenced using a 0 nM injection (i.e. buffer alone). Kinetics and overall affinities were determined using the 1:1 model inherent to the BioRad ProteOn XPR36 analysis software.

Any clones with confirmed binding activity were used for preparing total RNA and followed by PCR to recover the heavy chain variable region sequences. Standard 5'-RACE was carried out to analyse RNA transcripts from the transgenic heavy chain loci in the S2F and S3F mice. Additionally, deep sequence analysis of almost 2000 sequences produced by the mice was carried out.

Bionformatics Analysis

Sequences for analysis were obtained from two different methods:
  The first is from RNA extracted from the spleen: first cDNA strand was synthesized using an oligo based on the Cmu region of the mouse IGH locus as a PCR template. PCR was performed using this oligo with an oligo dT-anchor primer. Then PCR product was cloned into pDrive vector (Qiagen) and then sequenced.
  The second is from hybridomas generated through electro-fusion: total RNA was extracted from hybridoma lines of interest using standard Trizol methods and frozen at −80° C. for long term storage. cDNA was generated from 100 ng total RNA using standard Superscript III reverse transcriptase and a gene-specific reverse primer binding to all mouse IgG isotypes for heavy chain and a mouse kappa constant region primer for the light chain amplification. 2-3 ul of cDNA were then used as template in a PCR reaction using Pfu DNA polymerase and a panel of degenerate forward primers annealing to the leader sequence of the human immunoglobulin variable domain as well as one mouse pan-IgG reverse primer. PCR products were run out of a 1% agarose gel and bands of approximately 350-450 basepairs extracted and purified. DNA was then sequenced.

The sequences from the first method can either be from IgM from Naïve mice or IgG from immunised mice. The samples from the second method are all from IgG from immunised mice, and specific to the immunising antigen. Almost 2000 sequences were analysed.

The sequences were obtained as a pair of forward and reverse reads. These were first trimmed to remove low-quality base calls from the ends of the reads (trimmed from both ends until a 19 nucleotide window had an average quality score of 25 or more). The reads were combined together by taking the reverse complement of the reverse read, and aligning it against the forward read. The alignment scoring was 5 for a match, −4 for a mismatch, a gap open penalty of 10 and a gap extension penalty of 1. A consensus sequence, was then produced by stepping through the alignment and comparing bases. When there was a disagreement the base with the highest quality value from sequencing was used.

The BLAST+ (Basic Local Alignment Search Tool) (Camacho C., Coulouris G., Avagyan V., Ma N., Papadopoulos J., Bealer K., & Madden T. L. (2008) "BLAST+: architecture and applications." BMC Bioinformatics 10:421 http://www.ncbi.nlm.nih.gov/pubmed/20003500) program 'blastn' was then used to find the germline J and V segments used in each sequence. A wordsize of 30 was used for V matching, and 15 for J matching. The database searched against was constructed from the NGS sequencing of the BACs which were used to generate the Kymouse.

If a sequence matched both a V and a J segment, the sequence between the two was then compared to a database of germline D segments in the mouse using 'blastn' with a wordsize of 4 and the options 'blastn-short' and 'ungapped'. This was used to assign a D segment, if possible. The CDR3 was identified by searching for the conserved "TATTACTGT" sequence in the V segment, and the "CTGGGG" in the J segment. If these motifs were not found, then up to 4 mismatches were allowed. The IMGT definition of CDR3 was used, so the CDR3 length is calculated from after the "TGT" in the V to before the "TGG" in the J. Sequences with an out of frame junction (those which do not have a CDR3 nucleotide length divisible by 3) or which contained a stop codon ("TAA", "TAG" or "TGA") were excluded.

The identity of the matching V, J and D segments as well as the CDR3 length from this assignment were then saved as a table for downstream analysis. The ratio of IGHJ6*02 used increased from the naïve to immunised mice, as well as being enriched in the sub-population of sequences with a long HCDR3 (defined as consisting of 20 or more amino acids):

|  | All | | HCDR3>20 | | |
|---|---|---|---|---|---|
|  | JH6*02% | Total Count | JH6*02% | Total Count | % HCDR3>20 |
| Naïve | 22.31% | 1340 | 91.11% | 45 | 3.36% |
| Immunised | 37.50% | 256 | 66.67% | 9 | 3.52% |
| Hybridoma | 36.13% | 119 | 63.64% | 11 | 9.24% |

This shows that the JH6*02 gene segment is selected for by immunisation, as the proportion of JH6*02 usage increases after immunisation. JH6*02 is also used in the majority of antibodies with a long HCDR3 length, which is desirable for targets which are specifically bound by long HCDR3 length antibodies.

Additionally, the analysis revealed that certain VH and D gene segments frequently yielded HCDR3s of long length (in all of naïve, immunised and antigen-specific repertoires of heavy chains). See Table 2.

TABLE 2

A: Long HCDR3s from Naïve Repertoires

|  | Average CDR3Length | Count |
|---|---|---|
| V | | |
| IGHV1-2*02 | 21 | 3 |
| IGHV1-18*01 | 21 | 5 |
| IGHV3-7*01 | 22 | 3 |
| IGHV6-1*01 | 21 | 5 |
| IGHV3-9*01 | 20 | 2 |
| IGHV2-5*10 | 20 | 1 |
| IGHV7-4-1*01 | 21 | 3 |
| IGHV1-3*01 | 21 | 5 |
| IGHV4-4*02 | 20 | 3 |
| IGHV3-13*01 | 22 | 1 |
| IGHV3-23*04 | 20 | 1 |
| IGHV1-8*01 | 21 | 10 |
| IGHV3-21*03 | 23 | 3 |
| D | | |
| IGHD2-2*02 | 20 | 1 |
| IGHD3-9*01 | 21 | 13 |
| IGHD3-10*01 | 21 | 26 |
| IGHD6-13*01 | 20 | 1 |
| IGHD4-17*01 | 22 | 2 |
| IGHD6-19*01 | 23 | 1 |
| IGHD3-22*01 | 20 | 1 |

| CDR3Length (All Naïve) | Count |
|---|---|
| 20 | 23 |
| 21 | 10 |
| 22 | 7 |
| 23 | 3 |
| 24 | 1 |
| 26 | 1 |

B: Long HCDR3s from Immunised Repertoires

|  | Average CDR3Length | Count |
|---|---|---|
| V | | |
| IGHV4-4*02 | 20 | 1 |
| IGHV3-11*01 | 23 | 2 |
| IGHV3-7*01 | 21 | 6 |
| D | | |
| IGHD2-2*02 | 22 | 2 |
| IGHD3-10*01 | 22 | 5 |
| IGHD6-19*01 | 20 | 1 |
| IGHD1-26*01 | 20 | 1 |

| CDR3Length (All Immunised) | Count |
|---|---|
| 20 | 4 |
| 21 | 1 |
| 22 | 2 |
| 24 | 1 |
| 25 | 1 |

C: Long HCDR3s from Antigen-Specific Repertoires

|  | Average CDR3Length | Count |
|---|---|---|
| V | | |
| IGHV4-4*02 | 20 | 2 |
| IGHV1-3*01 | 21 | 3 |
| IGHV3-11*01 | 21 | 1 |
| IGHV3-7*01 | 22 | 1 |
| IGHV1-8*01 | 22 | 2 |
| IGHV3-20*d01 | 22 | 1 |
| IGHV3-9*01 | 20 | 1 |
| D | | |
| IGHD2-2*02 | 22 | 1 |
| IGHD3-9*01 | 21 | 1 |
| IGHD3-10*01 | 21 | 9 |

| CDR3Length (All Antigen-Specific) | Count |
|---|---|
| 20 | 4 |
| 22 | 2 |
| 21 | 4 |
| 24 | 1 |

The invention claimed is:

1. A method of isolating an antibody that binds a predetermined antigen, said antibody comprising a human heavy chain variable region, the method comprising
   (a) providing a mouse whose genome comprises:
      (i) an immunoglobulin heavy (IgH) chain locus comprising a plurality of human VH, one or more human D and one or more human JH gene segments at an endogenous locus upstream of and operably linked to a constant region;
         wherein said plurality of human VH gene segments is selected from at least two of the group consisting of: IGHV3-7*01, IGHV3-9*01, IGHV7-4-1*01, IGHV1-3*01, IGHV4-4*02, IGHV3-13*01, IGHV3-23*04 and VH3-20*d01, and where one or more human D gene segments is selected from the group consisting of: IGHD2-2*01, IGHD3-9*01, IGHD3-10*01, IGHD6-13*01, IGHD4-17*01, IGHD6-19*01, IGHD3-22*01 and IGHD1-26*01,
         said plurality of human VH gene segments each being capable of joining with a human D gene segment and a human JH gene segment to encode a variable region,
         said plurality of human VH gene segments being capable of joining with a human D gene segment and a human JH segment to encode a variable region comprising a HCDR3 of 20 or more amino acids in length in said mouse;
         said plurality of human VH gene segments capable of joining with a human D gene segment and a human JH segment to encode a variable region comprising a HCDR3 of 20 or more amino acids in length in said mouse and expresses an IgH heavy chain comprising a HCDR3 of 20 or more amino acids in length;
      (ii) an immunoglobulin light (IgL) chain locus comprising one or more human VL gene segments and one or more human JL gene segments upstream of and operatively linked to a constant region;
   (b) contacting said mouse with said antigen;
   (c) removing B lymphocytes from the mouse and selecting a B lymphocyte expressing antibody that binds to the antigen;
   (d) isolating an antibody expressed by the B lymphocytes, wherein in step (d) the antibody which is isolated has an HCDR3 length of at least 20 amino acids.

2. The method of claim 1, comprising the step of isolating from said B lymphocyte nucleic acid encoding said antibody that binds said antigen.

3. The method of claim 1, further comprising altering the antibody produced by the method of claim 1.

4. The method of claim 1, wherein said antibody is an IgG-type antibody.

5. A method of isolating an antibody that binds an antigen of an infectious disease pathogen, the method comprising
   (a) providing a mouse according to step (a) of claim 1;
   (b) contacting said mouse with said antigen;

(c) removing B lymphocytes from the mouse and selecting one or more B lymphocytes expressing antibodies that bind to the antigen;

(d) isolating an antibody expressed by the B lymphocytes; wherein in step (d) the antibody which is isolated has an HCDR3 length of at least 20 amino acids.

6. The method of claim 5, comprising the step of isolating from said B lymphocytes nucleic acid encoding said antibody that binds said antigen.

7. The method of claim 6, wherein said antibody is an IgG-type antibody.

8. The method of claim 5, further comprising altering the antibody produced by the method of claim 5.

9. The method of claim 1, wherein the human V region gene segments of said immunoglobulin heavy (IgH) chain locus step (a)(i) of said mouse genome consists of said a plurality of human VH, said one or more human D and said one or more human JH gene segments.

10. A method of isolating an antibody or fragment thereof, wherein said antibody binds a predetermined antigen, said antibody comprising a human heavy chain variable region, the method comprising:
(a) providing a mouse-whose genome comprises:
   (i) an immunoglobulin heavy (IgH) chain locus comprising a plurality of human VH, one or more human D and one or more human JH gene segments at an endogenous locus upstream of and operably linked to a constant region;
   wherein said plurality of human VH gene segments is selected from at least two of the group consisting of: IGHV3-7*01, IGHV3-9*01, IGHV7-4-1*01, IGHV1-3*01, IGHV4-4*02, IGHV3-13*01, IGHV3-23*04 and VH3-20*d01, and wherein said one or more human D gene segments is selected from the group consisting of: IGHD2-2*02, IGHD3-9*01, IGHD3-10*01, IGHD6-13*01, IGHD4-17*01, IGHD6-19*01, IGHD3-22*01 and IGHD1-26*01,
   wherein said plurality of human VH gene segments comprises: IGHV3-7*01, IGHV3-9*01, IGHV7-4-1*01, IGHV1-3*01, IGHV4-4*02, IGHV3-13*01, IGHV3-23*04, and VH3-20*d01;
   said plurality of human VH gene segments each being capable of joining with a human D gene segment and a human JH segment to encode a variable region;
   (ii) an immunoglobulin light (IgL) chain locus comprising one or more human VL gene segments and one or more human JL gene segments upstream of and operatively linked to a constant region;
(b) contacting said mouse with said antigen;
(c) isolating nucleic acid from the tissue or blood of said contacted mouse of (b), wherein said nucleic comprises nucleic acid encoding said antibody, wherein said antibody comprises a human Ig chain variable region and binds said antigen, (d) expressing from said nucleic acid one or more of:
   (i) an IgH chain or fragment thereof, of said antibody that binds said antigen, wherein said IgH chain or fragment thereof, comprises a human IgH chain variable region,
   (ii) an IgL chain or fragment thereof, of said antibody that binds said antigen, wherein said IgL chain or fragment thereof, comprises a human IgL chain variable region, or
   (iii) the IgH chain or fragment thereof, of (d)(i) and the IgL chain or fragment thereof, of (d)(ii),
(e) isolating an antibody or fragment thereof, wherein said isolated antibody or fragment thereof, comprises the IgH chain or fragment thereof, of (d)(i) and/or the IgL chain or fragment thereof, of (d)(ii), and wherein said antibody contains a said human Ig variable region and binds said antigen.

11. A method of isolating an antibody that binds a predetermined antigen, said antibody comprising a human heavy chain variable region, the method comprising
(a) providing a mouse whose genome comprises:
   (i) an immunoglobulin heavy (IgH) chain locus comprising a plurality of human VH, one or more human D and one or more human JH gene segments at an endogenous locus upstream of and operably linked to a constant region;
   wherein said plurality of human VH gene segments is selected from at least two of the group consisting of: IGHV3-7*01, IGHV3-9*01, IGHV7-4-1*01, IGHV1-3*01, IGHV4-4*02, IGHV3-13*01, IGHV3-23*04 and VH3-20*d01, and where one or more human D gene segments is selected from the group consisting of: IGHD2-2*01, IGHD3-9*01, IGHD3-10*01, IGHD6-13*01, IGHD4-17*01, IGHD6-19*01, IGHD3-22*01 and IGHD1-26*01,
   wherein said plurality of human VH gene segments comprises: IGHV3-7*01, IGHV3-9*01, IGHV7-4-1*01, IGHV1-3*01, IGHV4-4*02, IGHV3-13*01, IGHV3-23*04, and VH3-20*d01;
   said plurality of human VH gene segments each being capable of joining with a human D gene segment and a human JH gene segment to encode a variable region,
   (ii) an immunoglobulin light (IgL) chain locus comprising one or more human VL gene segments and one or more human JL gene segments upstream of and operatively linked to a constant region;
(b) contacting said mouse with said antigen;
(c) removing B lymphocytes from the mouse and selecting a B lymphocyte expressing antibody that binds to the antigen;
(d) isolating an antibody expressed by the B lymphocytes.

12. The method of claim 1, wherein said one or more human D gene segments comprises IGHD2-2*02, IGHD3-9*01, IGHD3-10*01, IGHD6-13*01, IGHD4-17*01, IGHD6-19*01, IGHD3-22*01 and IGHD1-26*01.

* * * * *